(12) United States Patent
Zhang et al.

(10) Patent No.: US 8,436,023 B2
(45) Date of Patent: May 7, 2013

(54) CYCLOHEXYL-AZETIDINYL ANTAGONISTS OF CCR2

(75) Inventors: Xuqing Zhang, Spring House, PA (US); Zhihua Sui, Spring House, PA (US); James C. Lanter, Spring House, PA (US)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 13/156,450

(22) Filed: Jun. 9, 2011

(65) Prior Publication Data

US 2011/0306592 A1    Dec. 15, 2011

Related U.S. Application Data

(60) Provisional application No. 61/353,003, filed on Jun. 9, 2010.

(51) Int. Cl.

| | | |
|---|---|---|
| *A61K 31/4418* | (2006.01) | |
| *A61K 31/427* | (2006.01) | |
| *A61K 31/422* | (2006.01) | |
| *A61K 31/423* | (2006.01) | |
| *A61K 31/416* | (2006.01) | |
| *A61K 31/4178* | (2006.01) | |
| *C07D 231/56* | (2006.01) | |
| *C07D 401/14* | (2006.01) | |
| *C07D 417/14* | (2006.01) | |
| *C07D 263/32* | (2006.01) | |
| *C07D 261/20* | (2006.01) | |
| *C07D 233/64* | (2006.01) | |

(52) U.S. Cl.
USPC ........... 514/338; 514/365; 514/374; 514/379; 514/397; 514/407; 546/272.1; 546/275.4; 548/181; 548/236; 548/241; 548/311.7; 548/362.1

(58) Field of Classification Search .................. None
See application file for complete search history.

(56) References Cited

U.S. PATENT DOCUMENTS

2003/0004151 A1   1/2003   Cherney et al.

FOREIGN PATENT DOCUMENTS

| WO | WO 9857641 | 12/1998 |
|---|---|---|
| WO | WO 0134598 | 5/2001 |
| WO | WO 2004/050024 | 6/2004 |
| WO | WO 2006/073592 | 7/2006 |
| WO | WO 2007003965 | 1/2007 |
| WO | WO 2010/068663 | 6/2010 |
| WO | WO 2010/121011 | 10/2010 |
| WO | WO 2010/121036 | 10/2010 |
| WO | WO 2010/121046 | 10/2010 |

OTHER PUBLICATIONS

Dawson J, et al., Targeting monocyte chemoattractant protein-1 signaling in disease, *Expert Opin. Ther. Targets*, Feb. 7, 2003 (1):35-48.
Rollins B J, Monocyte chemoattractant protein 1: a potential regulator of monocyte recruitment in inflammatory disease, *Mol. Med. Today*, 1996, 2:198.
International Search Report—PCT/US2011/039724—dated Jul. 12, 2009.
U.S. Appl. No. 13/161,572, filed Jun. 16, 2011.
Xia, et al., "Recent Developments in CCR2 Antagonists", Expert Opin. Ther. Patents, 19(3), 2009, pp. 295-303.

*Primary Examiner* — Joseph K. McKane
*Assistant Examiner* — Alicia L Otton
(74) *Attorney, Agent, or Firm* — Mary A. Appollina

(57) ABSTRACT

The present invention comprises compounds of Formula (I).

Formula (I)

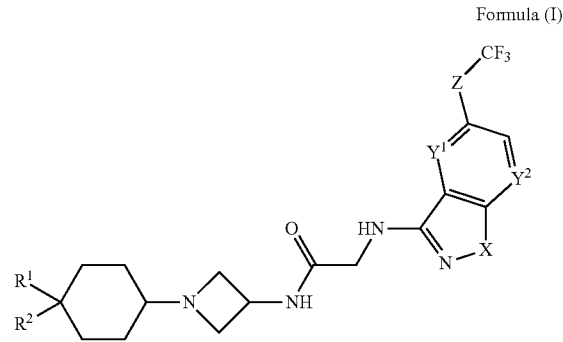

wherein: $R^1$, $R^2$, X, and Z are as defined in the specification. The invention also comprises a method of preventing, treating or ameliorating a syndrome, disorder or disease, wherein said syndrome, disorder or disease is type II diabetes, obesity and asthma. The invention also comprises a method of inhibiting CCR2 activity in a mammal by administration of a therapeutically effective amount of at least one compound of Formula (I).

15 Claims, No Drawings

CYCLOHEXYL-AZETIDINYL ANTAGONISTS OF CCR2

CROSS-REFERENCE TO RELATED APPLICATIONS

This application claims priority from U.S. Provisional Application Ser. No. 61/353,003 filed Jun. 9, 2010, the contents of each of which are hereby incorporated by reference in their entirety.

FIELD OF THE INVENTION

The invention is directed to substituted cyclohexyl azetidine compounds, which are antagonists to the chemoattractant cytokine receptor 2 (CCR2), pharmaceutical compositions, and methods for use thereof. More particularly, the CCR2 antagonists disclosed herein are useful for preventing, treating or ameliorating a CCR2 mediated syndrome, disorder or disease.

BACKGROUND OF THE INVENTION

CCR2 is a member of the GPCR family of receptors, as are all known chemokine receptors, and are expressed by monocytes and memory T-lymphocytes. The CCR2 signaling cascade involves activation of phospholipases (PLCβ2), protein kinases (PKC), and lipid kinases (PI-3 kinase).

Chemoattractant cytokines (i.e., chemokines) are relatively small proteins (8-10 kD), which stimulate the migration of cells. The chemokine family is divided into four subfamilies based on the number of amino acid residues between the first and second highly conserved cysteines. Monocyte chemotactic protein-1 (MCP-1) is a member of the CC chemokine subfamily (wherein CC represents the subfamily having adjacent first and second cysteines) and binds to the cell-surface chemokine receptor 2 (CCR2). MCP-1 is a potent chemotactic factor, which, after binding to CCR2, mediates monocyte and lymphocyte migration (i.e., chemotaxis) toward a site of inflammation. MCP-1 is also expressed by cardiac muscle cells, blood vessel endothelial cells, fibroblasts, chondrocytes, smooth muscle cells, mesangial cells, alveolar cells, T-lymphocytes, macrophages, and the like.

After monocytes enter the inflammatory tissue and differentiate into macrophages, monocyte differentiation provides a secondary source of several proinflammatory modulators, including tumor necrosis factor-α (TNF-α), interleukin-1 (IL-1), IL-8 (a member of the CXC chemokine subfamily, wherein CXC represents one amino acid residue between the first and second cysteines), IL-12, arachidonic acid metabolites (e.g., $PGE_2$ and $LTB_4$), oxygen-derived free radicals, matrix metalloproteinases, and complement components.

Animal model studies of chronic inflammatory diseases have demonstrated that inhibition of binding between MCP-1 and CCR2 by an antagonist suppresses the inflammatory response. The interaction between MCP-1 and CCR2 has been implicated (see Rollins B J, Monocyte chemoattractant protein 1: a potential regulator of monocyte recruitment in inflammatory disease, *Mol. Med. Today,* 1996, 2:198; and Dawson J, et al., Targeting monocyte chemoattractant protein-1 signaling in disease, *Expert Opin. Ther. Targets,* 2003 Feb. 7 (1):35-48) in inflammatory disease pathologies such as psoriasis, uveitis, atherosclerosis, rheumatoid arthritis (RA), multiple sclerosis, Crohn's Disease, nephritis, organ allograft rejection, fibroid lung, renal insufficiency, type II diabetes and diabetic complications, diabetic nephropathy, diabetic retinopathy, diabetic retinitis, diabetic microangiopathy, tuberculosis, sarcoidosis, invasive staphylococcia, inflammation after cataract surgery, allergic rhinitis, allergic conjunctivitis, chronic urticaria, Chronic Obstructive Pulmonary Disease (COPD), allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, and stomach.

Monocyte migration is inhibited by MCP-1 antagonists (either antibodies or soluble, inactive fragments of MCP-1), which have been shown to inhibit the development of arthritis, asthma, and uveitis. Both MCP-1 and CCR2 knockout (KO) mice have demonstrated that monocyte infiltration into inflammatory lesions is significantly decreased. In addition, such KO mice are resistant to the development of experimental allergic encephalomyelitis (EAE, a model of human MS), cockroach allergen-induced asthma, atherosclerosis, and uveitis. Rheumatoid arthritis and Crohn's Disease patients have improved during treatment with TNF-α antagonists (e.g., monoclonal antibodies and soluble receptors) at dose levels correlated with decreases in MCP-1 expression and the number of infiltrating macrophages.

MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e. to up-regulate) the expression of MCP-1 and other chemokines in the nasal mucosa of people with allergic rhinitis, suggesting the presence of a positive feedback loop in such patients.

There remains a need for small molecule CCR2 antagonists for preventing, treating or ameliorating a CCR2 mediated inflammatory syndrome, disorder or disease resulting from MCP-1 induced monocyte and lymphocyte migration to a site of inflammation.

All documents cited herein are incorporated by reference.

SUMMARY OF THE INVENTION

The invention relates to the compounds of Formula (I)

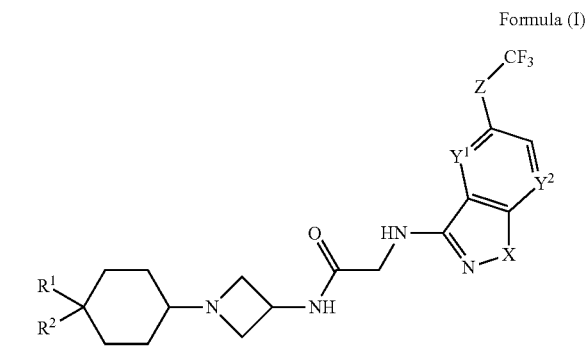

Formula (I)

wherein:
X is O or $NR^3$;
wherein $R^3$ is: H, $C_{(1-6)}$alkyl, $CH_2CF_3$, $C_{(1-6)}$alkylOH, $C_{(2-6)}$alkenyl, $CH_2OC_{(2-6)}$alkenyl, $CH_2OC_{(1-6)}$alkyl, $C(O)CO_{(1-6)}$alkyl, $CONH_2$, $CONHC_{(1-6)}$alkyl, $SONH_2$, $CH_2Ph$, $CH_2$heteroaryl, $CH_2$heterocyclyl, $CH_2$cycloalkyl, $C_{(3-6)}$cycloalkyl, or SO$_2$C$_{(1-2)}$alkyl; wherein said heteroaryl, heterocyclyl, or cycloalkyl may be optionally substituted with up to three substituents selected from the group consisting of: F, OCH$_3$, CH$_3$, and OH;

Y$^1$ and Y$^2$ are CH or N, provided that both Y$^1$ and Y$^2$ are not N; Z is O, CH$_2$, S, S(O), SO$_2$,

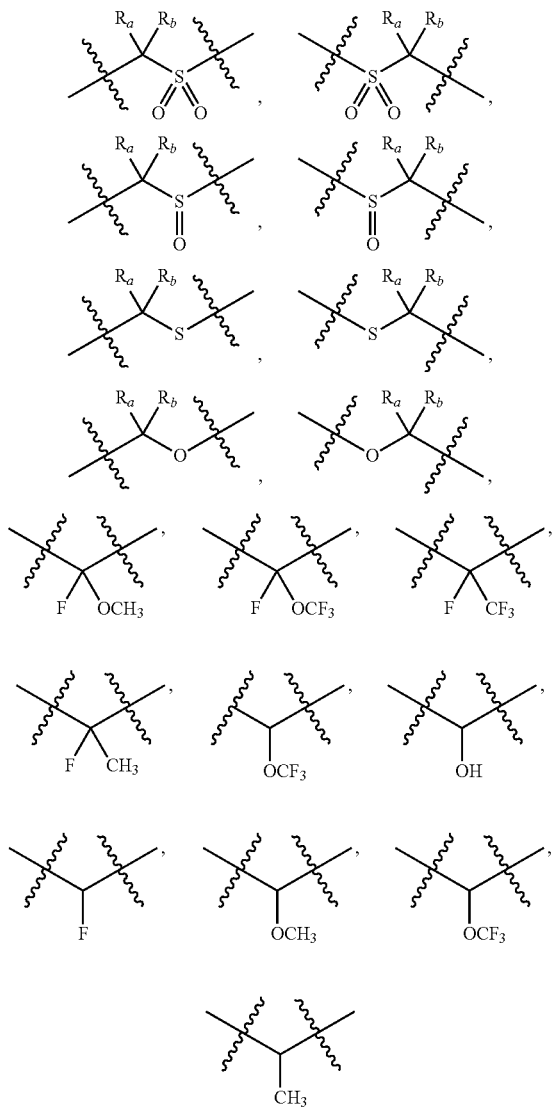

or a direct bond; wherein R$_a$ independently are selected from the group consisting of: H, OH, F, CH$_3$, CF$_3$, OCF$_3$, and OCH$_3$;

R$^1$ is

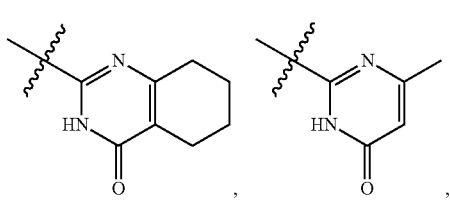

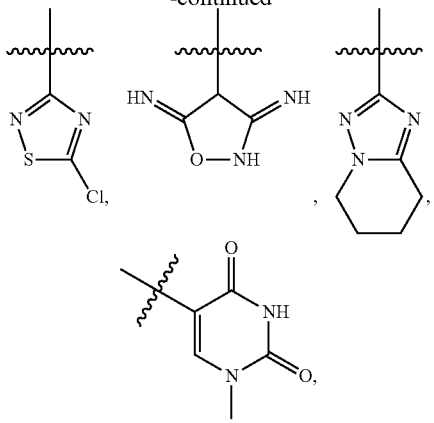

pyridyl, pyridyl-N-oxide, pyrimidyl, pyrazolyl, indolyl, thiazolyl, benzo[1,3]dioxol-5-yl, pyrazolyl, oxazolyl, isoxazolyl, imidazolyl, phenyl, thiazolyl, isothiazolyl, 3-H-thiazol-2-onyl, benzooxazolyl, furyl, [1,2,4]oxadiazolyl, [1,3,4]thiadiazolyl, C$_{(4-7)}$cycloalkyl, C$_{(1-6)}$alkyl, C$_{(1-4)}$alkylOH, CH$_2$OC$_{(3-6)}$alkenyl, CH$_2$OC$_{(1-4)}$alkyl, CH$_2$C(O)NH$_2$, CO$_2$C$_{(1-4)}$alkyl, —CN, C(O)NH$_2$, C(O)NHCH$_2$CH$_2$OH, OTBS, OH, OC$_{(1-4)}$alkyl, OC$_{(3-6)}$alkenyl, NH$_2$, or NHBOC, or pyridonyl; wherein said pyridyl, pyridyl-N-oxide, pyrimidyl, pyrazolyl, indolyl, thiazolyl, benzo[1,3]dioxol-5-yl, pyrazolyl, oxazolyl, isoxazolyl, imidazolyl, phenyl, thiazolyl, isothiazolyl, 3-H-thiazol-2-onyl, benzooxazolyl, furyl, [1,2,4]oxadiazolyl, [1,3,4]thiadiazolyl, C$_{(4-7)}$cycloalkyl, C$_{(1-6)}$alkyl, or pyridonyl, may be optionally substituted with two substituents, independently selected from the group consisting of: CH$_2$C(O)NH$_2$, C$_{(1-4)}$alkoxy, OC$_{(3-6)}$cycloalkyl, OCH$_2$CF$_3$, OCH$_2$Ph, F, CN, Cl, OCF$_3$, CF$_3$, CH$_2$CN, C$_{(1-4)}$alkyl, CH$_2$CF$_3$, N(C$_{(1-4)}$alkyl)$_2$, C$_{(1-4)}$alkylOH, Si(CH$_3$)$_3$, —C≡CH, SCH$_3$, S(O)CH$_3$, SO$_2$CH$_3$, pyrrolidinyl, OH, NH$_2$, NHCN, CO$_2$H, CONH$_2$, NHCO$_2$C$_{(1-4)}$alkyl, N(SO$_2$CH$_3$)$_2$, NHSO$_2$CH$_3$, NHC(O)CF$_3$, NHC$_{(1-4)}$alkyl, NHCO$_2$H, NHCO$_2$C$_{(1-4)}$alkyl, NHCOC$_{(1-4)}$alkyl, NHCONH$_2$, NHCONHC$_{(1-4)}$alkyl, and Br;

R$^2$ is F, NH$_2$, H, or OH;

and tautomers and pharmaceutically acceptable salts thereof.

DETAILED DESCRIPTION OF THE INVENTION

The invention relates to the compounds of Formula (I)

Formula (I)

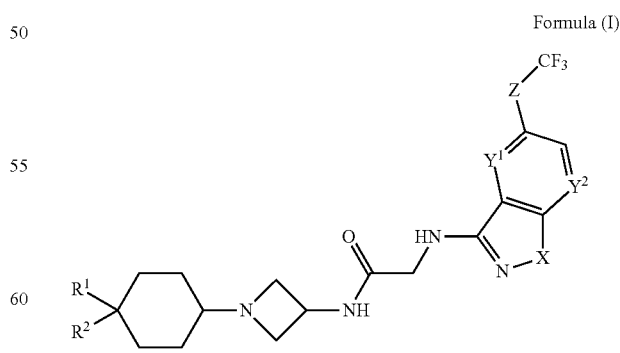

wherein:
X is O or NR$^3$;
wherein R$^3$ is: H, C$_{(1-6)}$alkyl, CH$_2$CF$_3$, C$_{(1-6)}$alkylOH, C$_{(2-6)}$alkenyl, CH$_2$OC$_{(2-6)}$alkenyl, CH$_2$OC$_{(1-6)}$alkyl, C(O)CO$_{(1-6)}$ alkyl, CONH$_2$, CONHC$_{(1-6)}$alkyl, SONH$_2$, CH$_2$Ph, CH$_2$heteroaryl, CH$_2$heterocyclyl, CH$_2$cycloalkyl, C$_{(3-6)}$cycloalkyl, or SO$_2$C$_{(1-2)}$alkyl; wherein said heteroaryl, heterocyclyl, or cycloalkyl may be optionally substituted with up to three substituents selected from the group consisting of: F, OCH$_3$, CH$_3$, and OH;

Y$^1$ and Y$^2$ are CH or N, provided that both Y$^1$ and Y$^2$ are not N;

Z is O, CH$_2$, S, S(O), SO$_2$,

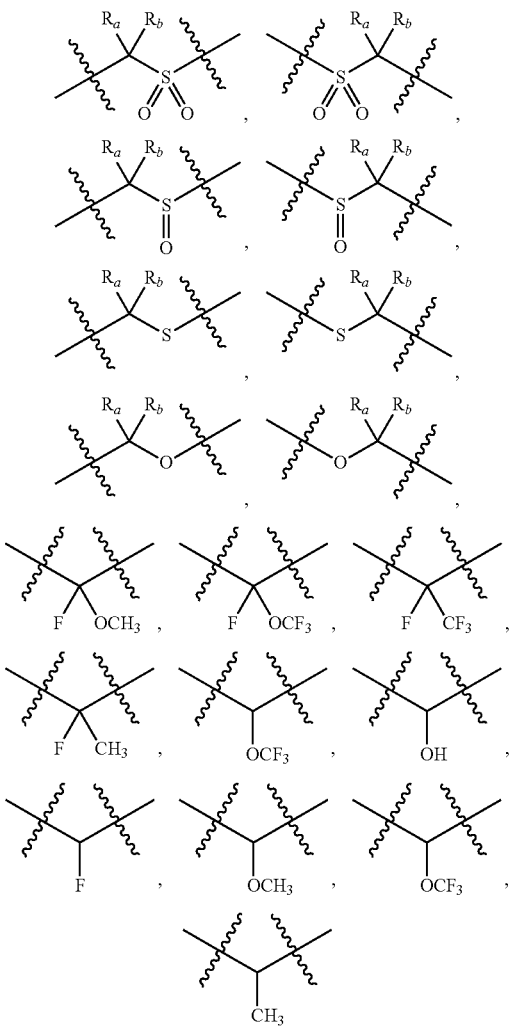

or a direct bond; wherein R$_a$ independently are selected from the group consisting of: H, OH, F, CH$_3$, CF$_3$, OCF$_3$, and OCH$_3$;

R$^1$ is

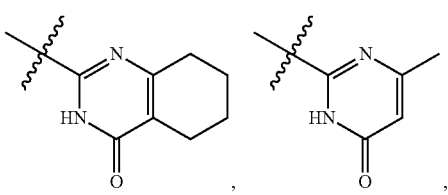

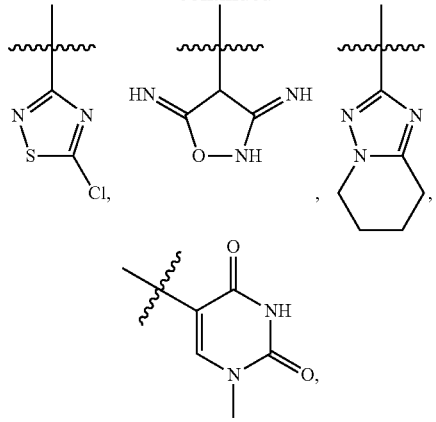

pyridyl, pyridyl-N-oxide, pyrimidyl, pyrazolyl, indolyl, thiazolyl, benzo[1,3]dioxol-5-yl, pyrazolyl, oxazolyl, isoxazolyl, imidazolyl, phenyl, thiazolyl, isothiazolyl, 3-H-thiazol-2-onyl, benzooxazolyl, furyl, [1,2,4]oxadiazolyl, [1,3,4]thiadiazolyl, C$_{(4-7)}$cycloalkyl, C$_{(1-6)}$alkyl, C$_{(1-4)}$alkylOH, CH$_2$OC$_{(3-6)}$alkenyl, CH$_2$OC$_{(1-4)}$alkyl, CH$_2$C(O)NH$_2$, CO$_2$C$_{(1-4)}$alkyl, —CN, C(O)NH$_2$, C(O)NHCH$_2$CH$_2$OH, OTBS, OH, OC$_{(1-4)}$alkyl, OC$_{(3-6)}$alkenyl, NH$_2$, or NHBOC, or pyridonyl; wherein said pyridyl, pyridyl-N-oxide, pyrimidyl, pyrazolyl, indolyl, thiazolyl, benzo[1,3]dioxol-5-yl, pyrazolyl, oxazolyl, isoxazolyl, imidazolyl, phenyl, thiazolyl, isothiazolyl, 3-H-thiazol-2-onyl, benzooxazolyl, furyl, [1,2,4]oxadiazolyl, [1,3,4]thiadiazolyl, C$_{(4-7)}$cycloalkyl, C$_{(1-6)}$alkyl, or pyridonyl, may be optionally substituted with two substituents, independently selected from the group consisting of: CH$_2$C(O)NH$_2$, C$_{(1-4)}$alkoxy, OC$_{(3-6)}$cycloalkyl, OCH$_2$CF$_3$, OCH$_2$Ph, F, CN, Cl, OCF$_3$, CF$_3$, CH$_2$CN, C$_{(1-4)}$alkyl, CH$_2$CF$_3$, N(C$_{(1-4)}$alkyl)$_2$, C$_{(1-4)}$alkylOH, Si(CH$_3$)$_3$, —C≡CH, SCH$_3$, S(O)CH$_3$, SO$_2$CH$_3$, pyrrolidinyl, OH, NH$_2$, NHCN, CO$_2$H, CONH$_2$, NHCO$_2$C$_{(1-4)}$alkyl, N(SO$_2$CH$_3$)$_2$, NHSO$_2$CH$_3$, NHC(O)CF$_3$, NHC$_{(1-4)}$alkyl, NHCO$_2$H, NHCO$_2$C$_{(1-4)}$alkyl, NHCOC$_{(1-4)}$alkyl, NHCONH$_2$, NHCONHC$_{(1-4)}$alkyl, and Br;

R$^2$ is F, NH$_2$, H, or OH;

and tautomers, and pharmaceutically acceptable salts thereof.

In another embodiment of the invention:

X is O or NR$^3$;

wherein R$^3$ is: H, C$_{(1-6)}$alkyl, CH$_2$CF$_3$, C$_{(1-6)}$alkylOH, C$_{(2-6)}$alkenyl, CH$_2$OC$_{(2-6)}$alkenyl, CH$_2$OC$_{(1-6)}$alkyl, C(O)C$_{(1-6)}$alkyl, CONH$_2$, CONHC$_{(1-6)}$alkyl, SONH$_2$, CH$_2$Ph, CH$_2$heteroaryl, CH$_2$heterocyclyl, CH$_2$cycloalkyl, C$_{(3-6)}$cycloalkyl, or SO$_2$C$_{(1-2)}$alkyl; wherein said heteroaryl, heterocyclyl, or cycloalkyl may be optionally substituted with up to three substituents selected from the group consisting of: F, OCH$_3$, CH$_3$, and OH;

Y$^1$ and Y$^2$ are CH;

Z is O, CH$_2$, S, S(O), SO$_2$,

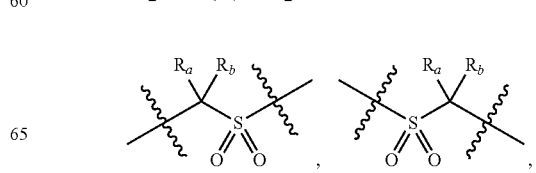

-continued

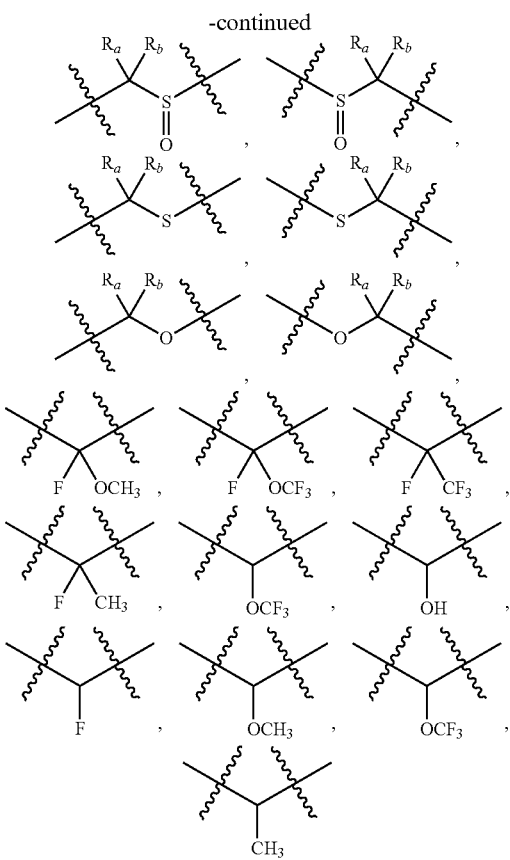

or a direct bond; wherein $R_a$ independently are selected from the group consisting of: H, OH, F, CH$_3$, CF$_3$, OCF$_3$, and OCH$_3$;

$R^1$ is pyridyl,

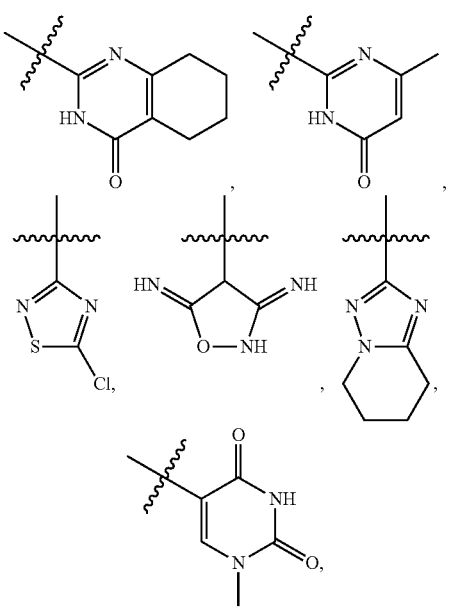

pyridyl, pyridyl-N-oxide, pyrimidyl, pyrazolyl, indolyl, thiazolyl, benzo[1,3]dioxol-5-yl, pyrazolyl, oxazolyl, isoxazolyl, imidazolyl, phenyl, thiazolyl, isothiazolyl, benzooxazolyl, furyl, [1,2,4]oxadiazolyl, [1,3,4]thiadiazolyl, C$_{(4-7)}$cycloalkyl, C$_{(1-6)}$alkyl, C$_{(1-4)}$alkylOH, CH$_2$OC$_{(3-6)}$alkenyl, CH$_2$OC$_{(1-4)}$alkyl, CH$_2$C(O)NH$_2$, CO$_2$C$_{(1-4)}$alkyl, —CN, C(O)NH$_2$, C(O)NHCH$_2$CH$_2$OH, OTBS, OH, OC$_{(1-4)}$alkyl, OC$_{(3-6)}$alkenyl, NH$_2$, or NHBOC, or pyridonyl; wherein said pyridyl, pyridyl-N-oxide, pyrimidyl, pyrazolyl, indolyl, thiazolyl, benzo[1,3]dioxol-5-yl, pyrazolyl, oxazolyl, isoxazolyl, imidazolyl, phenyl, thiazolyl, isothiazolyl, benzooxazolyl, furyl, [1,2,4]oxadiazolyl, [1,3,4]thiadiazolyl, C$_{(4-7)}$cycloalkyl, C$_{(1-6)}$alkyl, or pyridonyl, may be optionally substituted with two substituents, independently selected from the group consisting of: CH$_2$C(O)NH$_2$, C$_{(1-4)}$alkoxy, OC$_{(3-6)}$cycloalkyl, OCH$_2$CF$_3$, OCH$_2$Ph, F, CN, Cl, OCF$_3$, CF$_3$, CH$_2$CN, C$_{(1-4)}$alkyl, CH$_2$CF$_3$, N(C$_{(1-4)}$alkyl)$_2$, C$_{(1-4)}$alkylOH, Si(CH$_3$)$_3$, —C≡CH, SCH$_3$, S(O)CH$_3$, SO$_2$CH$_3$, pyrrolidinyl, OH, NH$_2$, NHCN, CO$_2$H, CONH$_2$, NHCO$_2$C$_{(1-4)}$alkyl, N(SO$_2$CH$_3$)$_2$, NHSO$_2$CH$_3$, NHC(O)CF$_3$, NHC$_{(1-4)}$alkyl, NHCO$_2$H, NHCO$_2$C$_{(1-4)}$alkyl, NHCOC$_{(1-4)}$alkyl, NHCONH$_2$, NHCONHC$_{(1-4)}$alkyl, and Br;

$R^2$ is F, NH$_2$, H, or OH;

and tautomers, and pharmaceutically acceptable salts thereof.

In another embodiment of the invention:

X is O or NR$^3$;

wherein R$^3$ is: H, C$_{(1-6)}$alkyl, CH$_2$CF$_3$, C$_{(1-6)}$alkylOH, C$_{(2-6)}$alkenyl, CH$_2$OC$_{(2-6)}$alkenyl, CH$_2$OC$_{(1-6)}$alkyl, C(O)C$_{(1-6)}$alkyl, CONH$_2$, CONHC$_{(1-6)}$alkyl, SONH$_2$, CH$_2$Ph, CH$_2$pyridyl, CH$_2$pyrrolyl, CH$_2$pyrimidyl, CH$_2$pyridazyl, CH$_2$imidazolyl, CH$_2$oxazolyl, CH$_2$isoxazolyl, CH$_2$furanyl, or SO$_2$C$_{(1-2)}$alkyl;

Y$^1$ and Y$^2$ are CH;

Z is O, CH$_2$,

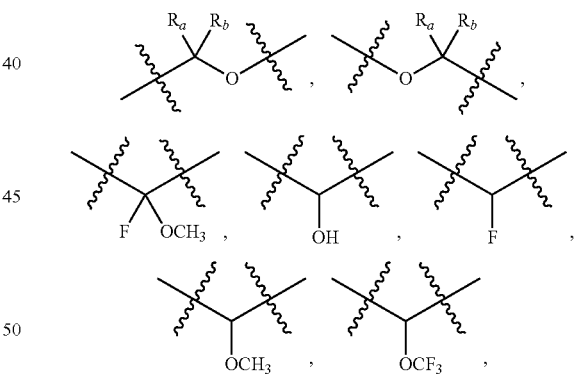

or a direct bond; wherein R$_a$ and R$_b$ are independently selected from the group consisting of: H, OH, F, and OCH$_3$;

R$^1$ is

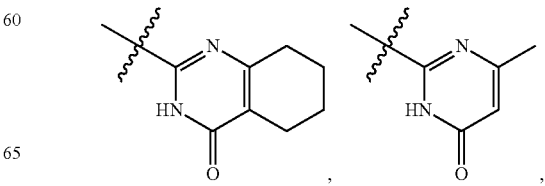

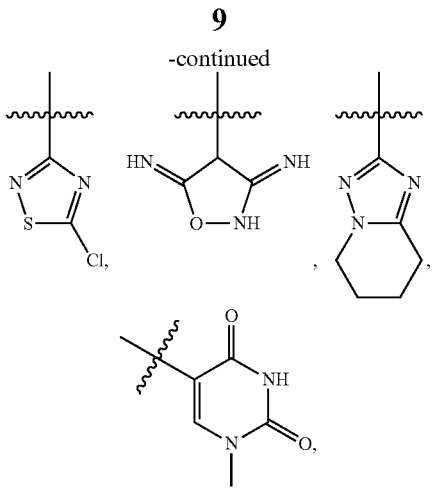

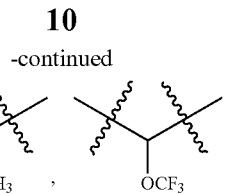

or a direct bond;

$R^1$ is pyridyl, thiazolyl, benzo[1,3]dioxol-5-yl, pyrazolyl, oxazolyl, imidazolyl, phenyl, $C_{(5-6)}$cycloalkyl, $C_{(2-6)}$alkyl, $C_{(1-4)}$alkylOH, $CH_2OC_{(3-6)}$alkenyl, $CH_2OC_{(1-4)}$alkyl, $CH_2C(O)NH_2$, $CO_2C_{(1-4)}$alkyl, —CN, $C(O)NH_2$, $C(O)NHCH_2CH_2OH$, OTBS, OH, $OC_{(1-4)}$alkyl, $OC_{(3-6)}$alkenyl, $NH_2$, NHBOC, or

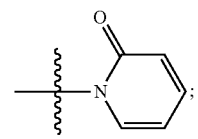

wherein said pyridyl, thiazolyl, benzo[1,3]dioxol-5-yl, pyrazolyl, oxazolyl, imidazolyl, phenyl, or $C_{(5-6)}$cycloalkyl may be optionally substituted with one substituent selected from the group consisting of: $C_{(1-3)}$alkyl, $C_{(1-3)}$alkoxy, $N(CH_3)_2$, or $CH_2C(O)NH_2$;

$R^2$ is H, or OH;

and tautomers, and pharmaceutically acceptable salts thereof.

In another embodiment of the invention:

X is O or $NR^3$;

wherein $R^3$ is: H, $C_{(1-6)}$alkyl, $CH_2CF_3$, $C_{(1-6)}$alkylOH, $CH_2CH=CH_2$, $CONH_2$, $CONHC_{(1-6)}$alkyl, $CH_2Ph$, $CH_2$pyridyl, or $SO_2C_{(1-2)}$alkyl;

$Y^1$ and $Y^2$ are CH;

Z is O, $CH_2$,

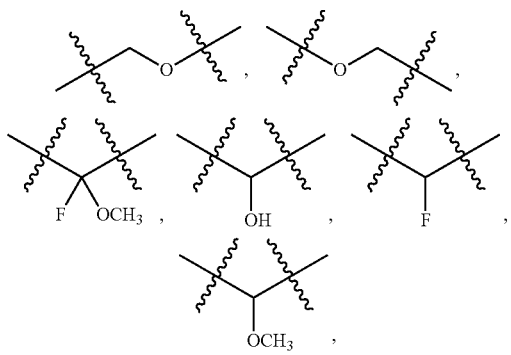

or a direct bond;

$R^1$ is pyrid-3-yl, pyrid-5-yl, pyrid-6-yl, thiazol-2-yl, thiazol-5-yl, benzo[1,3]dioxol-5-yl, pyrazol-4-yl, oxazol-2-yl, imidazol-2-yl, phenyl, cyclohexyl, $C_{(2-6)}$alkyl, $C_{(1-4)}$alkylOH, $CH_2OC_{(3-6)}$alkenyl, $CH_2OC_{(1-4)}$alkyl, $CH_2C(O)NH_2$, $CO_2C_{(1-4)}$alkyl, —CN, $C(O)NH_2$, $C(O)NHCH_2CH_2OH$, OTBS, OH, $OC_{(1-4)}$alkyl, $OC_{(3-6)}$alkenyl, $NH_2$, NHBOC, or pyridyl, pyrimidyl, pyrazolyl, thiazolyl, benzo[1,3]dioxol-5-yl, pyrazolyl, oxazolyl, isoxazolyl, imidazolyl, phenyl, thiazolyl, isothiazolyl, [1,2,4]oxadiazolyl, [1,3,4]thiadiazolyl, $C_{(4-7)}$cycloalkyl, $C_{(1-6)}$alkyl, $C_{(1-4)}$alkylOH, $CH_2OC_{(3-6)}$alkenyl, $CH_2OC_{(1-4)}$alkyl, $CH_2C(O)NH_2$, $CO_2C_{(1-4)}$alkyl, —CN, $C(O)NH_2$, $C(O)NHCH_2CH_2OH$, OTBS, OH, $OC_{(1-4)}$alkyl, $OC_{(3-6)}$alkenyl, $NH_2$, or NHBOC, or

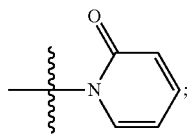

wherein said pyridyl, pyrimidyl, pyrazolyl, thiazolyl, benzo[1,3]dioxol-5-yl, pyrazolyl, oxazolyl, isoxazolyl, imidazolyl, phenyl, $C_{(4-7)}$cycloalkyl or $C_{(1-6)}$alkyl, may be optionally substituted with one substituent selected from the group consisting of: $OC_{(3-6)}$cycloalkyl, $OCH_2CF_3$, $OCH_2Ph$, $C_{(1-3)}$alkyl, OH, $C_{(1-3)}$alkoxy, $NH_2$, $NHCH_3$, $N(CH_3)_2$, $C(O)NH_2$, or $CH_2C(O)NH_2$;

$R^2$ is H, or OH;

and solvates, hydrates, tautomers, and pharmaceutically acceptable salts thereof.

In another embodiment of the invention:

X is O or $NR^3$;

wherein $R^3$ is: H, $C_{(1-6)}$alkyl, $CH_2CF_3$, $C_{(1-6)}$alkylOH, $C_{(2-6)}$alkenyl, $C(O)C_{(1-6)}$alkyl, $CONH_2$, $CONHC_{(1-6)}$alkyl, $SONH_2$, $CH_2Ph$, $CH_2$pyridyl, $CH_2$pyrrolyl, $CH_2$pyrimidyl, $CH_2$pyridazyl, or $SO_2C_{(1-2)}$alkyl;

$Y^1$ and $Y^2$ are CH;

Z is O, $CH_2$,

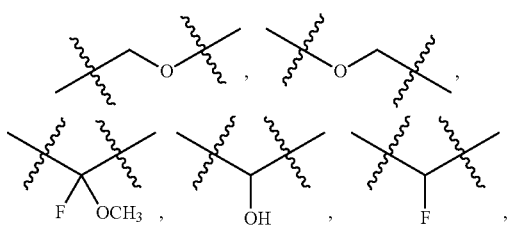

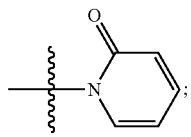 [SMILES: *n1ccccc1=O ; ";"]

wherein said pyrid-3-yl, pyrid-5-yl, pyrid-6-yl, thiazol-2-yl, thiazol-5-yl, benzo[1,3]dioxol-5-yl, pyrazol-4-yl, oxazol-2-yl, imidazol-2-yl, phenyl, or cyclohexyl may be optionally substituted with one substituent selected from the group consisting of: $C_{(1-3)}$alkyl, $C_{(1-3)}$alkoxy, $N(CH_3)_2$, or $CH_2C(O)NH_2$;
$R^2$ is H, or OH;
and tautomers, and pharmaceutically acceptable salts thereof.
In another embodiment of the invention:
X is O or $NR^3$;
wherein $R^3$ is: H, $C_{(1-3)}$alkyl, $CH_2CF_3$, $CH_2CH_2OH$, $CH_2CH=CH_2$, $CONH_2$, $CONHC(CH_3)_3$, $CONHCH(CH_3)_2$, $CH_2Ph$, or $SO_2CH_3$;
$Y^1$ and $Y^2$ are CH;
Z is O,

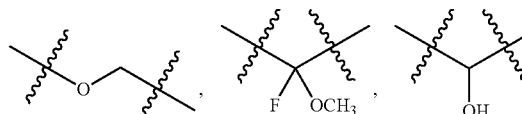

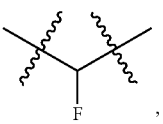

or a direct bond;
$R^1$ is pyrid-3-yl, 2-methoxy-pyrid-5-yl, 2-methoxy-pyrid-6-yl, 2-ethoxy-pyrid-5-yl, 2-methyl-pyrid-5-yl, thiazol-2-yl, thiazol-5-yl, 2-ethyl-thiazol-5-yl, 2-isopropyl-thiazol-5-yl, 2-methyl-thiazol-5-yl, 5-methyl-thiazol-2-yl, benzo[1,3]dioxol-5-yl, N-1-methyl-pyrazol-4-yl, oxazol-2-yl, N-methyl-imidazol-2-yl, phenyl,

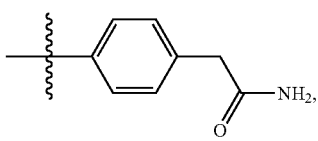 [SMILES: *c1ccc(CC(N)=O)cc1]

N,N-dimethylamino-phen-3-yl, cyclohexyl, $C_{(2-3)}$alkyl, $CH_2OH$, $CH_2OCH_2CH=CH_2$, $CH_2OCH_2CH_3$, $CH_2OCH_3$, $CH_2C(O)NH_2$, $CO_2CH_2CH_3$, —CN, $C(O)NH_2$, $C(O)NHCH_2CH_2OH$, OTBS, OH, $OCH_2CH_3$, $OCH_2CH=CH_2$, $NH_2$, NHBOC, or

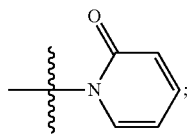 [SMILES: *n1ccccc1=O ; ";"]

$R^2$ is H, or OH;
and tautomers, and pharmaceutically acceptable salts thereof.
In another embodiment, the invention relates to a compound selected from the group consisting of:

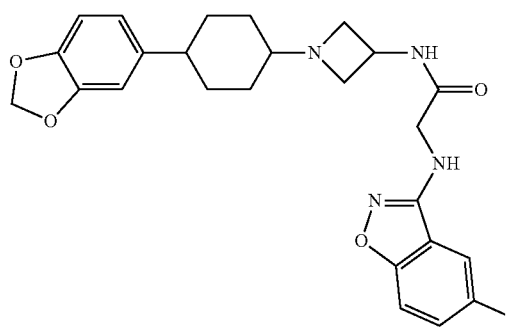

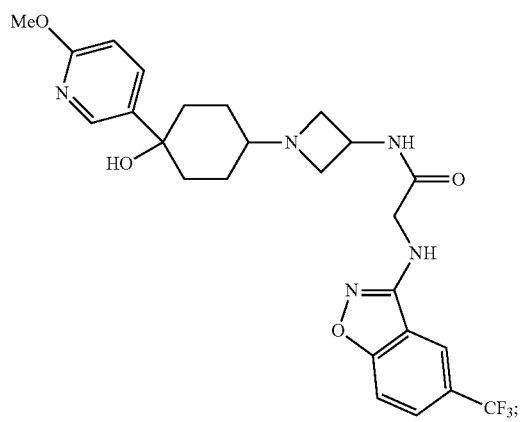

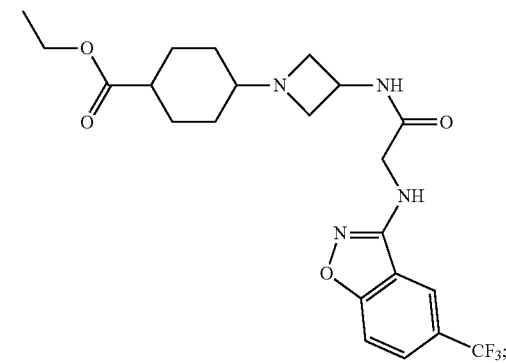

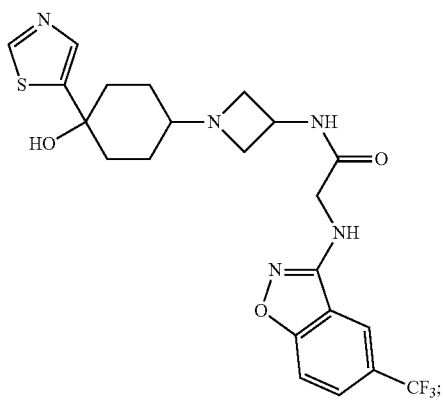

-continued
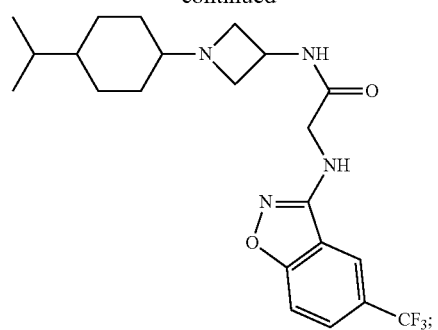
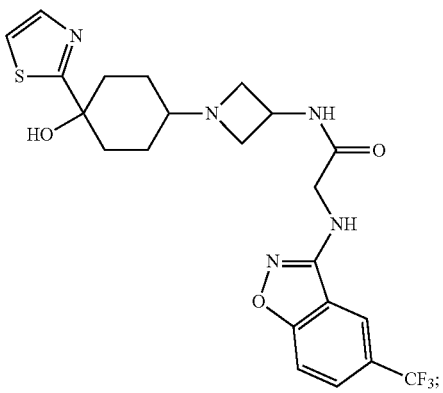
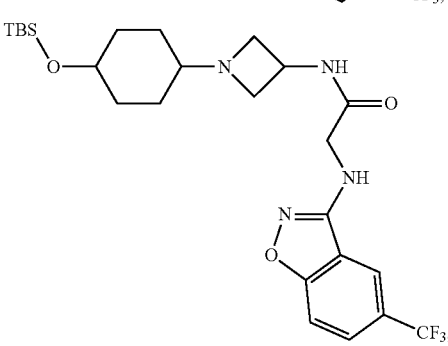
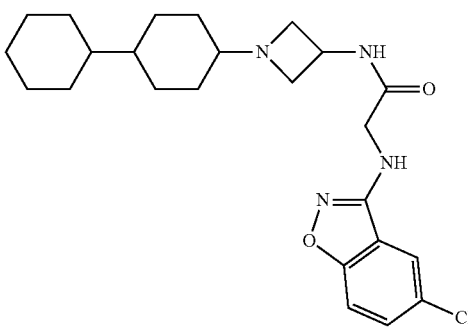
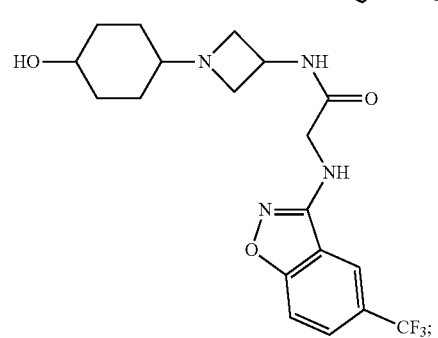
-continued
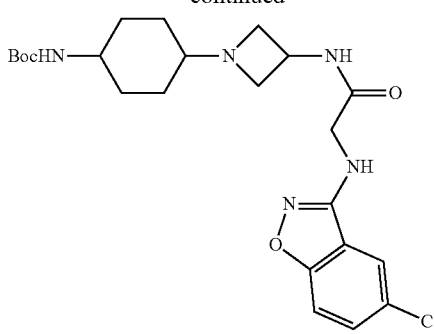
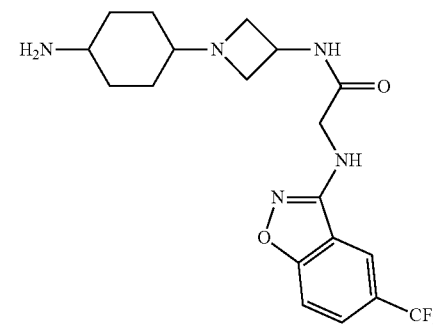
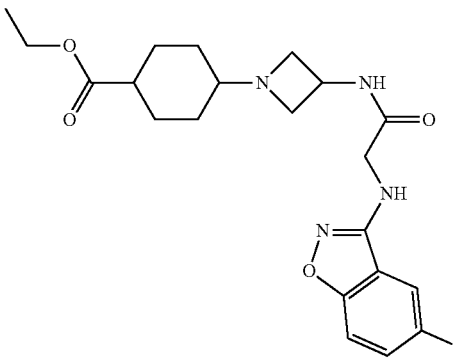
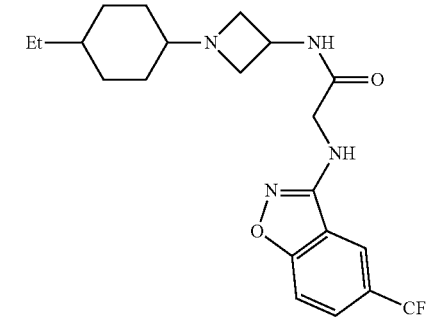
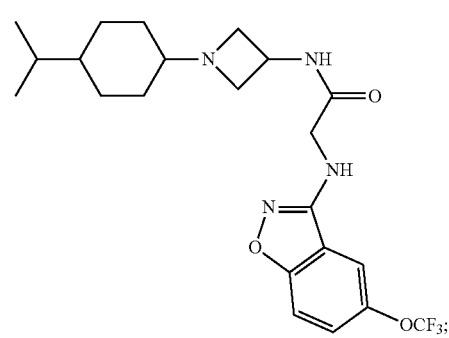

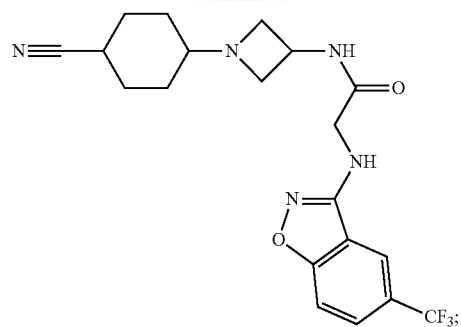
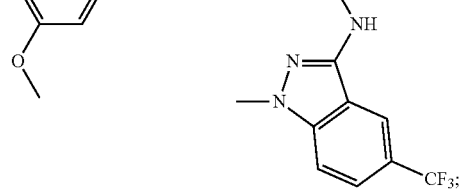
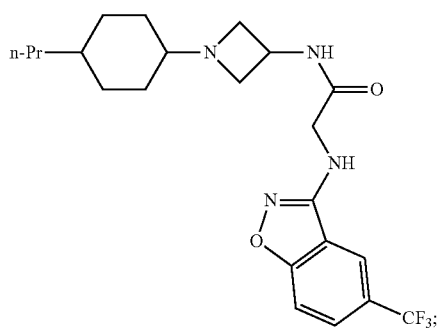
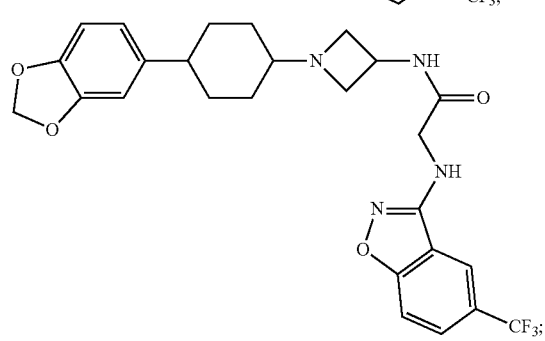
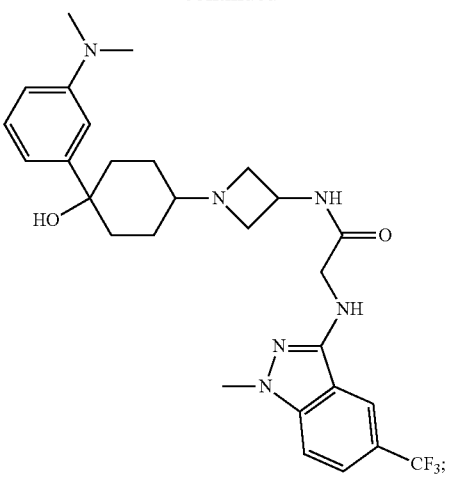
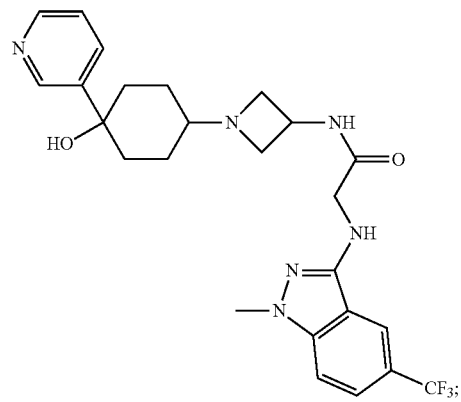

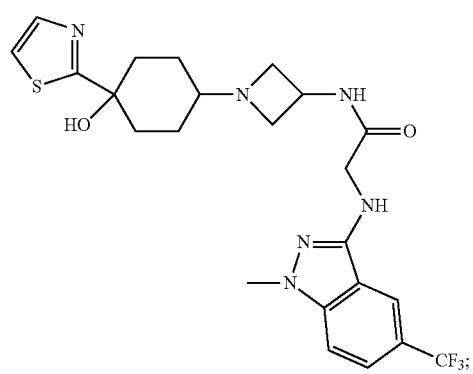
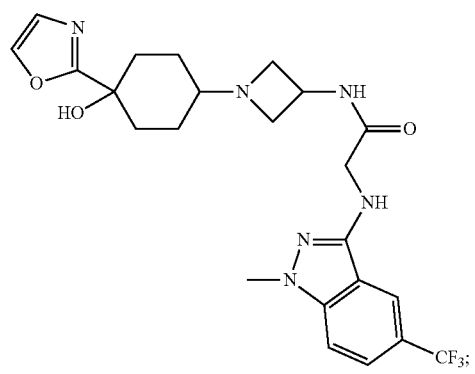
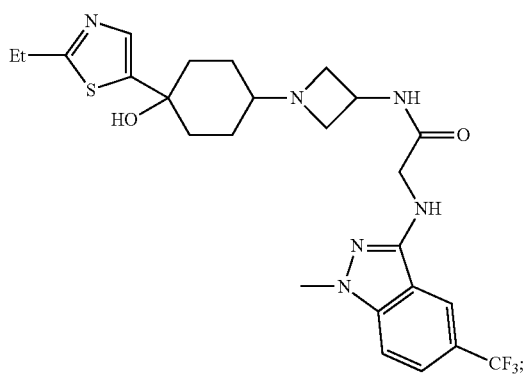
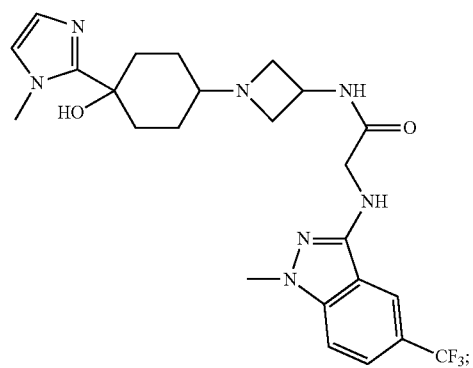
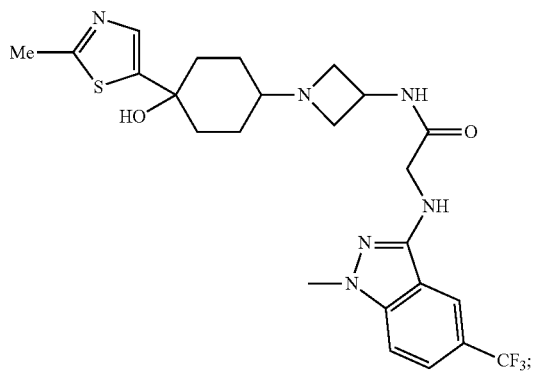
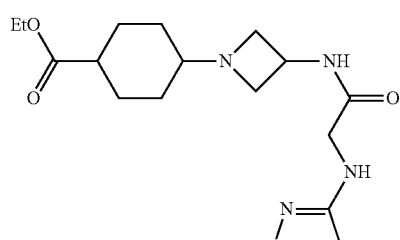
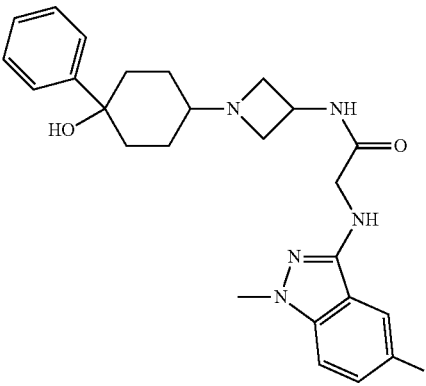
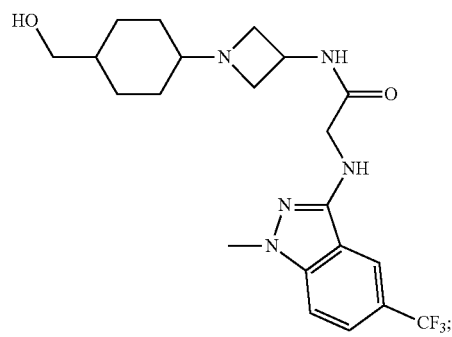

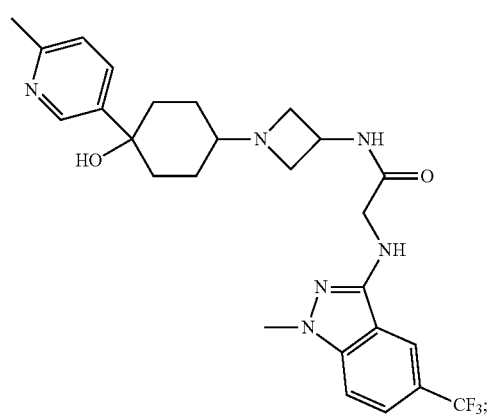
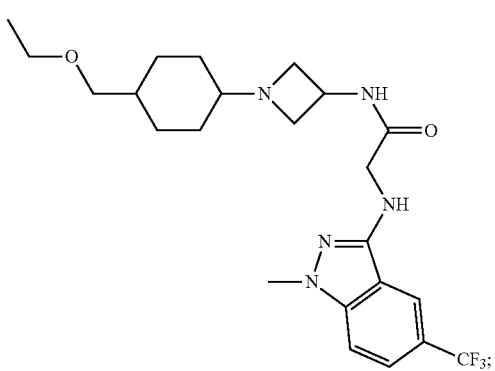
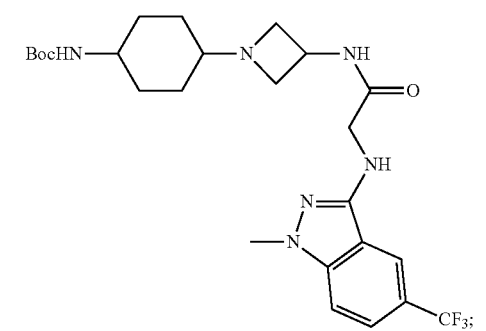
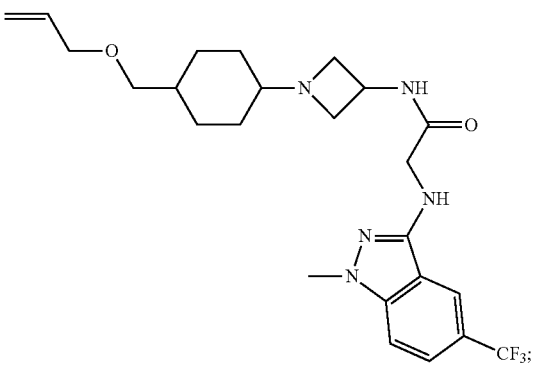
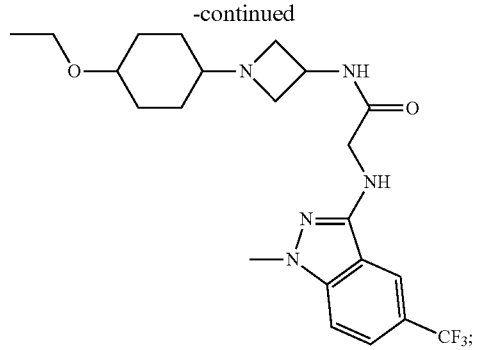
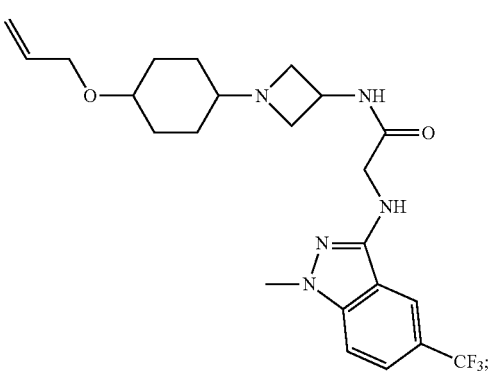
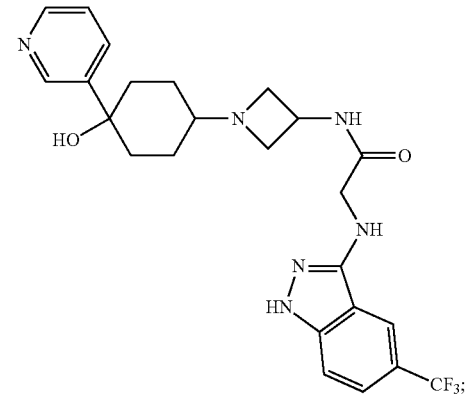
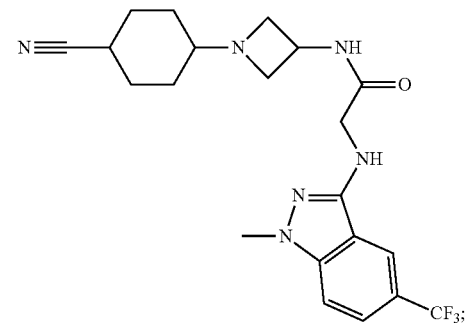

-continued
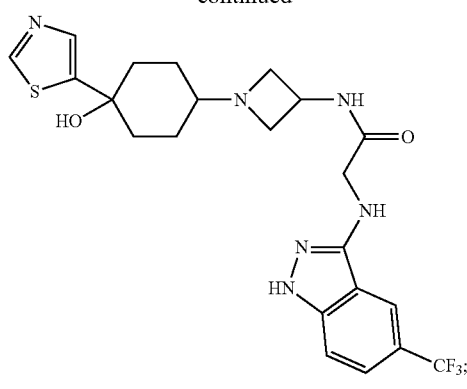
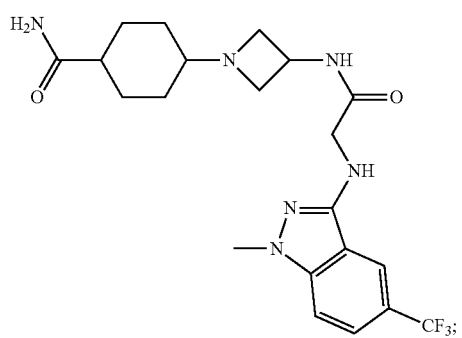
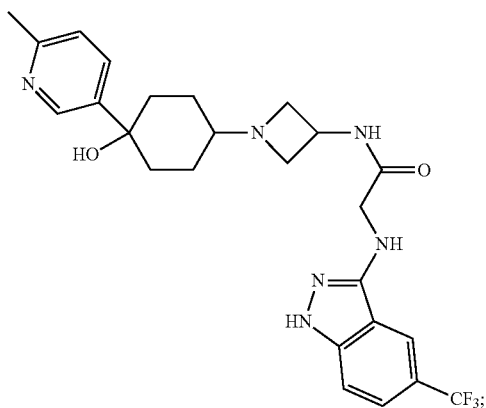
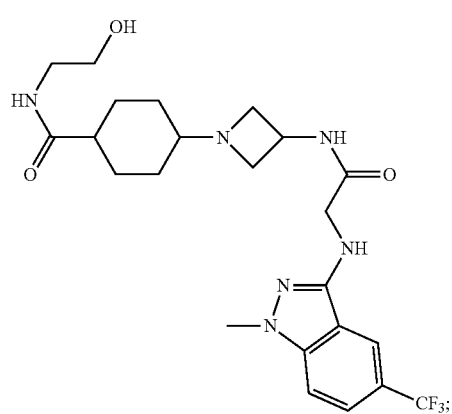
-continued
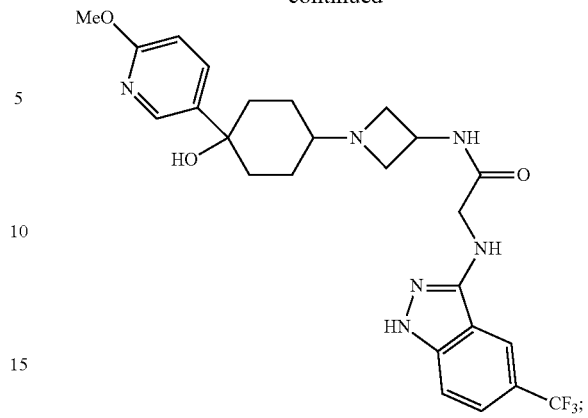
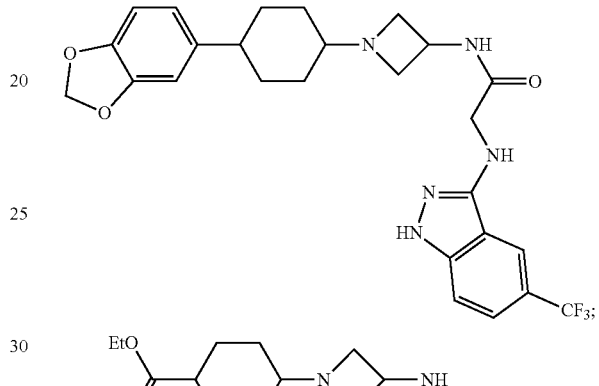
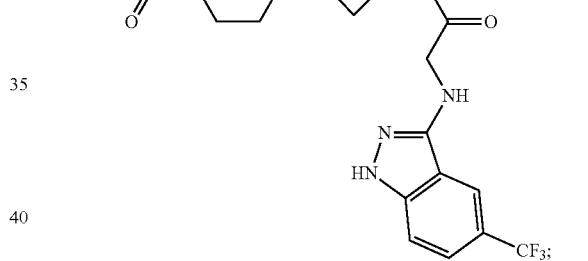
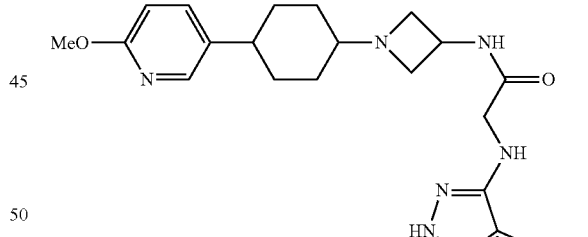
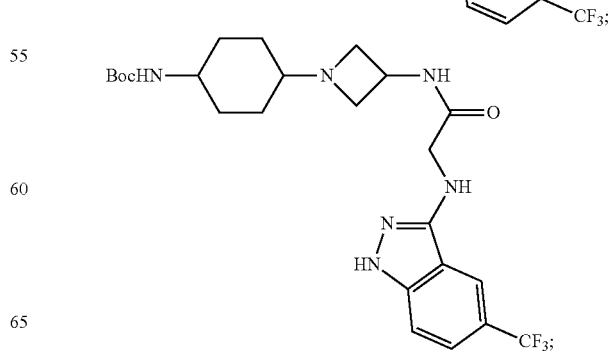

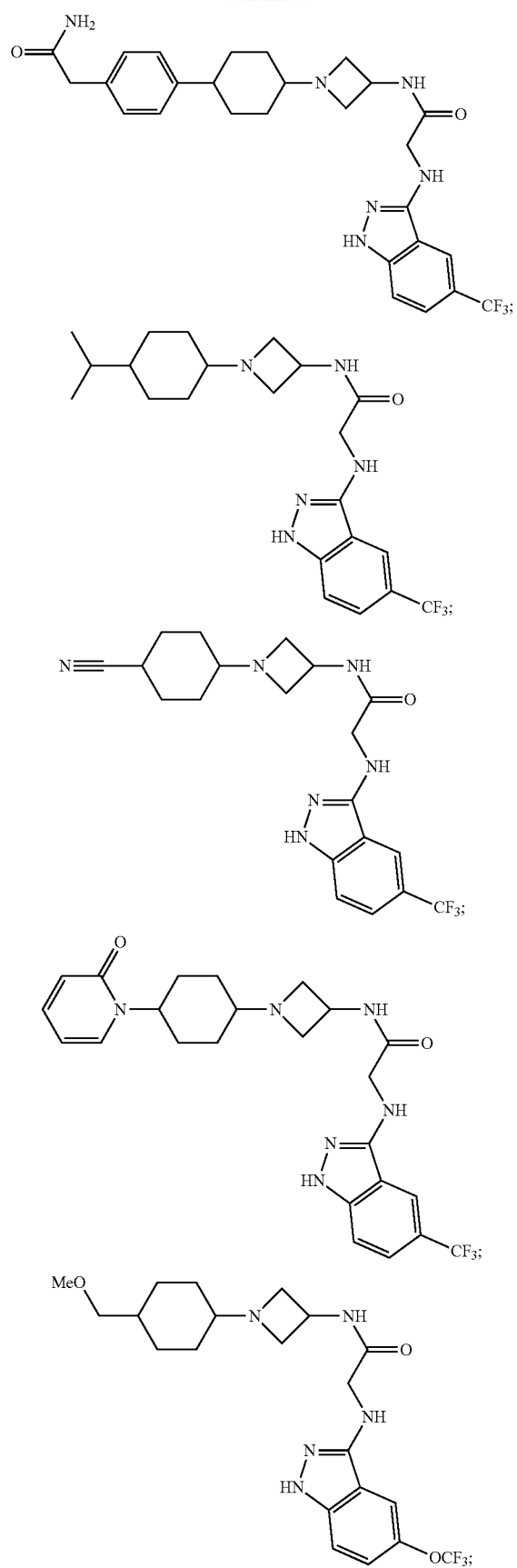
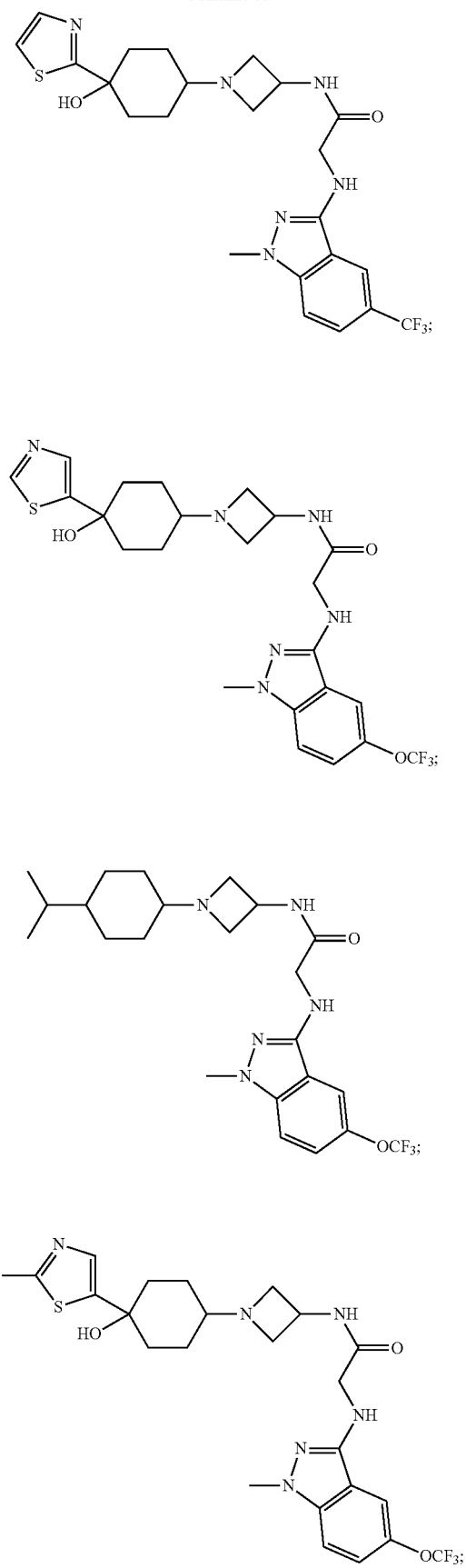

25
-continued
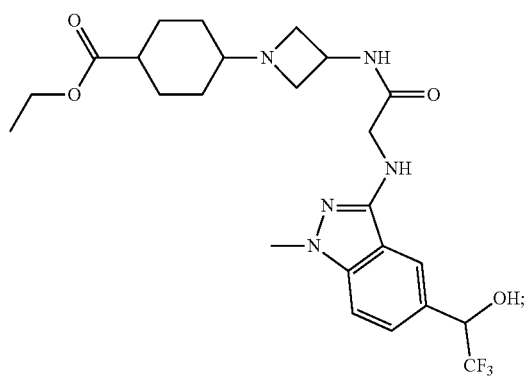
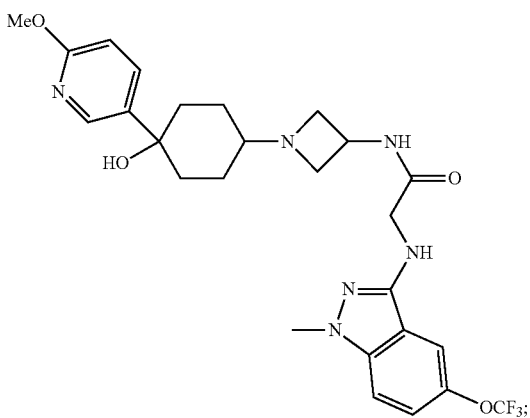
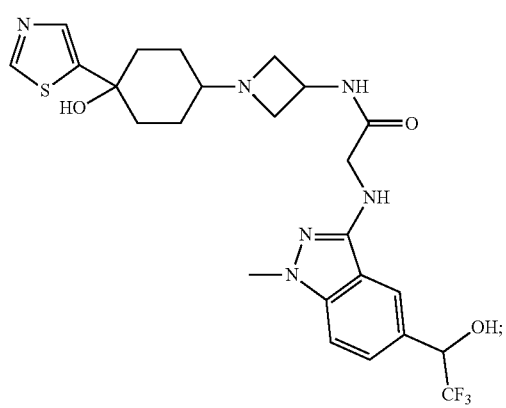
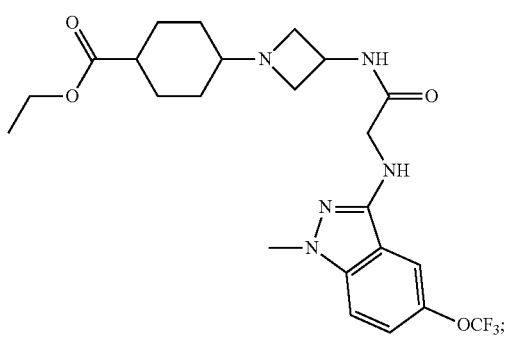
26
-continued
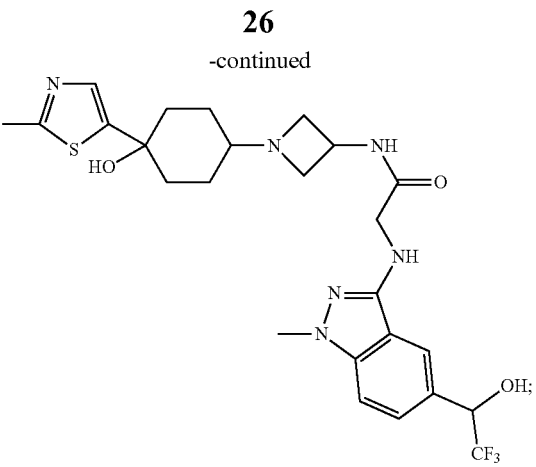
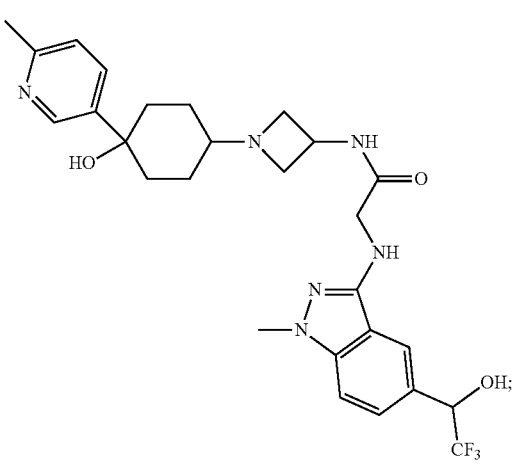
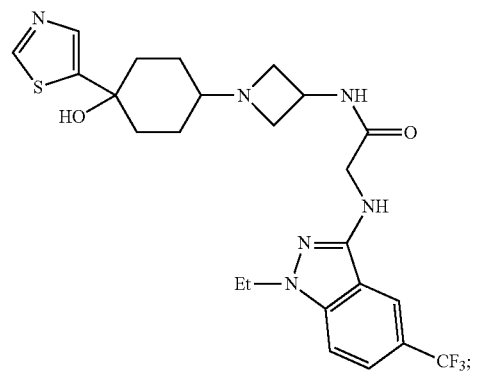
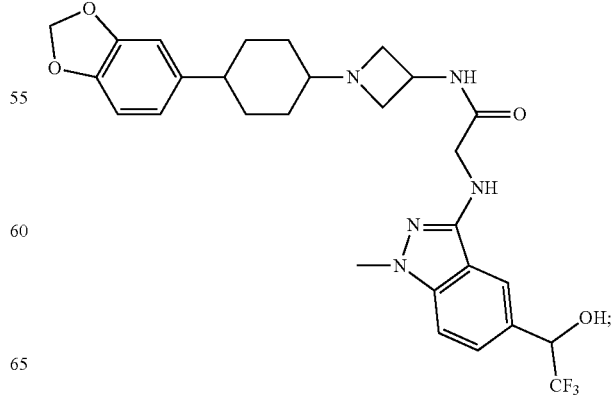

-continued
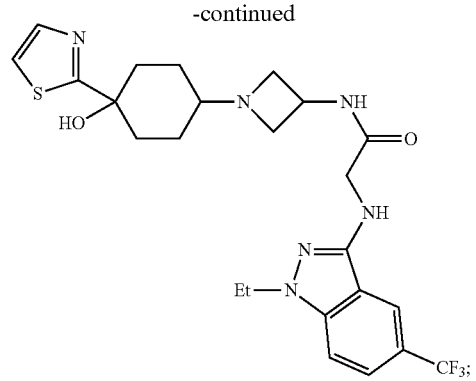
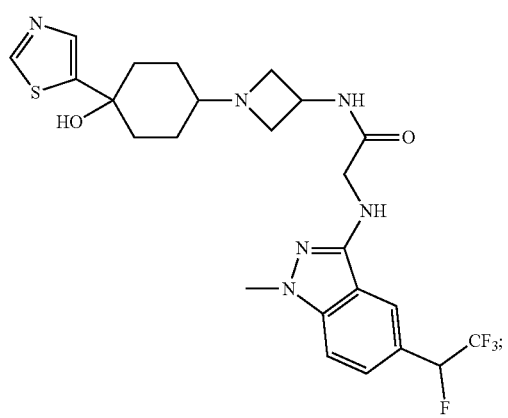
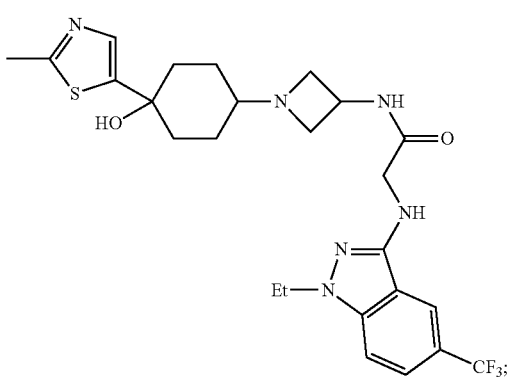
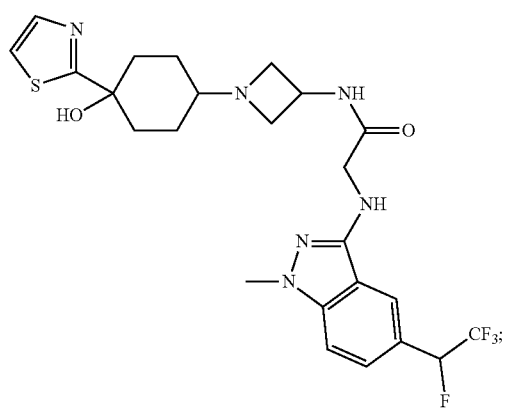
-continued
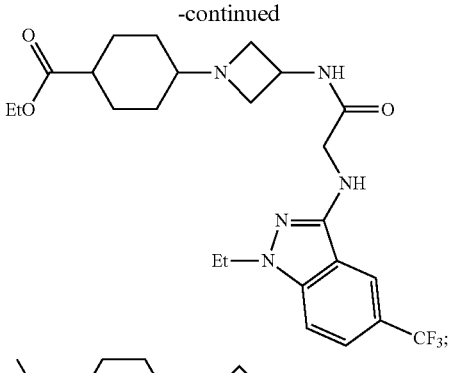
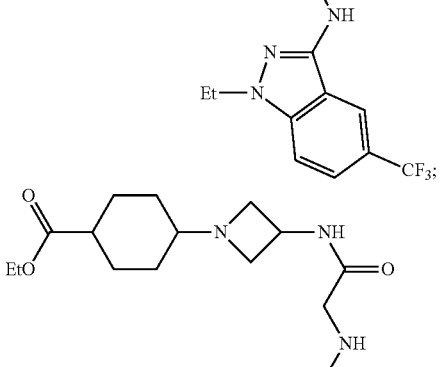
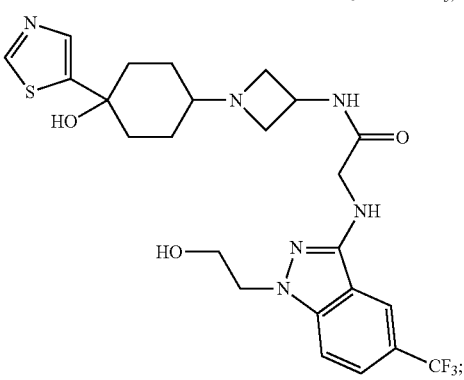
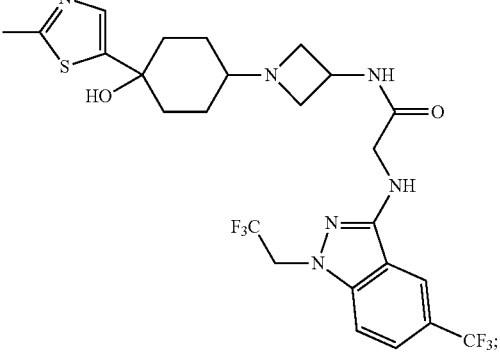

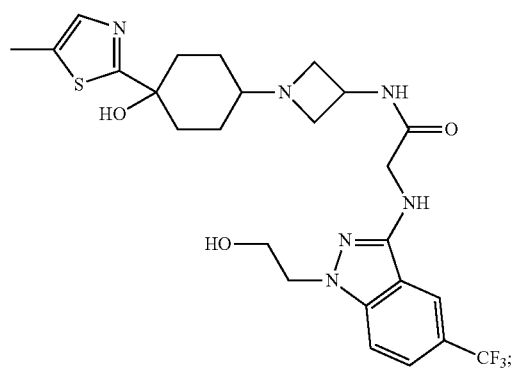
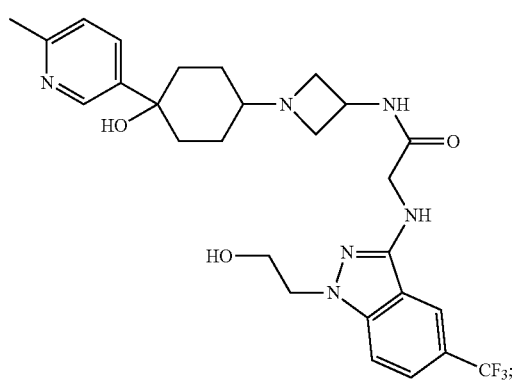
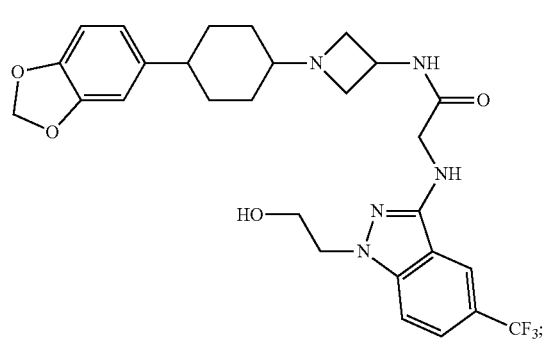
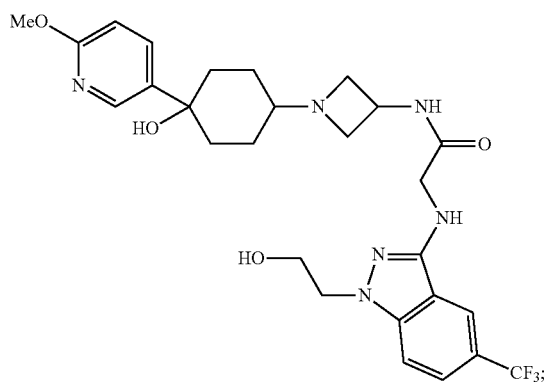
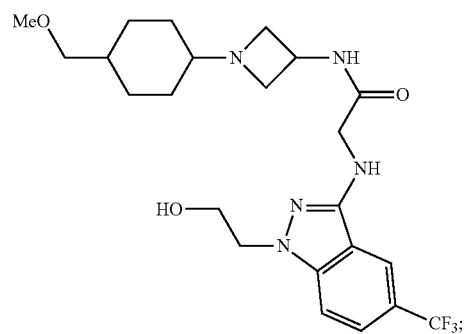
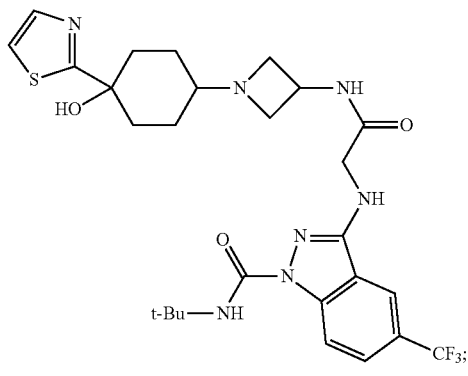
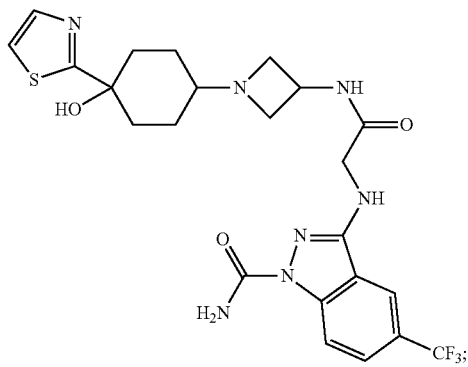
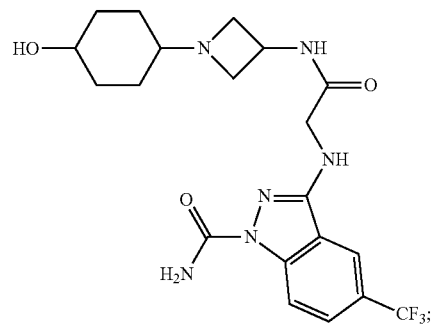

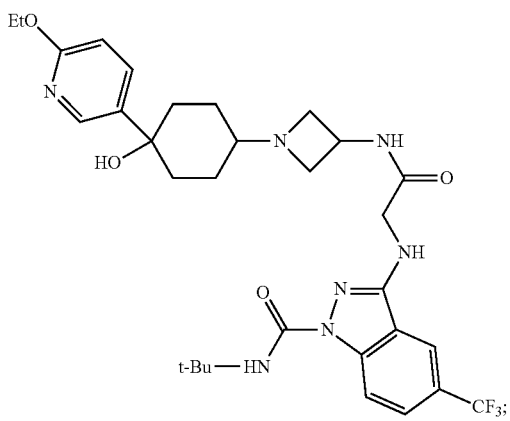
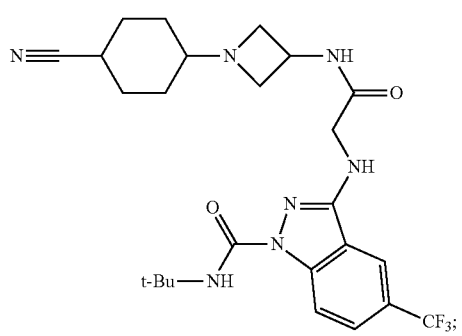
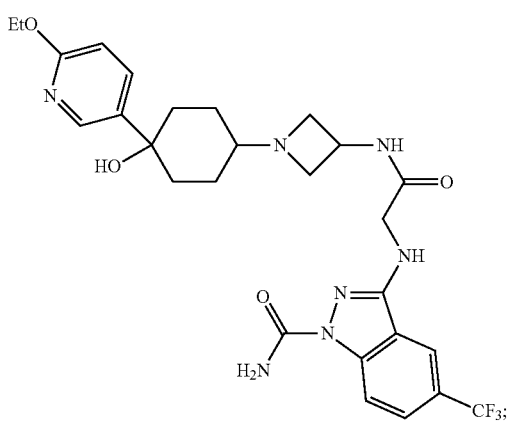
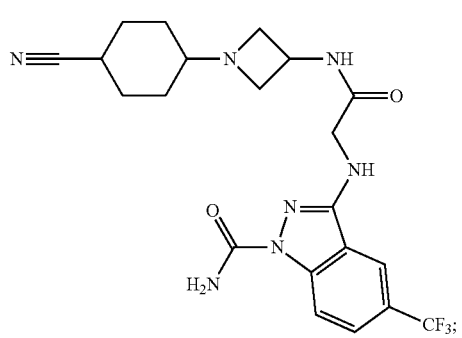
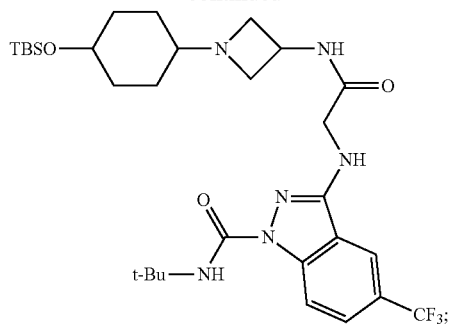
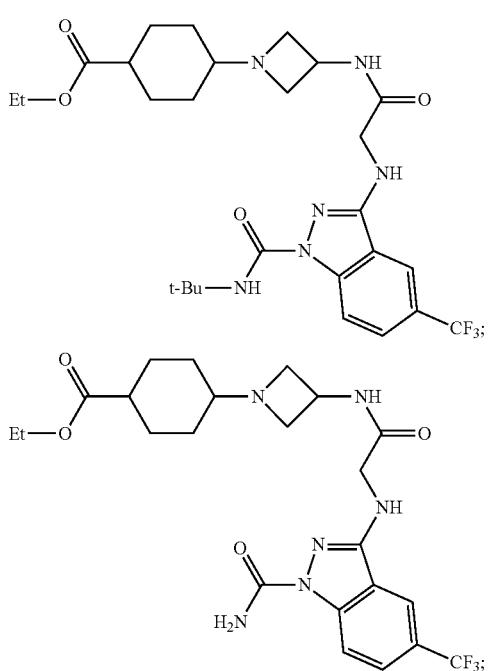
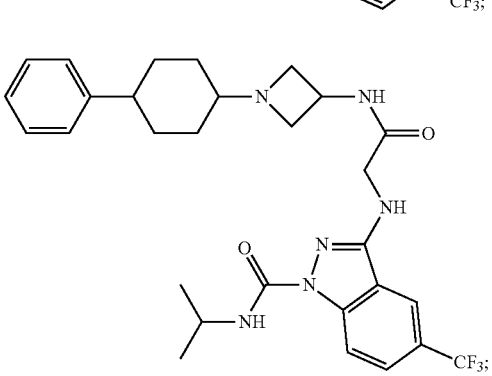
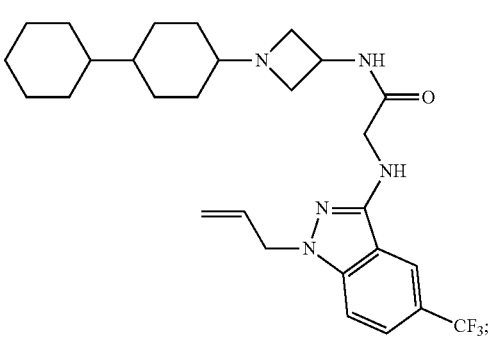

33
-continued
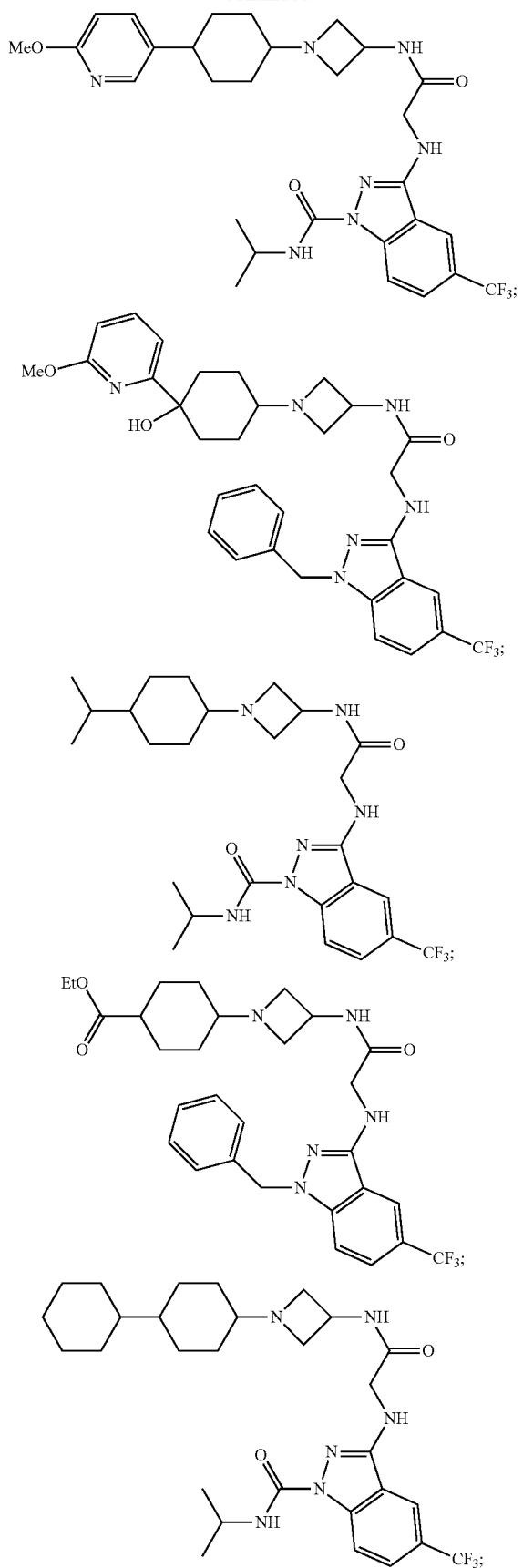
34
-continued
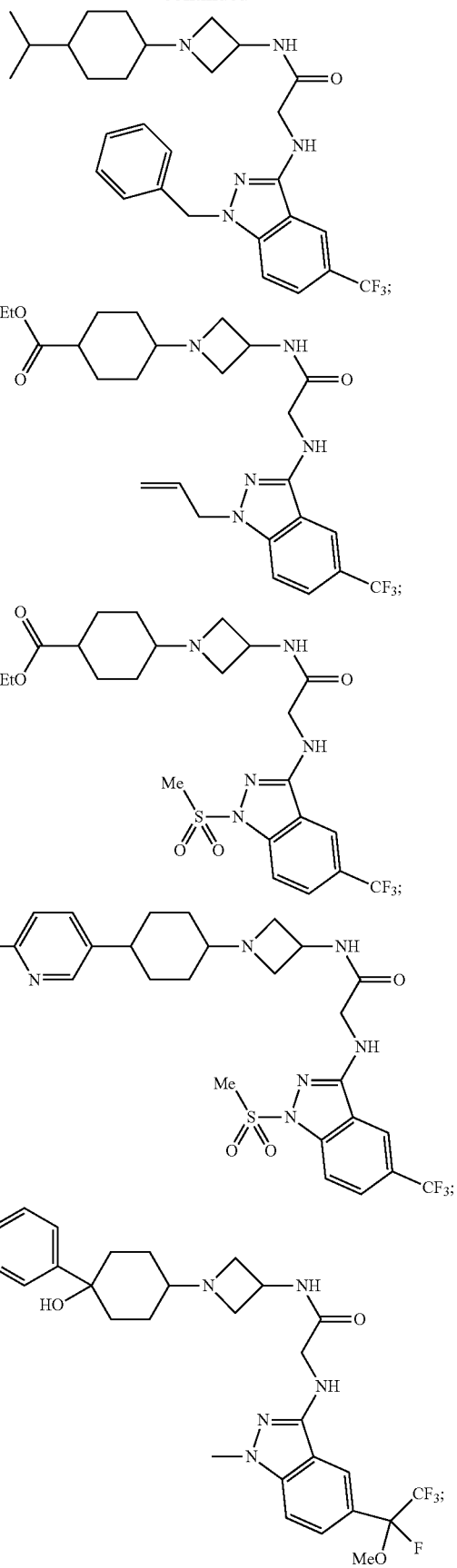

-continued
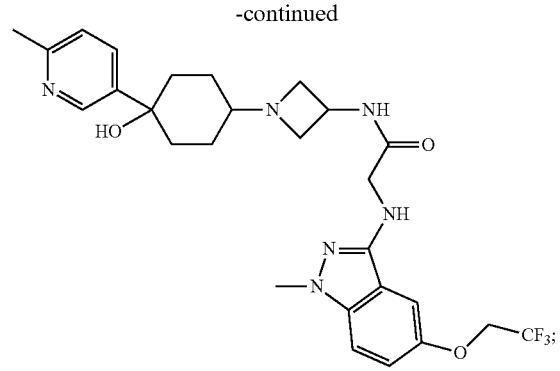
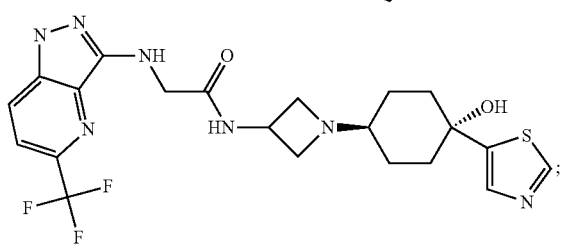
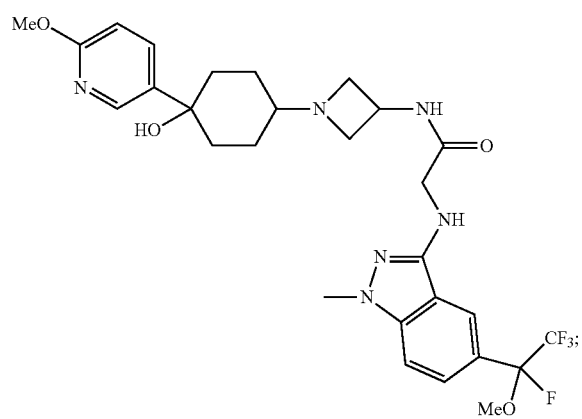
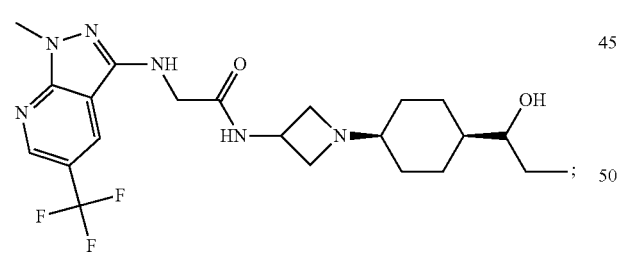
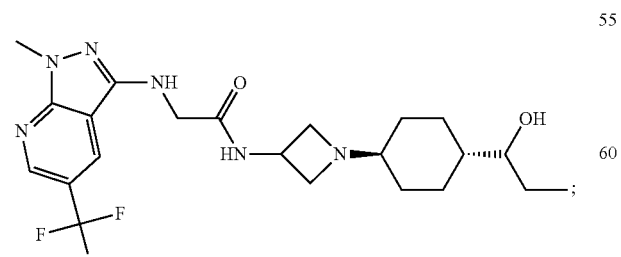
and tautomers, and pharmaceutically acceptable salts thereof.
In another embodiment, the invention relates to a compound selected from the group consisting of:
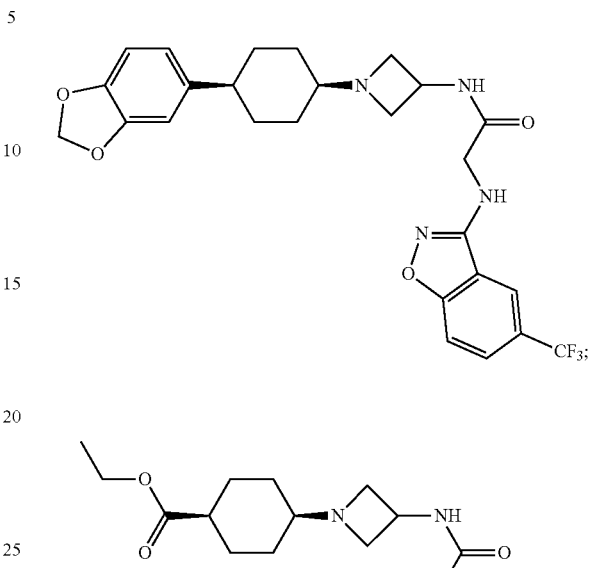
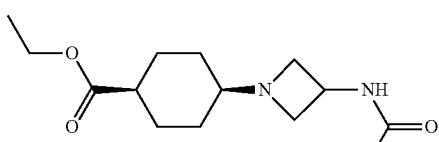
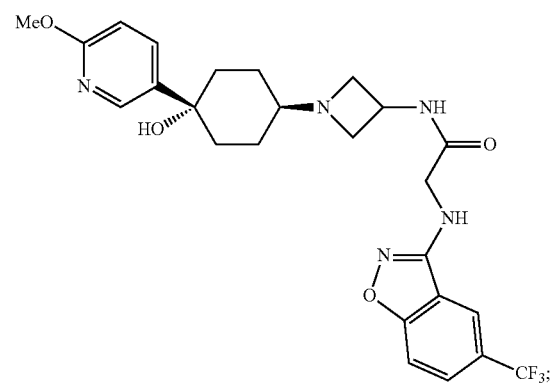
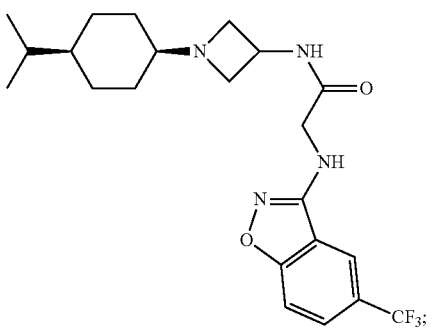

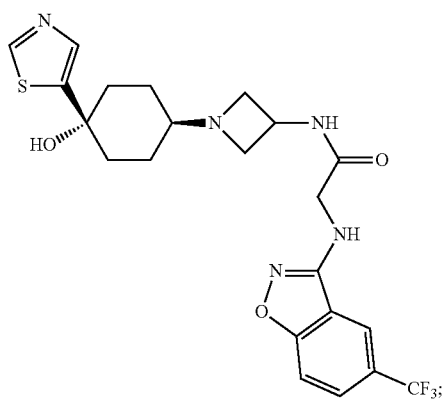
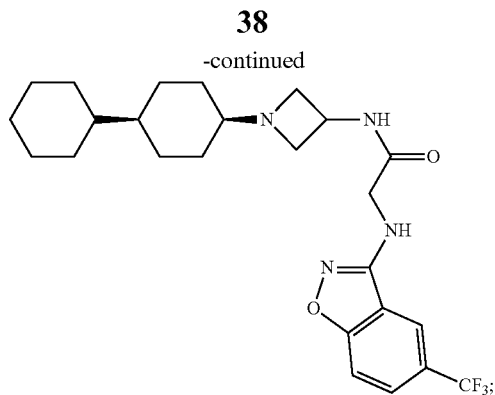
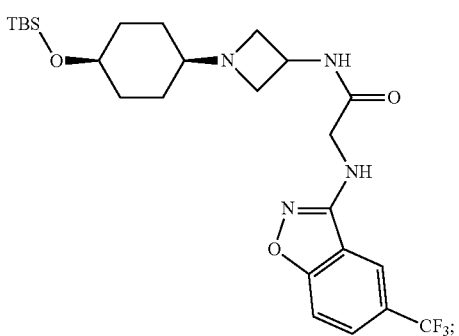
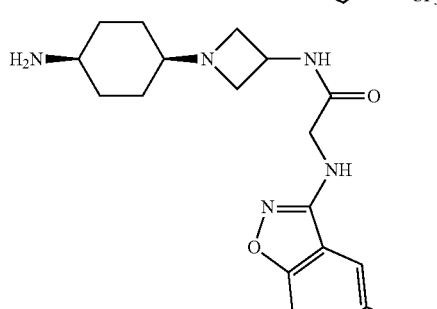
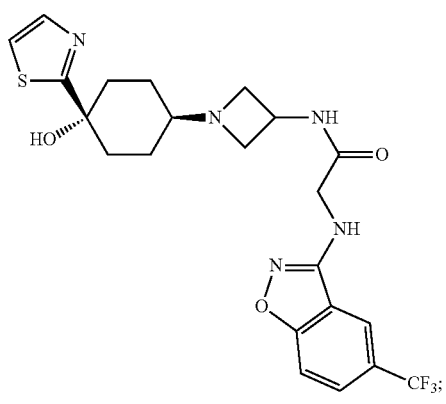
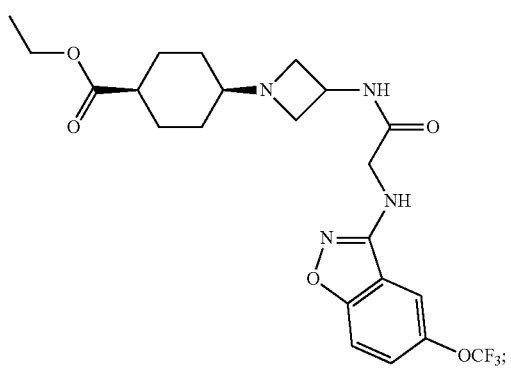
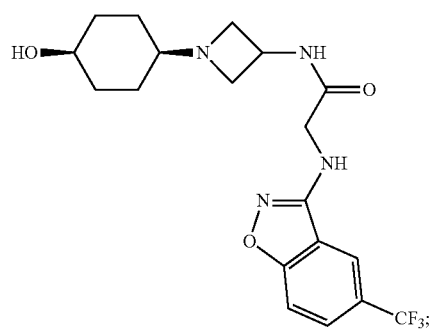
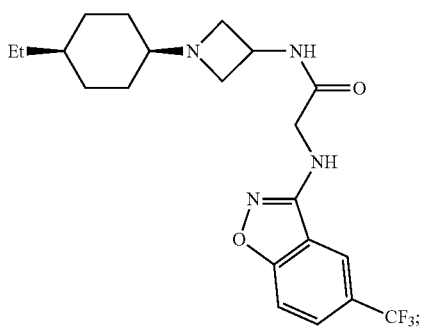

39
-continued
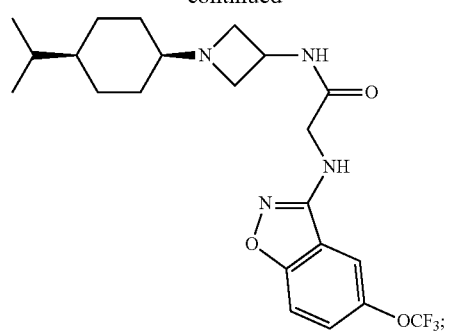
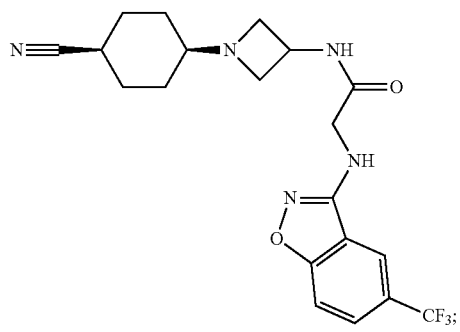
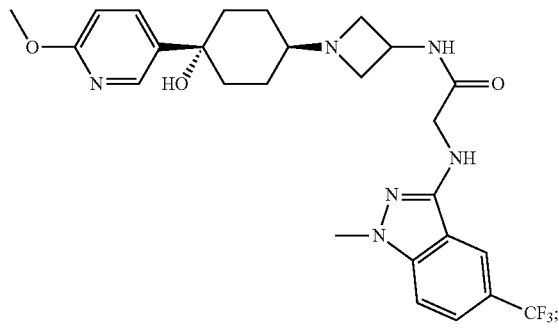
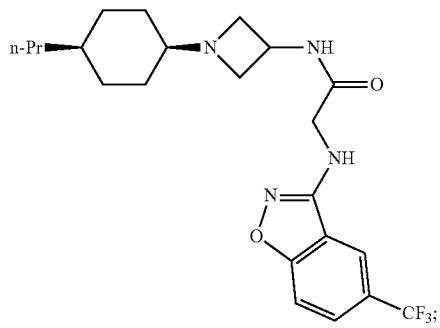
40
-continued
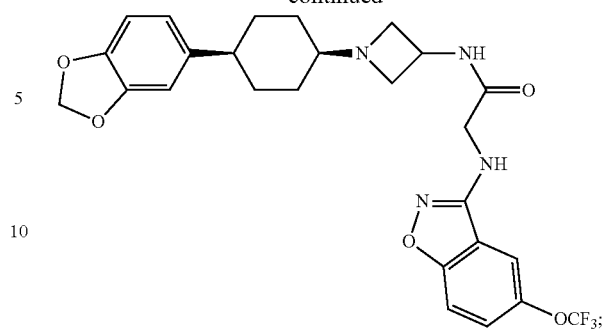
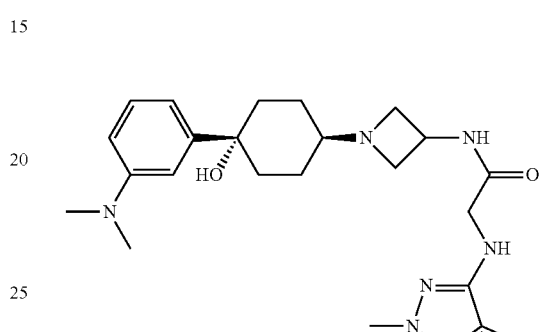
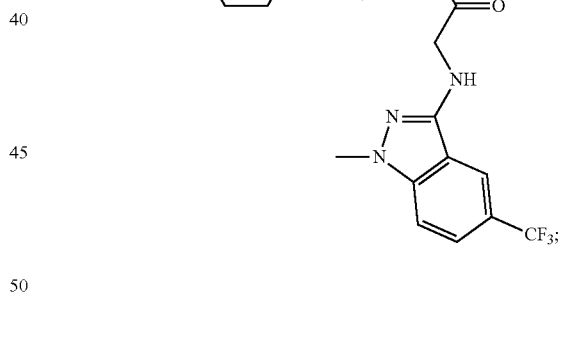
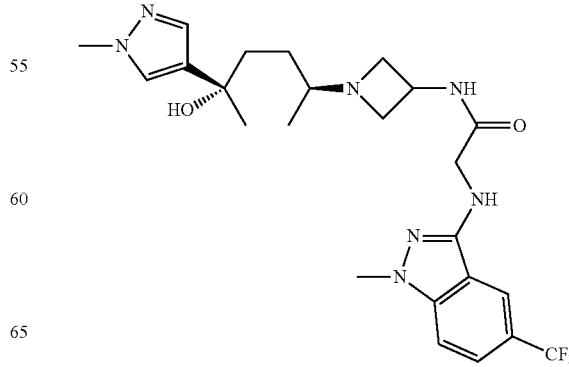
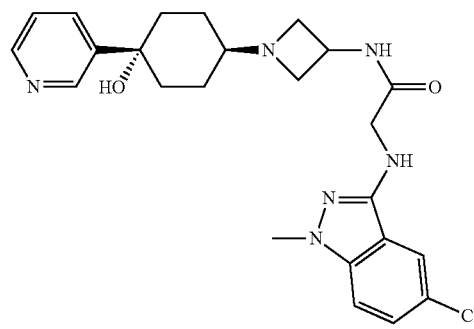

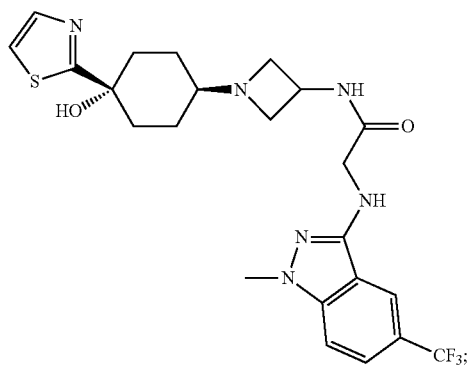
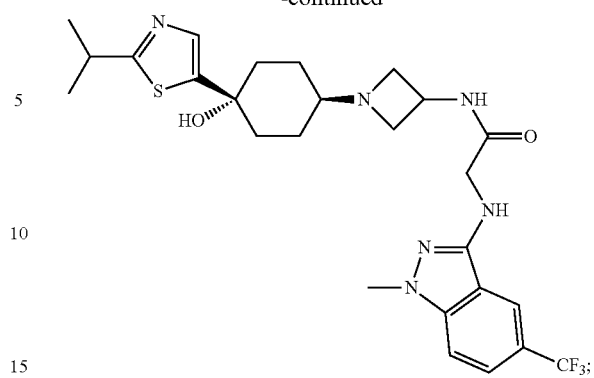
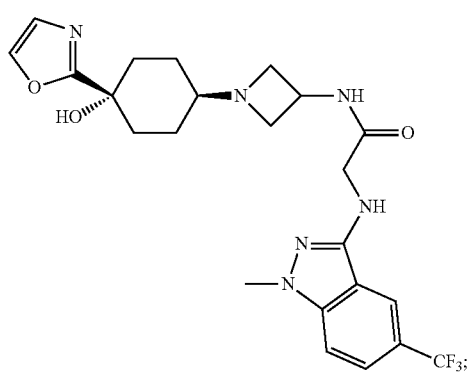
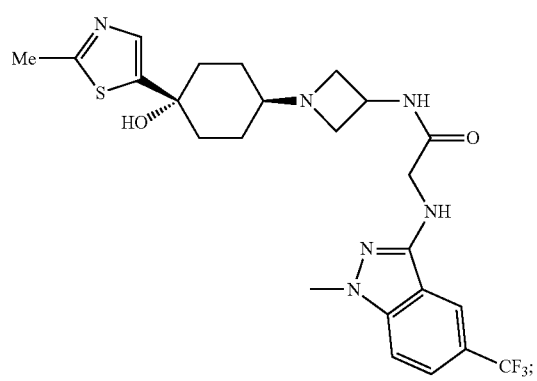 [SMILES: CC(C)c1ncc([C@]2(O)CC[C@H](N3CC(NC(=O)CNc4nn(C)c5ccc(C(F)(F)F)cc45)C3)CC2)s1]
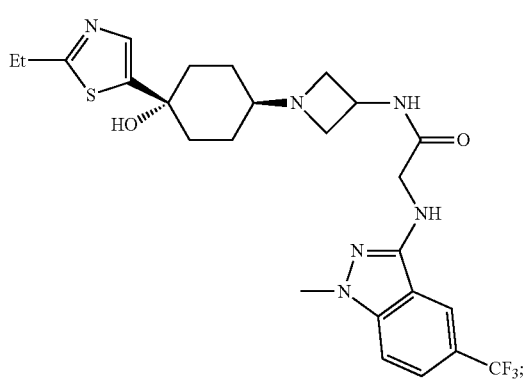
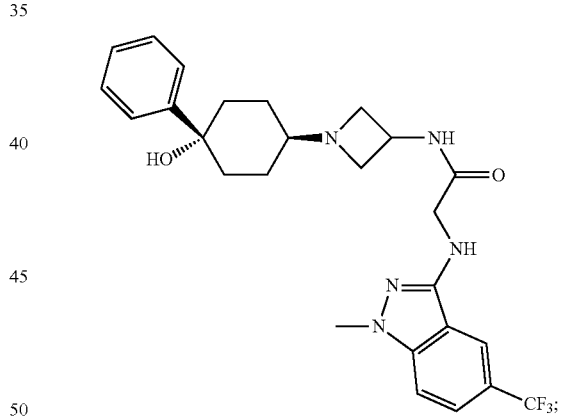
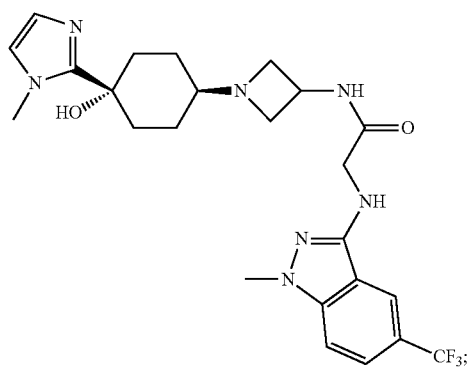
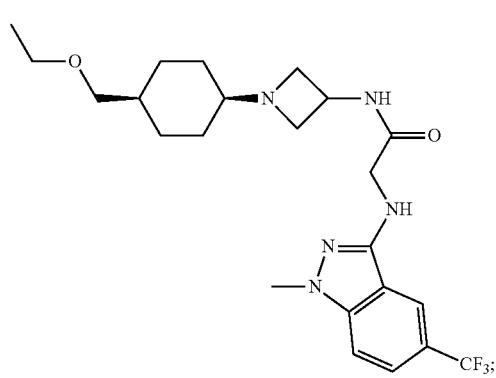

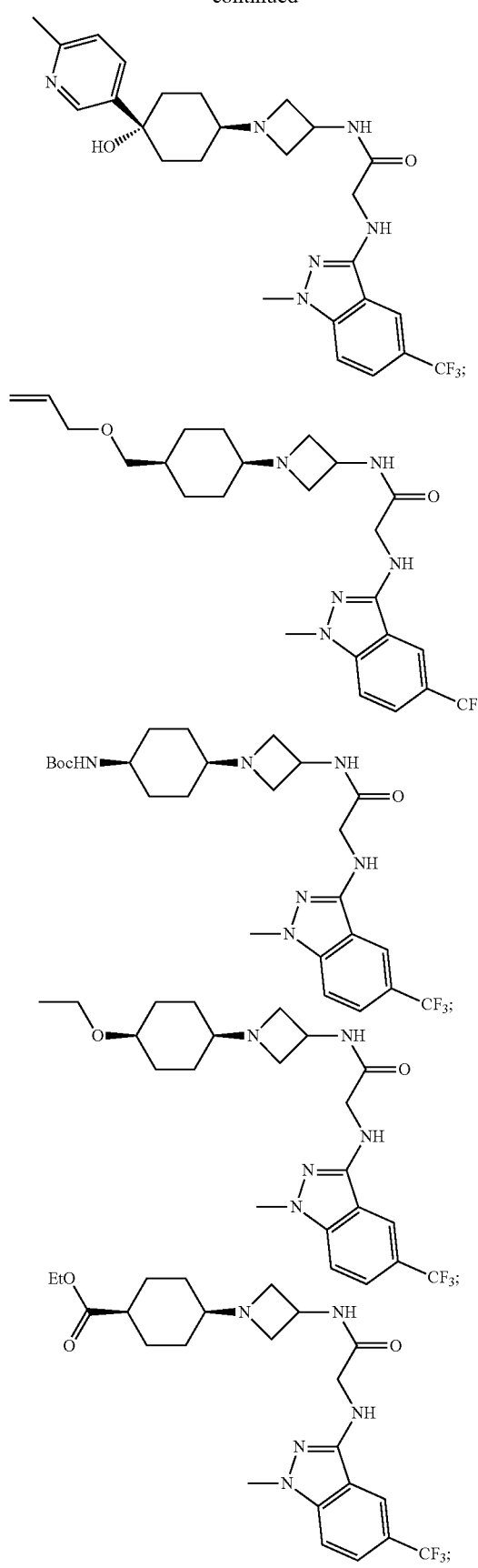
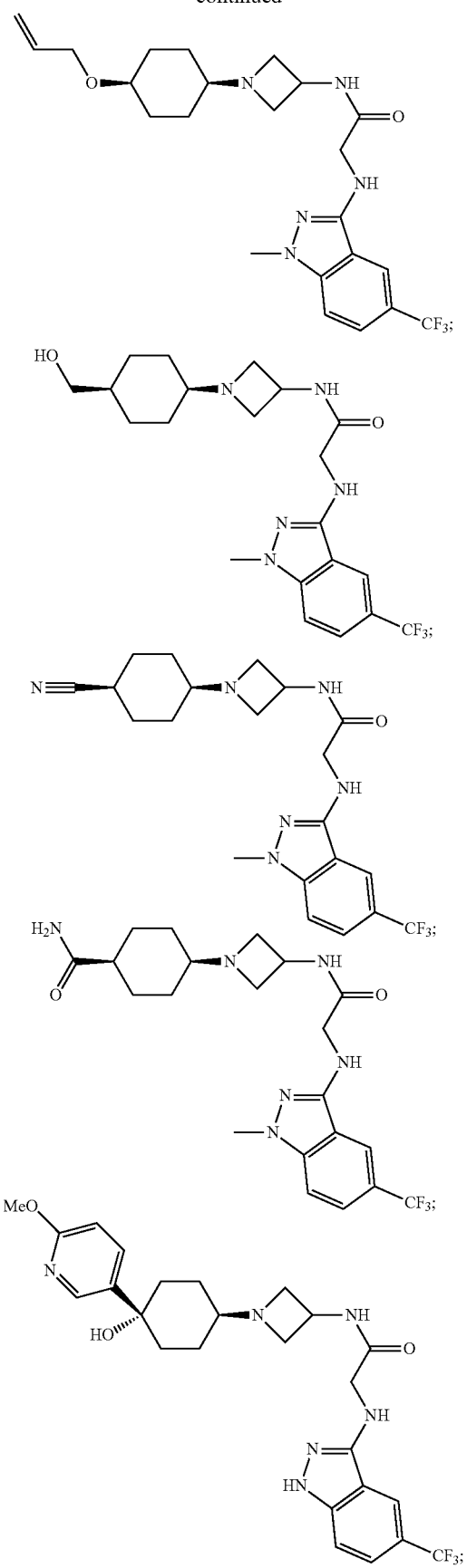

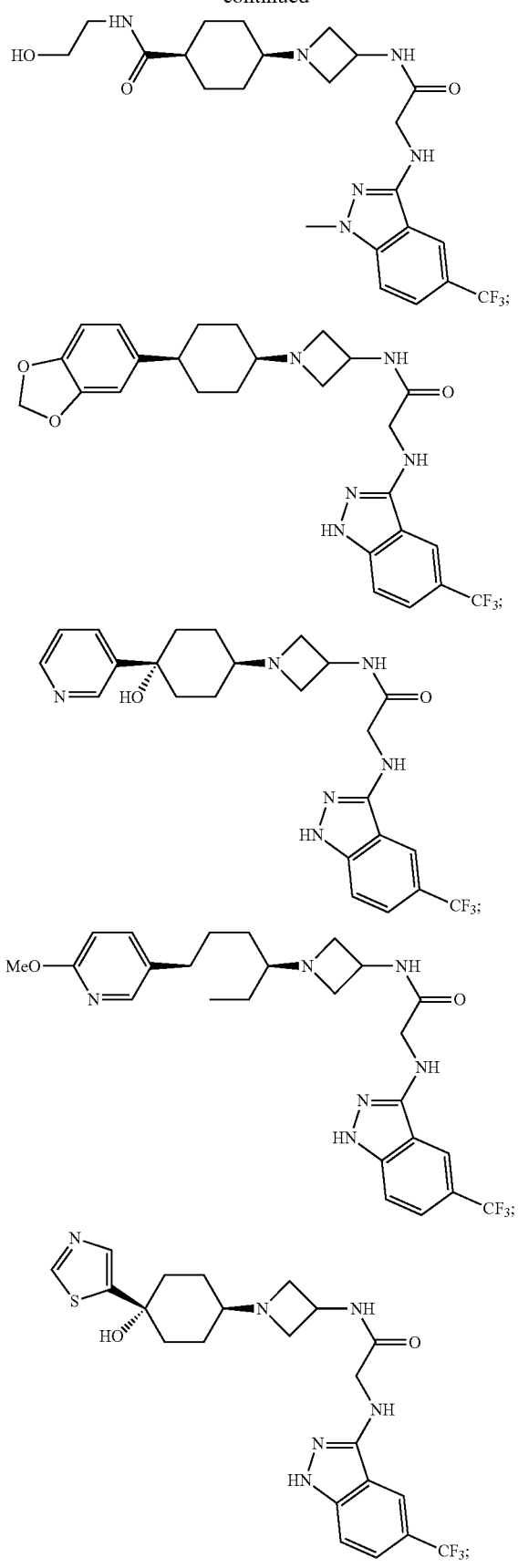
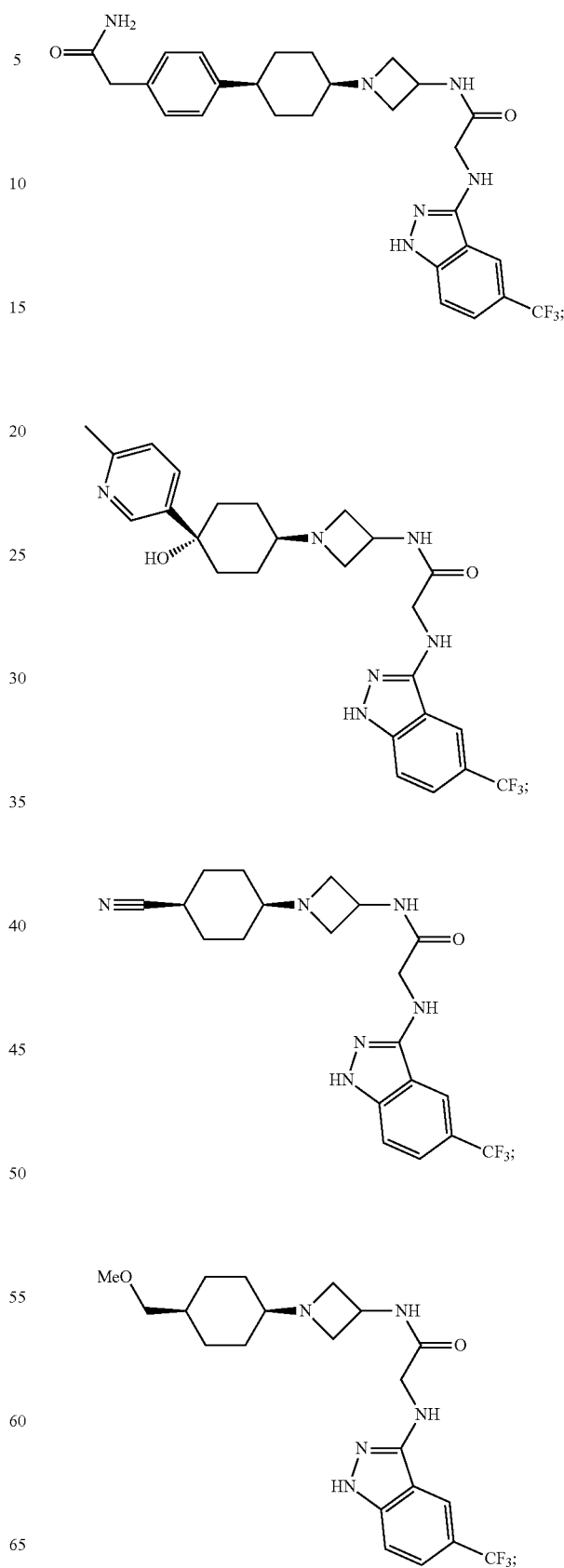

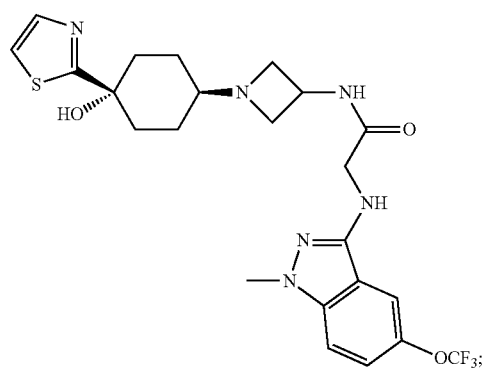
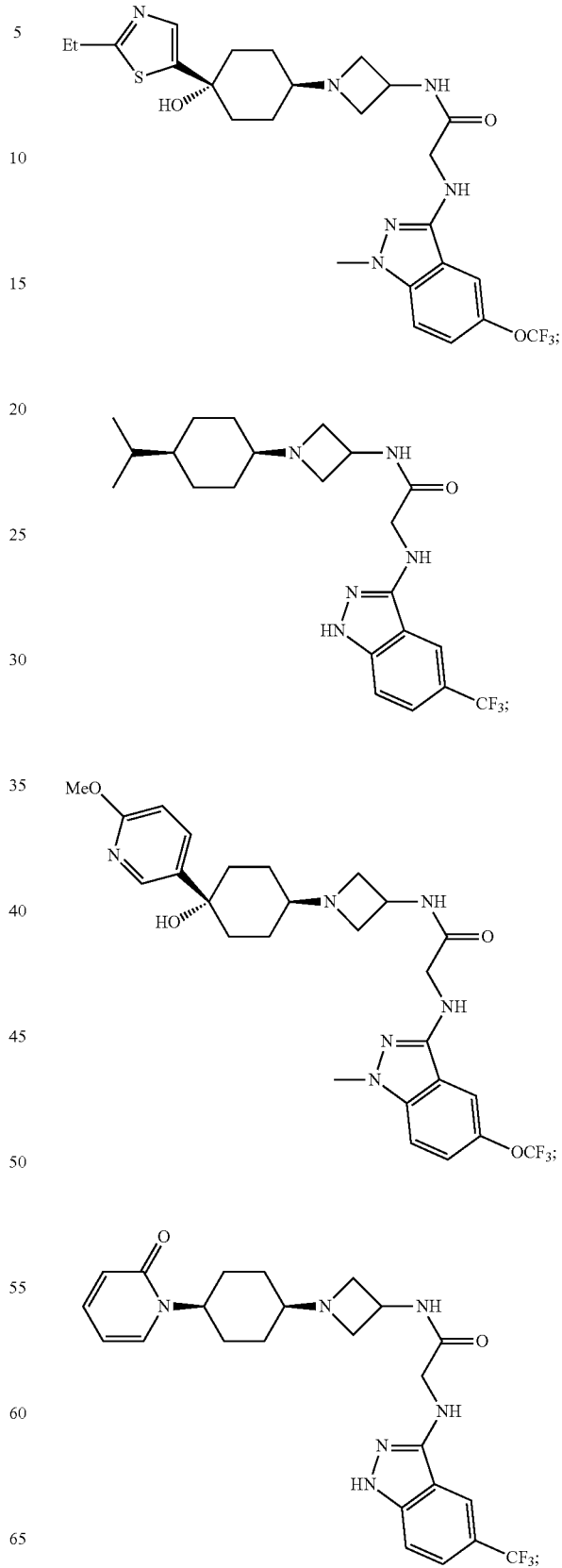

49
-continued
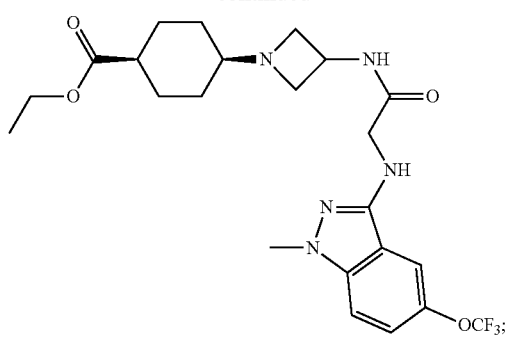
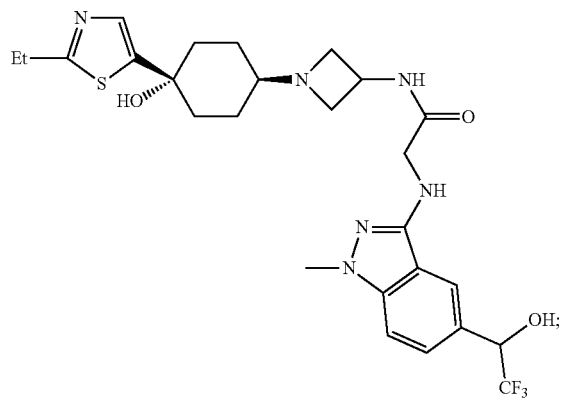
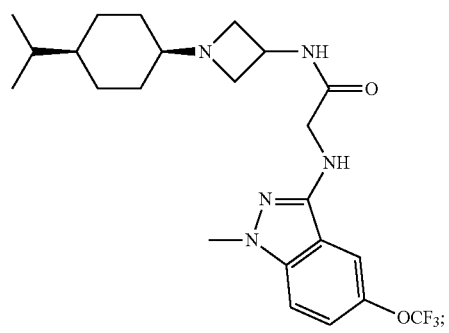
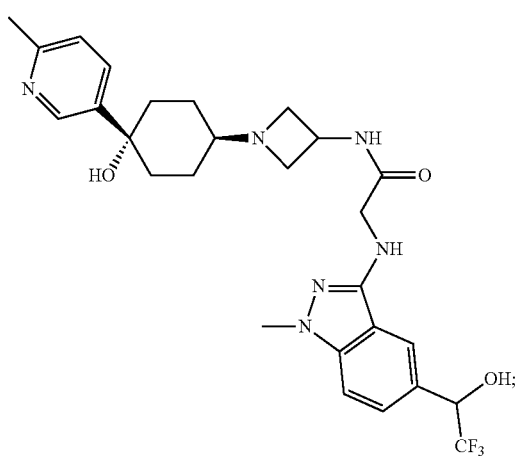
50
-continued
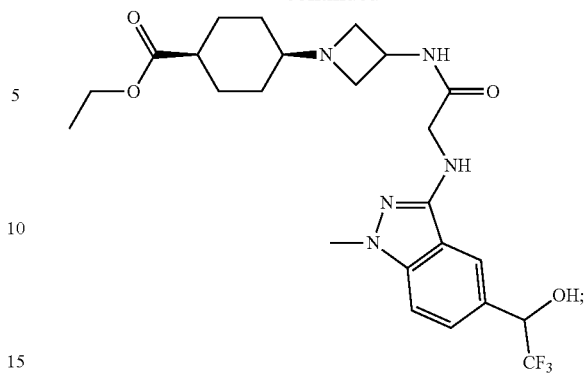
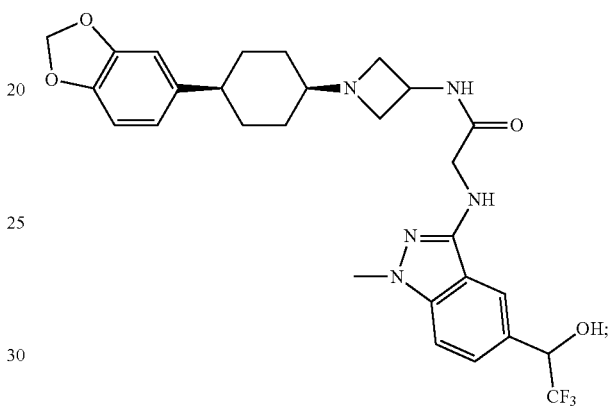
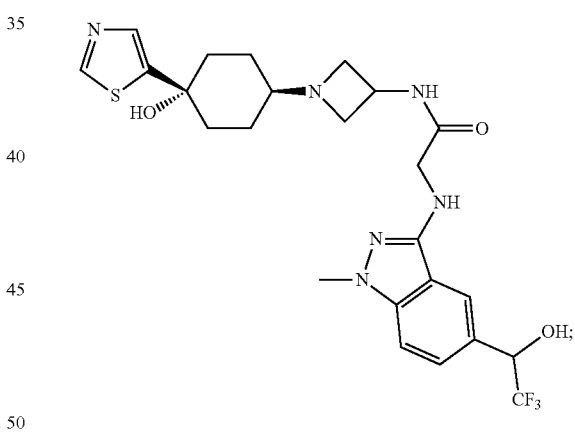
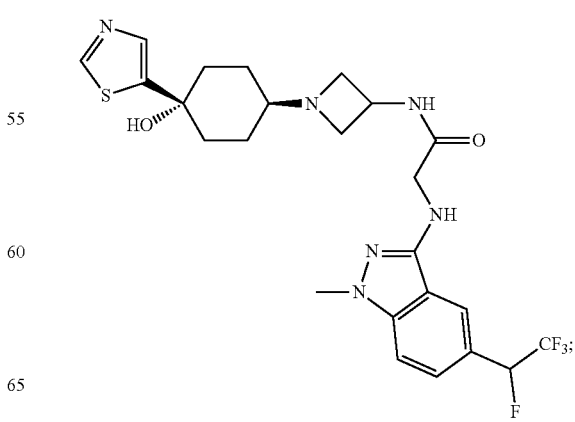

51
-continued
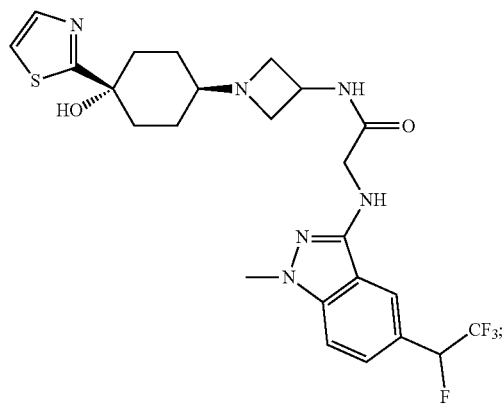
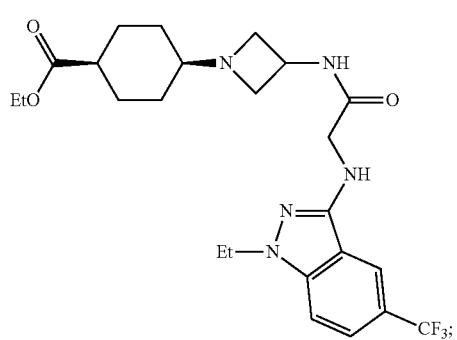
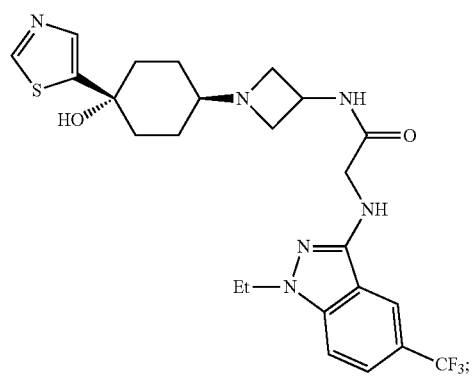
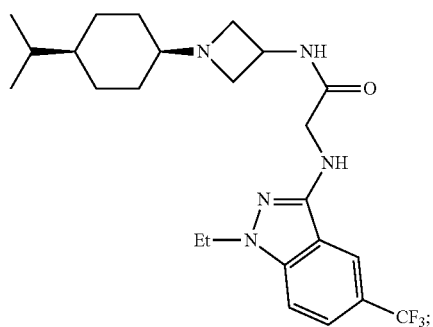
52
-continued
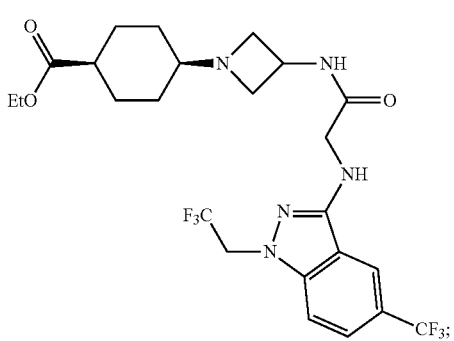
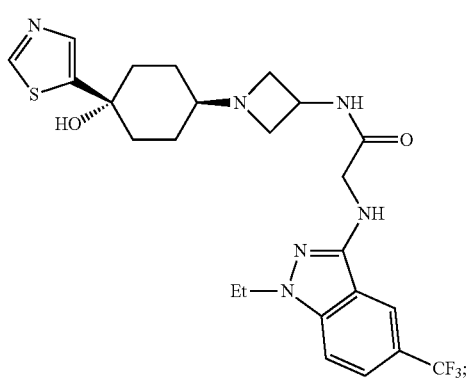
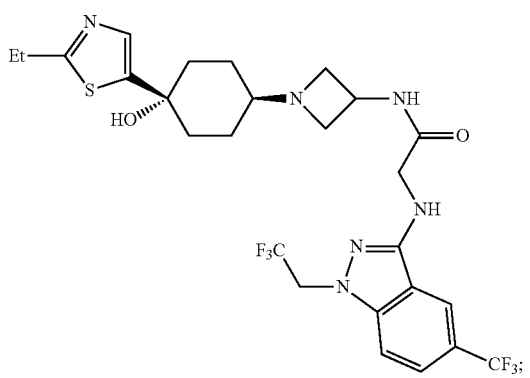
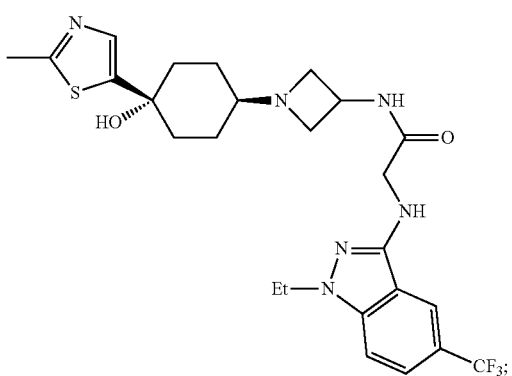

53
-continued
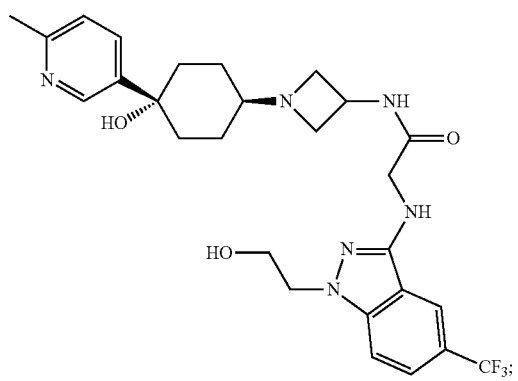
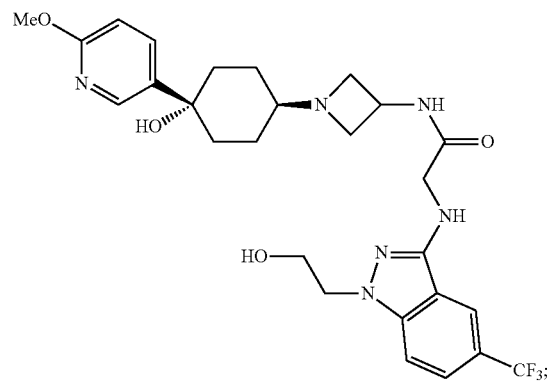
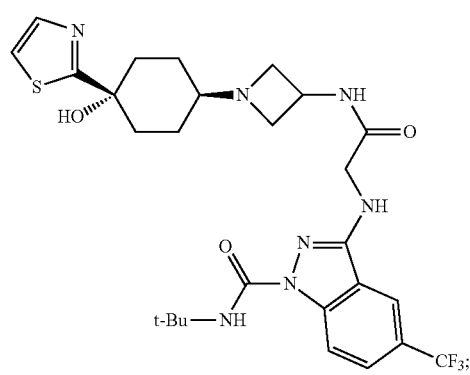
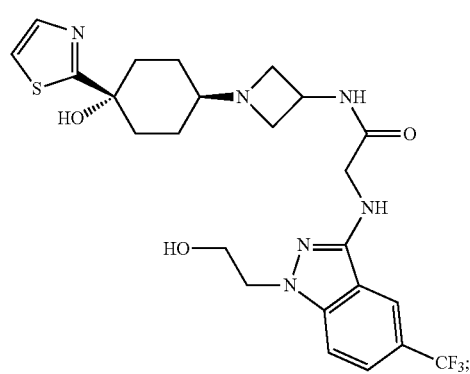
54
-continued
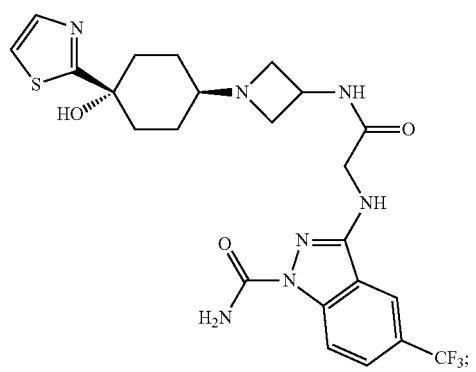
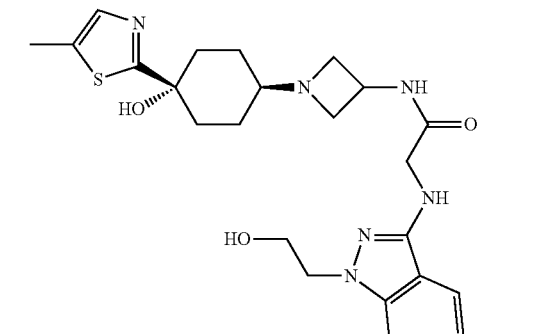
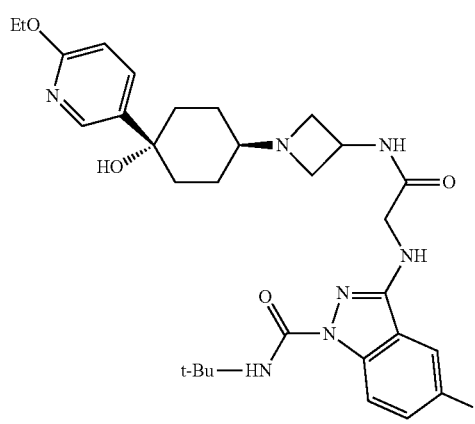
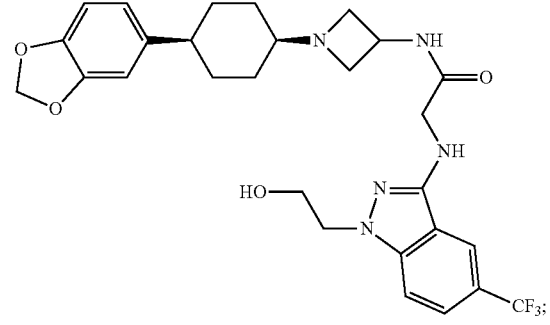

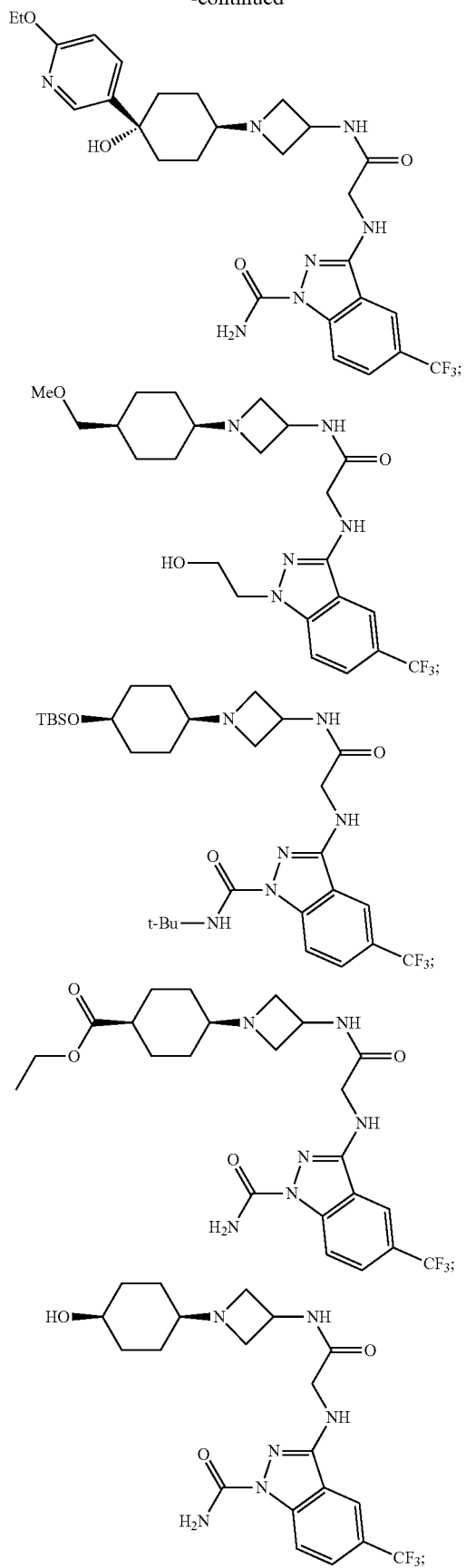
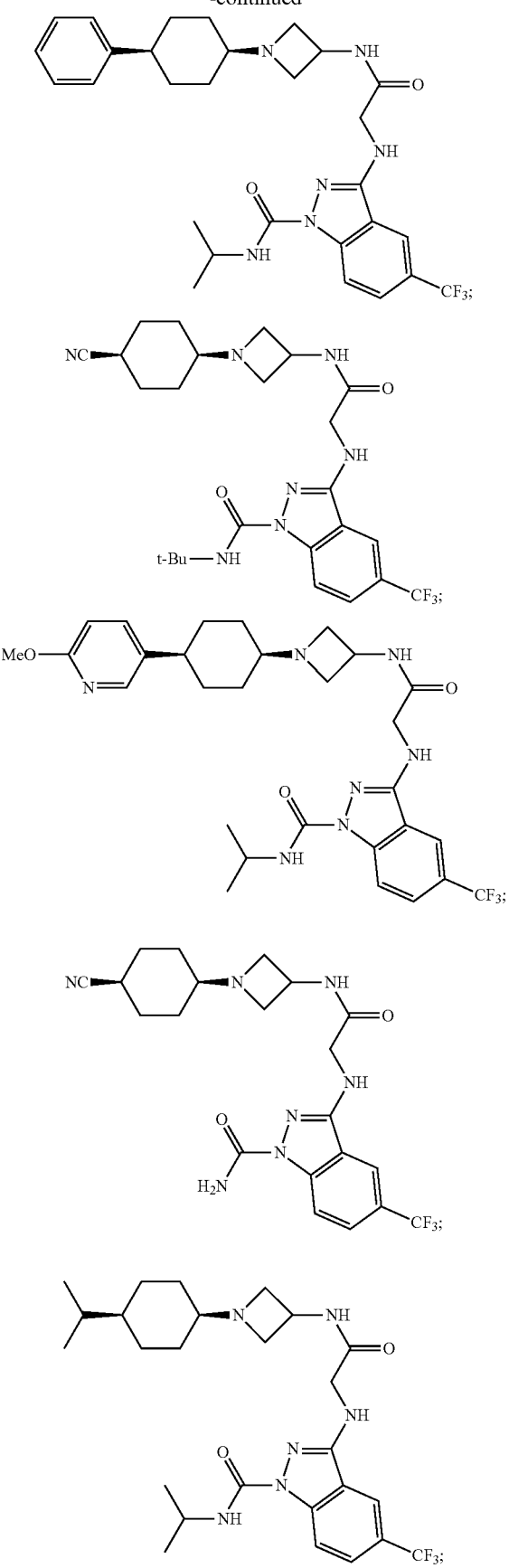

57
-continued
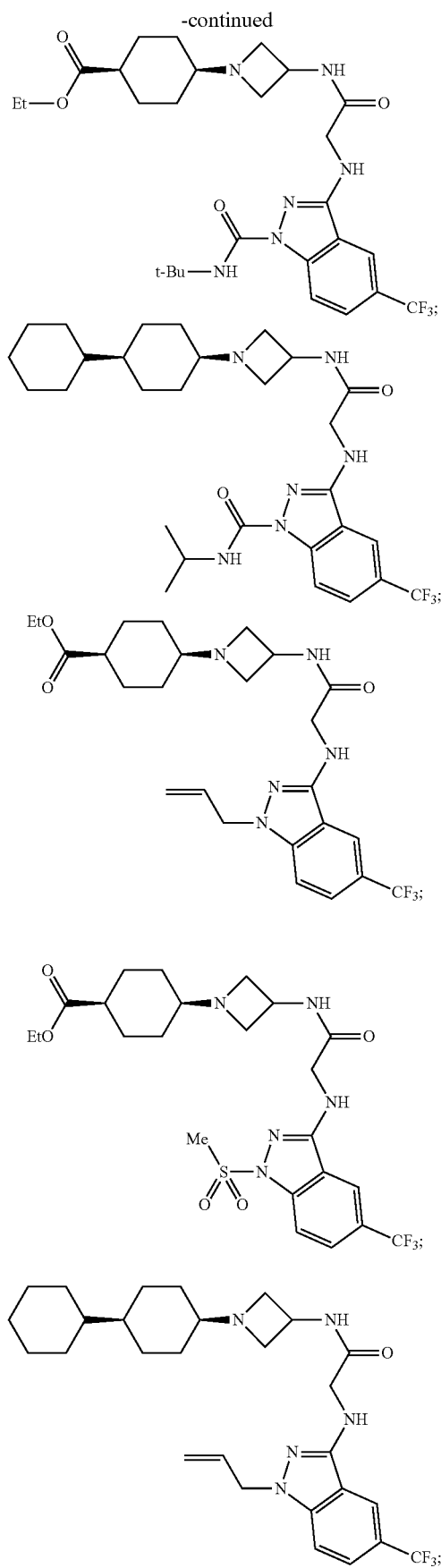
58
-continued
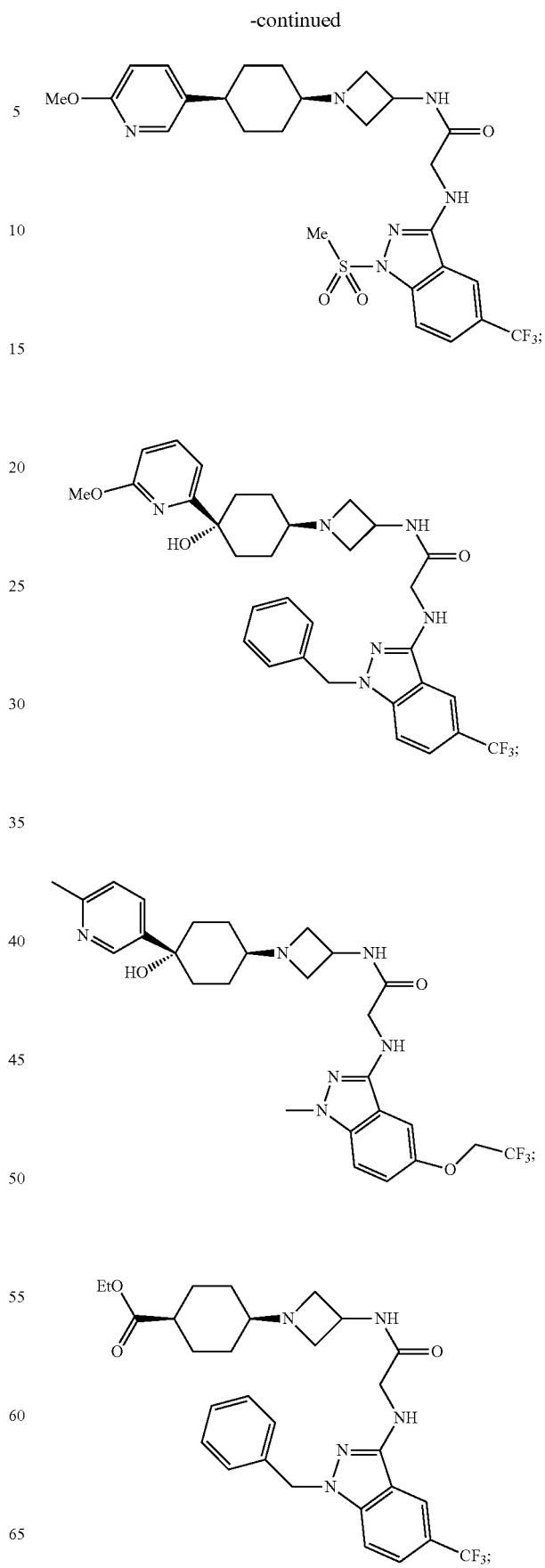

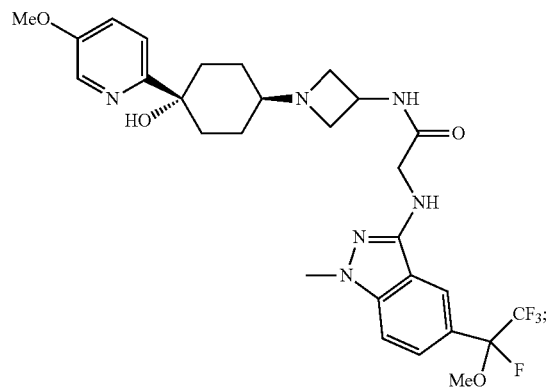
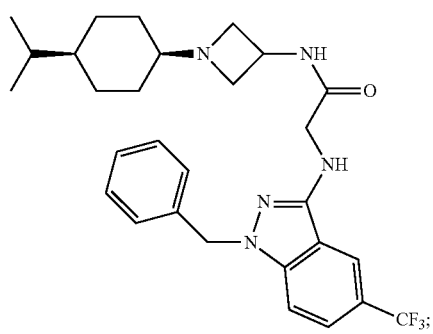
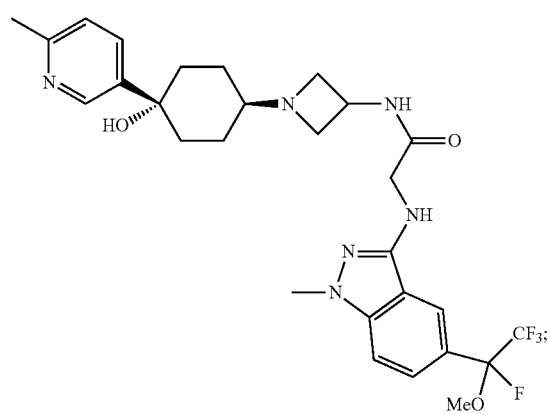
and tautomers, and pharmaceutically acceptable salts thereof.
In another embodiment, the invention relates to a compound selected from the group consisting of:
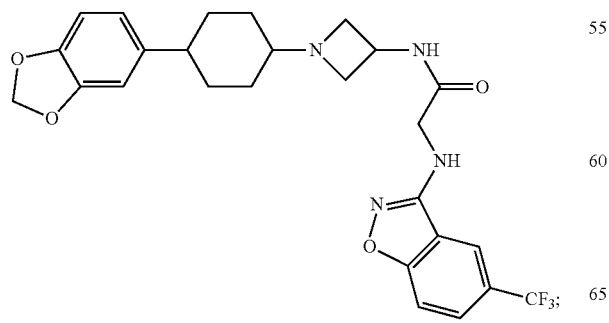
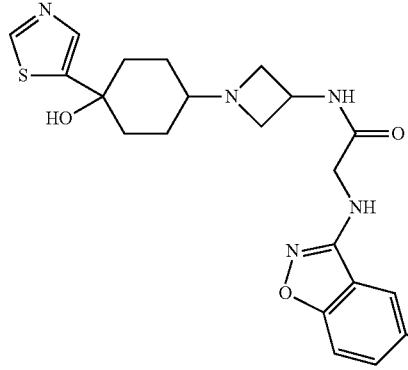
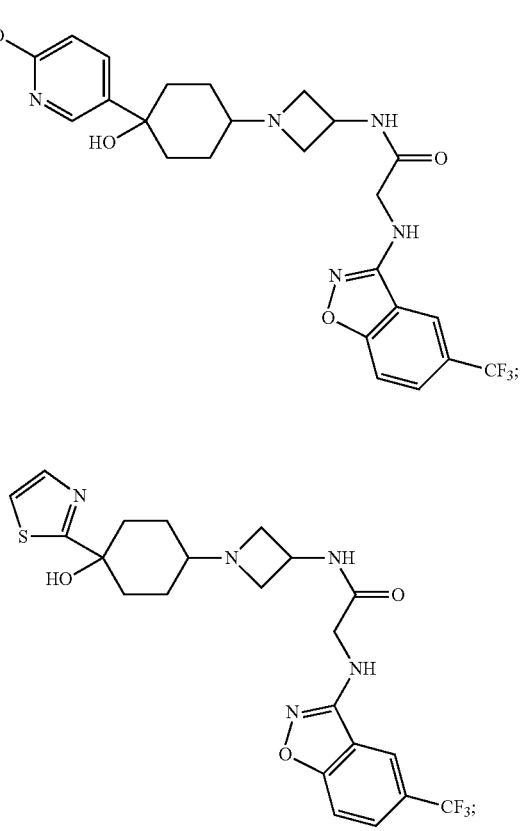
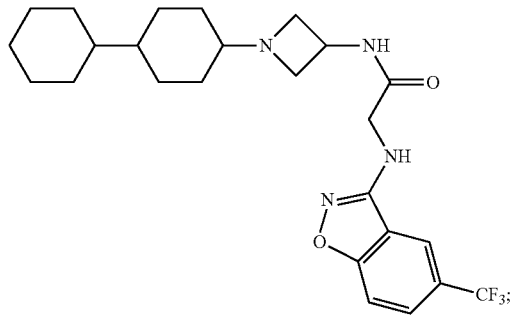

61
-continued
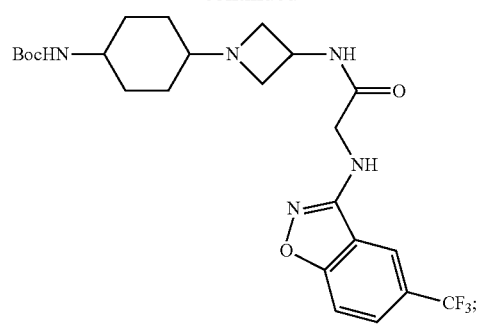
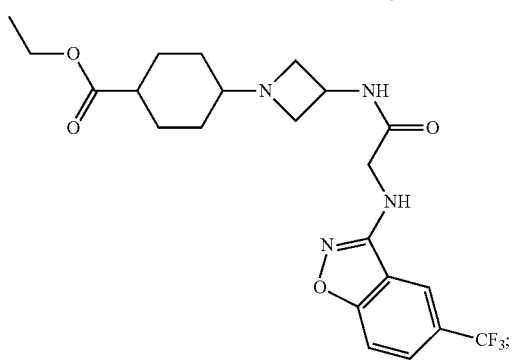
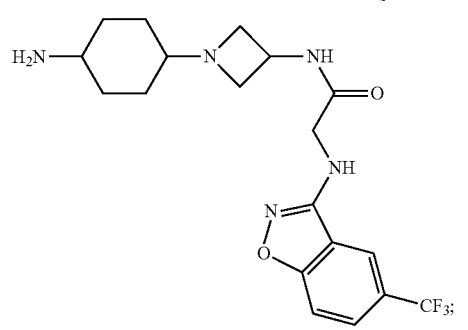
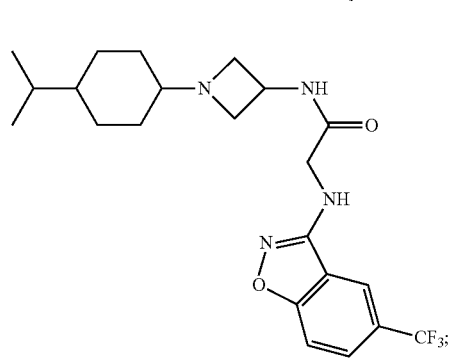
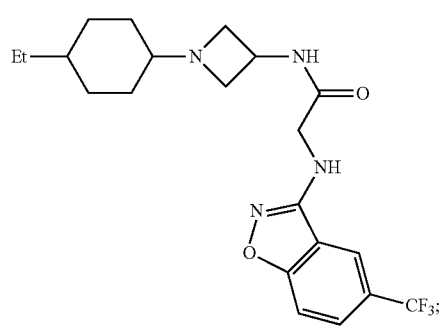
62
-continued
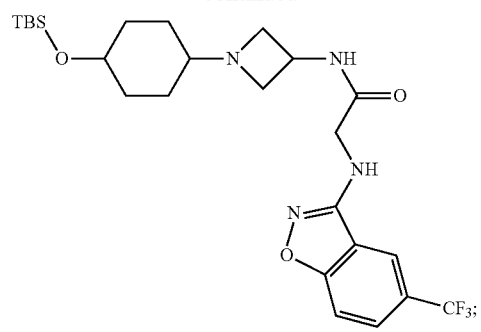
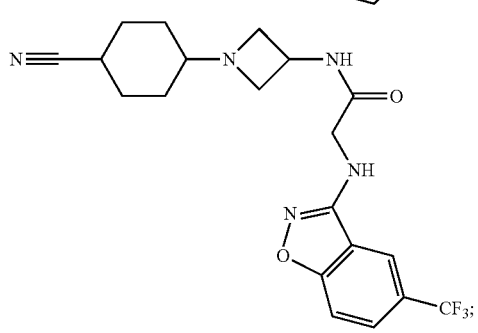
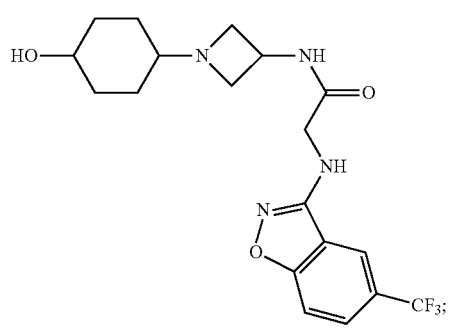
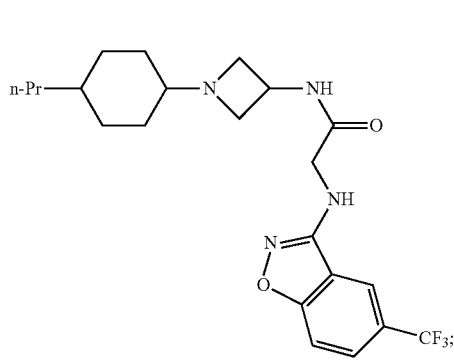
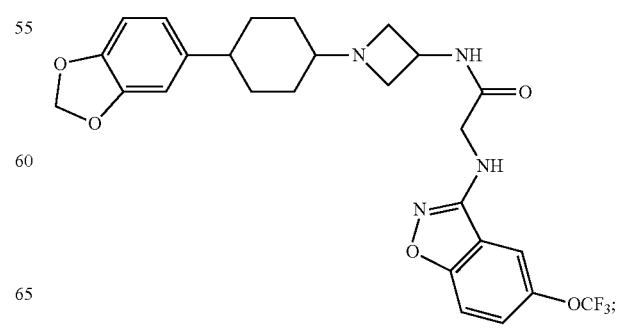

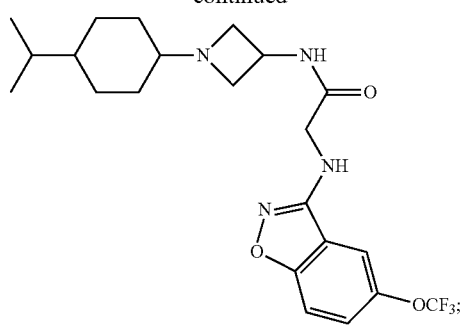
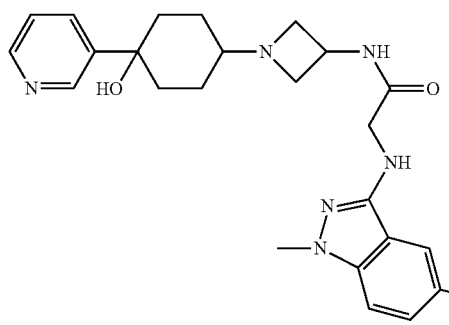
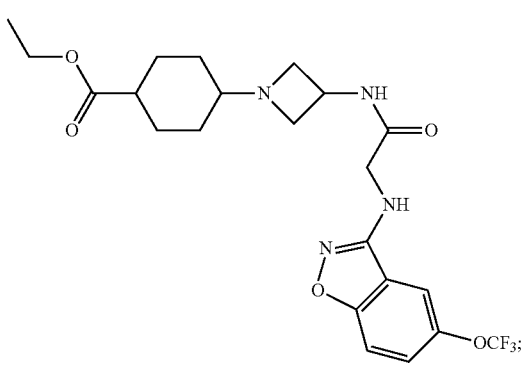
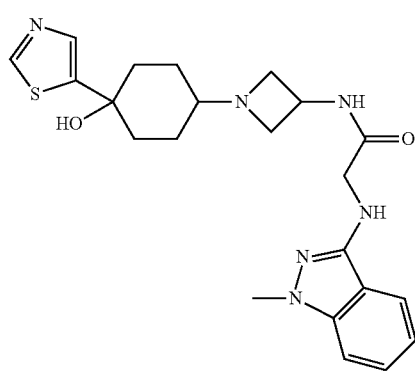
and tautomers, and pharmaceutically acceptable salts thereof.
In another embodiment, the invention relates to a compound selected from the group consisting of:
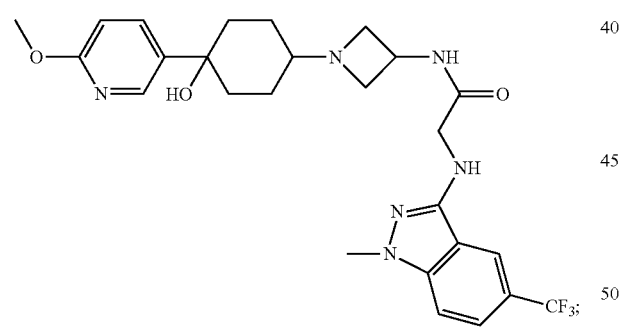
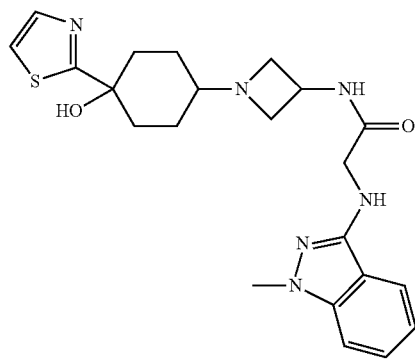
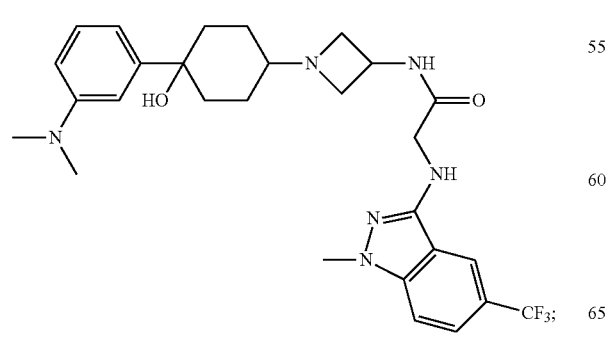
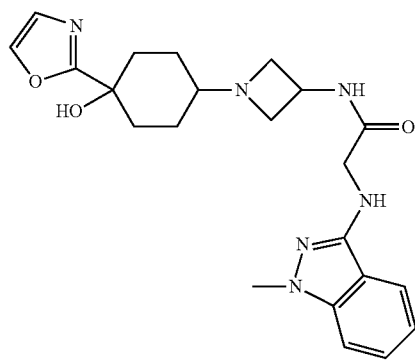

65
-continued
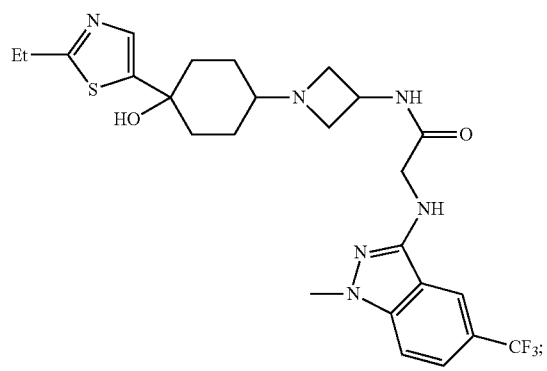
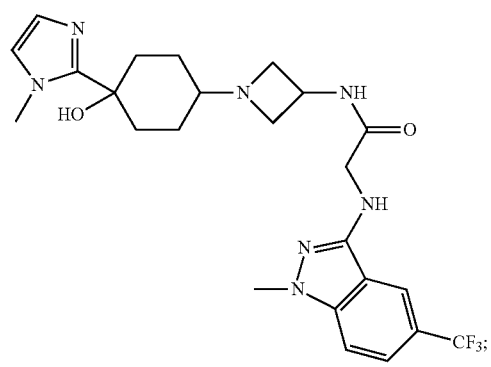
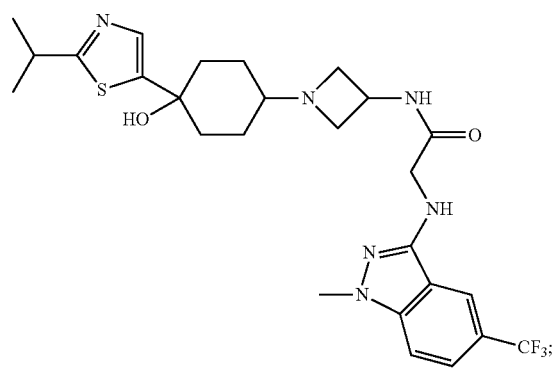
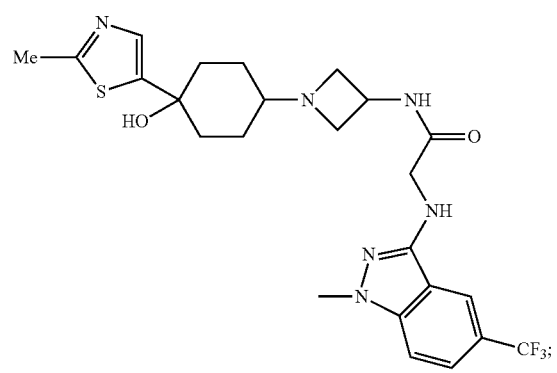
66
-continued
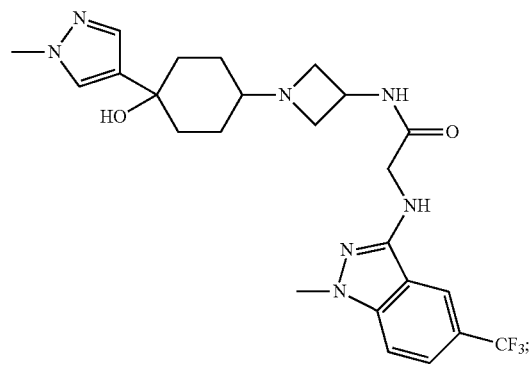
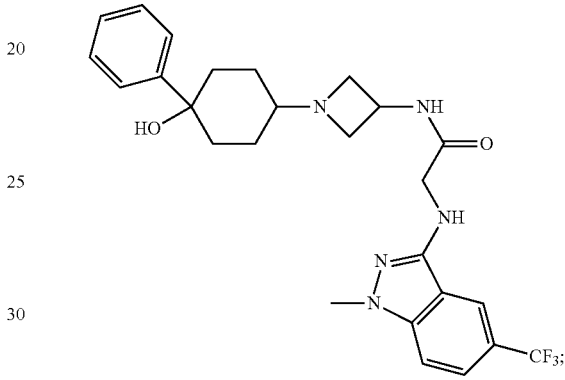
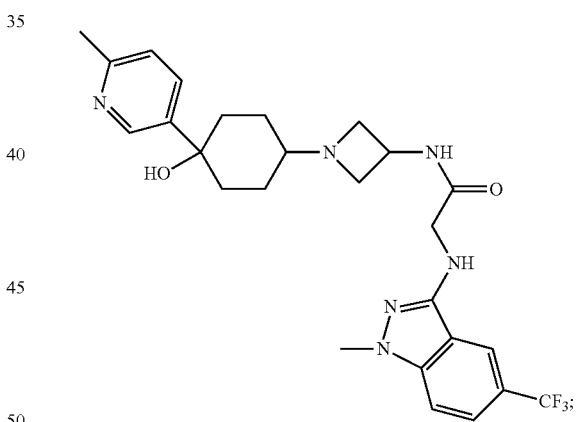
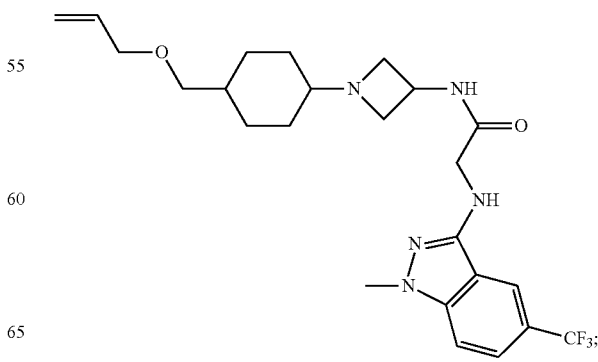

67
-continued
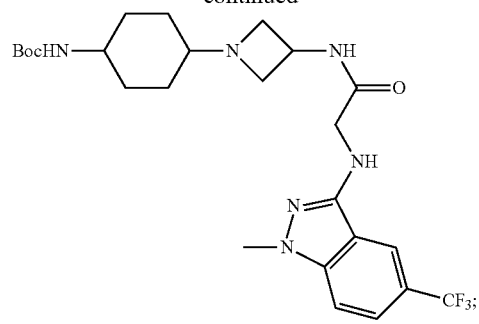
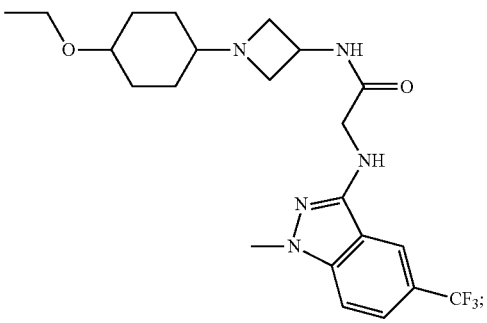
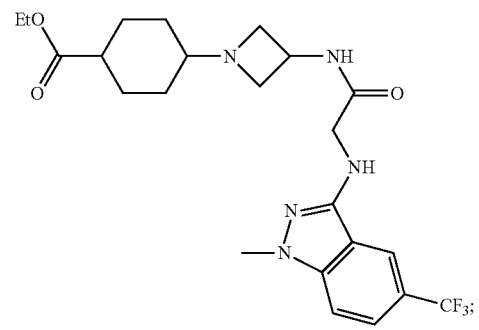
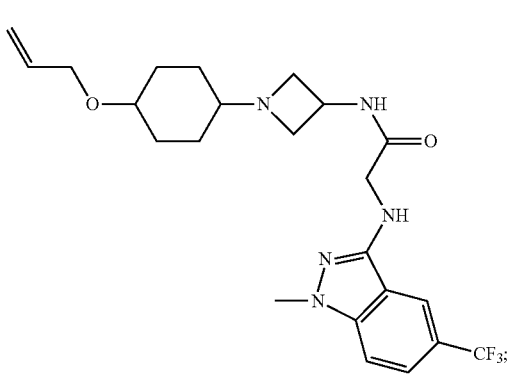
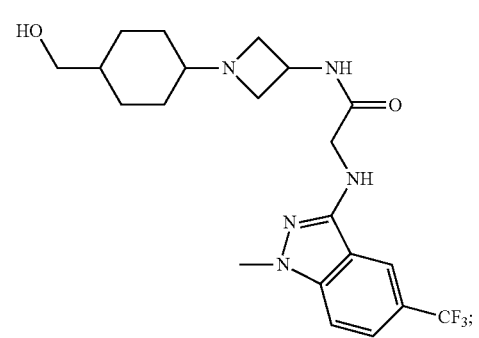
68
-continued
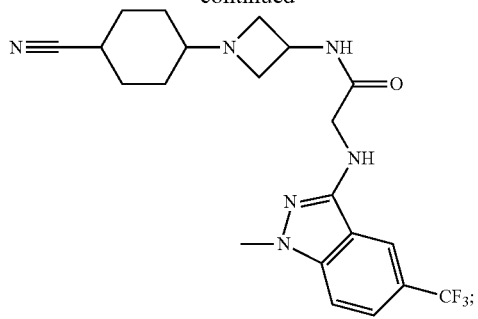
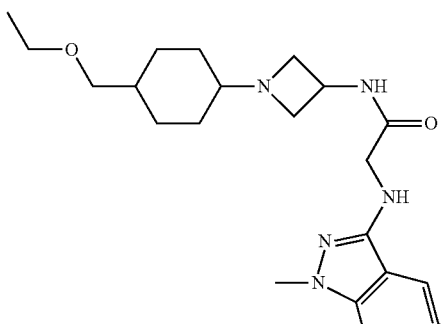
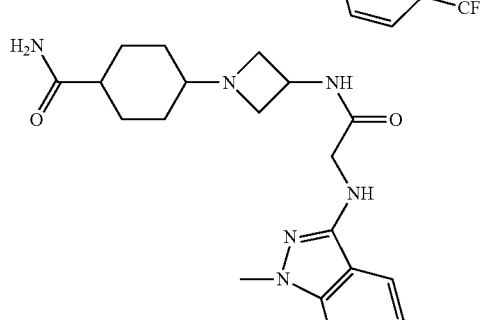
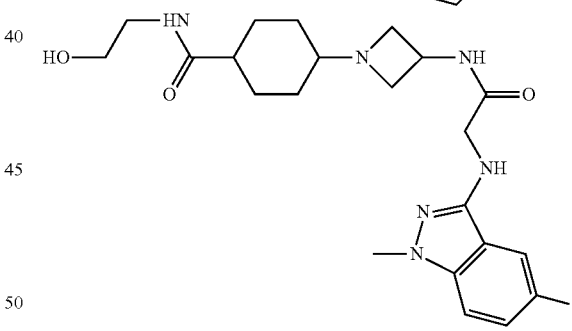
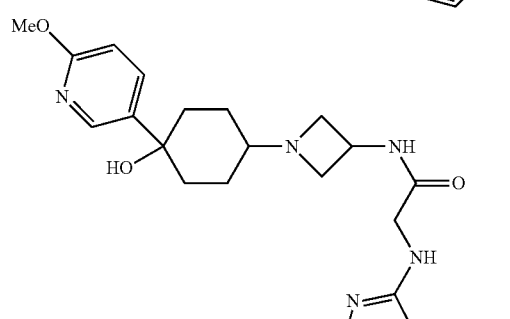

69
-continued
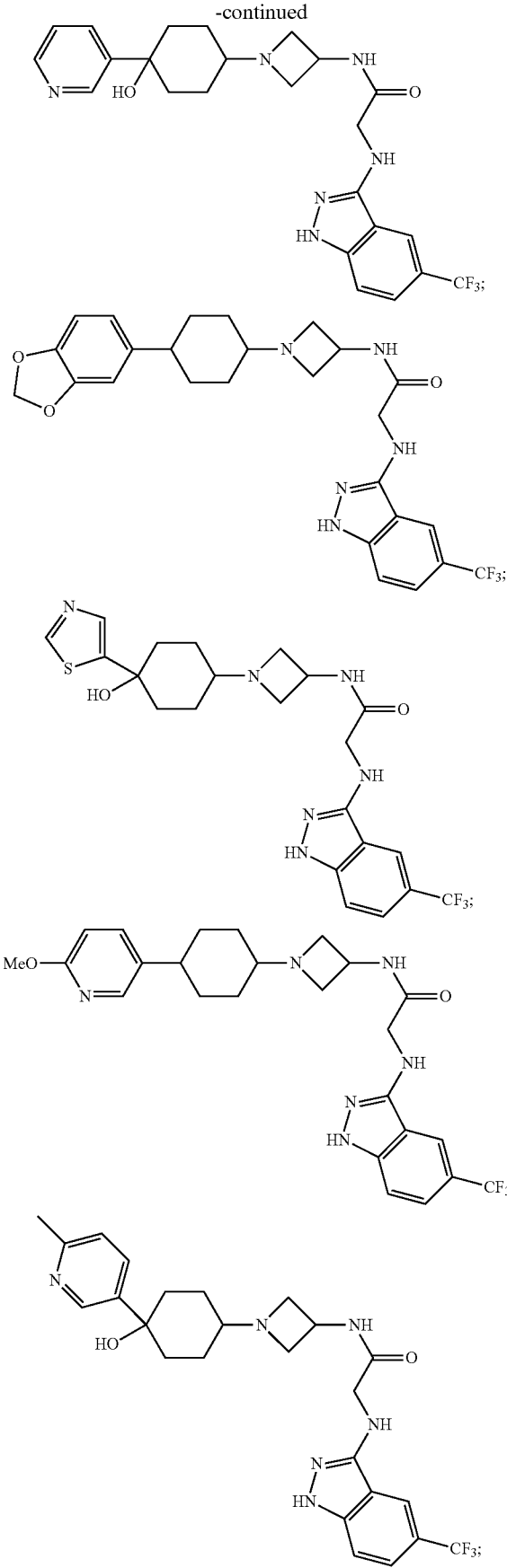
70
-continued
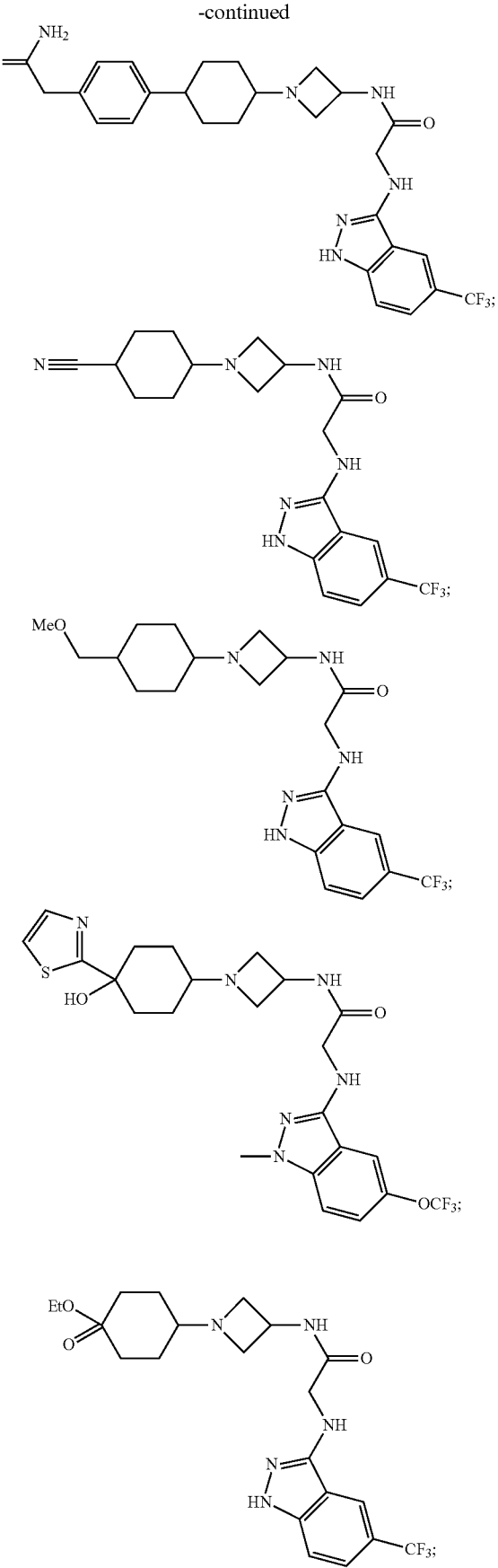

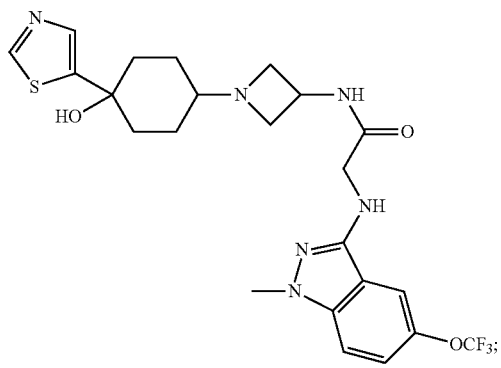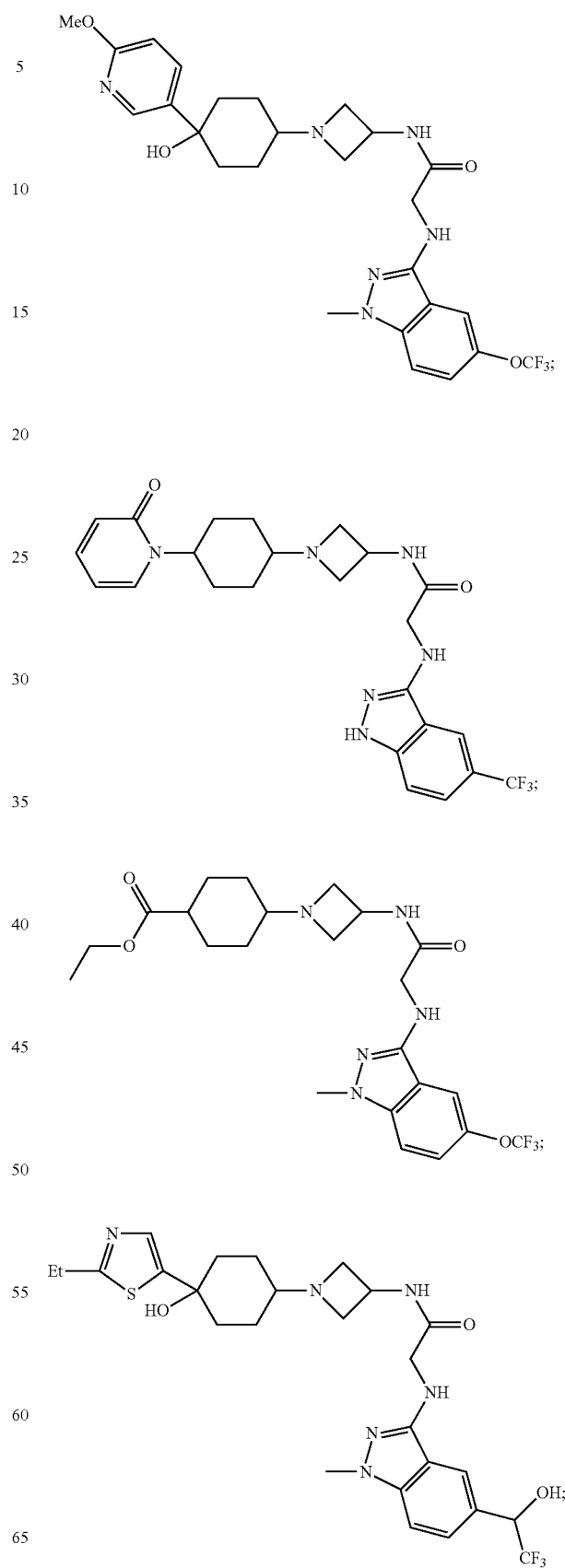

73
-continued
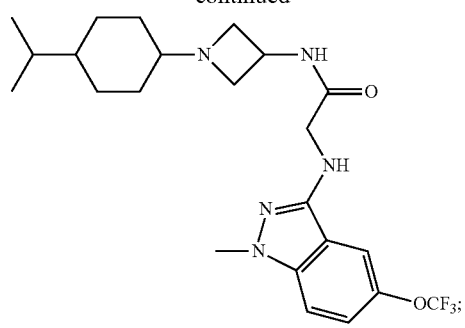
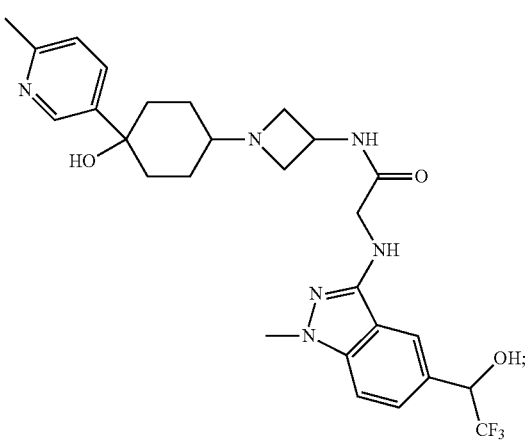
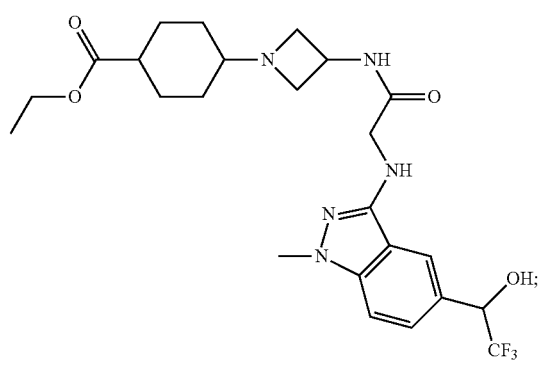
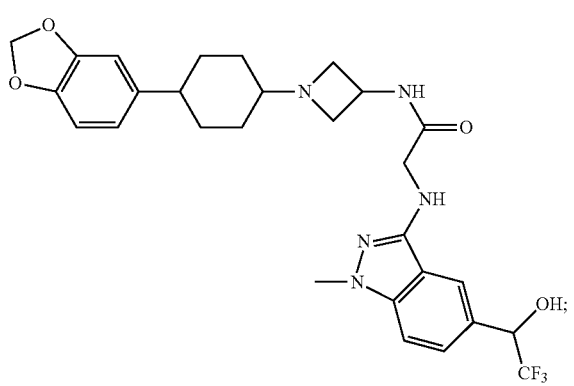
74
-continued
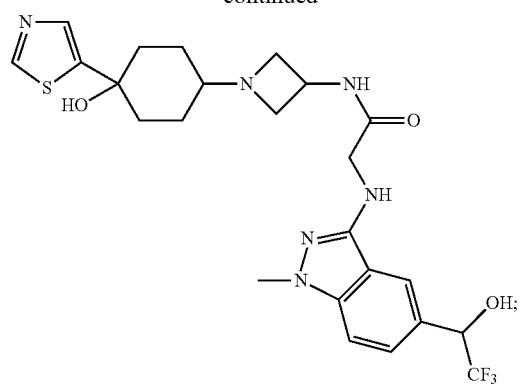
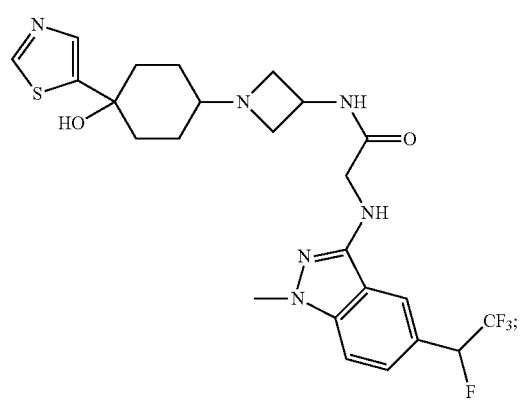
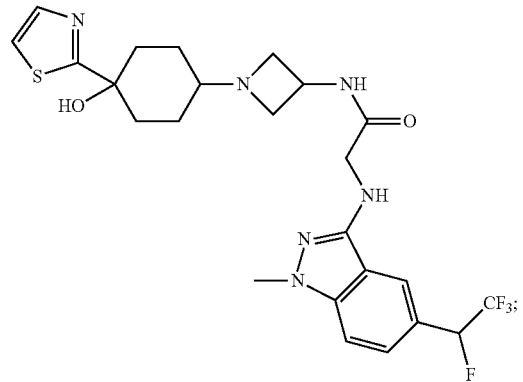
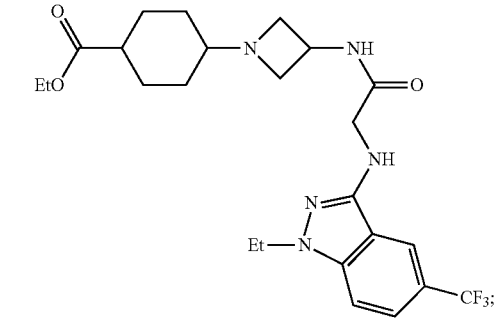

75
-continued
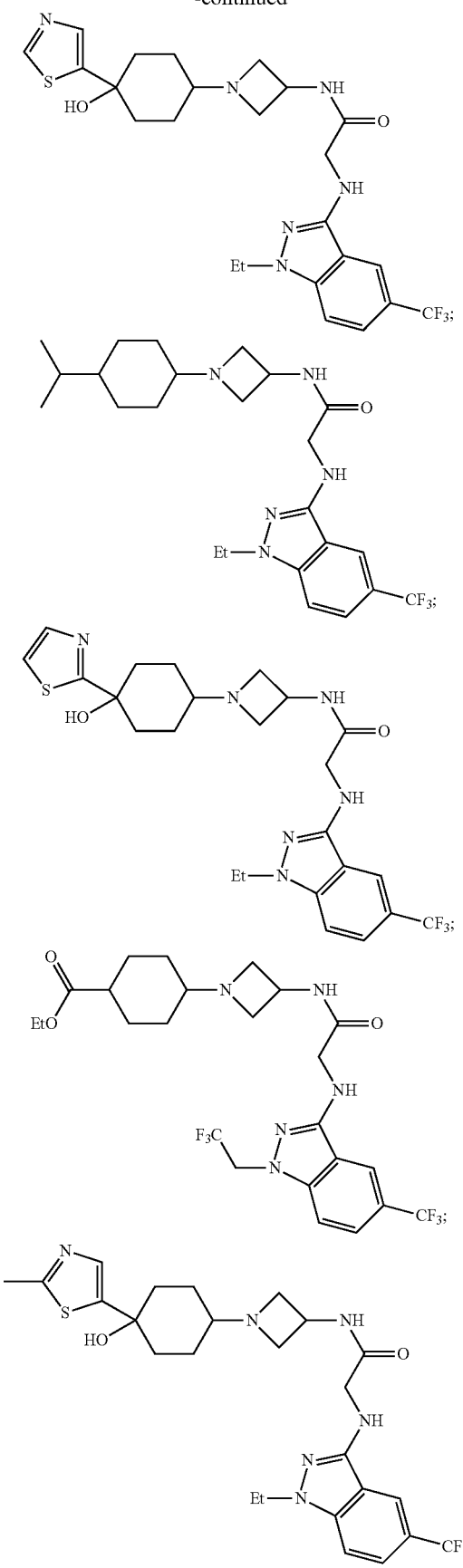
76
-continued
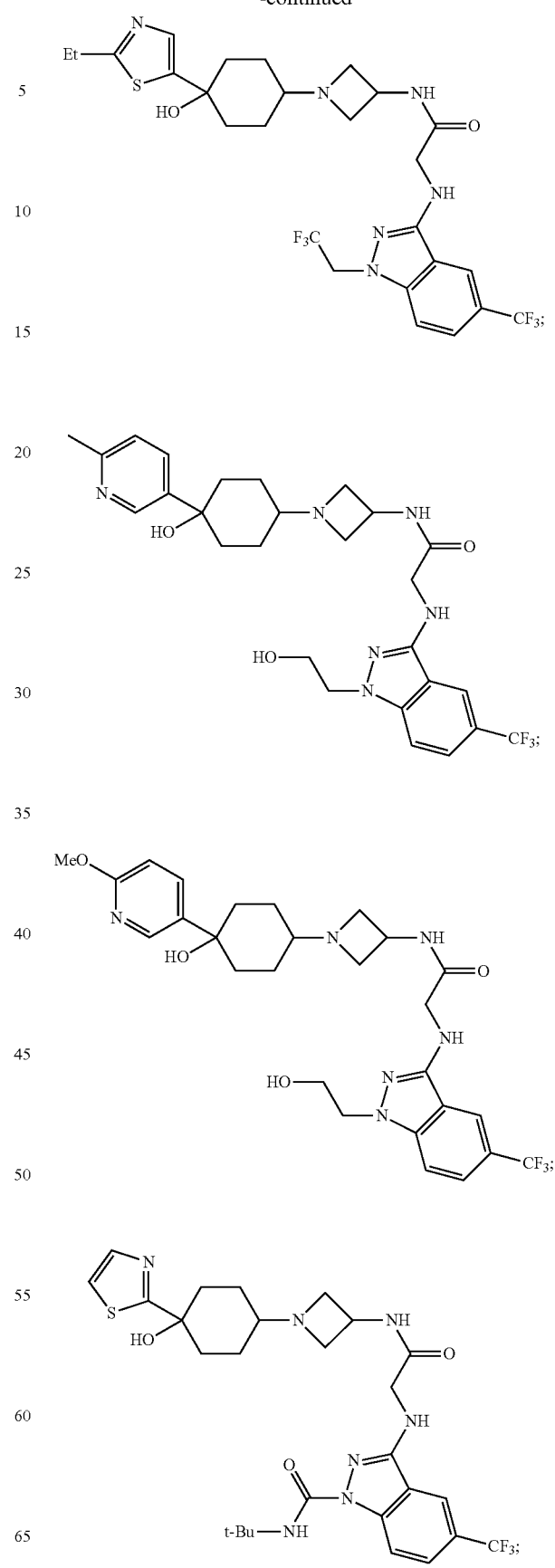

77
-continued
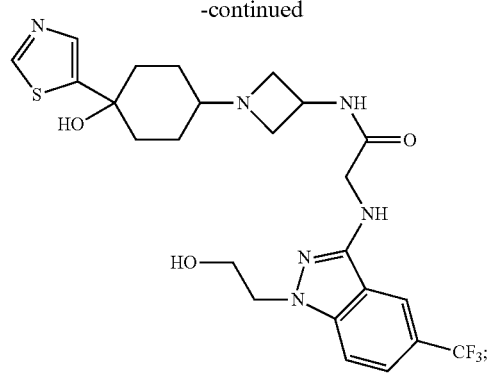
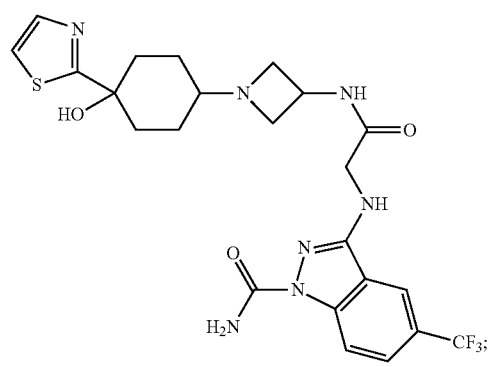
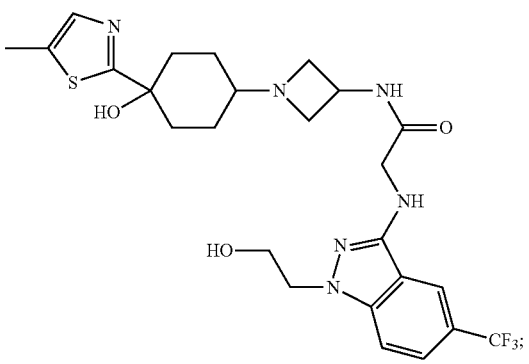
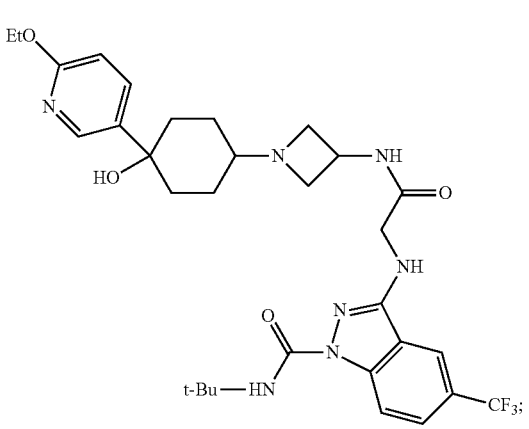
78
-continued
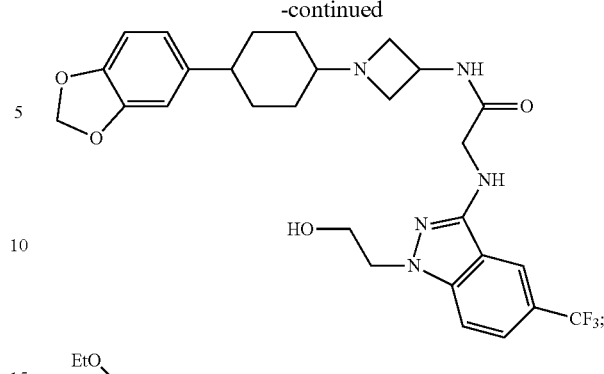
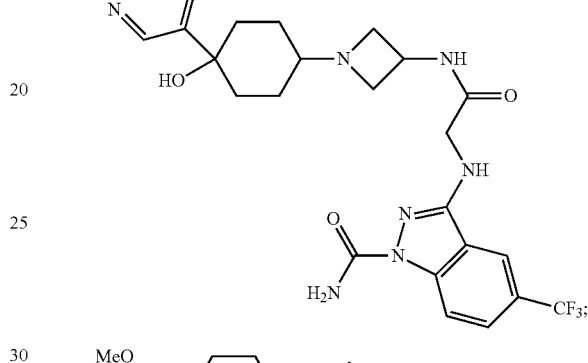
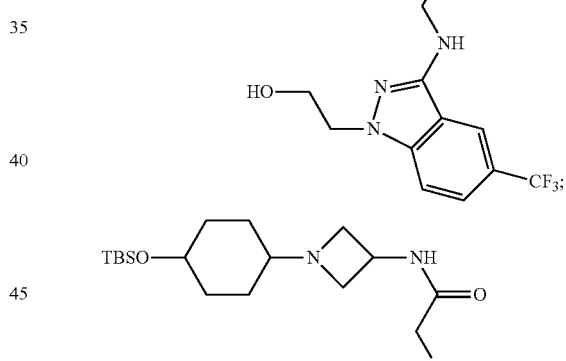
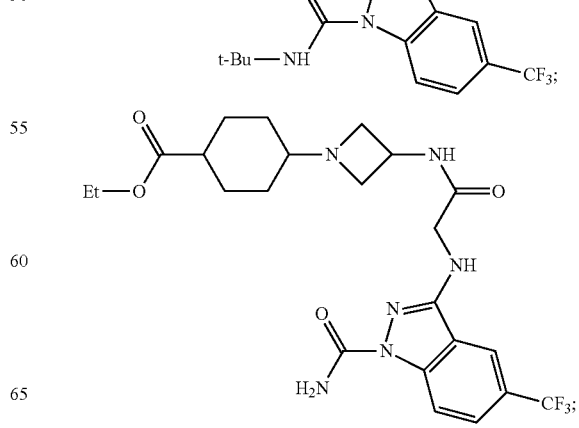

79
-continued
80
-continued
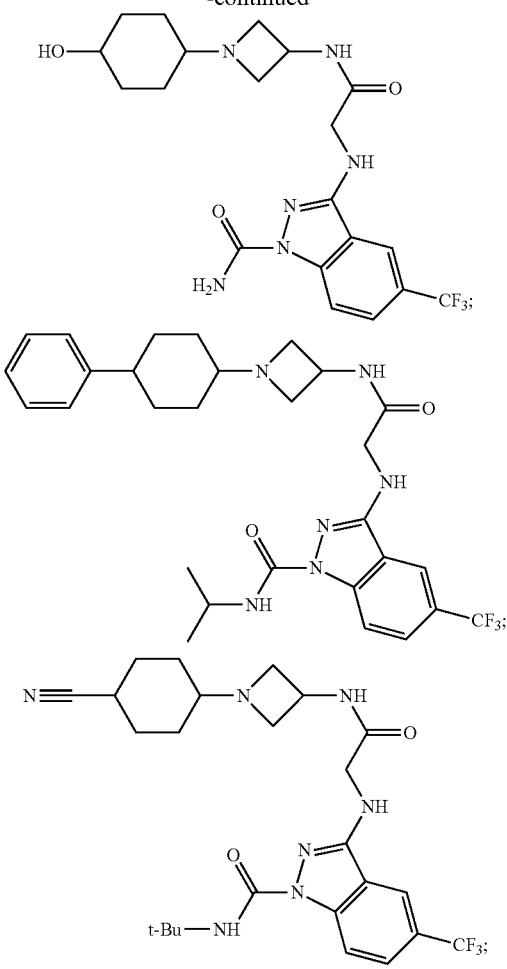
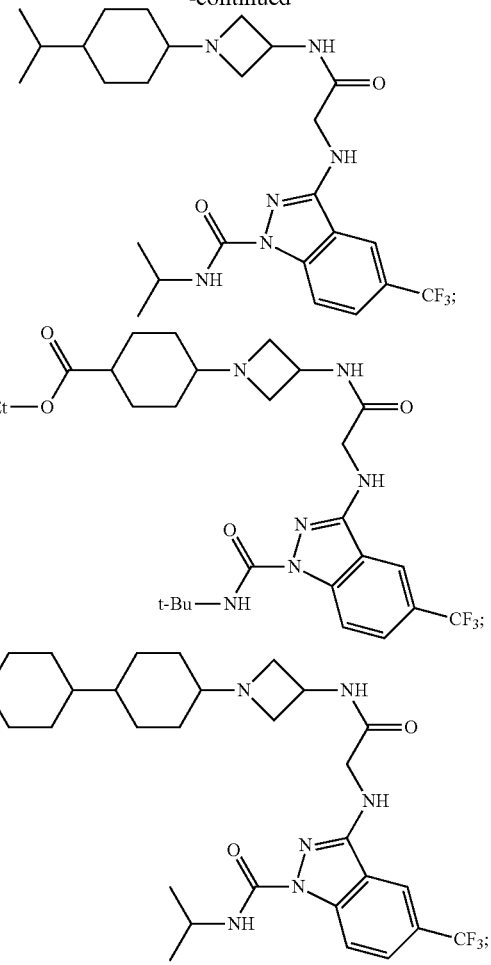
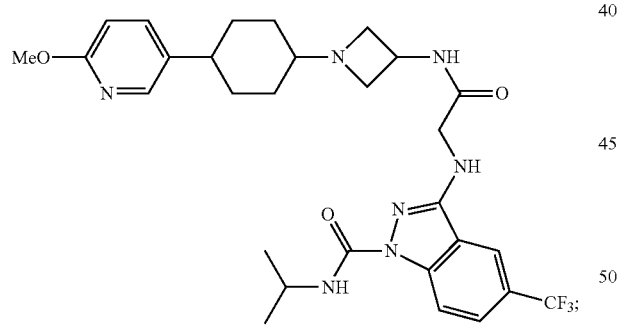
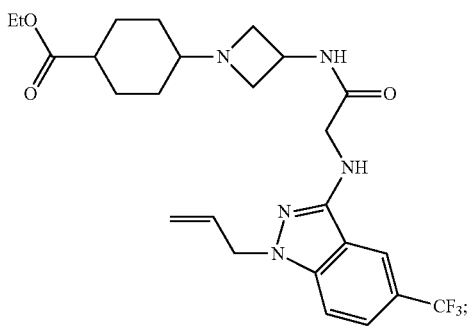
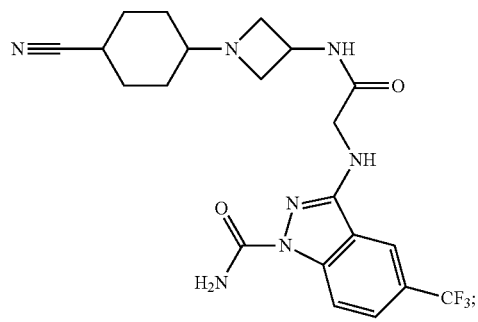
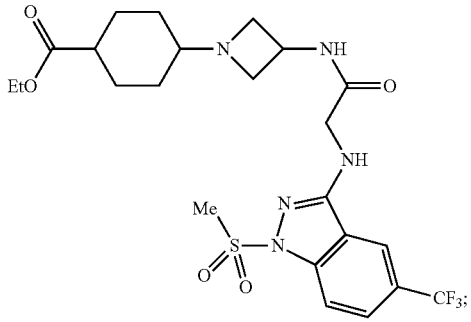

-continued

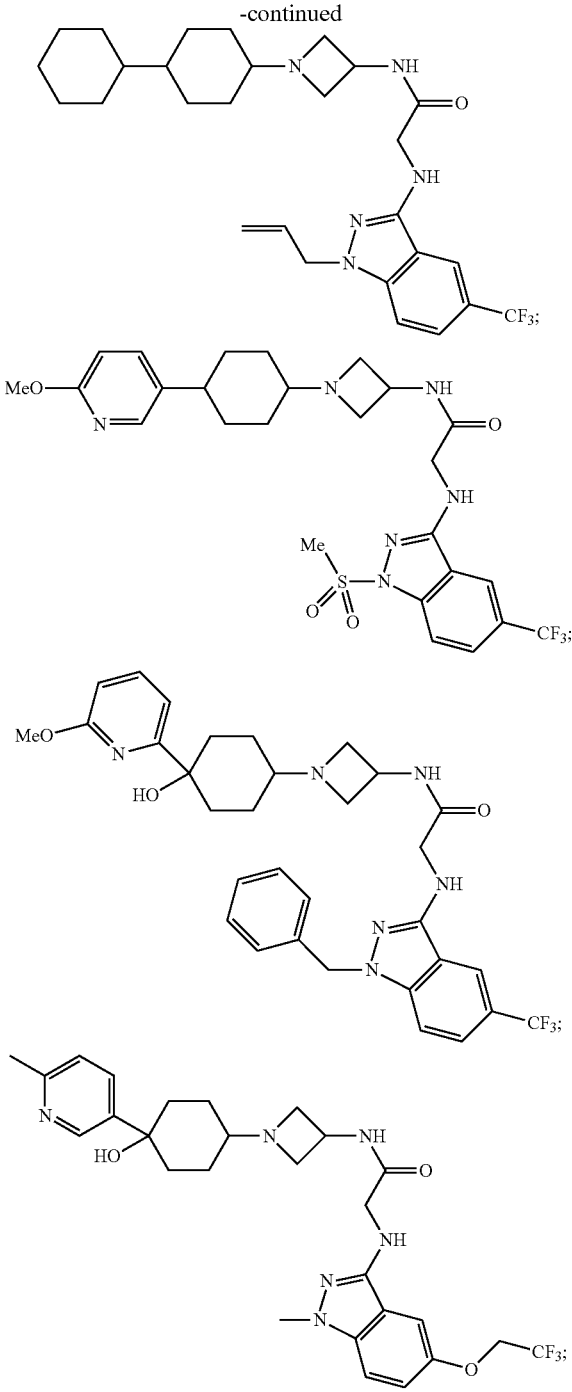

-continued

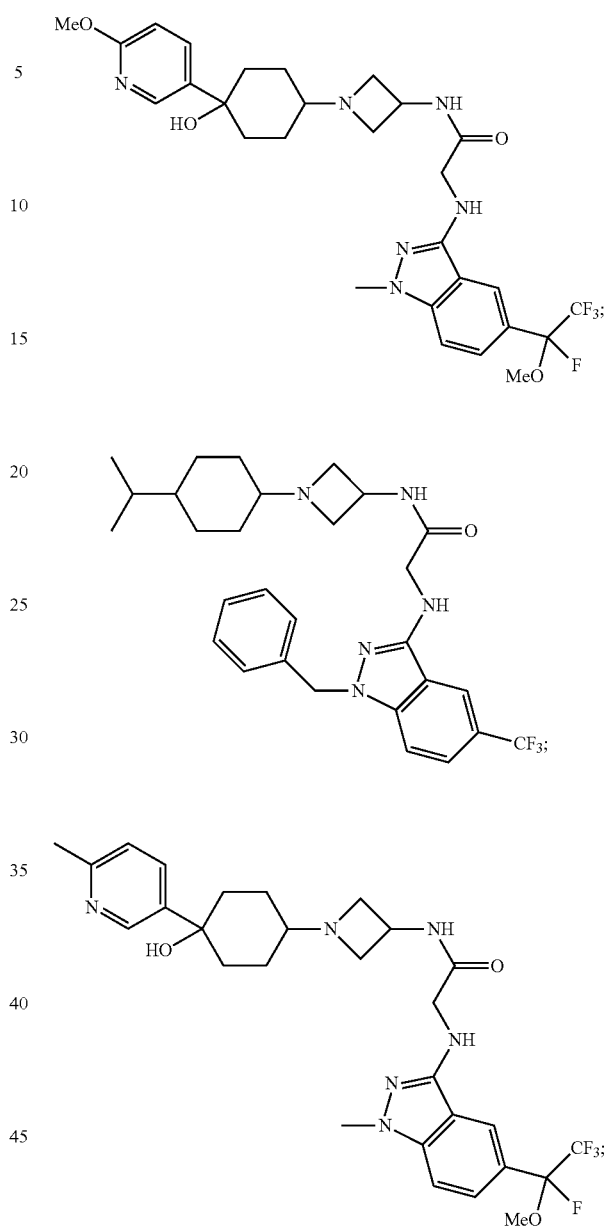

and tautomers, and pharmaceutically acceptable salts thereof.

In another embodiment, the invention relates to a pharmaceutical composition, comprising a compound of formula (I) and a pharmaceutically acceptable carrier.

In another embodiment, the invention relates to a pharmaceutical composition made by mixing a compound of formula (I) and a pharmaceutically acceptable carrier.

In another embodiment, the invention relates to a process for making a pharmaceutical composition comprising mixing a compound of formula (I) and a pharmaceutically acceptable carrier.

In another embodiment, the invention relates to a process for the preparation of a compound of Formula (I) of formula (I), comprising reacting a compound of Formula (IX)

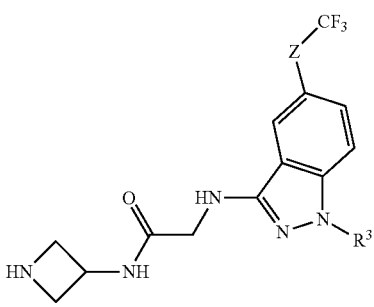

with a compound of Formula (X)

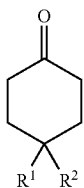

in the presence of a reducing agent to provide the compound of Formula (I). In another embodiment, the invention relates to a product made by the above-described process.

In another embodiment, the invention relates to a process for the preparation of a compound of Formula (I) of formula (I), comprising reacting a compound of Formula (XX)

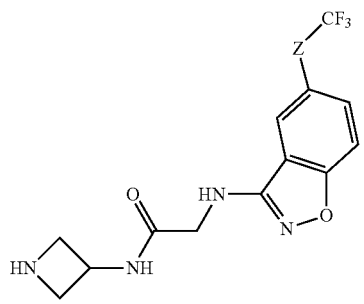

with a compound of Formula (X)

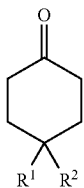

in the presence of a reducing agent to provide the compound of Formula (I). In another embodiment, the invention relates to a product made by the above-described process.

In another embodiment, the invention relates to a method for preventing, treating or ameliorating a CCR2 mediated syndrome, disorder or disease comprising administering to a subject in need thereof a therapeutically effective amount of a compound of formula (I).

In another embodiment, the invention relates to a method for preventing, treating or ameliorating a CCR2 mediated inflammatory syndrome, disorder or disease wherein the syndrome, disorder or disease is associated with elevated MCP-1 expression or MCP-1 overexpression, or is an inflammatory condition that accompanies syndromes, disorders or diseases associated with elevated MCP-1 expression or MCP-1 overexpression comprising administering to a subject in need thereof an effective amount of a compound of claim 1.

In another embodiment, the invention relates to a method of preventing, treating or ameliorating a syndrome, disorder or disease, wherein said syndrome, disorder or disease is selected from the group consisting of: Chronic Obstructive Pulmonary Disease (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes and diabetic complications, diabetic nephropathy, diabetic retinopathy, diabetic retinitis, diabetic microangiopathy, overweight, obesity, obesity-associated insulin resistance, metabolic syndrome, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodontis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of formula (I).

In another embodiment, the invention relates to a method of preventing, treating or ameliorating a syndrome, disorder or disease, wherein said syndrome, disorder or disease is selected from the group consisting of: type I diabetes, type II diabetes, diabetic complications, diabetic nephropathy, diabetic retinopathy, diabetic retinitis, diabetic microangiopathy, obesity, obesity-associated insulin resistance, metabolic syndrome, asthma, and allergic asthma, comprising administering to a subject in need thereof a therapeutically effective amount of a compound of formula (I).

In another embodiment, the invention relates to a method of treating a disorder selected from the group consisting of type II diabetes, obesity and asthma comprising administering to a subject in need thereof a therapeutically effective amount of a compound of formula (I).

In another embodiment, the invention relates to a compound of formula (I), which is the less polar isomer of any of Examples #1-106.

In another embodiment, the invention relates to a compound of formula (I), which is the less polar isomer of Example #20.

In another embodiment, the invention relates to a product made by the process of any of Examples from Example 1 to Example 106.

DEFINITIONS

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-8)}$cycloalkyl, $C_{(5-8)}$cycloalkyl, $C_{(3-12)}$cycloalkyl, $C_{(3-20)}$cycloalkyl, decahydronaphthalenyl, and 2,3,4,5,6,7-hexahydro-1H-indenyl.

The term "heterocyclyl" refers to a saturated or partially unsaturated monocyclic cycloalkyl ring radical wherein from 1 to 3 ring carbon atoms have been replaced with heteroatoms selected from N, O, or S. Said heteroatoms may exist in any allowed oxidation state. The radical may be derived from the removal of a hydrogen atom from a carbon or a nitrogen atom. Typical heterocyclyl radicals include, but are not limited to, 2H-pyrrolyl, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azepanyl, hexahydro-1,4-diazepinyl and the like.

The term "heteroaromatic" or "heteroaryl" refers to 5- to 7-membered mono- or 8- to 10-membered bicyclic aromatic ring systems, containing from one to four heteroatoms selected from N, O, or S where the nitrogen and sulfur atoms can exist in any allowed oxidation state. Examples include, but are not limited to, benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

For use in medicines, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p1) include pharmaceutically acceptable acidic/anionic or basic/cationic salts.

Throughout this specification, compounds are described as being separated, usually by silica gel column, although preporatory thin layer chromatography, or high or low pressure liquid choromatography may also be used. It is generally accepted that when eluting compounds through a silica gel-type separation medium, that the least polar compounds elute before the more polar compounds. Therefore, the term "less polar isomer", refers to the isomer that will elute first from a silica gel type separation medium.

Abbreviations

Herein and throughout this application, the following abbreviations may be used.
BOC or Boc tert-butyloxycarbonyl
Bu butyl
DAST diethylaminosulfur trifluoride
DCC dicyclohexylcarbodiimide
DCM dicholomethane
DMF dimethylformamide
DMSO dimethylsulfoxide
EDCI 1-ethyl-3-(3'-dimethylaminopropyl)carbodiimide
Et ethyl
EtOAc ethyl acetate
DIPEA diisopropylethylamine
HOBt hydroxybenzotriazole
IPA isopropyl alcohol
LAH lithium aluminum hydride
LDA lithium diisopropyl amine
Me methyl
NMP N-methylpyrrolidine
OAc acetate
$PdCl_2$(dppf) [1,1'-bis(diphenylphosphino)ferrocene]dichloropalladium(II)
Ph phenyl
iPr isopropyl
PyBrop bromo-tris-pyrrolidinophosphonium hexafluorophosphate
RT or rt room temperature
TEA triethylamine
TFA trifluoroacetic acid
THF tetrahydrofuran
Ts tosylate Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethylpropane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine or zinc.

Methods of Use

The present invention is directed to a method for preventing, treating or ameliorating a CCR2 mediated syndrome, disorder or disease comprising administering to a subject in need thereof an effective amount of a compound of Formula (I) or a form, composition or medicament thereof.

Examples of a CCR2 mediated syndrome, disorder or disease for which the compounds of Formula (I) are useful include chronic obstructive pulmonary disorder (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes, diabetic complications, diabetic nephropathy, diabetic retinopathy, diabetic retinitis, diabetic microangiopathy, overweight, obesity, obesity-associated insulin resistance, metabolic syndrome, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, aortic abdominal aneurism, multiple sclerosis, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, and chronic neuroinflammatory disorders including, but not limited to, Alzheimer's disease, ischemic stroke, spinal cord injury, nerve crush injury and traumatic brain injury.

The term "administering" with respect to the methods of the invention, means a method for therapeutically or prophylactically preventing, treating or ameliorating a syndrome, disorder or disease as described herein by using a compound of Formula (I) or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment. In one aspect of the invention, the subject is at risk of (or susceptible to) developing a syndrome, disorder or disease that is associated with elevated MCP-1 expression or MCP-1 overexpression, or a patient with an inflammatory condition that accompanies syndromes, disorders or diseases associated with elevated MCP-1 expression or MCP-1 overexpression.

The term "therapeutically effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

The term "uveitis" generically refers to any inflammatory disease involving the eye. Uveitis can be divided into clinically distinct subtypes based on the part of the eye in which the inflammation is present (percentages correspond to patients known to fit these categories): anterior (51%), intermediate (13%), posterior (20%), or panuveitis (16%) and, according to the course of the disease, as either acute (16%), recurring (26%), or chronic (58%). Those with anterior uveitis (0.19%) eventually develop irreparable vision damage despite aggressive treatment such as unilateral blindness (9%), bilateral blindness (2%), or unilateral or bilateral vision impairment (8%). Most cases of uveitis are idiopathic, but known causes include infection (e.g., toxoplasmosis, cytomegalovirus, and the like) or development as a component of a systemic inflammatory and/or autoimmune disorder (e.g., juvenile RA, HLA-B27 associated spondyloarthropathies, sarcoidosis, and the like). (HLA-B27: Human Leukocyte Antigen B*27—is a class I surface antigen encoded by the B locus in the major histocompatibility complex (MHC) on chromosome 6 and presents micobial antigens to T cells. HLA-B27 is strongly associated with a certain set of autoimmune diseases referred to as the seronegative spondyloarthropathies.)

When employed as CCR2 inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula (I) may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula (I) include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well

89 as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in the Examples or Formula (I) for use as a medicament.

In another embodiment, the invention relates to the use of a compound as described in the Examples of Formula (I) for the preparation of a medicament for the treatment of a disease associated with an elevated or inappropriate CCR2 activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base.

90

The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

General Reaction Scheme

Representative compounds of the present invention can be synthesized in accordance with the general synthetic methods described below. Compounds of Formula (I) can be prepared by methods known to those who are skilled in the art. The following reaction schemes are only meant to represent examples of the invention and are in no way meant to be a limit of the invention.

Compounds of Formula (I) may be prepared according to the processes outlined in Scheme 1.

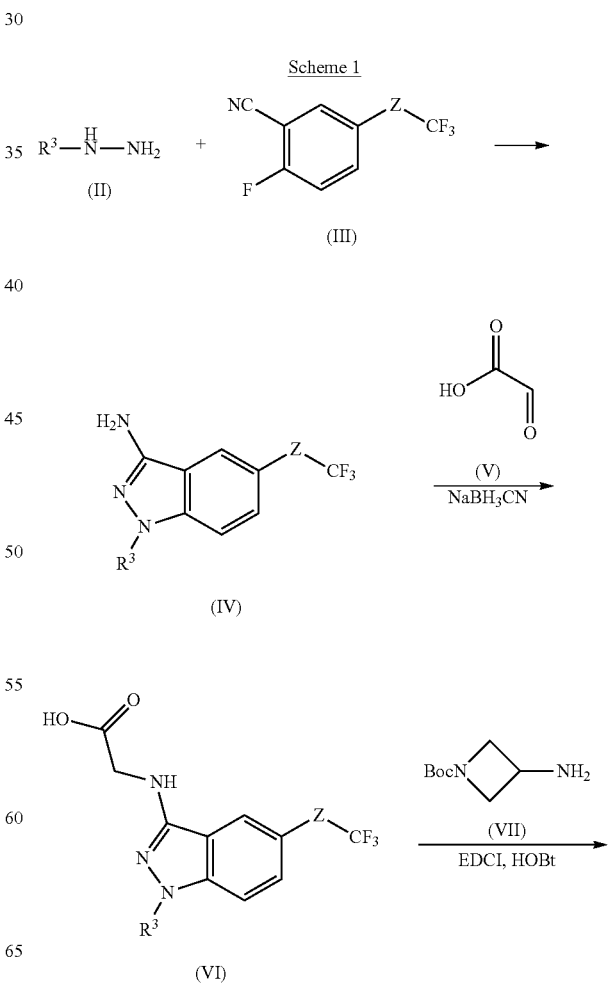

91

-continued

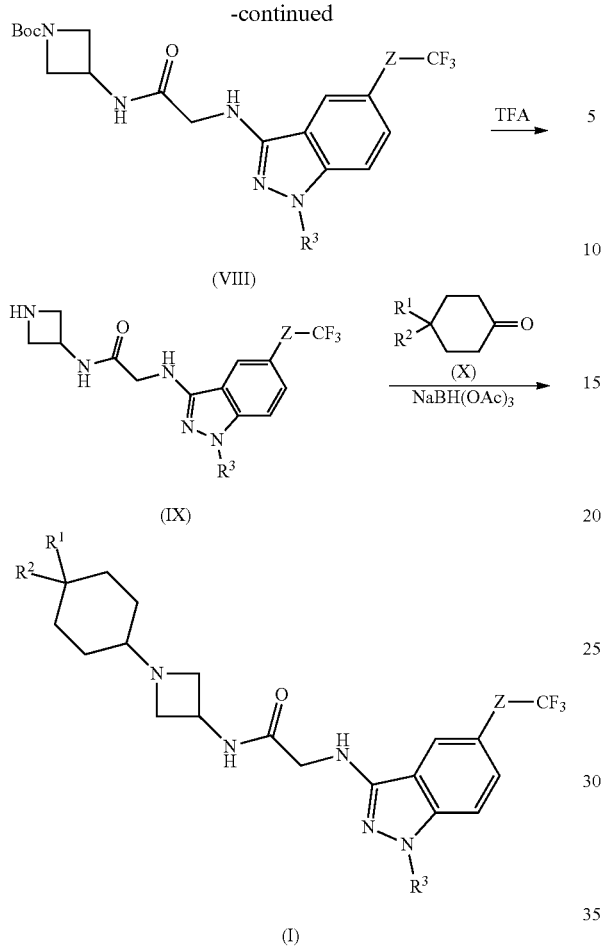

Alternatively, compounds of Formula (IV) may be prepared according to the processes outlined in Scheme 2.

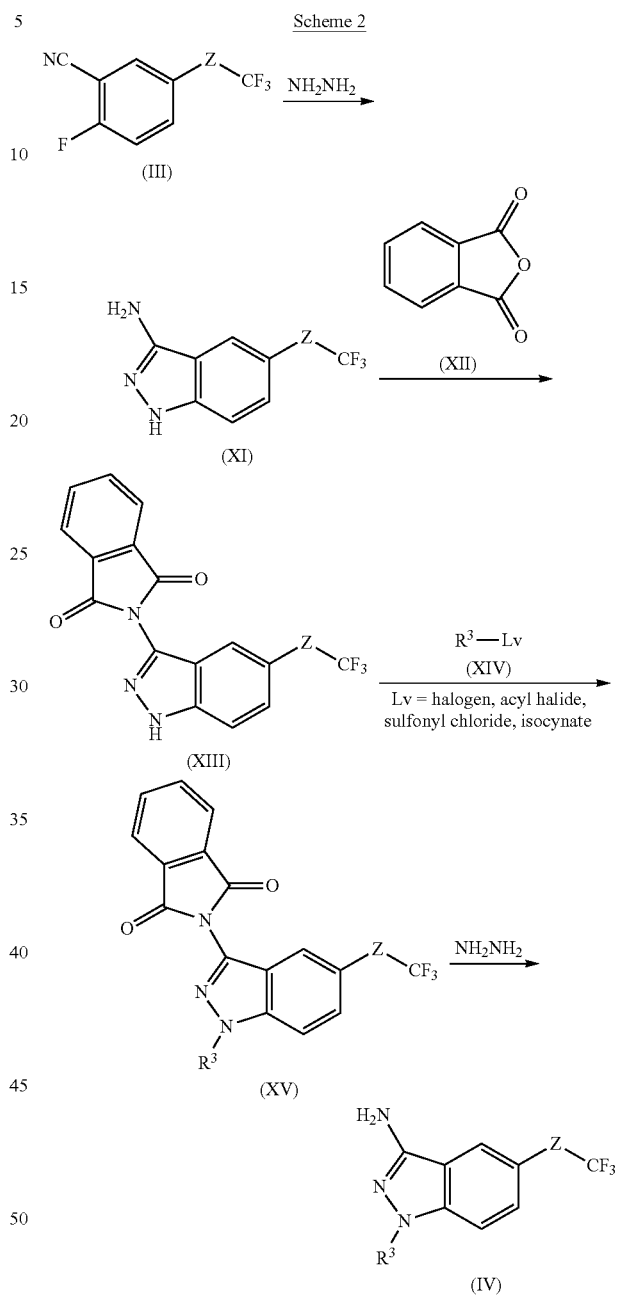

Scheme 1 illustrates a synthetic route leading to compounds of Formula (I). Commercially available hydrazine (II) is reacted with a suitable substituted fluorobenzonitrile (III), in an organic solvent such as IPA, n-BuOH or t-BuOH, at a temperature in the range of about 100° C. to about 150° C., to yield the corresponding amino-indazole (IV).

Amino-indazole (IV) is reacted with glyoxylic acid (V), in the presence of a reducing reagent such as $NaBH_4$, $NaBH_3CN$ or $NaBH(OAc)_3$, in an organic solvent such as MeOH, EtOH or IPA with catalytic amount of acid such as acetic acid, trifluoroacetic acid or formic acid, at a temperature in the range of 25° C. to about 60° C., to yield the corresponding acid (VI).

Acid (VI) is reacted with commercially available amine (VII), in the presence of a coupling reagent such as EDCI/HOBt, PyBrop or DCC, in an organic solvent such as THF, dichloromethane or 1,2-dichloroethane, at a temperature in the range of about 0° C. to about 25° C., to yield the corresponding azetidine (VIII).

Azetidine (VIII) is treated with an acid such as 1N HCl, 1N $H_2SO_4$ or trifluoroacetic acid in an organic solvent such as diethyl ether, THF, dichloromethane or dioxane, at a temperature in the range of about 0° C. to about 25° C. to yield amine (IX).

Amine (IX) is reacted with a suitably substituted ketone (X), in the presence of a reducing reagent such as $NaBH_4$, $NaBH_3CN$ or $NaBH(OAc)_3$, in an organic base such as triethylamine, diethylpropylamine or N-methylmorpholine with or without molecule sieves, in an organic solvent such as dichloromethane, 1,2-dichloroethane or THF, at a temperature in the range of 0° C. to about 25° C., to yield the corresponding azetidine (I).

Commercially available hydrazine is reacted with a suitably substituted fluorobenzonitrile (III), in an organic solvent such as IPA, n-BuOH or t-BuOH, at a temperature in the range of about 100° C. to about 150° C., to yield the corresponding amino-indazole (XI). Amino-indazole (XI) is reacted with commercially available isobenzofuran-1,3-dione (XII), in an organic solvent such as toluene, xylene or chlorobenzene, or without any solvent (neat), at a temperature in the range of 110° C. to about 180° C., to yield the corresponding indazole (XIII). Indazole (XIII) is reacted with a commercially available reagent (XIV), in the presence of an organic base such as TEA, DIPEA or pyridine, in an organic solvent such as DCM, dichloromethane or DMF, at a temperature in the range of about 0° C. to about 25° C., to yield the corresponding indazole (XV).

Indazole (XV) is treated with hydrazine in an organic solvent such as THF, dioxane or dichloromethane, at a temperature in the range of about 0° C. to about 25° C., to yield the corresponding indazole (IV).

Alternatively, compounds of Formula (I) may be prepared according to the processes outlined in Scheme 3.

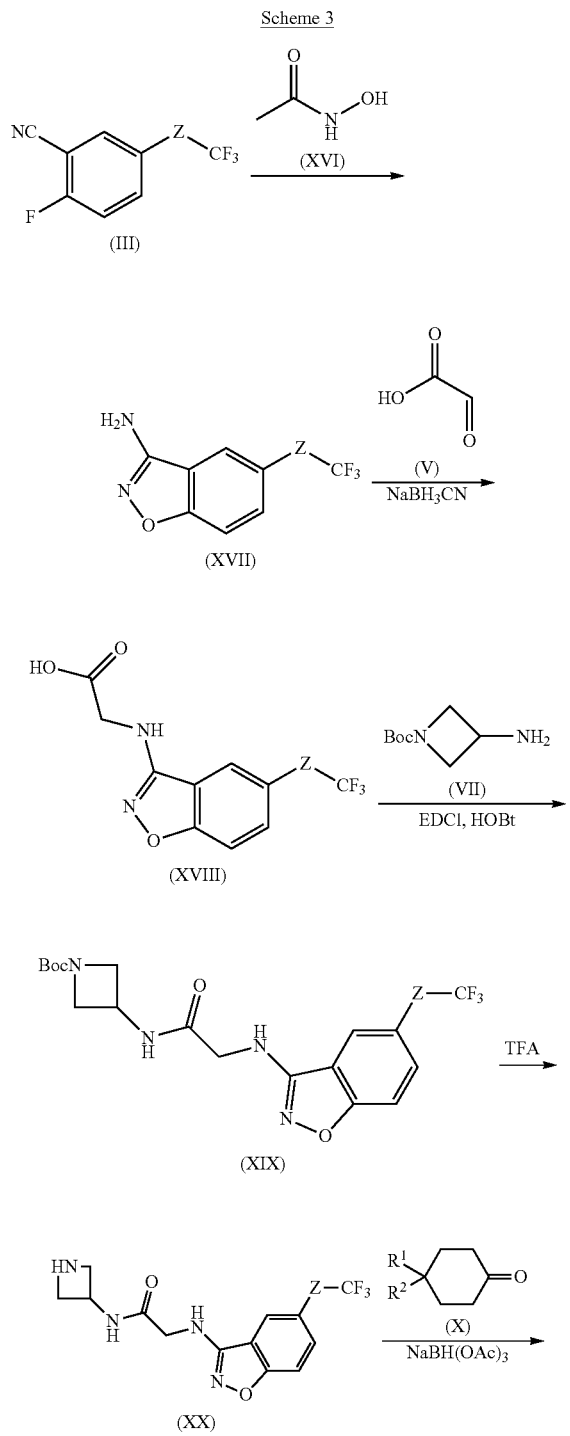

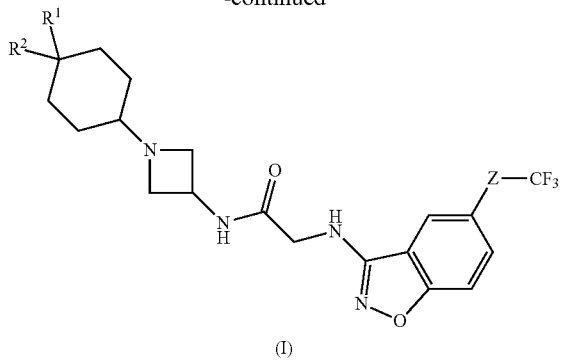

Commercially available N-hydroxy-acetamide (XVI) is reacted with a suitable substituted fluorobenzonitrile (III), in the presence of an organic base such as t-BuOK, t-BuONa or n-BuOK, in an organic solvent such as DMF, DMSO or NMP, at a temperature in the range of about 80° C. to about 120° C., to yield the corresponding amino-benzoisoxazole (XVII). Amino-bezoisoxazole (XVII) is reacted with glyoxylic acid (V), in the presence of a reducing reagent such as $NaBH_4$, $NaBH_3CN$ or $NaBH(OAc)_3$, in an organic solvent such as MeOH, EtOH or IPA with catalytic amount of acid such as acetic acid, trifluoroacetic acid or formic acid, at a temperature in the range of 25° C. to about 60° C., to yield the corresponding acid (XVIII).

Acid (XVIII) is reacted with commercially available amine (VII), in the presence of a coupling reagent such as EDCI/HOBt, PyBrop or DCC, in an organic solvent such as THF, dichloromethane or 1,2-dichloroethane, at a temperature in the range of about 0° C. to about 25° C., to yield the corresponding azetidine (XIX).

Azetidine (XIX) is treated with an acid such as 1N HCl, 1N $H_2SO_4$ or trifluoroacetic acid in an organic solvent such as diethyl ether, THF, dichloromethane or dioxane, at a temperature in the range of about 0° C. to about 25° C. to yield amine (XX).

Amine (XX) is reacted with a suitably substituted ketone (X), in the presence of a reducing reagent such as $NaBH_4$, $NaBH_3CN$ or $NaBH(OAc)_3$, in an organic base such as triethylamine, diethylpropylamine or N-methylmorpholine with or without molecule sieves, in an organic solvent such as dichloromethane, 1,2-dichloroethane or THF, at a temperature in the range of 0° C. to about 25° C., to yield the corresponding azetidine (I).

Compounds of Formula (I) may be derived from ketone (XXI). Preparation of (XXI) is outlined in Scheme 4.

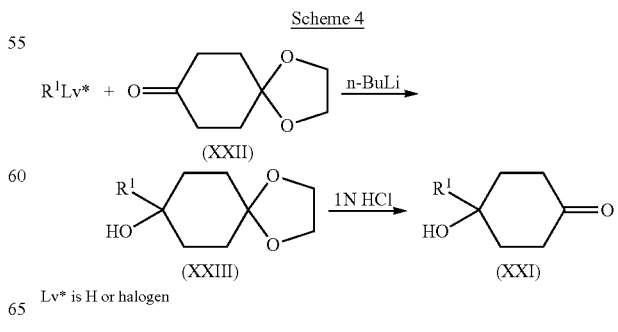

Lv* is H or halogen

Commercially available aryl halide or aryl alkane R¹Lv* (where R¹ is as defined in Formula (I), and Lv* is H or a halogen) is reacted with commercially available ketone (XXII) in the presence of organometalic agent such as n-BuLi, i-PrMgBr or i-PrMgCl, in an organic solvent such as ether, THF or dioxane, at a temperature in the range of about −78° C. to about 0° C., to yield the corresponding ketal (XXIII).

Ketal (XXIII) is treated with an acid such as 1N HCl or 1N $H_2SO_4$ in an organic solvent such as acetone, acetonitrile or THF, at a temperature in the range of about 0° C. to about 25° C., to yield the corresponding ketone (XXI).

Compounds of Formula (I) may be derived from ketone (XXIV). Preparation of (XXIV) is outlined in Scheme 5.

Scheme 5

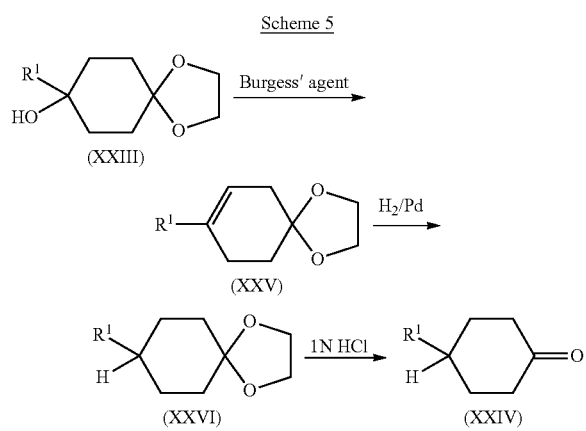

Ketal (XXIII) is treated with a dehydrating agent such as Burgess' reagent, in an organic solvent such as ether, THF or dioxane, at a temperature in the range of about 0° C. to about 25° C., to yield the corresponding alkene (XXV).

Alkene (XXV) is treated with hydrogen gas under pressure from 5 to 50 psi catalyzed by 5-10% Pd/C, in an organic solvent such as methanol, at a temperature in the range of about 25° C. to about 50° C., to yield the corresponding alkane (XXVI).

Alkane (XXVI) is treated with 1N HCl or 1N $H_2SO_4$, in an organic solvent such as acetone, acetonitrile or THF, at a temperature in the range of about 0° C. to about 25° C., to yield the corresponding ketone (XXIV).

Alternatively compound (XXV) may be prepared according to the processes outlined in Scheme 6.

Scheme 6

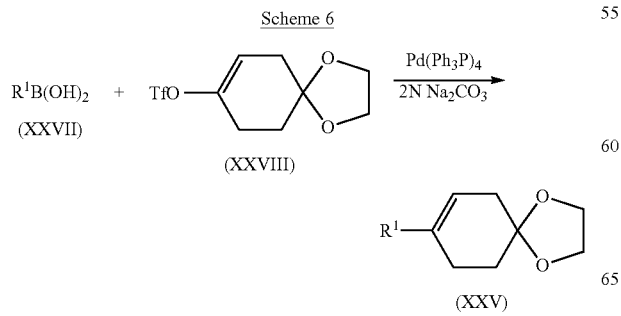

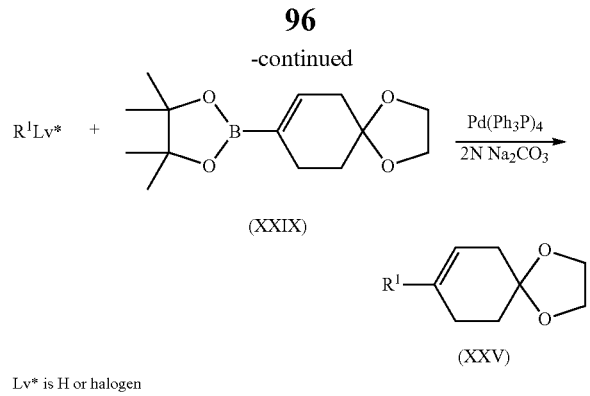

Lv* is H or halogen

Commercially available aryl boronic acid (XXVII), (wherein R¹ is as defined in Formula (I)) is reacted with vinyl triflate (XXIII) prepared according to the procedure of Pearson, W. et. al., *J. Org. Chem.* 2004, 69, 9109-9122, in the presence of a catalyst such as $Pd(Ph_3P)_4$, $PdCl_2(Ph_3P)_2$ or $PdCl_2(dppf)$ and a base such as $2N\ Na_2CO_3$ or $K_2CO_3$, in an organic solvent such as toluene, dioxane or THF, at a temperature in the range of about 80° C. to about 120° C., to yield the corresponding alkene (XXV).

Alternatively, commercially available aryl or heteroaryl halide R¹Lv* is reacted with vinyl boronic ester (XXIX) prepared according to Birch, A. M. et. al., PCT Int. Appl. 2006, WO 2006064189, in the presence of a catalyst such as $Pd(Ph_3P)_4$, $PdCl_2(Ph_3P)_2$ or $PdCl_2(dppf)$ and a base such as $2N\ Na_2CO_3$ or $K_2CO_3$, in an organic solvent such as toluene, dioxane or THF, at a temperature in the range of about 80° C. to about 120° C., to yield the corresponding alkene (XXV).

EXAMPLES

Representative compounds of the present invention can be synthesized in accordance with the general synthetic methods described below. Compounds of Formula (I) can be prepared by methods known to those who are skilled in the art. The following examples are only meant to represent examples of the invention and are in no way meant to be a limit of the invention.

Example 1

N-[1-(4-Benzo[1,3]dioxol-5-yl-cyclohexyl)-azetidin-3-yl]-2-(5-trifluoromethyl-benzo[d]isoxazol-3-ylamino)-acetamide

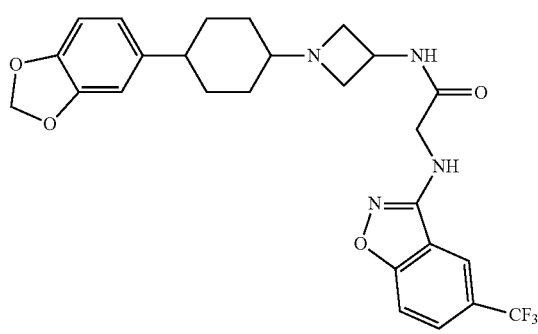 [SMILES: O=C(CNc1noc2ccc(C(F)(F)F)cc12)NC1CN(C2CCC(c3ccc4c(c3)OCO4)CC2)C1]

Step A

5-Trifluoromethyl-benzo[d]isoxazol-3-ylamine

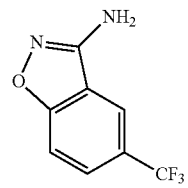

2-Fluoro-5-trifluoro-benzonitrile (Matrix, 5 g, 26.4 mmol), N-hydroxy-acetamide (Aldrich, 2.9 g, 39.7 mmol) and $K_2CO_3$ (5.48 g, 39.7 mmol) in DMF (20 mL) were heated at 80° C. overnight. The reaction was partitioned between ethyl acetate and water. The aqueous layer was extracted two times with ethyl acetate. The combined organic layers were washed with brine, dried over anhydrous $Na_2SO_4$, filtered and concentrated to give the crude material, which was purified by silica gel column (hexanes:ethyl acetate 2:1) to afford the title compound as white solid (4.1 g, 76.7%).

MS: 203 (MH$^+$).

Step B

(5-Trifluoromethyl-benzo[d]isoxazol-3-ylamino)-acetic acid

5-Trifluoromethyl-benzo[d]isoxazol-3-ylamine (2.5 g, 12.4 mmol) and glyoxylic acid monohydrate (Aldrich, 1.14 g, 12.4 mmol) in MeOH (10 mL) were treated with a few drop of AcOH and heated at 80° C. for 30 min. The reaction was then cooled to room temperature and NaBCNH$_3$ (Aldrich, 1.17 g, 18.6 mmol) was added in one portion and the resulting solution was stirred at room temperature for another 2 hours. The solvent was removed and the residue was partitioned between ether and 1 N NaOH. The aqueous layer was then acidified with 1 N HCl to pH=3 and then extracted three times with ethyl acetate. The combined organic layer was washed with brine, dried over anhydrous $Na_2SO_4$, filtered and concentrated to give the title compound as white solid.

MS: 261 (MH$^+$).

Step C

3-[2-(5-Trifluoromethyl-benzo[d]isoxazol-3-ylamino)-acetylamino]-azetidine-1-carboxylic acid tert-butyl ester

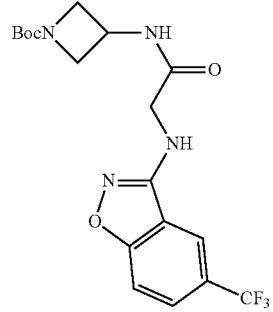 [SMILES: CC(C)(C)OC(=O)N1CC(NC(=O)CNc2noc3ccc(C(F)(F)F)cc23)C1]

(5-Trifluoromethyl-benzo[d]isoxazol-3-ylamino)-acetic acid (2.6 g, 9.99 mmol), 3-amino-azetidine-1-carboxylic acid tert-butyl ester (1.72 g, 9.99 mmol), EDCI (2.3 g, 12.0 mmol), HOBt (1.62 g, 12.0 mmol) in DCM (20 mL) were stirred at room temperature for 4 hours. The reaction was then partitioned between DCM and water. The aqueous layer was extracted two times with DCM. The combined organic layer was washed with brine, dried over anhydrous $Na_2SO_4$, filtered and concentrated to give the crude material, which was purified by silica gel column (hexanes:ethyl acetate 1:1) to afford the title compound as white foam.

MS: 415 (MH$^+$).

Step D

N-Azetidin-3-yl-2-(5-trifluoromethyl-benzo[d]isoxazol-3-ylamino)-acetamide TFA salt

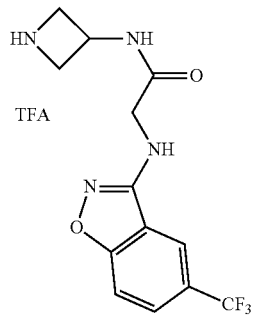

3-[2-(5-Trifluoromethyl-benzo[d]isoxazol-3-ylamino)-acetylamino]-azetidine-1-carboxylic acid tert-butyl ester (500 mg, 1.21 mmol) in DCM (5 mL) and TFA (5 mL) was stirred at room temperature for 1 hour. The solvent was removed and then lyophilized overnight to give the title compound as colorless oil.

MS: 315 (MH$^+$).

Step E

N-[1-(4-Benzo[1,3]dioxol-5-yl-cyclohexyl)-azetidin-3-yl]-2-(5-trifluoromethyl-benzo[d]isoxazol-3-ylamino)-acetamide

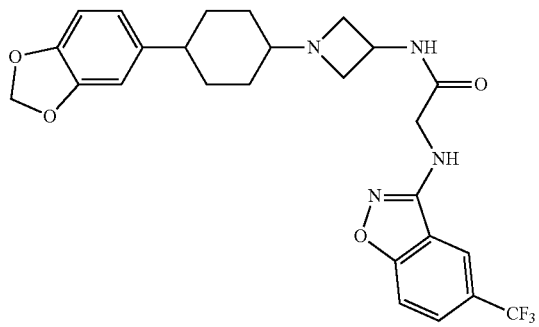 [SMILES: O=C(CNc1noc2ccc(C(F)(F)F)cc12)NC1CN(C2CCC(c3ccc4c(c3)OCO4)CC2)C1]

To a solution of N-azetidin-3-yl-2-(5-trifluoromethyl-benzo[d]isoxazol-3-ylamino)-acetamide (100 mg, 0.318 mmol) and 4-benzo[1,3]dioxol-5-yl-cyclohexanone (69 mg, 0.318 mmol) in DCM (10 mL) was added TEA (55 μL, 0.382 mmol) and the resulting solution was stirred at RT for 30 minutes. Sodium triacetoxyborohydride (81 mg, 0.382 mmol) was then added and the reaction was and stirred at RT overnight. The reaction was dissolved into DCM/IPA (3:1) solution and washed with saturated NaHCO$_3$. The organic layers were dried over anhydrous Na$_2$SO$_4$, concentrated in vacuo and purified by column chromatography using EtOAc (A) and 7N NH$_3$ in MeOH (B) (from 100% A to 10% B in A) to give the above products as white solids. The less polar isomer from the silica gel column was tested in vitro as described in Example 107.

$^1$H NMR (400 MHz, CDCl$_3$) δ: 7.90 (s, 1H), 7.75 (d, J=10.4 Hz, 1H), 7.50 (d, J=8.8 Hz, 1H), 6.60-6.85 (m, 3H), 6.33-6.50 (m, 1H), 5.90 (br. s., 2H), 5.42-5.53 (m, 1H), 5.35 (br. s., 1H), 4.51-4.64 (m, 1H), 4.10 (d, J=5.3 Hz, 2H), 3.53-3.65 (m, 2H), 2.80-2.96 (m, 2H), 2.43 (t, J=11.6 Hz, 1H), 2.32 (br. s., 1H), 2.16-2.26 (m, 1H), 1.95-2.06 (m, 1H), 1.72-1.85 (m, 3H), 1.70 (br. s., 2H), 1.64 (br. s., 3H), 1.42-1.57 (m, 5H), 1.31 (br. s., 3H), 1.25 (br. s., 4H).

Example 2

N-{1-[4-Hydroxy-4-(6-methoxy-pyridin-3-yl)-cyclohexyl]-azetidin-3-yl}-2-(5-trifluoromethyl-benzo[d]isoxazol-3-ylamino)-acetamide

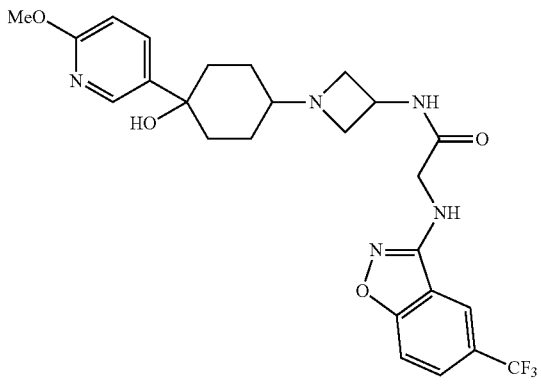 [SMILES: COc1ccc(C2(O)CCC(N3CC(NC(=O)CNc4noc5ccc(C(F)(F)F)cc45)C3)CC2)cn1]

The title compound was prepared as a white solid from reaction of (N-Azetidin-3-yl-2-(5-trifluoromethyl-benzo[d]isoxazol-3-ylamino)-acetamide TFA salt (as prepared in Example 1, Step D) and 4-hydroxy-4-(6-methoxy-pyridin-3-yl)-cyclohexanone, using the procedure described in Step E of Example 1.

The less polar isomer from the silica gel column was tested in vitro as described in Example 107.

$^1$H NMR (400 MHz, d$_4$-MeOH) δ: 8.27 (d, J=2.5 Hz, 1H), 8.21 (s, 1H), 7.77-7.89 (m, 2H), 7.58 (d, J=8.8 Hz, 1H), 6.78 (d, J=8.6 Hz, 1H), 4.51 (t, J=7.1 Hz, 1H), 4.11 (q, J=7.2 Hz, 2H), 4.03 (s, 2H), 3.90 (s, 3H), 3.67 (t, J=7.7 Hz, 2H), 3.26-3.37 (m, 3H), 2.99 (t, J=7.7 Hz, 2H), 2.33-2.43 (m, 1H), 2.20 (t, J=10.1 Hz, 2H), 1.81-1.93 (m, 2H), 1.56 (d, J=14.1 Hz, 2H), 1.33-1.46 (m, 2H)

Example 3

N-[1-(4-Hydroxy-4-thiazol-5-yl-cyclohexyl)-azetidin-3-yl]-2-(5-trifluoromethyl-benzo[d]isoxazol-3-ylamino)-acetamide

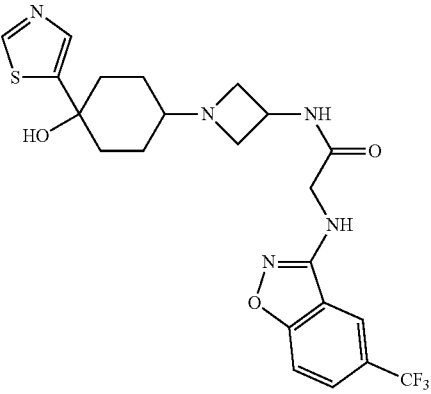 [SMILES: O=C(CNc1noc2ccc(C(F)(F)F)cc12)NC1CN(C2CCC(O)(c3cncs3)CC2)C1]

The title compound was prepared as a white solid from reaction of (N-Azetidin-3-yl-2-(5-trifluoromethyl-benzo[d]isoxazol-3-ylamino)-acetamide TFA salt (as prepared in Example 1, Step D) and 4-hydroxy-4-thiazol-5-yl-cyclohexanone using the procedure described in Step E of Example 1.

The less polar isomer from the silica gel column was tested in vitro as described in Example 107.

$^1$H NMR (400 MHz, d$_4$-MeOH) δ: 8.75 (s, 1H), 7.95 (s, 1H), 7.80 (s, 1H), 7.75 (d, J=6.5 Hz, 1H), 7.48 (d, J=6.8 Hz, 1H), 4.55 (m, 1H), 4.11 (s, 2H), 3.60 (t, J=7.7 Hz, 2H), 3.12 (t, J=7.5 Hz, 2H), 2.34 (br. s., 1H), 1.85 (m, 4H), 1.70 (m, 2H), 1.55 (m, 2H).

Example 4

N-[1-(4-Hydroxy-4-thiazol-2-yl-cyclohexyl)-azetidin-3-yl]-2-(5-trifluoromethyl-benzo[d]isoxazol-3-ylamino)-acetamide

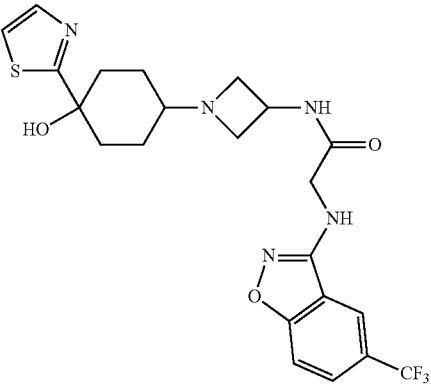 [SMILES: O=C(CNc1noc2ccc(C(F)(F)F)cc12)NC1CN(C2CCC(O)(c3nccs3)CC2)C1]

The title compound was prepared as a white solid from reaction of (N-Azetidin-3-yl-2-(5-trifluoromethyl-benzo[d]isoxazol-3-ylamino)-acetamide TFA salt (as prepared in Example 1, Step D) and 4-hydroxy-4-thiazol-2-yl-cyclohexanone using the procedure described in Step E of Example 1.

The less polar isomer from the silica gel column was tested in vitro as described in Example 107.

¹H NMR (400 MHz, d₄-MeOH) δ: 8.20 (s, 1H), 7.85 (d, J=7.0 Hz, 1H), 7.70 (d, J=3.0 Hz, 1H), 7.60 (d, J=6.5 Hz, 1H), 7.50 (d, J=2.5 Hz, 1H), 4.48 (m, 1H), 4.05 (s, 2H), 3.65 (t, J=7.7 Hz, 2H), 3.00 (t, J=7.5 Hz, 2H), 2.40 (m, 3H), 1.85 (m, 4H), 1.65 (m, 2H), 1.50 (m, 2H).

Example 5

N-(1-Bicyclohexyl-4-yl-azetidin-3-yl)-2-(5-trifluoromethyl-benzo[d]isoxazol-3-ylamino)-acetamide

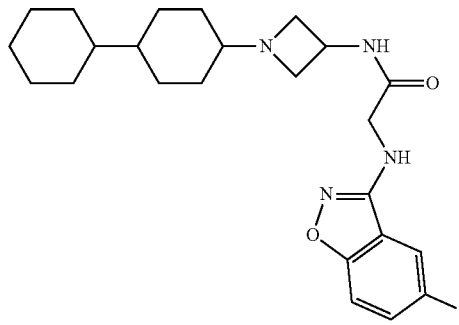

The title compound was prepared as a white solid from reaction of (N-Azetidin-3-yl-2-(5-trifluoromethyl-benzo[d]isoxazol-3-ylamino)-acetamide TFA salt (as prepared in Example 1, Step D) and bicyclohexyl-4-one using the procedure described in Step E of Example 1.

The less polar isomer from the silica gel column was tested in vitro as described in Example 107.

¹H NMR (400 MHz, d₄-MeOH) δ: 8.23 (s, 1H), 7.85 (dd, J=8.8, 1.5 Hz, 1H), 7.61 (d, J=8.8 Hz, 1H), 4.49 (t, J=7.1 Hz, 1H), 4.02 (s, 2H), 3.58-3.72 (m, 3H), 2.92-3.06 (m, 2H), 1.84 (d, J=10.9 Hz, 3H), 1.59-1.79 (m, 10H), 1.16-1.30 (m, 5H), 0.91-1.06 (m, 9H)

Example 6

4-{3-[2-(5-Trifluoromethyl-benzo[d]isoxazol-3-ylamino)-acetylamino]-azetidin-1-yl}-cyclohexanecarboxylic acid ethyl ester

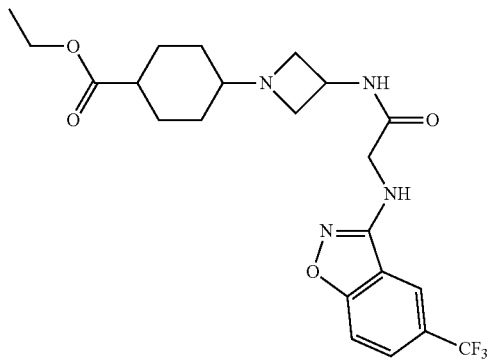 [SMILES: CCOC(=O)C1CCC(N2CC(NC(=O)CNc3noc4ccc(C(F)(F)F)cc34)C2)CC1]

The title compound was prepared as a white solid from reaction of (N-Azetidin-3-yl-2-(5-trifluoromethyl-benzo[d]isoxazol-3-ylamino)-acetamide TFA salt (as prepared in Example 1, Step D) and 4-oxo-cyclohexanecarboxylic acid ethyl ester using the procedure described in Step E of Example 1.

The less polar isomer from the silica gel column was tested in vitro as described in Example 107.

¹H NMR (400 MHz, d₄-MeOH) δ: 8.22 (s, 1H), 7.85 (d, J=10.4 Hz, 1H), 7.60 (d, J=8.6 Hz, 1H), 4.48 (quin, J=7.0 Hz, 1H), 4.13 (q, J=7.1 Hz, 2H), 3.63 (t, J=7.8 Hz, 2H), 2.99 (t, J=7.6 Hz, 2H), 2.51 (t, J=4.9 Hz, 1H), 2.14-2.27 (m, 1H), 1.97-2.11 (m, 2H), 1.46-1.67 (m, 5H), 1.20-1.38 (m, 6H).

Example 7

N-[1-(4-Isopropyl-cyclohexyl)-azetidin-3-yl]-2-(5-trifluoromethyl-benzo[d]isoxazol-3-ylamino)-acetamide

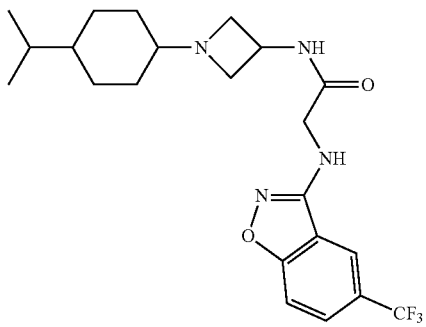 [SMILES: CC(C)C1CCC(N2CC(NC(=O)CNc3noc4ccc(C(F)(F)F)cc34)C2)CC1]

The title compound was prepared as a white solid from reaction of (N-Azetidin-3-yl-2-(5-trifluoromethyl-benzo[d]isoxazol-3-ylamino)-acetamide TFA salt (as prepared in Example 1, Step D) and 4-isopropyl-cyclohexanone using the procedure described in Step E of Example 1.

The less polar isomer from the silica gel column was tested in vitro as described in Example 107.

¹H NMR (400 MHz, d₄-MeOH) δ: 8.23 (s, 1H), 7.85 (d, J=10.6 Hz, 1H), 7.61 (d, J=8.8 Hz, 1H), 4.50 (s, 1H), 4.02 (s, 2H), 3.53-3.76 (m, 2H), 3.34 (s, 22H), 2.92 (s, 2H), 2.26 (br. s., 1H), 1.49 (br. s., 6H), 1.42 (br. s., 4H), 1.36 (s, 3H), 1.09 (br. s., 2H), 0.88 (s, 8H)

Example 8

N-{1-[4-(tert-Butyl-dimethyl-silanyloxy)-cyclohexyl]-azetidin-3-yl}-2-(5-trifluoromethyl-benzo[d]isoxazol-3-ylamino)-acetamide

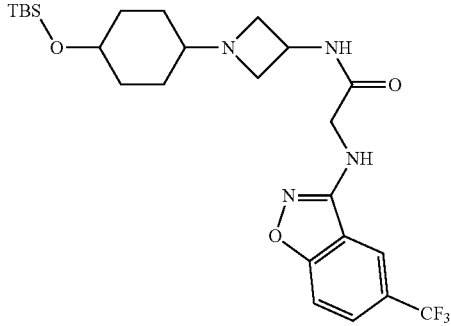

The title compound was prepared as a white solid from reaction of (N-azetidin-3-yl-2-(5-trifluoromethyl-benzo[d]isoxazol-3-ylamino)-acetamide TFA salt (as prepared in Example 1, Step D) and 4-(tert-butyl-dimethyl-silanyloxy)-cyclohexanone using the procedure described in Step E of Example 1.

The less polar isomer from the silica gel column was tested in vitro as described in Example 107.

$^1$H NMR (400 MHz, d$_4$-MeOH) δ: 7.87 (s, 1H), 7.69 (dd, J=1.4, 8.7 Hz, 1H), 7.43 (d, J=8.8 Hz, 1H), 6.82 (d, J=7.6 Hz, 1H), 5.91 (t, J=5.3 Hz, 1H), 4.54 (d, J=7.1 Hz, 1H), 4.08 (d, J=5.6 Hz, 2H), 3.71-3.91 (m, 1H), 3.57 (t, J=7.5 Hz, 2H), 2.99 (dd, J=5.4, 8.0 Hz, 2H), 1.96 (td, J=4.0, 8.3 Hz, 3H), 1.66 (dd, J=4.5, 9.3 Hz, 2H), 1.20-1.50 (m, 7H), 0.68-0.92 (m, 10H), -0.13-0.14 (m, 7H).

Example 9

N-[1-(4-Hydroxy-cyclohexyl)-azetidin-3-yl]-2-(5-trifluoromethyl-benzo[d]isoxazol-3-ylamino)-acetamide

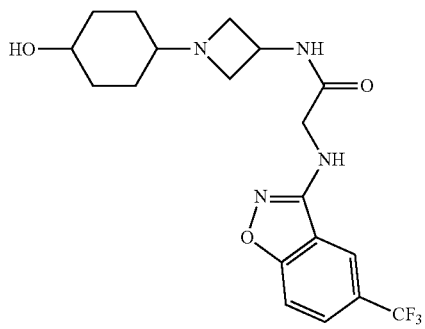 [SMILES: O=C(CNc1noc2ccc(C(F)(F)F)cc12)NC1CN(C2CCC(O)CC2)C1]

To a solution of N-{1-[4-(tert-butyl-dimethyl-silanyloxy)-cyclohexyl]-azetidin-3-yl}-2-(5-trifluoro-methyl-benzo[d]isoxazol-3-ylamino)-acetamide (as prepared in Example 8, 20 mg, 0.033 mmol) in THF (2 mL) was added 1 N HCl (200 L) and stirred at RT for 1.5 hours. The reaction was quenched with 1 N NaOH to pH=10 and then extracted with EtOAc and dried over anhydrous Na$_2$SO$_4$, filtered and concentrated to give the title product.

The less polar isomer from the silica gel column was tested in vitro as described in Example 107.

$^1$H NMR (400 MHz, MeOH) δ: 7.63-7.70 (m, 2H), 7.57 (dd, J=3.4, 5.7 Hz, 2H), 7.46 (s, 1H), 5.61 (dd, J=2.0, 6.1 Hz, 1H), 5.54 (dd, J=2.0, 6.1 Hz, 1H), 5.40 (dd, J=2.0, 5.8 Hz, 1H), 4.30 (t, J=7.1 Hz, 1H), 4.12-4.21 (m, 5H), 3.77-3.89 (m, 8H), 2.43 (d, J=8.3 Hz, 1H), 1.93-2.04 (m, 4H), 1.83-1.92 (m, 5H), 1.73-1.82 (m, 7H), 1.18-1.43 (m, 21H), 0.80-0.98 (m, 17H)

Example 10

(4-{3-[2-(5-Trifluoromethyl-benzo[d]isoxazol-3-ylamino)-acetylamino]-azetidin-1-yl}-cyclohexyl)-carbamic acid tert-butyl ester

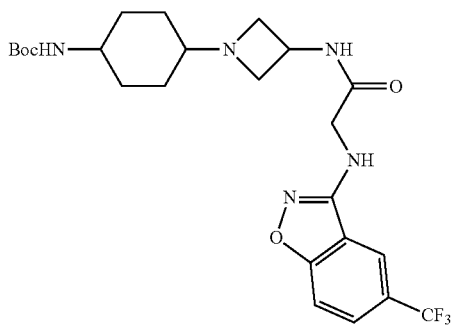 [SMILES: CC(C)(C)OC(=O)NC1CCC(N2CC(NC(=O)CNc3noc4ccc(C(F)(F)F)cc34)C2)CC1]

The title compound was prepared as a white solid from reaction of (N-Azetidin-3-yl-2-(5-trifluoromethyl-benzo[d]isoxazol-3-ylamino)-acetamide TFA salt (as prepared in Example 1, Step D) and (4-oxo-cyclohexyl)-carbamic acid tert-butyl ester using the procedure described in Step E of Example 1.

The less polar isomer from the silica gel column was tested in vitro as described in Example 107.

$^1$H NMR (400 MHz, CDCl$_3$) δ: 7.89 (s, 1H), 7.65-7.77 (m, 1H), 7.46 (d, J=8.8 Hz, 1H), 6.85 (d, J=7.3 Hz, 1H), 5.88 (t, J=5.3 Hz, 1H), 4.47-4.60 (m, 1H), 4.38 (d, J=7.8 Hz, 1H), 4.00-4.17 (m, 3H), 3.59 (t, J=7.5 Hz, 3H), 3.02 (dd, J=5.4, 8.0 Hz, 2H), 1.91-2.03 (m, 5H), 1.70-1.82 (m, 3H), 1.40-1.49 (m, 14H), 1.03-1.14 (m, 5H).

Example 11

N-[1-(4-Amino-cyclohexyl)-azetidin-3-yl]-2-(5-trifluoromethyl-benzo[d]isoxazol-3-ylamino)-acetamide TFA salt

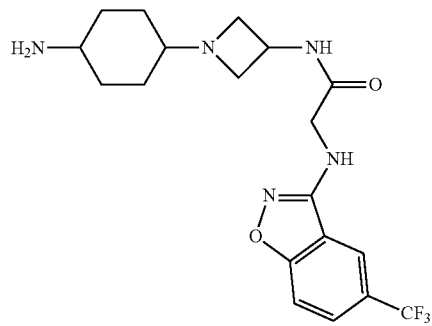 [SMILES: NC1CCC(N2CC(NC(=O)CNc3noc4ccc(C(F)(F)F)cc34)C2)CC1]

(4-{3-[2-(5-Trifluoromethyl-benzo[d]isoxazol-3-ylamino)-acetylamino]-azetidin-1-yl}-cyclohexyl)-carbamic acid tert-butyl ester (as prepared in Example 10, 50 mg) was treated with TFA (100 μL) in DCM (2 L) at room temperature for 1 hour. Solvent was removed to give the product as TFA salt.

$^1$H NMR (400 MHz, d$_4$-MeOH) δ: 8.21 (s, 1H), 7.86 (dd, J=1.5, 8.6 Hz, 1H), 7.60 (d, J=8.6 Hz, 1H), 4.36 (s, 4H), 4.05 (s, 2H), 3.05-3.17 (m, 1H), 2.16 (d, J=9.6 Hz, 4H), 1.45 (br. s., 3H), 1.28 (s, 4H).

Example 12

N-[1-(4-Ethyl-cyclohexyl)-azetidin-3-yl]-2-(5-trifluoromethyl-benzo[d]isoxazol-3-ylamino)-acetamide

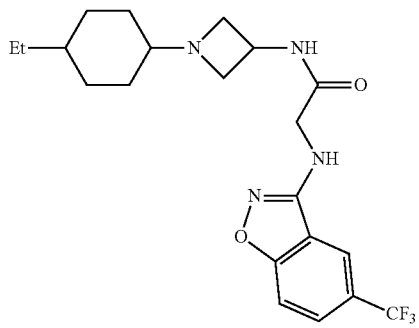 [SMILES: CCC1CCC(N2CC(NC(=O)CNc3noc4ccc(C(F)(F)F)cc34)C2)CC1]

The title compound was prepared as a white solid from reaction of (N-Azetidin-3-yl-2-(5-trifluoromethyl-benzo[d]isoxazol-3-ylamino)-acetamide TFA salt (as prepared in Example 1, Step D) and 4-ethyl-cyclohexanone using the procedure described in Step E of Example 1.

The less polar isomer from the silica gel column was tested in vitro as described in Example 107.

$^1$H NMR (400 MHz, d$_4$-MeOH) δ: 8.22 (s, 1H), 7.78-7.92 (m, 1H), 7.60 (d, J=8.8 Hz, 1H), 4.50 (t, J=7.1 Hz, 1H), 3.64 (t, J=7.7 Hz, 2H), 2.96 (t, J=7.7 Hz, 2H), 2.22 (br. s., 1H), 1.40-1.50 (m, 7H), 1.22-1.37 (m, 4H), 0.89 (t, J=7.2 Hz, 4H).

Example 13

N-[1-(4-Cyano-cyclohexyl)-azetidin-3-yl]-2-(5-trifluoromethyl-benzo[d]isoxazol-3-ylamino)-acetamide

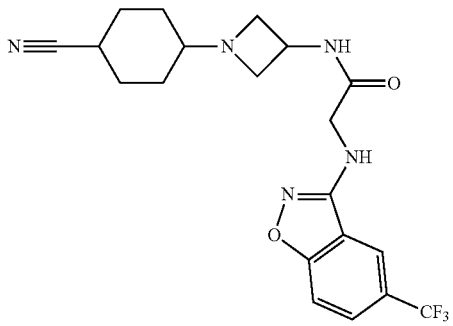 [SMILES: N#CC1CCC(N2CC(NC(=O)CNc3noc4ccc(C(F)(F)F)cc34)C2)CC1]

The title compound was prepared as a white solid from reaction of (N-Azetidin-3-yl-2-(5-trifluoromethyl-benzo[d]isoxazol-3-ylamino)-acetamide TFA salt (as prepared in Example 1, Step D) and 4-cyano-cyclohexanone using the procedure described in Step E of Example 1.

The less polar isomer from the silica gel column was tested in vitro as described in Example 107.

LC-MS: 422 (MH$^+$).

Example 14

N-[1-(4-Propyl-cyclohexyl)-azetidin-3-yl]-2-(5-trifluoromethyl-benzo[d]isoxazol-3-ylamino)-acetamide

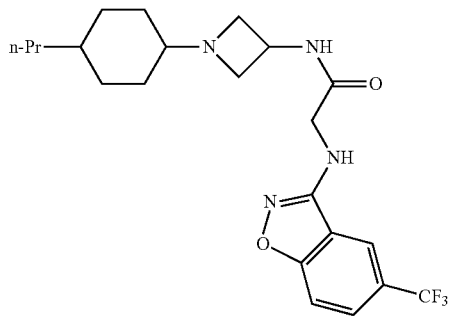

The title compound was prepared as a white solid from reaction of (N-Azetidin-3-yl-2-(5-trifluoromethyl-benzo[d]isoxazol-3-ylamino)-acetamide TFA salt (as prepared in Example 1, Step D) and 4-n-propyl-cyclohexanone using the procedure described in Step E of Example 1.

LC-MS: 439 (MH$^+$).

Example 15

N-[1-(4-Benzo[1,3]dioxol-5-yl-cyclohexyl)-azetidin-3-yl]-2-(5-trifluoromethoxy-benzo[d]isoxazol-3-ylamino)-acetamide

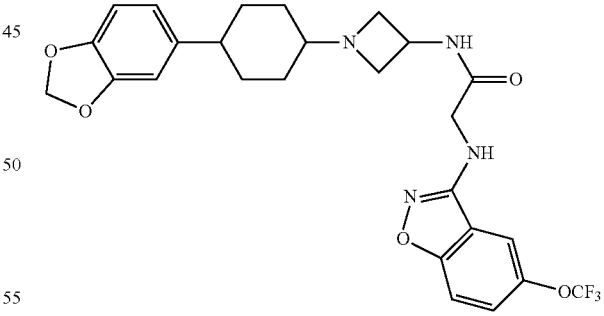

The title compound was prepared as a white solid from reaction of N-azetidin-3-yl-2-(5-trifluoromethoxy-benzo[d]isoxazol-3-ylamino)-acetamide TFA salt (as prepared in Example 1, Step D) and 4-benzo[1,3]dioxol-5-yl-cyclohexanone using the procedure described in Step E of Example 1.

The less polar isomer from the silica gel column was tested in vitro as described in Example 107.

$^1$H NMR (400 MHz, d$_4$-MeOH) δ: 7.80 (s, 1H), 7.51 (s, 2H), 6.82 (s, 1H), 6.72 (s, 2H), 5.89 (s, 2H), 4.61 (d, J=7.6 Hz,

1H), 4.05-4.14 (m, 3H), 4.04 (s, 2H), 3.54-3.68 (m, 2H), 2.98 (br. s., 1H), 2.00-2.06 (m, 1H), 1.97 (s, 3H), 1.76-1.89 (m, 3H), 1.57-1.76 (m, 6H).

Example 16

4-{3-[2-(5-Trifluoromethoxy-benzo[d]isoxazol-3-ylamino)-acetylamino]-azetidin-1-yl}-cyclohexanecarboxylic acid ethyl ester

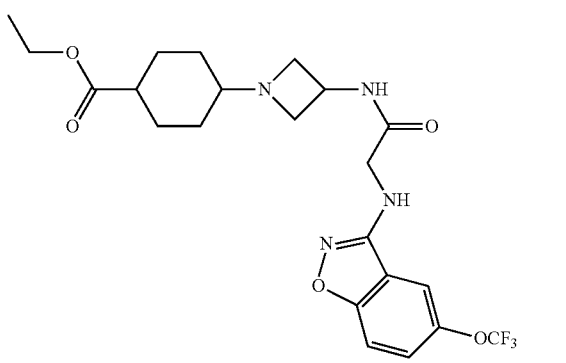 [SMILES: CCOC(=O)C1CCC(N2CC(NC(=O)CNc3noc4ccc(OC(F)(F)F)cc34)C2)CC1]

The title compound was prepared as a white solid from reaction of N-azetidin-3-yl-2-(5-trifluoromethoxy-benzo[d]isoxazol-3-ylamino)-acetamide TFA salt (as prepared in Example 1, Step D) and 4-oxo-cyclohexane carboxylic acid ethyl ester using the procedure described in Step E of Example 1.

MS: 485 (MH+).

Example 17

N-[1-(4-Isopropyl-cyclohexyl)-azetidin-3-yl]-2-(5-trifluoromethoxy-benzo[d]isoxazol-3-ylamino)-acetamide

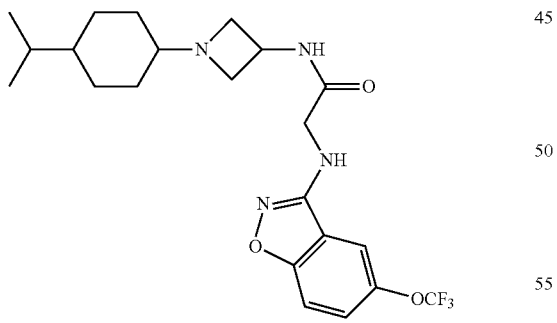

The title compound was prepared as a white solid from reaction of N-azetidin-3-yl-2-(5-trifluoromethoxy-benzo[d]isoxazol-3-ylamino)-acetamide TFA salt (as prepared in Example 1, Step D) and 4-isopropyl-cyclohexanone using the procedure described in Step E of Example 1.

The less polar isomer from the silica gel column was tested in vitro as described in Example 107.

¹H NMR (400 MHz, d₄-MeOH) δ: 7.78 (s, 1H), 7.49 (s, 2H), 4.50 (t, J=7.2 Hz, 1H), 3.57-3.71 (m, 2H), 2.94 (dd, J=7.1, 8.3 Hz, 2H), 2.26 (t, J=3.8 Hz, 1H), 1.29-1.58 (m, 10H), 1.01-1.15 (m, 1H), 0.88 (d, J=6.6 Hz, 7H).

Example 18

N-{-[4-Hydroxy-4-(6-methoxy-pyridin-3-yl)-cyclohexyl]-azetidin-3-yl}-2-(1-methyl-5-trifluoromethyl-1H-indazol-3-ylamino)-acetamide

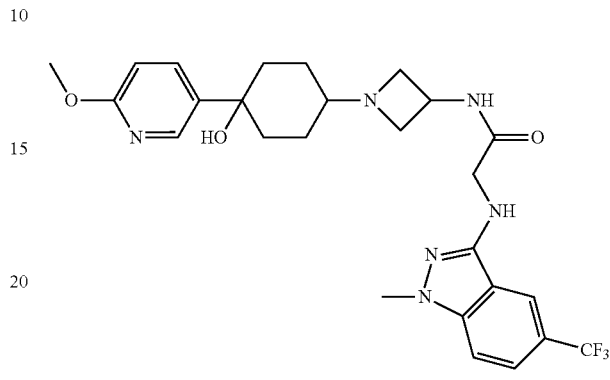

Step A

1-Methyl-5-trifluoromethyl-1H-indazol-3-ylamine

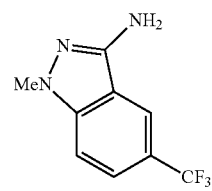 [SMILES: Cn1nc(N)c2cc(C(F)(F)F)ccc21]

2-Fluoro-5-trifluoromethyl-benzonitrile (Matrix, 6.5 g, 34.4 mmol) and methylhydrazine (Aldrich, 2.72 mL, 51.6 mmol) in IPA (10 mL) were heated to reflux for 2 hours. The solvent was removed to afford the title compound as white solid.

MS: 216 (MH+).

Step B (1-Methyl-5-trifluoromethyl-1H-indazol-3-ylamino)-acetic acid

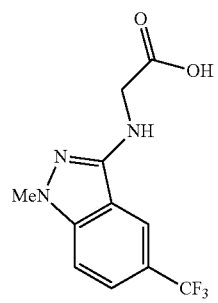 [SMILES: Cn1nc(NCC(=O)O)c2cc(C(F)(F)F)ccc21]

The title compound was prepared as white solid from reductive amination of 1-methyl-5-trifluoromethyl-1H-indazol-3-ylamine (as prepared in the previous step) and glyoxylic acid using the procedure described in Step B of Example 1.

¹H NMR (400 MHz, CDCl₃) δ: 8.10 (s, 1H), 7.55 (d, J=6.1 Hz, 1H), 7.42 (d, J=7.0 Hz, 1H), 4.15 (d, J=2.0 Hz, 2H), 3.85 (s, 3H).

Step C

3-[2-(1-Methyl-5-trifluoromethyl-1H-indazol-3-ylamino)-acetylamino]-azetidine-1-carboxylic acid tert-butyl ester

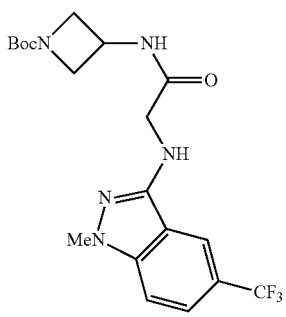 [SMILES: Cn1nc(NCC(=O)NC2CN(C(=O)OC(C)(C)C)C2)c2cc(C(F)(F)F)ccc21]

The title compound was prepared as white foam from EDCI coupling of (1-methyl-5-trifluoromethyl-1H-indazol-3-ylamino)-acetic acid (as prepared in the previous step) and 3-amino-azetidine-1-carboxylic acid tert-butyl ester using the procedure described in Step C of Example 1.

¹H NMR (400 MHz, d₄-MeOH) δ: 7.95 (s, 1H), 7.41 (d, J=6.5 Hz, 1H), 7.28 (d, J=6.5 Hz, 1H), 4.42 (m, 1H), 4.05 (t, J=6.0 Hz, 2H), 3.92 (t, J=6.0 Hz, 2H), 3.89 (s, 2H), 3.68 (s, 3H), 1.28 (s, 9H).

Step D

N-Azetidin-3-yl-2-(1-methyl-5-trifluoromethyl-1H-indazol-3-ylamino)-acetamide TFA salt

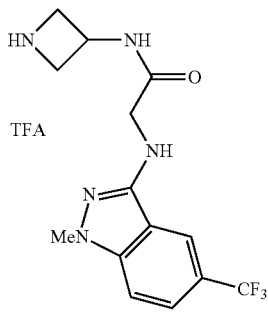 [SMILES: Cn1nc(NCC(=O)NC2CNC2)c2cc(C(F)(F)F)ccc21]

The title compound was prepared as colorless oil from TFA treatment of 3-[2-(1-Methyl-5-trifluoromethyl-1H-indazol-3-ylamino)-acetylamino]-azetidine-1-carboxylic acid tert-butyl ester using the procedure described in Step D of Example 1.

MS: 328 (MH⁺).

Step E

N-{1-[4-Hydroxy-4-(6-methoxy-pyridin-3-yl)-cyclohexyl]-azetidin-3-yl}-2-(1-methyl-5-trifluoromethyl-1H-indazol-3-ylamino)-acetamide

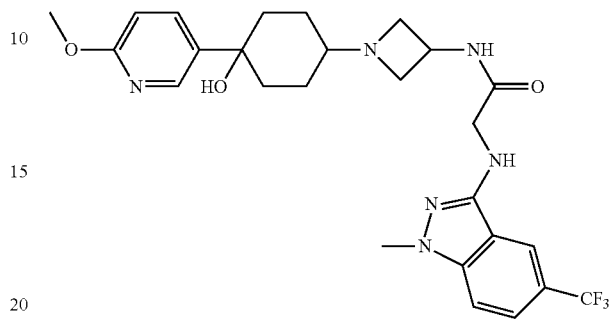

The title compound was prepared as a white solid from reaction of N-azetidin-3-yl-2-(1-methyl-5-trifluoromethyl-1H-indazol-3-ylamino)-acetamide TFA salt (as prepared in the previous step) and 4-hydroxy-4-(6-methoxy-pyridin-3-yl)-cyclohexanone using the procedure described in Step E of Example 1.

The less polar isomer from the silica gel column was tested in vitro as described in Example 107.

¹H NMR (400 MHz, d₄-MeOH) δ: 8.11 (d, J=2.5 Hz, 1H), 7.95 (s, 1H), 7.69 (dd, J=8.7, 2.7 Hz, 1H), 7.36-7.46 (m, 1H), 7.29 (d, J=8.8 Hz, 1H), 6.62 (d, J=8.6 Hz, 1H), 4.36 (quin, J=6.9 Hz, 1H), 3.86 (s, 2H), 3.70 (s, 3H), 3.50 (t, J=7.7 Hz, 2H), 3.21 (s, 1H), 2.83 (t, J=7.6 Hz, 2H), 2.16-2.28 (m, 1H), 1.97-2.09 (m, 2H), 1.69 (d, J=6.3 Hz, 2H), 1.39 (d, J=10.1 Hz, 2H), 1.22 (br. s., 2H).

Example 19

N-[1-(4-Hydroxy-4-pyridin-3-yl-cyclohexyl)-azetidin-3-yl]-2-(1-methyl-5-trifluoromethyl-1H-indazol-3-ylamino)-acetamide

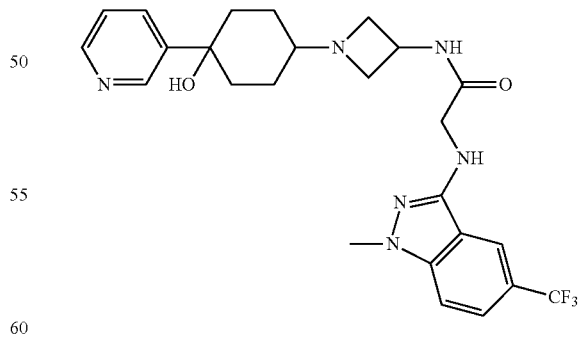

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-hydroxy-4-pyridin-3-yl-cyclohexanone using the procedure described in Step E of Example 1.

The less polar isomer from the silica gel column was tested in vitro as described in Example 107.

$^1$H NMR (400 MHz, d$_4$-MeOH) δ: 8.75 (s, 1H), 8.38 (s, 1H), 8.15 (s, 1H), 8.02 (d, J=6.5 Hz, 1H), 7.60 (d, J=6.0 Hz, 1H), 7.45 (m, 1H), 7.40 (m, 1H), 4.55 (m, 1H), 4.05 (s, 2H), 3.85 (s, 3H), 3.68 (t, J=7.0 Hz, 2H), 3.05 (t, J=7.0 Hz, 2H), 2.50 (m, 1H), 2.18 (m, 2H), 1.95 (m, 2H), 1.60 (m, 2H), 1.45 (m, 2H).

Example 20

N-{1-[4-(3-Dimethylamino-phenyl)-4-hydroxy-cyclohexyl]-azetidin-3-yl}-2-(1-methyl-5-trifluoromethyl-1H-indazol-3-ylamino)-acetamide

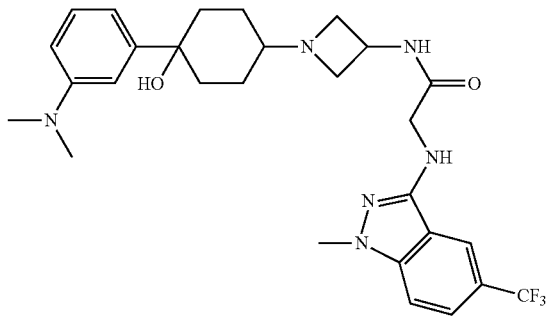 [SMILES: CN(C)c1cccc(C2(O)CCC(N3CC(NC(=O)CNc4nn(C)c5ccc(C(F)(F)F)cc45)C3)CC2)c1]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-(3-dimethylamino-phenyl)-4-hydroxy-cyclohexanone using the procedure described in Step E of Example 1.

The less polar isomer from the silica gel column was tested in vitro as described in Example 107.

$^1$H NMR (400 MHz, d$_4$-MeOH) δ: 7.96 (s, 1H), 7.42 (d, J=8.8 Hz, 1H), 7.29 (d, J=8.8 Hz, 1H), 7.00 (t, J=8.0 Hz, 1H), 6.85 (d, J=4.0 Hz, 1H), 6.74 (d, J=8.3 Hz, 1H), 6.52 (d, J=10.1 Hz, 1H), 4.37 (t, J=7.1 Hz, 1H), 3.94 (dq, J=13.6, 6.8 Hz, 1H), 3.85 (s, 2H), 3.69 (s, 3H), 3.51 (t, J=7.7 Hz, 2H), 2.85 (t, J=7.7 Hz, 2H), 2.23 (t, J=3.5 Hz, 1H), 2.01-2.16 (m, 2H), 1.88 (br. s., 1H), 1.79 (s, 4H), 1.57-1.76 (m, 2H), 1.32-1.43 (m, 2H), 1.17-1.28 (m, 2H).

Example 21

N-[1-(4-Hydroxy-4-thiazol-5-yl-cyclohexyl)-azetidin-3-yl]-2-(1-methyl-5-trifluoromethyl-1H-indazol-3-ylamino)-acetamide

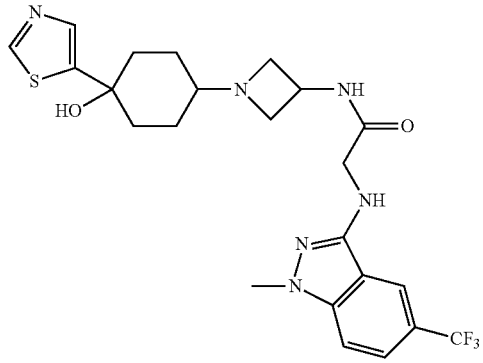 [SMILES: Cn1nc(NCC(=O)NC2CN(C3CCC(O)(c4cncs4)CC3)C2)c2cc(C(F)(F)F)ccc21]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-hydroxy-4-thiazol-5-yl-cyclohexanone using the procedure described in Step E of Example 1.

The less polar isomer from the silica gel column was tested in vitro as described in Example 107.

$^1$H NMR (400 MHz, d$_4$-MeOH) δ: 8.90 (s, 1H), 8.11 (s, 1H), 7.85 (s, 1H), 7.60 (d, J=6.5 Hz, 1H), 7.45 (d, J=6.5 Hz, 1H), 4.51 (m, 1H), 4.05 (s, 2H), 3.90 (s, 3H), 3.62 (t, J=6.0 Hz, 2H), 3.15 (m, 1H), 3.05 (t, J=6.0 Hz, 2H), 2.40 (m, 1H), 2.30 (m, 2H), 1.92 (m, 2H), 1.75 (m, 2H), 1.38 (m, 2H).

Example 22

N-[1-(4-Hydroxy-4-thiazol-2-yl-cyclohexyl)-azetidin-3-yl]-2-(1-methyl-5-trifluoromethyl-1H-indazol-3-ylamino)-acetamide

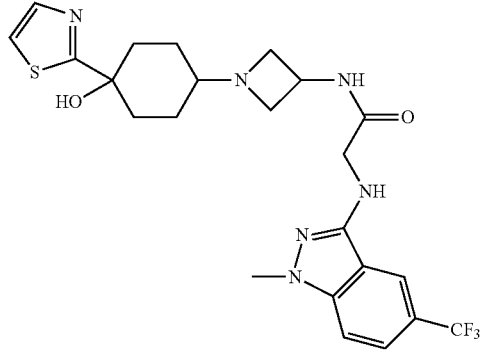 [SMILES: Cn1nc(NCC(=O)NC2CN(C3CCC(O)(c4nccs4)CC3)C2)c2cc(C(F)(F)F)ccc21]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-hydroxy-4-thiazol-2-yl-cyclohexanone using the procedure described in Step E of Example 1.

The less polar isomer from the silica gel column was tested in vitro as described in Example 107.

$^1$H NMR (400 MHz, d$_4$-MeOH) δ: 7.70 (s, 1H), 7.65 (s, 1H), 7.51 (s, 1H), 7.38 (d, J=6.0 Hz, 1H), 7.25 (d, J=6.0 Hz, 1H), 4.50 (m, 1H), 4.01 (s, 2H), 3.81 (s, 3H), 3.62 (t, J=5.0 Hz, 2H), 3.02 (t, J=5.0 Hz, 2H), 2.38 (m, 3H), 1.80 (m, 2H), 1.70 (m, 2H), 1.45 (m, 2H).

Example 23

N-{1-[4-(2-Ethyl-thiazol-5-yl)-4-hydroxy-cyclohexyl]-azetidin-3-yl}-2-(1-methyl-5-trifluoromethyl-1H-indazol-3-ylamino)-acetamide

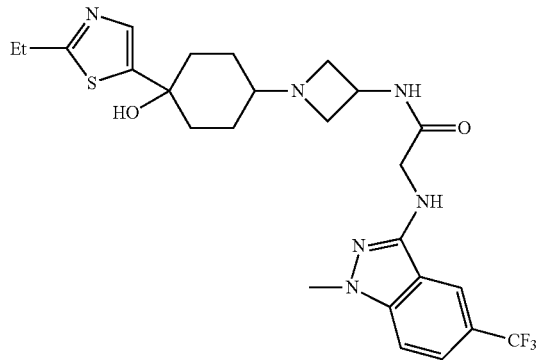 [SMILES: CCc1ncc(C2(O)CCC(N3CC(NC(=O)CNc4nn(C)c5ccc(C(F)(F)F)cc45)C3)CC2)s1]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-(2-ethyl-thiazol-5-yl)-4-hydroxy-cyclohexanone using the procedure described in Step E of Example 1.

The less polar isomer from the silica gel column was tested in vitro as described in Example 107.

$^1$H NMR (400 MHz, d$_4$-MeOH) δ: 8.27 (s, 1H), 7.44-7.59 (m, 2H), 7.42 (s, 1H), 4.39 (quin, J=7.2 Hz, 1H), 3.96 (q, J=7.0 Hz, 1H), 3.91 (s, 3H), 3.50-3.59 (m, 2H), 3.01 (t, J=7.8 Hz, 2H), 2.85 (q, J=7.6 Hz, 3H), 2.25 (dt, J=7.3, 3.7 Hz, 1H), 2.00-2.14 (m, 3H), 1.66-1.77 (m, 2H), 1.56-1.66 (m, 2H), 1.40-1.52 (m, 1H), 1.21 (t, J=7.6 Hz, 5H).

Example 24

N-{1-[4-Hydroxy-4-(2-isopropyl-thiazol-5-yl)-cyclohexyl]-azetidin-3-yl}-2-(1-methyl-5-trifluoromethyl-1H-indazol-3-ylamino)-acetamide

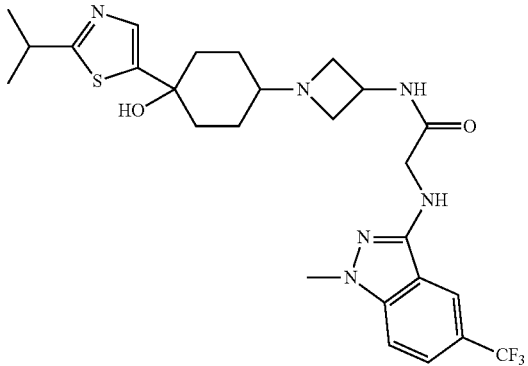 [SMILES: CC(C)c1ncc(C2(O)CCC(N3CC(NC(=O)CNc4nn(C)c5ccc(C(F)(F)F)cc45)C3)CC2)s1]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-hydroxy-4-(2-isopropyl-thiazol-5-yl)-cyclohexanone using the procedure described in Step E of Example 1.

The less polar isomer from the silica gel column was tested in vitro as described in Example 107.

$^1$H NMR (400 MHz, d$_4$-MeOH) δ: 8.15 (s, 1H), 7.58 (d, J=6.0 Hz, 1H), 7.55 (s, 1H), 7.42 (d, J=6.0 Hz, 1H), 4.55 (m, 1H), 4.05 (s, 2H), 3.90 (s, 3H), 3.58 (m, 2H), 3.15 (m, 2H), 2.75 (m, 1H), 2.25 (m, 2H), 1.98 (m, 2H), 1.80 (m, 2H), 1.35 (m, 2H), 1.30 (d, J=7.0 Hz, 6H).

Example 25

N-{1-[4-Hydroxy-4-(1-methyl-1H-pyrazol-4-yl)-cyclohexyl]-azetidin-3-yl}-2-(1-methyl-5-trifluoromethyl-1H-indazol-3-ylamino)-acetamide

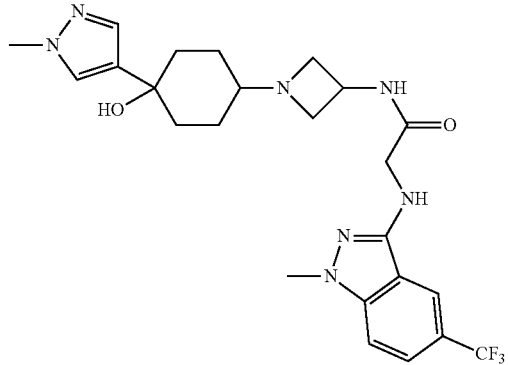 [SMILES: Cn1cc(C2(O)CCC(N3CC(NC(=O)CNc4nn(C)c5ccc(C(F)(F)F)cc45)C3)CC2)cn1]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-hydroxy-4-(1-methyl-1H-pyrazol-4-yl)-cyclohexanone using the procedure described in Step E of Example 1.

The less polar isomer from the silica gel column was tested in vitro as described in Example 107.

$^1$H NMR (400 MHz, d$_4$-MeOH) δ: 8.10 (s, 1H), 7.58 (d, J=6.5 Hz, 1H), 7.48 (d, J=6.0 Hz, 1H), 6.96 (s, 1H), 6.79 (s, 1H), 4.48 (m, 1H), 4.01 (s, 2H), 3.86 (s, 3H), 3.83 (s, 3H), 3.49 (t, J=7.5 Hz, 2H), 3.01 (t, J=7.5 Hz, 2H), 2.40 (m, 2H), 2.28 (m, 1H), 1.80 (m, 2H), 1.72 (m, 2H), 1.38 (m, 2H).

Example 26

N-[1-(4-Hydroxy-4-oxazol-2-yl-cyclohexyl)-azetidin-3-yl]-2-(1-methyl-5-trifluoromethyl-1H-indazol-3-ylamino)-acetamide

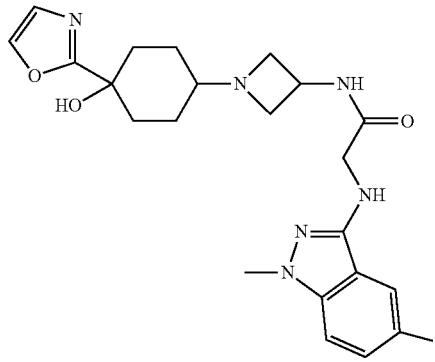

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-hydroxy-4-oxazol-2-yl-cyclohexanone using the procedure described in Step E of Example 1.

The less polar isomer from the silica gel column was tested in vitro as described in Example 107.

Example 27

N-{1-[4-Hydroxy-4-(1-methyl-1H-imidazol-2-yl)-cyclohexyl]-azetidin-3-yl}-2-(1-methyl-5-trifluoromethyl-1H-indazol-3-ylamino)-acetamide

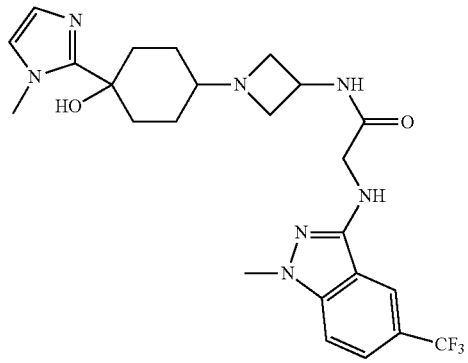 [SMILES: Cn1ccnc1C1(O)CCC(N2CC(NC(=O)CNc3nn(C)c4ccc(C(F)(F)F)cc34)C2)CC1]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-hydroxy-4-(1-methyl-1H-imidazol-2-yl)-cyclohexanone using the procedure described in Step E of Example 1.

The less polar isomer from the silica gel column was tested in vitro as described in Example 107.

$^1$H NMR (400 MHz, d$_4$-MeOH) δ: 8.21 (s, 1H), 7.60 (d, J=7.0 Hz, 1H), 7.35 (d, J=7.0 Hz, 1H), 6.92 (s, 1H), 6.58 (s, 1H), 4.46 (m, 1H), 3.98 (s, 2H), 3.88 (s, 3H), 3.82 (s, 3H), 3.65 (t, J=6.5 Hz, 2H), 2.95 (t, J=6.5 Hz, 2H), 2.42 (m, 2H), 2.25 (m, 1H), 1.80 (m, 2H), 1.65 (m, 2H), 1.36 (m, 2H).

Example 28

N-{-[4-Hydroxy-4-(2-methyl-thiazol-5-yl)-cyclohexyl]-azetidin-3-yl}-2-(1-methyl-5-trifluoromethyl-1H-indazol-3-ylamino)-acetamide

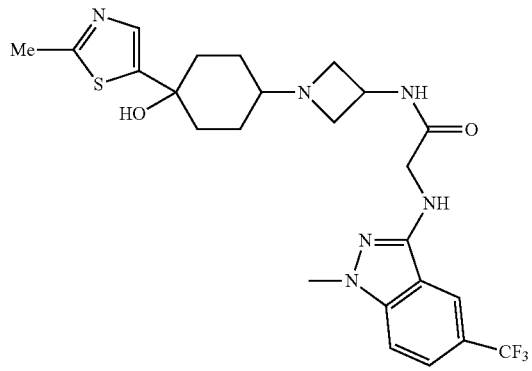 [SMILES: Cc1ncc(C2(O)CCC(N3CC(NC(=O)CNc4nn(C)c5ccc(C(F)(F)F)cc45)C3)CC2)s1]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-hydroxy-4-(2-methyl-thiazol-5-yl)-cyclohexanone using the procedure described in Step E of Example 1.

The less polar isomer from the silica gel column was tested in vitro as described in Example 107.

$^1$H NMR (400 MHz, d$_4$-MeOH) δ: 8.20 (s, 1H), 8.13 (d, J=6.5 Hz, 1H), 7.80 (d, J=6.0 Hz, 1H), 7.62 (t, J=7.2 Hz, 1H), 4.55 (m, 1H), 3.83 (s, 3H), 3.65 (t, J=7.5 Hz, 2H), 3.28 (s, 3H), 2.98 (t, J=7.2 Hz, 2H), 2.30 (m, 2H), 1.80 (m, 2H), 1.65 (m, 2H), 1.42 (m, 2H).

Example 29

N-[1-(4-Hydroxy-4-phenyl-cyclohexyl)-azetidin-3-yl]-2-(1-methyl-5-trifluoromethyl-1H-indazol-3-ylamino)-acetamide

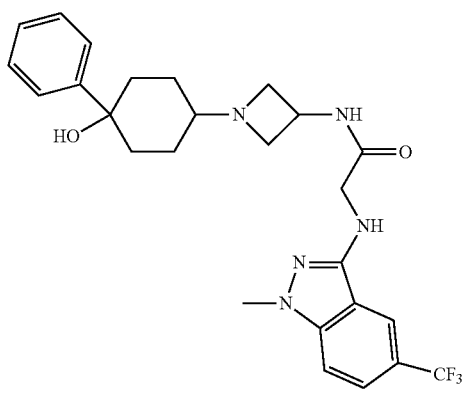 [SMILES: Cn1nc(NCC(=O)NC2CN(C3CCC(O)(c4ccccc4)CC3)C2)c2cc(C(F)(F)F)ccc21]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-hydroxy-4-phenyl-cyclohexanone using the procedure described in Step E of Example 1.

The less polar isomer from the silica gel column was tested in vitro as described in Example 107.

$^1$H NMR (400 MHz, CDCl$_3$) δ: 8.15 (s, 1H), 8.04 (d, J=6.5 Hz, 1H), 7.75 (d, J=6.4 Hz, 1H), 7.54 (t, J=6.8 Hz, 1H), 7.38 (d, J=6.0 Hz, 2H), 7.35 (m, 1H), 7.26 (m, 2H), 7.15 (d, J=5.8 Hz, 1H), 7.12 (m, 1H), 6.96 (d, J=6.8 Hz, 1H), 4.58 (m, 1H), 4.05 (d, J=3.2 Hz, 2H), 3.83 (s, 3H), 3.60 (t, J=7.2 Hz, 2H), 2.95 (t, J=7.5 Hz, 2H), 2.25 (m, 2H), 1.80 (m, 2H), 1.55 (m, 2H), 1.40 (m, 2H).

Example 30

N-{1-[4-Hydroxy-4-(6-methyl-pyridin-3-yl)-cyclohexyl]-azetidin-3-yl}-2-(1-methyl-5-trifluoromethyl-1H-indazol-3-ylamino)-acetamide

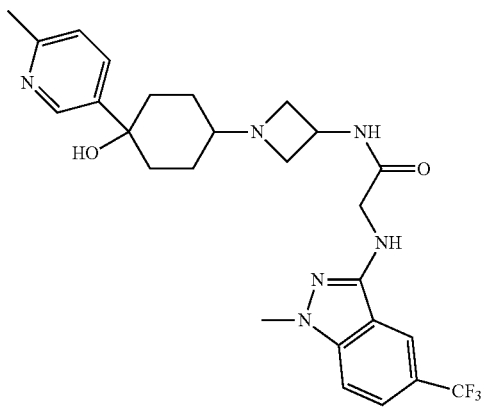 [SMILES: Cc1ccc(C2(O)CCC(N3CC(NC(=O)CNc4nn(C)c5ccc(C(F)(F)F)cc45)C3)CC2)cn1]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-hydroxy-4-(6-methyl-pyridin-3-yl)-cyclohexanone using the procedure described in Step E of Example 1.

The less polar isomer from the silica gel column was tested in vitro as described in Example 107.

$^1$H NMR (400 MHz, CDCl$_3$) δ: 8.60 (s, 1H), 8.13 (s, 1H), 8.00 (d, J=6.5 Hz, 1H), 7.65 (m, 2H), 7.62 (m, 1H), 7.53 (d, J=6.5 Hz, 1H), 7.25 (s, 1H), 7.10 (d, J=6.8 Hz, 1H), 4.58 (m, 1H), 4.00 (d, J=6.0 Hz, 2H), 3.85 (s, 3H), 3.62 (t, J=7.5 Hz, 2H), 2.98 (t, J=7.8 Hz, 2H), 2.50 (s, 3H), 2.25 (m, 2H), 1.85 (m, 2H), 1.55 (m, 4H).

Example 31

(4-{3-[2-(1-Methyl-5-trifluoromethyl-1H-indazol-3-ylamino)-acetylamino]-azetidin-1-yl}-cyclohexyl)-carbamic acid tert-butyl ester

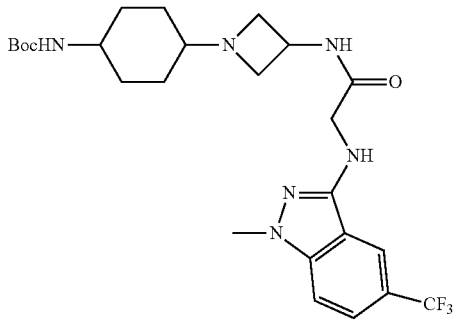 [SMILES: Cn1nc(NCC(=O)NC2CN(C3CCC(NC(=O)OC(C)(C)C)CC3)C2)c2cc(C(F)(F)F)ccc21]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and (4-oxo-cyclohexyl)-carbamic acid tert-butyl ester using the procedure described in Step E of Example 1.

The less polar isomer from the silica gel column was tested in vitro as described in Example 107.

$^1$H NMR (400 MHz, CDCl$_3$) δ: 7.95 (s, 1H), 7.55 (d, J=6.5 Hz, 1H), 7.23 (d, J=6.5 Hz, 1H), 5.25 (br, s, 1H), 4.95 (br, s, 1H), 4.65 (m, 1H), 4.45 (m, 1H), 4.10 (s, 2H), 3.85 (s, 3H), 3.50 (t, J=6.0 Hz, 2H), 3.11 (t, J=6.0 Hz, 2H), 2.40 (m, 1H), 2.15 (m, 2H), 1.80 (m, 2H), 1.70 (m, 2H), 1.50 (m, 2H), 1.45 (s, 9H).

Example 32

4-{3-[2-(1-Methyl-5-trifluoromethyl-1H-indazol-3-ylamino)-acetylamino]-azetidin-1-yl}-cyclohexane carboxylic acid ethyl ester

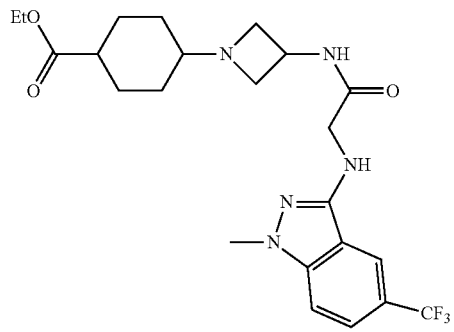 [SMILES: CCOC(=O)C1CCC(N2CC(NC(=O)CNc3nn(C)c4ccc(C(F)(F)F)cc34)C2)CC1]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-oxo-cyclohexanecarboxylic acid ethyl ester using the procedure described in Step E of Example 1.

The less polar isomer from the silica gel column was tested in vitro as described in Example 107.

MS: 482 (MH$^+$).

Example 33

N-[1-(4-Hydroxymethyl-cyclohexyl)-azetidin-3-yl]-2-(1-methyl-5-trifluoromethyl-1H-indazol-3-ylamino)-acetamide

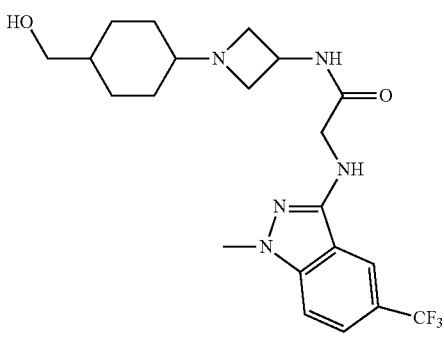 [SMILES: Cn1nc(NCC(=O)NC2CN(C3CCC(CO)CC3)C2)c2cc(C(F)(F)F)ccc21]

Step A

4-Hydroxymethyl-cyclohexanone

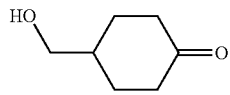

4-Oxo-cyclohexanecarboxylic acid ethyl ester (Aldrich, 6.1 g, 35.8 mmol), ethylene glycol (3.34 g, 53.8 mmol), pTSA (123 mg, 0.717 mmol) in toluene (100 mL) was refluxed in Dean-Stark until no water was observed. The resulting solution was washed with saturated NaHCO$_3$ and brine, dried over anhydrous Na$_2$SO$_4$, filtered and concentrated to give 1,4-dioxa-spiro[4.5]decane-8-carboxylic acid ethyl ester as colorless solid.

To 1,4-dioxa-spiro[4.5]decane-8-carboxylic acid ethyl ester (5.7 g, 26.6 mmol) in THF (15 mL) at 0° C. was treated with LAH (1N in THF, 32 mL, 32 mmol) dropwise for 30 min. The reaction was then slowly warmed to room temperature and quenched with MeOH (~0.5 mL) and filtered through a pad of Celite to give (1,4-dioxa-spiro[4.5]dec-8-yl)-methanol, which was then treated with 1N HCl (5 mL) in acetone (10 mL) at room temperature for 2 hours. The solvent was removed and the solution was then partitioned between ethyl acetate and saturated NaHCO$_3$. The combined organic layers were washed with brine, dried over anhydrous Na$_2$SO$_4$, filtered and concentrated to give the crude material, which was purified by silica gel column (hexanes:ethyl acetate 4:1) to afford the title compound as colorless solid.

$^1$H NMR (400 MHz, CDCl$_3$) δ: 3.95 (s, 4H), 3.48 (d, J=5.6 Hz, 2H), 1.68 (m, 4H), 1.52 (m, 2H), 1.23 (m, 2H).

Step B

N-[1-(4-Hydroxymethyl-cyclohexyl)-azetidin-3-yl]-2-(1-methyl-5-trifluoromethyl-1H-indazol-3-ylamino)-acetamide

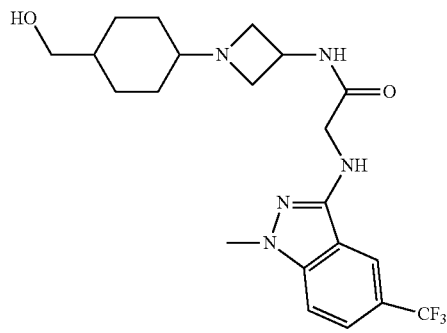 [SMILES: Cn1nc(NCC(=O)NC2CN(C3CCC(CO)CC3)C2)c2cc(C(F)(F)F)ccc21]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-hydroxymethyl-cyclohexanone using the procedure described in Step E of Example 1.

The less polar isomer from the silica gel column was tested in vitro as described in Example 107.

$^1$H NMR (400 MHz, CDCl$_3$) δ: 8.10 (s, 1H), 7.61 (d, J=7.0 Hz, 1H), 7.46 (d, J=7.0 Hz, 1H), 4.51 (m, 1H), 4.02 (s, 2H), 3.85 (s, 3H), 3.65 (t, J=6.5 Hz, 2H), 3.45 (d, J=6.0 Hz, 2H), 3.35 (s, 3H), 3.02 (t, J=6.5 Hz, 2H), 2.38 (m, 1H), 1.95 (M, 2H), 1.45 (M, 4H), 1.32 (M, 2H).

Example 34

N-[1-(4-Ethoxymethyl-cyclohexyl)-azetidin-3-yl]-2-(1-methyl-5-trifluoromethyl-1H-indazol-3-ylamino)-acetamide

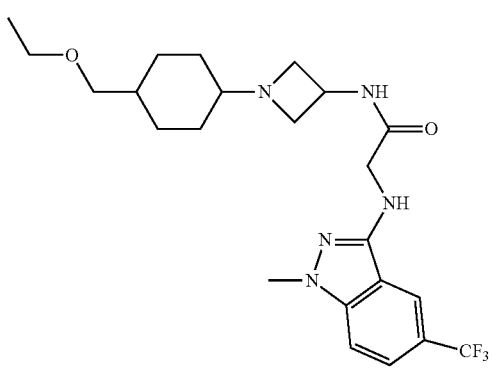 [SMILES: CCOCC1CCC(N2CC(NC(=O)CNc3nn(C)c4ccc(C(F)(F)F)cc34)C2)CC1]

Step A

4-Ethoxymethyl-cyclohexanone

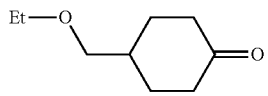

(1,4-Dioxa-spiro[4.5]dec-8-yl)-methanol (from Example 33, 765 mg, 4.44 mmol) in DMF (3 mL) at 0° C. was treated with NaH (Aldrich, 60% in mineral oil, 355 mg, 8.88 mmol) followed by EtI (Aldrich, 0.7 mL, 8.88 mmol). The resulting solution was slowly warmed to room temperature for 2 hours and heated at 60° C. for additional 30 min. The solution was then partitioned between ethyl acetate and saturated NH$_4$Cl. The combined organic layers were washed with brine, dried over anhydrous Na$_2$SO$_4$, filtered and concentrated to give the crude material, which was treated with 1N HCl (2 mL) and acetone (6 mL) at room temperature for 2 hours. The solvent was removed and the solution was then partitioned between ethyl acetate and saturated NaHCO$_3$. The combined organic layers were washed with brine, dried over anhydrous Na$_2$SO$_4$, filtered and concentrated to give the crude material, purified by silica gel column (hexanes:ethyl acetate 5:1) to afford the title compound as colorless solid.

$^1$H NMR (400 MHz, CDCl$_3$) δ: 3.51 (t, J=6.0 Hz, 2H), 3.35 (d, J=5.0 Hz, 2H), 2.41 (m, 4H), 2.08 (m, 4H), 1.49 (m, 4H), 1.21 (t, J=6.0 Hz, 2H).

Step B

N-[1-(4-Ethoxymethyl-cyclohexyl)-azetidin-3-yl]-2-(1-methyl-5-trifluoromethyl-1H-indazol-3-ylamino)-acetamide

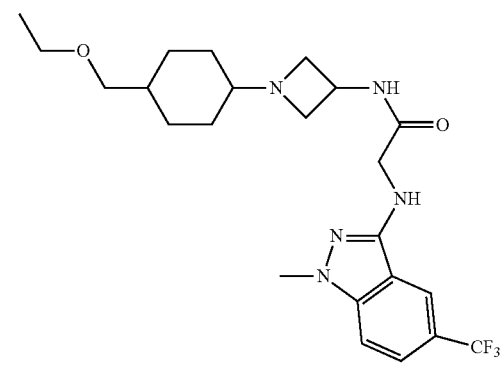 [SMILES: CCOCC1CCC(N2CC(NC(=O)CNc3nn(C)c4ccc(C(F)(F)F)cc34)C2)CC1]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-ethoxymethyl-cyclohexanone using the procedure described in Step E of Example 1.

The less polar isomer from the silica gel column was tested in vitro as described in Example 107.

MS: 468 (MH$^+$).

Example 35

N-[1-(4-Allyloxymethyl-cyclohexyl)-azetidin-3-yl]-2-(1-methyl-5-trifluoromethyl-1H-indazol-3-ylamino)-acetamide

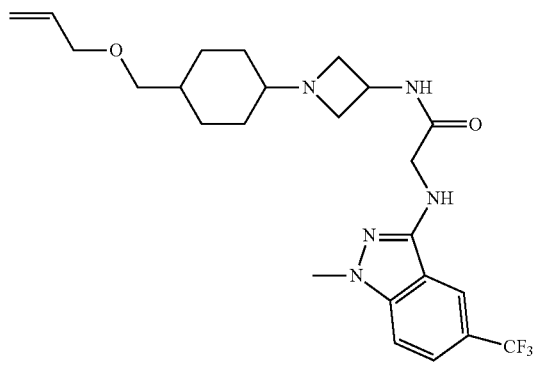 [SMILES: C=CCOCC1CCC(N2CC(NC(=O)CNc3nn(C)c4ccc(C(F)(F)F)cc34)C2)CC1]

Step A

4-Allyloxymethyl-cyclohexanone

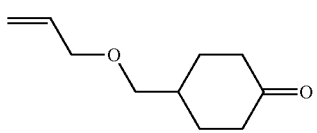

The title compound was prepared as white solid from reaction of (1,4-dioxa-spiro[4.5]dec-8-yl)-methanol and allyl bromide (Aldrich) followed by de-protection using the procedure described in Example 34.

¹H NMR (400 MHz, CDCl₃) δ: 5.91 (m, 1H), 5.35 (d, J=9.5 Hz, 1H), 5.21 (d, J=7.5 Hz, 1H), 3.95 (s, 2H), 3.32 (d, J=5.5 Hz, 2H), 2.42 (m, 4H), 2.15 (m, 3H), 1.52 (m, 2H).

Step B

N-[1-(4-Allyloxymethyl-cyclohexyl)-azetidin-3-yl]-2-(1-methyl-5-trifluoromethyl-1H-indazol-3-ylamino)-acetamide

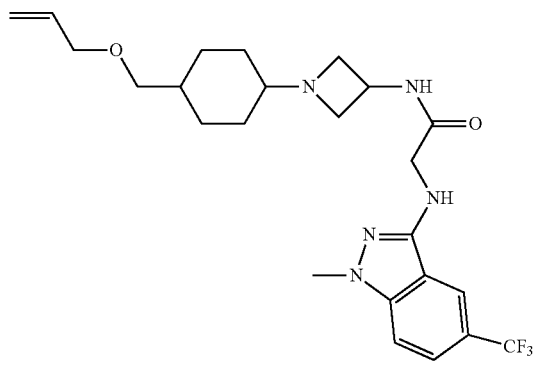 [SMILES: C=CCOCC1CCC(N2CC(NC(=O)CNc3nn(C)c4ccc(C(F)(F)F)cc34)C2)CC1]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-allyloxymethyl-cyclohexanone using the procedure described in Step E of Example 1.

The less polar isomer from the silica gel column was tested in vitro as described in Example 107.

¹H NMR (400 MHz, CDCl₃) δ: 7.90 (s, 1H), 7.61 (s, br, 1H), 7.54 (d, J=6.5 Hz, 1H), 7.25 (d, J=6.5 Hz, 1H), 5.90 (m, 1H), 5.38 (m, 1H), 5.27 (d, J=9.5 Hz, 1H), 5.18 (d, J=9.5 Hz, 1H), 4.58 (m, 1H), 4.10 (d, J=2.5 Hz, 2H), 3.95 (d, J=3.0 Hz, 2H), 3.88 (s, 3H), 3.63 (t, J=7.5 Hz, 2H), 3.30 (d, J=4.5 Hz, 2H), 3.05 (m, 2H), 2.35 (m, 1H), 1.75 (m, 1H), 1.48 (m, 7H).

Example 36

N-[1-(4-Ethoxy-cyclohexyl)-azetidin-3-yl]-2-(1-methyl-5-trifluoromethyl-1H-indazol-3-ylamino)-acetamide

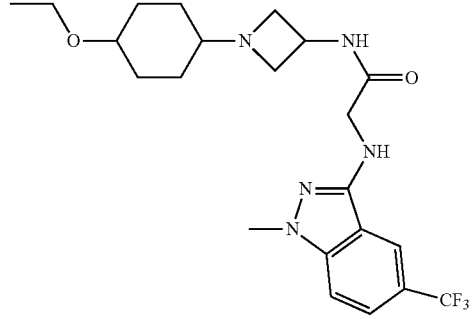 [SMILES: CCOC1CCC(N2CC(NC(=O)CNc3nn(C)c4ccc(C(F)(F)F)cc34)C2)CC1]

Step A

4-Ethoxy-cyclohexanone

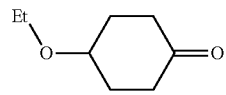

The title compound was prepared as white solid from reaction of 1,4-dioxa-spiro[4.5]decan-8-ol and EtI (Aldrich) followed by de-protection using the procedure described in Example 34.

MS: 143 (MH⁺).

Step B

N-[1-(4-Ethoxy-cyclohexyl)-azetidin-3-yl]-2-(1-methyl-5-trifluoromethyl-1H-indazol-3-ylamino)-acetamide

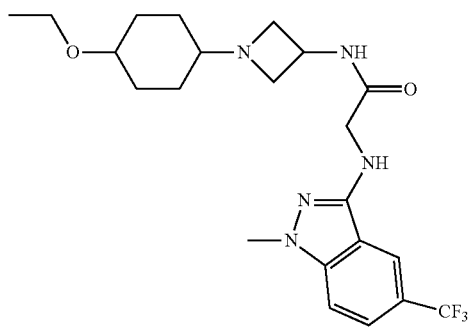 [SMILES: CCOC1CCC(N2CC(NC(=O)CNc3nn(C)c4ccc(C(F)(F)F)cc34)C2)CC1]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-ethoxy-cyclohexanone using the procedure described in Step E of Example 1.

The less polar isomer from the silica gel column was tested in vitro as described in Example 107.

$^1$H NMR (400 MHz, CDCl$_3$) δ: 7.95 (s, 1H), 7.52 (d, J=6.5 Hz, 1H), 7.25 (d, J=6.0 Hz, 1H), 4.52 (m, 1H), 4.10 (s, 2H), 4.08 (m, 1H), 3.92 (s, 3H), 3.62 (m, 1H), 3.60 (t, J=6.5 Hz, 2H), 3.45 (q, J=6.5 Hz, 2H), 3.08 (t, J=6.5 Hz, 2H), 2.10 (m, 2H), 1.85 (m, 2H), 1.46 (m, 4H), 1.23 (t, J=6.5 Hz, 3H).

Example 37

N-[1-(4-Allyloxy-cyclohexyl)-azetidin-3-yl]-2-(1-methyl-5-trifluoromethyl-1H-indazol-3-ylamino)-acetamide

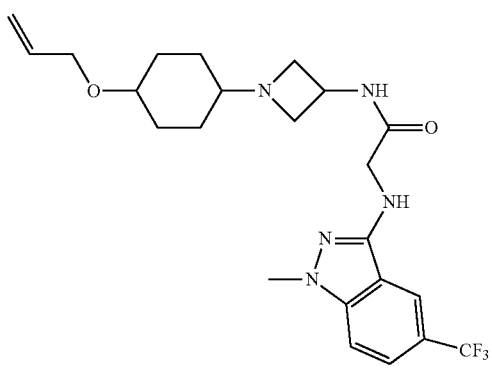 [SMILES: C=CCOC1CCC(N2CC(NC(=O)CNc3nn(C)c4ccc(C(F)(F)F)cc34)C2)CC1]

Step A

4-allyoxy-cyclohexanone

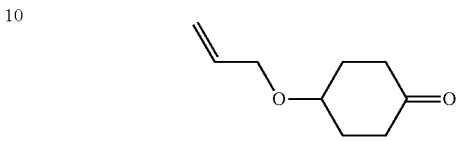

The title compound was prepared as white solid from reaction of 1,4-dioxa-spiro[4.5]decan-8-ol and allyl bromide (Aldrich) followed by de-protection using the procedure described in Example 34.

$^1$H NMR (400 MHz, CDCl$_3$) δ: 5.95 (m, 1H), 5.38 (d, J=10.2 Hz, 1H), 5.24 9d, J=7.6 Hz, 1H), 4.05 (s, 2H), 3.72 (m, 1H), 2.62 (m, 2H), 2.32 (m, 2H), 2.18 (m, 2H), 1.93 (m, 2H).

Step B

N-[1-(4-Allyloxy-cyclohexyl)-azetidin-3-yl]-2-(1-methyl-5-trifluoromethyl-1H-indazol-3-ylamino)-acetamide

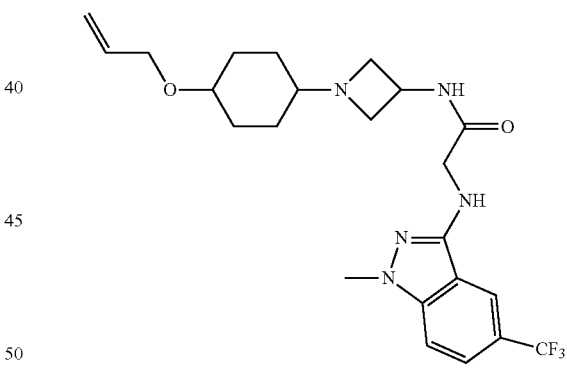

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-allyoxy-cyclohexanone using the procedure described in Step E of Example 1.

The less polar isomer from the silica gel column was tested in vitro as described in Example 107.

$^1$H NMR (400 MHz, CDCl$_3$) δ: 7.95 (s, 1H), 7.52 (d, J=6.5 Hz, 1H), 7.23 (d, J=6.0 Hz, 1H), 5.95 (m, 1H), 5.25 (d, J=10.0 Hz, 1H), 5.15 (t, J=4.5 Hz, 1H), 4.50 (m, 1H), 4.10 (t, J=6.5 Hz, 2H), 4.01 (m, 1H), 3.95 (s, 2H), 3.85 (s, 3H), 3.52 (t, J=6.0 Hz, 2H), 3.00 (t, J=6.0 Hz, 2H), 2.10 (m, 2H), 1.80 (m, 4H), 1.41 (m, 2H).

Example 38

N-[1-(4-Cyano-cyclohexyl)-azetidin-3-yl]-2-(1-methyl-5-trifluoromethyl-1H-indazol-3-ylamino)-acetamide

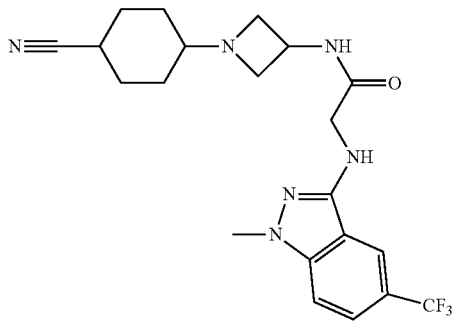 [SMILES: Cn1nc(NCC(=O)NC2CN(C3CCC(C#N)CC3)C2)c2cc(C(F)(F)F)ccc21]

The title compound was prepared as a white solid from reaction of N-azetidin-3-yl-2-(1-methyl-5-trifluoromethyl-1H-indazol-3-ylamino)-acetamide TFA salt (as prepared in Example 18, Step D) and 4-cynao-cyclohexanone using the procedure described in Step E of Example 1.

The less polar isomer from the silica gel column was tested in vitro as described in Example 107.

$^1$H NMR (400 MHz, $d_4$-MeOH) δ: 8.12 (s, 1H), 7.58 (d, J=6.5 Hz, 1H), 7.43 (d, J=6.0 Hz, 1H), 4.53 (m, 1H), 4.01 (s, 2H), 3.85 (s, 3H), 3.60 (t, J=7.0 Hz, 2H), 3.05 (t, J=7.0 Hz, 2H), 2.50 (m, 1H), 2.20 (m, 2H), 1.85 (m, 4H), 1.38 (m, 2H).

Example 39

4-{3-[2-(1-Methyl-5-trifluoromethyl-1H-indazol-3-ylamino)-acetylamino]-azetidin-1-yl}-cyclohexane carboxylic acid amide

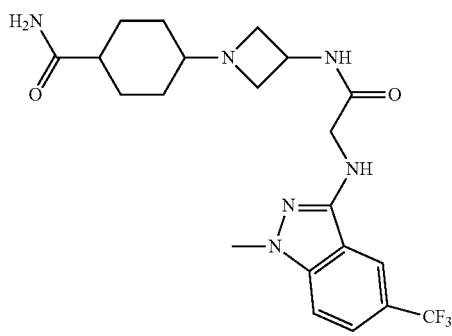

Step A

4-{3-[2-(1-Methyl-5-trifluoromethyl-1H-indazol-3-ylamino)-acetylamino]-azetidin-1-yl}-cyclohexane carboxylic acid

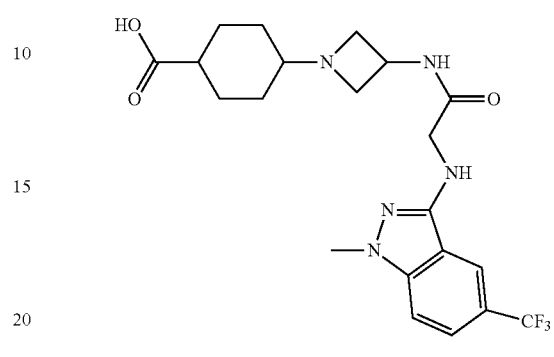

4-{3-[2-(1-Methyl-5-trifluoromethyl-1H-indazol-3-ylamino)-acetylamino]-azetidin-1-yl}-cyclohexane carboxylic acid ethyl ester (from Example 32, 350 mg, 0.773 mmol) in THF (2 mL), MeOH (2 mL) and distilled water (2 mL) was treated with lithium hydroxide monohydrate (87 mg, 1.93 mmol) at room temperature for 1 hour. The reaction mixture was acidified to pH=5 and extracted with DCM:IPA (3:1) solvent three times. The combined organic layer was washed with brine, dried over anhydrous $Na_2SO_4$, filtered and concentrated to give the title compound as colorless solid.

MS: 454 (MH$^+$).

Step B

4-{3-[2-(1-Methyl-5-trifluoromethyl-1H-indazol-3-ylamino)-acetylamino]-azetidin-1-yl}-cyclohexane carboxylic acid amide

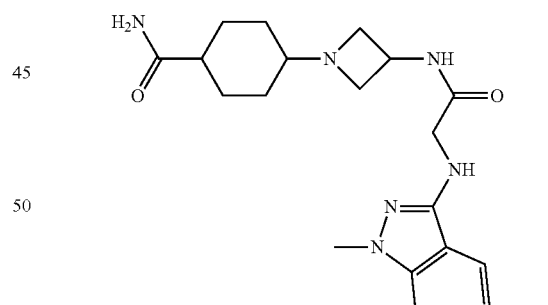

4-{3-[2-(1-Methyl-5-trifluoromethyl-1H-indazol-3-ylamino)-acetylamino]-azetidin-1-yl}-cyclohexane carboxylic acid (as prepared in the previous step, 100 mg, 0.22 mmol), EDCI (Aldrich, 65 mg, 0.33 mmol), HOBt (Aldrich, 45 mg, 0.33 mmol) and ammonia in THF (1N, Aldrich, 0.5 mL) in DCM (5 mL) was stirred at room temperature overnight. The solvent was removed and the residue was purified by silica gel column chromatography using DCM: 7N $NH_3$ in MeOH (10:1) as eluent to give the title compound as white solid.

MS: 453 (MH$^+$).

Example 40

4-{3-[2-(1-Methyl-5-trifluoromethyl-1H-indazol-3-ylamino)-acetylamino]-azetidin-1-yl}-cyclohexane carboxylic acid (2-hydroxy-ethyl)-amide

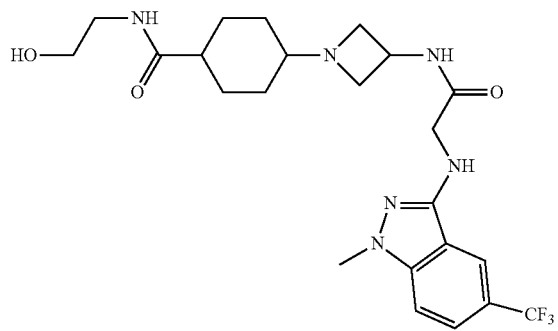 [SMILES: Cn1nc(NCC(=O)NC2CN(C3CCC(C(=O)NCCO)CC3)C2)c2cc(C(F)(F)F)ccc21]

The title compound was prepared from EDCI coupling of 4-{3-[2-(1-methyl-5-trifluoromethyl-1H-indazol-3-ylamino)-acetylamino]-azetidin-1-yl}-cyclohexanecarboxylic acid (as prepared in Example 39, Step A) and 2-aminoethanol using the procedure described in Example 39.
MS: 497 (MH$^+$).

Example 41

N-[1-(4-Hydroxy-4-pyridin-3-yl-cyclohexyl)-azetidin-3-yl]-2-(5-trifluoromethyl-1H-indazol-3-ylamino)-acetamide

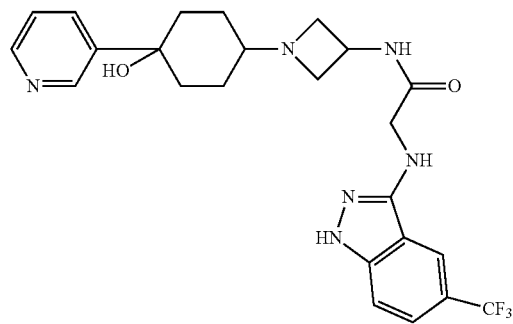 [SMILES: O=C(CNc1n[nH]c2ccc(C(F)(F)F)cc12)NC1CN(C2CCC(O)(c3cccnc3)CC2)C1]

Step A

N-Azetidin-3-yl-2-(5-trifluoromethyl-1H-indazol-3-ylamino)-acetamide

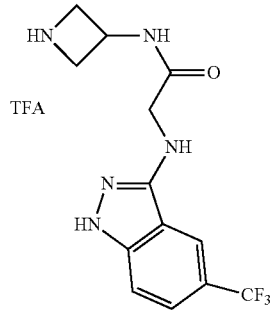 [SMILES: O=C(CNc1n[nH]c2ccc(C(F)(F)F)cc12)NC1CNC1]

The title compound was prepared from hydrazine and 2-fluoro-5-trifluoromethyl-benzonitrile using the procedures described in Example 18 (A to D) as a colorless oil.
MS: 314 (MH$^+$).

Step B

N-[1-(4-Hydroxy-4-pyridin-3-yl-cyclohexyl)-azetidin-3-yl]-2-(5-trifluoromethyl-1H-indazol-3-ylamino)-acetamide

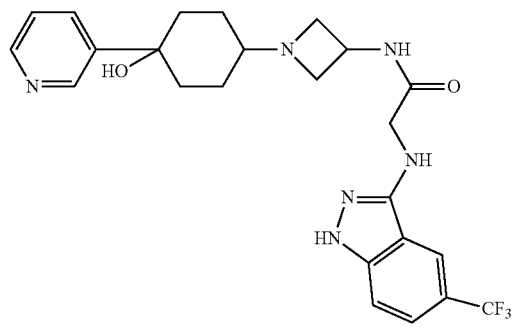 [SMILES: O=C(CNc1n[nH]c2ccc(C(F)(F)F)cc12)NC1CN(C2CCC(O)(c3cccnc3)CC2)C1]

The title compound was prepared as a white solid from reaction of N-azetidin-3-yl-2-(5-trifluoromethyl-1H-indazol-3-ylamino)-acetamide (as prepared in the previous step) and 4-hydroxy-4-pyridin-3-yl-cyclohexanone using the procedure described in Step E of Example 1.

The less polar isomer from the silica gel column was tested in vitro as described in Example 107.
$^1$H NMR (400 MHz, d$_4$-MeOH) δ: 8.70 (s, 1H), 8.45 (d, J=7.5 Hz, 1H), 8.27 (d, J=7.0 Hz, 1H), 8.19 (s, 1H), 7.61 (d, J=5.7 Hz, 1H), 7.45 (d, J=6.0 Hz, 1H), 7.40 (d, J=6.5 Hz, 1H), 4.50 (m, 1H), 4.06 (s, 2H), 3.70 (t, J=6.5 Hz, 2H), 3.05 (t, J=6.5 Hz, 2H), 2.42 (m, 1H), 2.25 (m, 2H), 1.95 (m, 2H), 1.67 (m, 2H), 1.55 (m, 2H).

Example 42

N-[1-(4-Hydroxy-4-thiazol-5-yl-cyclohexyl)-azetidin-3-yl]-2-(5-trifluoromethyl-1H-indazol-3-ylamino)-acetamide

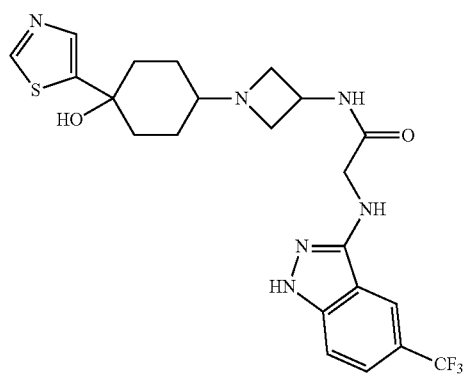 [SMILES: O=C(CNc1n[nH]c2ccc(C(F)(F)F)cc12)NC1CN(C2CCC(O)(c3cncs3)CC2)C1]

The title compound was prepared as a white solid from reaction of N-azetidin-3-yl-2-(5-trifluoromethyl-1H-indazol-3-ylamino)-acetamide (as prepared in Example 41, Step A) and 4-hydroxy-4-thiazol-5-yl-cyclohexanone using the procedure described in Step E of Example 1.

The less polar isomer from the silica gel column was tested in vitro as described in Example 107.

$^1$H NMR (400 MHz, d$_4$-MeOH) δ: 8.90 (s, 1H0, 8.15 (s, 1H), 7.82 (s, 1H), 7.55 (d, J=7.0 Hz, 1H), 7.45 (d, J=7.0 Hz, 1H), 4.50 (m, 1H), 4.05 (s, 2H), 3.62 (t, J=8.0 Hz, 2H), 3.15 (m, 1H0, 3.00 (t, J=8.0 Hz, 2H), 2.32 (m, 1H), 2.25 (m, 2H), 1.90 (m, 2H), 1.82 (m, 2H), 1.38 (m, 2H).

Example 43

N-{1-[4-Hydroxy-4-(6-methyl-pyridin-3-yl)-cyclohexyl]-azetidin-3-yl}-2-(5-trifluoromethyl-1H-indazol-3-ylamino)-acetamide

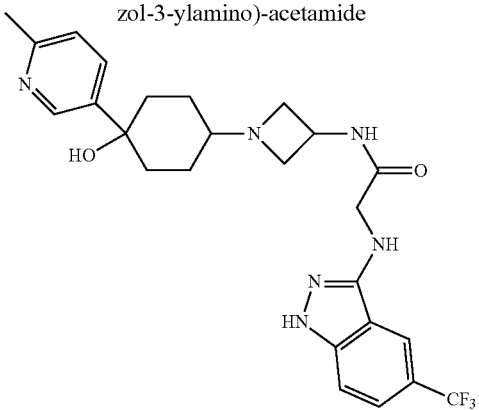

The title compound was prepared as a white solid from reaction of N-azetidin-3-yl-2-(5-trifluoromethyl-1H-indazol-3-ylamino)-acetamide (as prepared in Example 41, Step A) and 4-hydroxy-4-(6-methyl-pyridin-3-yl)-cyclohexanone using the procedure described in Step E of Example 1.

The less polar isomer from the silica gel column was tested in vitro as described in Example 107.

$^1$H NMR (400 MHz, d$_4$-MeOH) δ: 8.60 (s, 1H), 8.15 (s, 1H), 7.90 (d, J=6.0 Hz, 1H), 7.58 (d, J=6.5 Hz, 1H), 7.49 (d, J=7.5 Hz, 1H), 7.28 (d, J=6.0 Hz, 1H), 4.52 (m, 1H), 4.05 (s, 2H), 3.70 (t, J=6.5 Hz, 2H), 3.01 (t, J=6.0 Hz, 2H), 2.55 (s, 2H), 2.45 (s, 1H), 2.20 (m, 2H), 1.90 (m, 2H), 1.55 (m, 2H), 1.45 (m, 2H).

Example 44

N-{1-[4-Hydroxy-4-(6-methoxy-pyridin-3-yl)-cyclohexyl]-azetidin-3-yl}-2-(5-trifluoromethyl-1H-indazol-3-ylamino)-acetamide

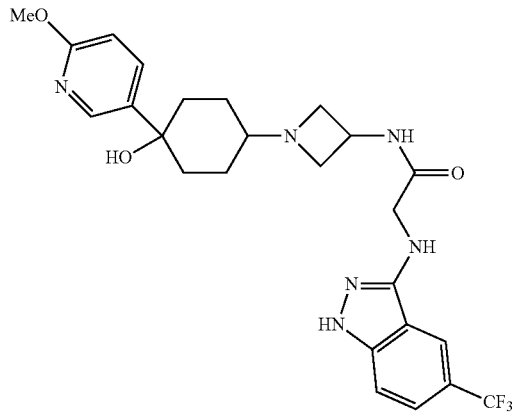 [SMILES: COc1ccc(C2(O)CCC(N3CC(NC(=O)CNc4n[nH]c5ccc(C(F)(F)F)cc45)C3)CC2)cn1]

The title compound was prepared as a white solid from reaction of N-azetidin-3-yl-2-(5-trifluoromethyl-1H-indazol-3-ylamino)-acetamide (as prepared in Example 41, Step A) and 4-hydroxy-4-(6-methoxy-pyridin-3-yl)-cyclohexanone using the procedure described in Step E of Example 1.

The less polar isomer from the silica gel column was tested in vitro as described in Example 107.

$^1$H NMR (400 MHz, d$_4$-MeOH) δ: 8.25 (d, J=4.5 Hz, 1H), 8.15 (s, 1H), 7.85 (d, J=6.5 Hz, 1H), 7.54 (d, J=6.5 Hz, 1H), 7.41 (d, J=7.5 Hz, 1H), 6.80 (d, J=6.0 Hz, 1H), 4.45 (m, 1H), 3.98 (s, 2H), 3.90 (s, 3H), 3.64 (t, J=6.5 Hz, 2H), 2.95 (t, J=6.0 Hz, 2H), 2.45 (m, 1H), 2.21 (m, 2H), 1.90 (m, 2H), 1.55 (m, 2H), 1.40 (m, 2H).

Example 45

N-[1-(4-Benzo[1,3]dioxol-5-yl-cyclohexyl)-azetidin-3-yl]-2-(5-trifluoromethyl-1H-indazol-3-ylamino)-acetamide

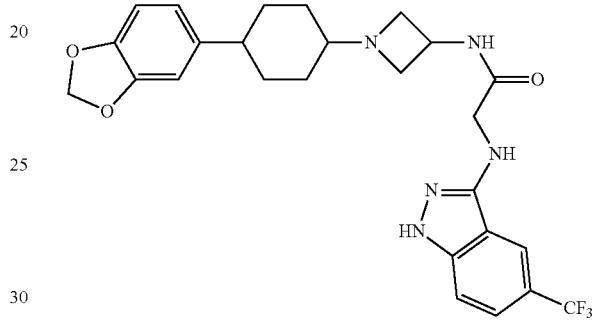

The title compound was prepared as a white solid from reaction of N-azetidin-3-yl-2-(5-trifluoromethyl-1H-indazol-3-ylamino)-acetamide (as prepared in Example 41, Step A) and 4-benzo[1,3]dioxol-5-yl-cyclohexanone using the procedure described in Step E of Example 1.

The less polar isomer from the silica gel column was tested in vitro as described in Example 107.

$^1$H NMR (400 MHz, d$_4$-MeOH) δ: 8.11 (s, 1H), 8.02 (d, J=6.8 Hz, 1H), 7.85 (m, 1H), 7.74 (d, J=7.0 Hz, 2H), 7.55 (t, J=6.8 Hz, 1H), 7.40 (d, J=7.0 Hz, 1H), 6.72 (d, J=6.5 Hz, 1H), 6.70 (s, 1H), 6.62 (d, J=6.2 Hz, 1H), 5.92 (s, 2H), 4.53 (m, 1H), 4.01 (s, 2H), 3.88 (s, 3H), 3.65 (t, J=6.5 Hz, 2H), 2.98 (t, J=6.0 Hz, 2H), 2.55 (m, 1H), 2.18 (m, 2H), 1.85 (m, 2H), 1.45 (m, 2H), 1.25 (m, 2H).

Example 46

N-{1-[4-(6-Methoxy-pyridin-3-yl)-cyclohexyl]-azetidin-3-yl}-2-(5-trifluoromethyl-1H-indazol-3-ylamino)-acetamide

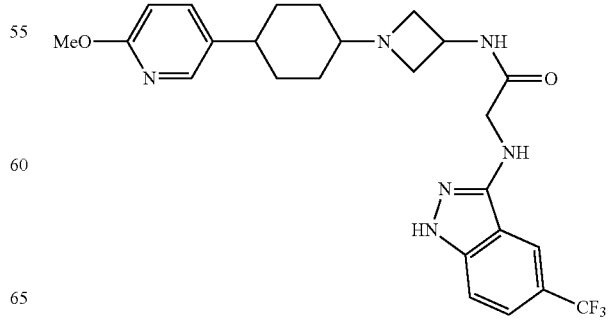

The title compound was prepared as a white solid from reaction of N-azetidin-3-yl-2-(5-trifluoromethyl-1H-indazol-3-ylamino)-acetamide (as prepared in Example 41, Step A) and 4-(6-methoxy-pyridin-3-yl)-cyclohexanone using the procedure described in Step E of Example 1.

The less polar isomer from the silica gel column was tested in vitro as described in Example 107.

MS: 503 (MH+).

Example 47

2-[4-(4-{3-[2-(5-Trifluoromethyl-1H-indazol-3-ylamino)-acetylamino]-azetidin-1-yl}-cyclohexyl)-phenyl]-acetamide

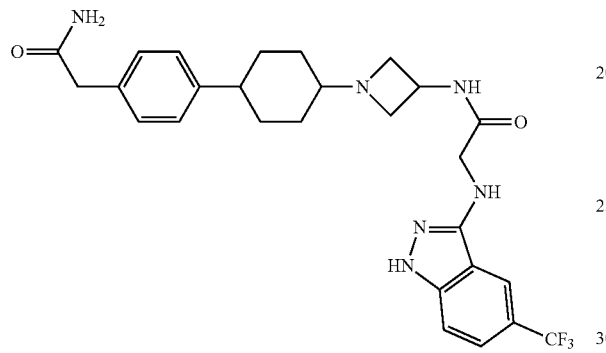

The title compound was prepared as a white solid from reaction of N-azetidin-3-yl-2-(5-trifluoromethyl-1H-indazol-3-ylamino)-acetamide (as prepared in Example 41, Step A) and 2-[4-(4-oxo-cyclohexyl)-phenyl]-acetamide using the procedure described in Step E of Example 1.

The less polar isomer from the silica gel column was tested in vitro as described in Example 107.

$^1$H NMR (400 MHz, d$_4$-MeOH) δ 8.11 (s, 1H), 8.05 (d, J=6.5 Hz, 1H), 7.75 (d, J=6.0 Hz, 1H), 7.60 (d, J=6.5 Hz, 1H), 7.10 (s, 4H), 4.55 (m, 1H), 4.01 (s, 2H), 3.58 (t, J=6.5 Hz, 2H), 3.02 (t, J=6.6 Hz, 2H), 2.55 (m, 1H), 2.35 (m, 1H), 2.20 (m, 2H), 1.80 (m, 2H), 1.65 (m, 2H), 1.45 (m, 2H).

Example 48

N-[1-(4-Cyano-cyclohexyl)-azetidin-3-yl]-2-(5-trifluoromethyl-1H-indazol-3-ylamino)-acetamide

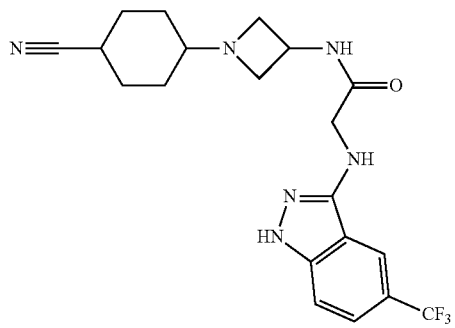

The title compound was prepared as a white solid from reaction of N-azetidin-3-yl-2-(5-trifluoromethyl-1H-indazol-3-ylamino)-acetamide (as prepared in Example 41, Step A) and 4-cyano-cyclohexanone using the procedure described in Step E of Example 1.

The less polar isomer from the silica gel column was tested in vitro as described in Example 107.

$^1$H NMR (400 MHz, d$_4$-MeOH) δ: 8.11 (s, 1H), 7.55 (d, J=6.0 Hz, 1H), 7.40 (d, J=6.0 Hz, 1H), 4.50 (m, 1H), 4.06 (s, 2H), 3.66 (t, J=7.0 Hz, 2H), 3.10 (t, J=7.1 Hz, 2H), 2.45 (m, 1H), 2.30 (m, 2H), 2.05 (m, 1H), 1.78 (m, 2H), 1.65 (m, 2H), 1.38 (m, 2H).

Example 49

N-[1-(4-Methoxymethyl-cyclohexyl)-azetidin-3-yl]-2-(5-trifluoromethyl-1H-indazol-3-ylamino)-acetamide

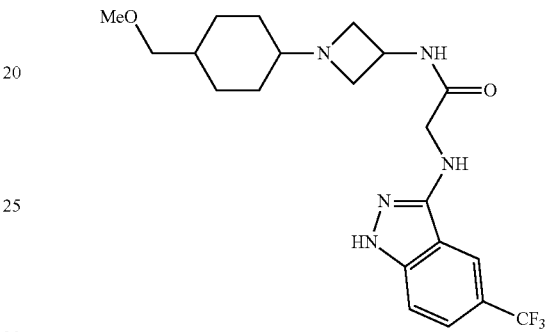

The title compound was prepared as a white solid from reaction of N-azetidin-3-yl-2-(5-trifluoromethyl-1H-indazol-3-ylamino)-acetamide (as prepared in Example 41, Step A) and 4-methoxymethyl-cyclohexanone (following the procedure described in Example 34, substituting methyl iodide for ethyl iodide) using the procedure described in Step E of Example 1.

The less polar isomer from the silica gel column was isolated and characterized by NMR.

$^1$H NMR (400 MHz, d$_4$-MeOH) δ: 8.15 (s, 1H), 7.60 (d, J=7.5 Hz, 1H), 7.41 (d, J=7.3 Hz, 1H), 4.50 (m, 1H), 4.05 (s, 2H), 3.62 (t, J=6.0 Hz, 2H), 3.35 (s, 3H), 3.30 (d, J=7.0 Hz, 2H), 3.00 (t, J=6.0 Hz, 2H), 2.30 (m, 3H), 1.85 (m, 2H), 1.70 (m, 2H), 1.50 (m, 2H).

Example 50

4-{3-[2-(5-Trifluoromethyl-1H-indazol-3-ylamino)-acetylamino]-azetidin-1-yl}-cyclohexane carboxylic acid ethyl ester

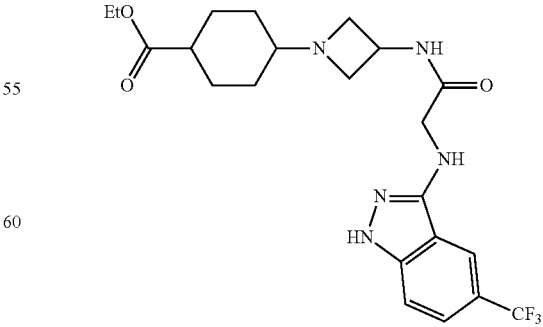

The title compound was prepared as a white solid from reaction of N-azetidin-3-yl-2-(5-trifluoromethyl-1H-indazol-3-ylamino)-acetamide (as prepared in Example 41, Step A) and 4-oxo-cyclohexanecarboxylic acid ethyl ester using the procedure described in Step E of Example 1.

The less polar isomer from the silica gel column was tested in vitro as described in Example 107.

$^1$H NMR (400 MHz, d$_4$-MeOH) δ: 8.15 (s, 1H), 7.55 (d, J=6.0 Hz, 1H), 7.44 (d, J=6.5 Hz, 1H), 4.41 (m, 1H), 4.15 (q, J=8.5 Hz, 2H), 4.06 (s, 2H), 3.61 (t, J=7.0 Hz, 2H), 2.95 (t, J=7.0 Hz, 2H), 2.50 (m, 1H), 2.25 (m, 1H), 2.08 (m, 2H), 1.62 (m, 4H), 1.35 (m, 2H), 1.25 9 t, J=8.5 Hz, 3H).

Example 51

(4-{3-[2-(5-Trifluoromethyl-1H-indazol-3-ylamino)-acetylamino]-azetidin-1-yl}-cyclohexyl)-carbamic acid tert-butyl ester

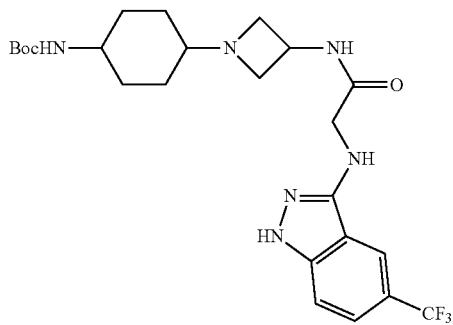

The title compound was prepared as a white solid from reaction of N-azetidin-3-yl-2-(5-trifluoromethyl-1H-indazol-3-ylamino)-acetamide (as prepared in Example 41, Step A) and (4-oxo-cyclohexyl)-carbamic acid tert-butyl ester using the procedure described in Step E of Example 1.

The less polar isomer from the silica gel column was tested in vitro as described in Example 107.

$^1$H NMR (400 MHz, d$_4$-MeOH) δ: 8.15 (s, 1H), 7.56 (d, J=6.0 Hz, 1H), 7.42 (d, J=6.0 Hz, 1H), 4.51 (m, 1H), 4.42 (m, 1H), 4.02 (s, 2H), 3.70 (t, J=5.0 Hz, 2H), 3.55 (br, s, 1H), 2.95 (t, J=7.5 Hz, 2H), 2.22 (m, 1H), 1.72 (m, 2H), 1.58 (m, 4H), 1.49 (s, 9H), 1.35 (m, 2H).

Example 52

N-[1-(4-Isopropyl-cyclohexyl)-azetidin-3-yl]-2-(5-trifluoromethyl-1H-indazol-3-ylamino)-acetamide

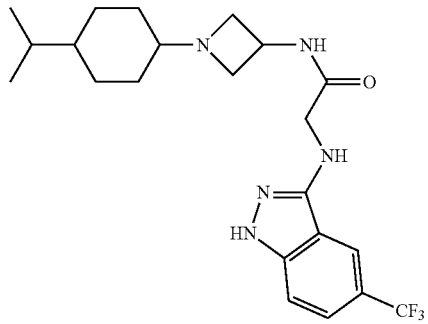

The title compound was prepared as a white solid from reaction of N-azetidin-3-yl-2-(5-trifluoromethyl-1H-indazol-3-ylamino)-acetamide (as prepared in Example 41, Step A) and 4-isopropyl-cyclohexanone using the procedure described in Step E of Example 1.

The less polar isomer from the silica gel column was tested in vitro as described in Example 107.

$^1$H NMR (400 MHz, d$_4$-MeOH) δ: 8.16 (s, 1H), 7.55 (d, J=6.0 Hz, 1H), 7.42 (d, J=6.0 Hz, 1H), 4.02 (, 2H), 3.78 (t, J=5.5 Hz, 3H), 3.15 (t, J=5.5 Hz, 2H), 2.48 (m, 1H), 1.50 (m, 8H), 1.15 (m, 1H), 0.90 (d, J=8.5 Hz, 6H).

Example 53

N-{1-[4-(2-Oxo-2H-pyridin-1-yl)-cyclohexyl]-azetidin-3-yl}-2-(5-trifluoromethyl-1H-indazol-3-ylamino)-acetamide

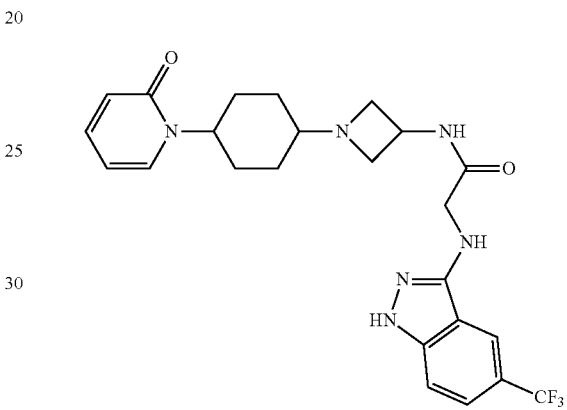

The title compound was prepared as a white solid from reaction of N-azetidin-3-yl-2-(5-trifluoromethyl-1H-indazol-3-ylamino)-acetamide and 1-(4-oxo-cyclohexyl)-1H-pyridin-2-one using the procedure described in Step E of Example 1.

MS: 489 (MH$^+$).

Example 54

N-[1-(4-Hydroxy-4-thiazol-2-yl-cyclohexyl)-azetidin-3-yl]-2-(1-methyl-5-trifluoromethoxy-1H-indazol-3-ylamino)-acetamide

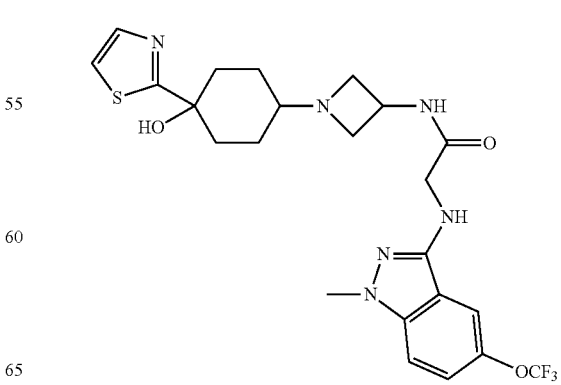

Step A

N-Azetidin-3-yl-2-(1-methyl-5-trifluoromethoxy-1H-indazol-3-ylamino)-acetamide

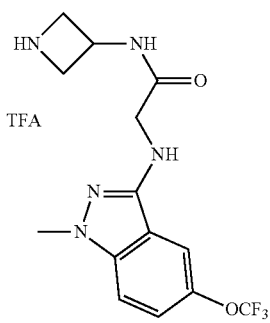 [SMILES: Cn1nc(NCC(=O)NC2CNC2)c2cc(OC(F)(F)F)ccc21]

The title compound was prepared from methyl hydrazine and 2-fluoro-5-trifluoromethoxy-benzonitrile according to the procedures described in Example 18 (A to D) as a colorless oil.

MS: 344 (MH$^+$).

Step B

N-[1-(4-Hydroxy-4-thiazol-2-yl-cyclohexyl)-azetidin-3-yl]-2-(1-methyl-5-trifluoromethoxy-1H-indazol-3-ylamino)-acetamide

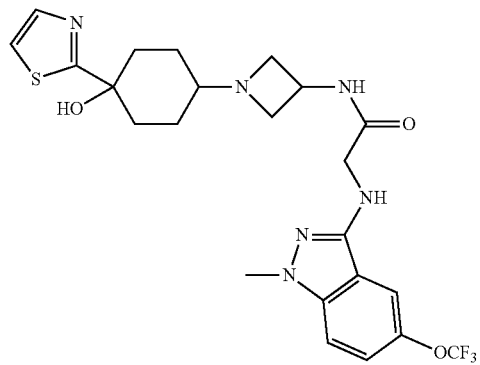 [SMILES: Cn1nc(NCC(=O)NC2CN(C3CCC(O)(c4nccs4)CC3)C2)c2cc(OC(F)(F)F)ccc21]

The title compound was prepared as a white solid from reaction of N-azetidin-3-yl-2-(1-methyl-5-trifluoromethoxy-1H-indazol-3-ylamino)-acetamide (as prepared in the previous step) and 4-hydroxy-4-thiazol-2-yl-cyclohexanone using the procedure described in Step E of Example 1.

The less polar isomer from the silica gel column was tested in vitro as described in Example 107.

$^1$H NMR (400 MHz, CDCl$_3$) δ: 8.14 (s, 1H), 8.05 (d, J=6.0 Hz, 1H), 7.72 (d, J=6.5 Hz, 1H), 7.65 (m, 1H), 7.62 (s, 1H), 7.52 (t, J=6.8 Hz, 1H), 7.40 (d, J=6.0 Hz, 1H), 7.18 (d, J=6.2 Hz, 1H), 4.53 (m, 1H), 4.05 (d, J=6.7 Hz, 2H), 3.80 (s, 3H), 3.50 (t, J=7.0 Hz, 2H), 2.98 (t, J=7.0 Hz, 2H), 2.30 (m, 2H), 1.81 (m, 2H), 1.68 (m, 2H), 1.48 (m, 2H).

Example 55

N-[1-(4-Hydroxy-4-thiazol-5-yl-cyclohexyl)-azetidin-3-yl]-2-(1-methyl-5-trifluoromethoxy-1H-indazol-3-ylamino)-acetamide

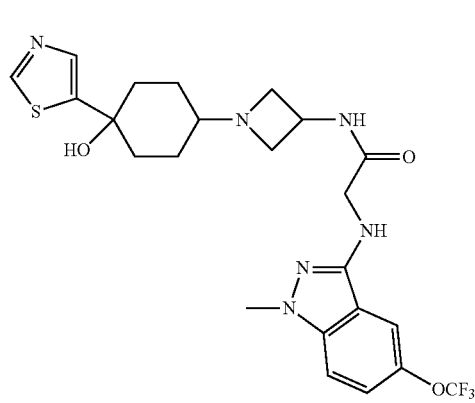 [SMILES: Cn1nc(NCC(=O)NC2CN(C3CCC(O)(c4cncs4)CC3)C2)c2cc(OC(F)(F)F)ccc21]

The title compound was prepared as a white solid from reaction of N-azetidin-3-yl-2-(1-methyl-5-trifluoromethoxy-1H-indazol-3-ylamino)-acetamide (as prepared in Example 54, Step A) and 4-hydroxy-4-thiazol-2-yl-cyclohexanone using the procedure described in Step E of Example 1.

The less polar isomer from the silica gel column was tested in vitro as described in Example 107.

$^1$H NMR (400 MHz, d$_4$-MeOH) δ: 8.95 (s, 1H), 8.18 (s, 1H), 8.15 (d, J=6.3 Hz, 1H), 7.85 (d, J=6.5 Hz, 1H), 7.80 (s, 1H), 7.66 (t, J=6.5 Hz, 1H), 4.53 (m, 1H), 4.00 (s, 2H), 3.87 (s, 3H), 3.58 (t, J=7.0 Hz, 2H), 3.02 (t, J=7.0 Hz, 2H), 2.35 (s, br, 1H), 2.25 (m, 2H), 1.90 (m, 2H), 1.82 (m, 2H), 1.38 (m, 2H).

Example 56

2-{1-[4-(2-Ethyl-thiazol-5-yl)-4-hydroxy-cyclohexyl]-azetidin-3-ylamino}-N-(1-methyl-5-trifluoromethoxy-1H-indazol-3-yl)-acetamide

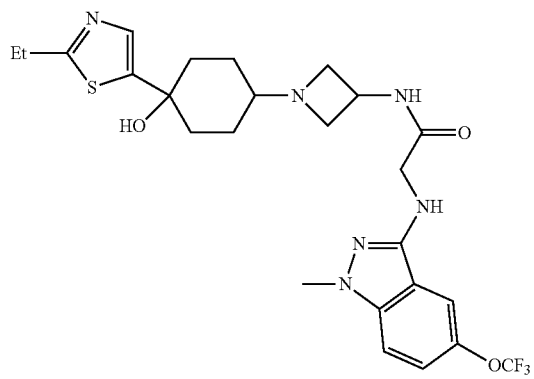 [SMILES: CCc1ncc(C2(O)CCC(N3CC(NC(=O)CNc4nn(C)c5ccc(OC(F)(F)F)cc45)C3)CC2)s1]

The title compound was prepared as a white solid from reaction of N-azetidin-3-yl-2-(1-methyl-5-trifluoromethoxy-1H-indazol-3-ylamino)-acetamide (as prepared in Example 41, Step A) and 4-(5-ethyl-thiazol-2-yl)-4-hydroxy-cyclohexanone using the procedure described in Step E of Example 1.

The less polar isomer from the silica gel column was tested in vitro as described in Example 107.

$^1$H NMR (400 MHz, d$_4$-MeOH) δ: 7.65 (s, 1H), 7.55 (d, J=5.6 Hz, 2H), 7.37 (d, J=9.1 Hz, 1H), 7.24-7.31 (m, 1H), 4.45-4.53 (m, 1H), 4.39 (quin, J=7.1 Hz, 1H), 3.98 (s, 2H), 3.83 (s, 3H), 3.63 (q, J=7.1 Hz, 3H), 2.99 (q, J=7.4 Hz, 3H), 3.00 (q, J=7.6 Hz, 3H), 2.92 (t, J=7.7 Hz, 2H), 2.27-2.36 (m, 2H), 2.13-2.26 (m, 4H), 2.03 (d, J=1.8 Hz, 2H), 1.94 (s, 2H), 1.69-1.89 (m, 7H), 1.36 (td, J=7.6, 3.8 Hz, 7H).

Example 57

2-{1-[4-Hydroxy-4-(6-methoxy-pyridin-3-yl)-cyclohexyl]-azetidin-3-ylamino}-N-(1-methyl-5-trifluoromethoxy-1H-indazol-3-yl)-acetamide

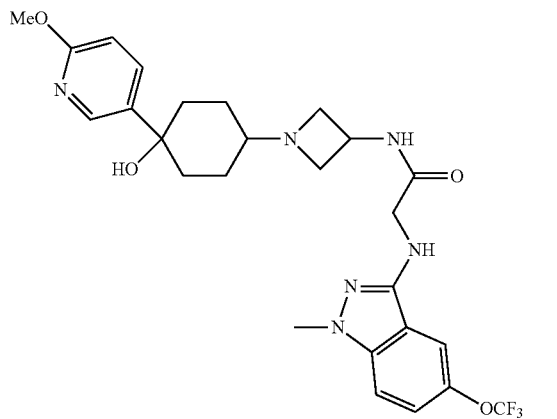 [SMILES: COc1ccc(C2(O)CCC(N3CC(NC(=O)CNc4nn(C)c5ccc(OC(F)(F)F)cc45)C3)CC2)cn1]

The title compound was prepared as a white solid from reaction of N-azetidin-3-yl-2-(1-methyl-5-trifluoromethoxy-1H-indazol-3-ylamino)-acetamide (as prepared in Example 41, Step A) and 4-hydroxy-4-(6-methoxy-pyridin-3-yl)-cyclohexanone using the procedure described in Step E of Example 1.

The less polar isomer from the silica gel column was tested in vitro as described in Example 107.

$^1$H NMR (400 MHz, d$_4$-MeOH) δ: 8.27 (dd, J=5.8, 2.5 Hz, 1H), 7.75-7.96 (m, 1H), 7.66 (s, 1H), 7.37 (d, J=9.1 Hz, 1H), 7.28 (d, J=8.3 Hz, 1H), 6.78 (dd, J=8.3, 6.1 Hz, 1H), 4.52 (t, J=7.1 Hz, 1H), 4.43 (t, J=7.1 Hz, 1H), 4.03-4.21 (m, 1H), 4.00 (s, 2H), 3.90 (s, 4H), 3.83 (s, 2H), 3.66 (q, J=7.0 Hz, 2H), 3.33 (s, 4H), 2.99 (t, J=7.6 Hz, 1H), 2.91 (t, J=7.7 Hz, 1H), 2.37 (br. s., 1H), 2.20 (d, J=10.4 Hz, 2H), 1.95 (s, 2H), 1.88 (d, J=10.1 Hz, 2H), 1.57 (d, J=13.4 Hz, 3H), 1.39 (d, J=7.3 Hz, 3H).

Example 58

4-(3-{[(1-Methyl-5-trifluoromethoxy-1H-indazol-3-ylcarbamoyl)-methyl]-amino}-azetidin-1-yl)-cyclohexanecarboxylic acid ethyl ester

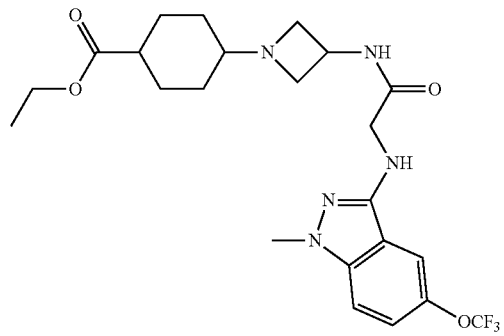 [SMILES: CCOC(=O)C1CCC(N2CC(NC(=O)CNc3nn(C)c4ccc(OC(F)(F)F)cc34)C2)CC1]

The title compound was prepared as a white solid from reaction of N-azetidin-3-yl-2-(1-methyl-5-trifluoromethoxy-1H-indazol-3-ylamino)-acetamide (as prepared in Example 41, Step A) and 4-oxo-cyclohexanecarboxylic acid ethyl ester using the procedure described in Step E of Example 1.

The less polar isomer from the silica gel column was tested in vitro as described in Example 107.

$^1$H NMR (400 MHz, d$_4$-MeOH) δ: 7.65 (s, 1H), 7.32-7.40 (m, 1H), 7.21-7.31 (m, 1H), 4.48 (quin, J=6.9 Hz, 1H), 4.08-4.18 (m, 3H), 3.99 (s, 2H), 3.82 (s, 3H), 3.56-3.69 (m, 3H), 3.28-3.38 (m, 3H), 2.94-3.03 (m, 2H), 2.92 (d, J=7.1 Hz, 1H), 2.46-2.57 (m, 1H), 2.12-2.24 (m, 2H), 2.03 (d, J=1.8 Hz, 3H), 1.94 (d, J=7.3 Hz, 2H), 1.46-1.64 (m, 6H), 1.23-1.29 (m, 5H)

Example 59

2-[1-(4-Isopropyl-cyclohexyl)-azetidin-3-ylamino]-N-(1-methyl-5-trifluoromethoxy-1H-indazol-3-yl)-acetamide

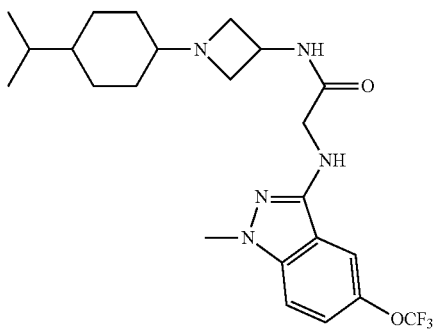 [SMILES: CC(C)C1CCC(N2CC(NC(=O)CNc3nn(C)c4ccc(OC(F)(F)F)cc34)C2)CC1]

The title compound was prepared as a white solid from reaction of N-azetidin-3-yl-2-(1-methyl-5-trifluoromethoxy-1H-indazol-3-ylamino)-acetamide (as prepared in Example 41, Step A) and 4-isopropyl-cyclohexanone using the procedure described in Step E of Example 1.

The less polar isomer from the silica gel column was tested in vitro as described in Example 107.

¹H NMR (400 MHz, d₄-MeOH) δ: 7.66 (s, 1H), 7.36 (s, 1H), 7.20-7.32 (m, 1H), 4.46-4.58 (m, 1H), 4.41 (t, J=7.2 Hz, 1H), 3.99 (s, 2H), 3.83 (s, 3H), 3.51-3.70 (m, 4H), 2.94 (d, J=1.5 Hz, 2H), 2.86 (t, J=7.8 Hz, 1H), 2.25 (br. s., 2H), 1.94 (s, 2H), 1.31-1.60 (m, 16H), 0.89 (t, J=6.9 Hz, 11H).

Example 60

4-(3-{2-[1-Methyl-5-(2,2,2-trifluoro-1-hydroxy-ethyl)-1H-indazol-3-ylamino]-acetylamino}-azetidin-1-yl)-cyclohexanecarboxylic acid ethyl ester

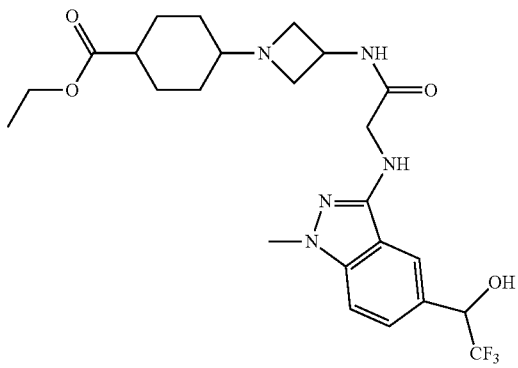 [SMILES: CCOC(=O)C1CCC(N2CC(NC(=O)CNc3nn(C)c4ccc(C(O)C(F)(F)F)cc34)C2)CC1]

Step A

2-Fluoro-5-(2,2,2-trifluoro-1-hydroxy-ethyl)-benzonitrile

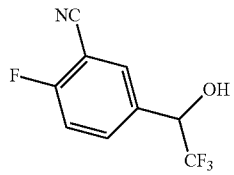

2-Fluoro-5-formyl-benzonitrile (5 g, 33.5 mmol) and CsF (51 mg, 0.335 mmol) in THF (10 mL) were treated with TMSCF₃ (4.77 g, 33.5 mmol) at room temperature for 2 hours. The reaction was then treated with 4 N HCl (5 mL) and stirred at room temperature for 30 min. The solvent was removed and the residue was partitioned between ether and water. The organic layer was washed with brine, dried over anhydrous Na₂SO₄, filtered and concentrated to give the crude material, purified by silica gel column (hexanes:ethyl acetate 3:1) to afford the title compound as colorless solid (4.5 g, 61%).

¹H NMR (400 MHz, CDCl₃) δ: 7.80 (d, J=6.5 Hz, 1H), 7.75 (d, J=6.0 Hz, 1H), 7.30 (t, J=8.5 Hz, 1H), 5.10 (q, J=6.0 Hz, 1H).

Step B

N-Azetidin-3-yl-2-[1-methyl-5-(2,2,2-trifluoro-1-hydroxy-ethyl)-1H-indazol-3-ylamino]-acetamide TFA salt

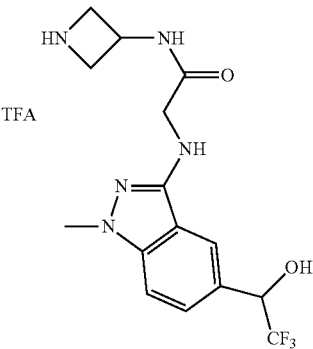 [SMILES: Cn1nc(NCC(=O)NC2CNC2)c2cc(C(O)C(F)(F)F)ccc21]

The title compound was prepared from starting material hydrazine and 2-fluoro-5-(2,2,2-trifluoro-1-hydroxy-ethyl)-benzonitrile by following the sequences described in Example 18 (A to D) as a colorless oil.

MS: 358 (MH⁺).

Step C 4-(3-{2-[1-Methyl-5-(2,2,2-trifluoro-1-hydroxy-ethyl)-1H-indazol-3-ylamino]-acetylamino}-azetidin-1-yl)-cyclohexanecarboxylic acid ethyl ester

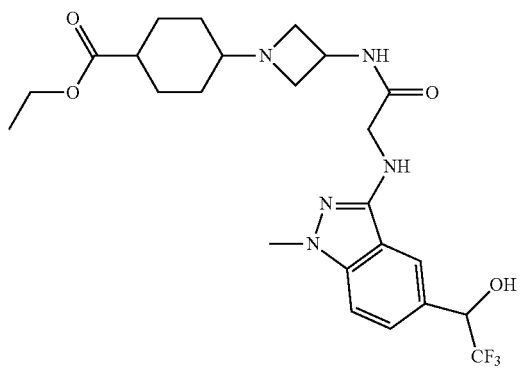 [SMILES: CCOC(=O)C1CCC(N2CC(NC(=O)CNc3nn(C)c4ccc(C(O)C(F)(F)F)cc34)C2)CC1]

The title compound was prepared as a white solid from reaction of N-azetidin-3-yl-2-[1-methyl-5-(2,2,2-trifluoro-1-hydroxy-ethyl)-1H-indazol-3-ylamino]-acetamide TFA salt (as prepared in the previous step) and 4-oxo-cyclohexanecarboxylic acid ethyl ester using the procedure described in Step E of Example 1.

The less polar isomer from the silica gel column was tested in vitro as described in Example 107.

¹H NMR (400 MHz, d₄-MeOH) δ: 7.72 (s, 1H), 7.37 (d, J=8.6 Hz, 1H), 7.19 (d, J=8.6 Hz, 1H), 4.98 (q, J=7.1 Hz, 1H), 4.36 (t, J=6.9 Hz, 1H), 4.27 (d, J=17.4 Hz, 1H), 4.00 (qd,

J=7.1, 2.7 Hz, 5H), 3.87 (s, 2H), 3.69 (s, 3H), 3.54 (t, J=7.8 Hz, 2H), 3.48 (t, J=7.7 Hz, 3H), 2.77-2.93 (m, 4H), 2.38 (t, J=4.9 Hz, 2H), 2.11-2.17 (m, 1H), 2.00-2.10 (m, 2H), 1.85-1.97 (m, 6H), 1.35-1.50 (m, 6H), 1.07-1.16 (m, 9H).

Example 61

N-[1-(4-Hydroxy-4-thiazol-5-yl-cyclohexyl)-azetidin-3-yl]-2-[1-methyl-5-(2,2,2-trifluoro-1-hydroxyethyl)-1H-indazol-3-ylamino]-acetamide

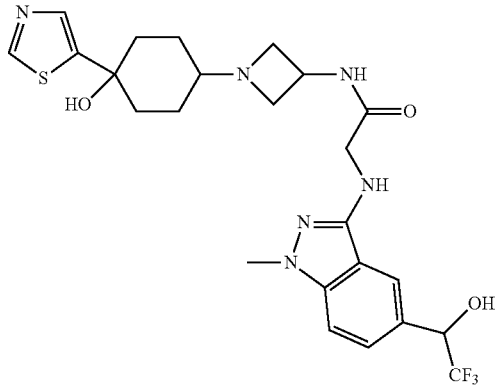 [SMILES: Cn1nc(NCC(=O)NC2CN(C3CCC(O)(c4cncs4)CC3)C2)c2cc(C(O)C(F)(F)F)ccc21]

The title compound was prepared as a white solid from reaction of N-azetidin-3-yl-2-[1-methyl-5-(2,2,2-trifluoro-1-hydroxy-ethyl)-1H-indazol-3-ylamino]-acetamide TFA salt (as prepared in Example 60, Step B) and 4-hydroxy-4-thiazol-5-yl-cyclohexanone using the procedure described in Step E of Example 1.

The less polar isomer from the silica gel column was tested in vitro as described in Example 107.

$^{1}$H NMR (400 MHz, d$_{4}$-MeOH) δ: 8.89 (s, 1H), 7.82 (s, 1H), 7.79 (s, 1H), 7.55 (d, J=7.1 Hz, 1H), 7.29 (d, J=7.1 Hz, 1H), 5.10 (m, 1H), 4.51 (m, 1H), 4.03 (s, 2H), 3.81 (s, 3H), 3.61 (t, J=7.5 Hz, 2H), 2.98 (t, J=7.5 Hz, 2H), 2.40 (m, 1H), 2.20 (m, 2H), 1.91 (m, 2H), 1.72 (m, 2H), 1.35 (m, 2H).

Example 62

N-{1-[4-(2-Ethyl-thiazol-5-yl)-4-hydroxy-cyclohexyl]-azetidin-3-yl}-2-[1-methyl-5-(2,2,2-trifluoro-1-hydroxy-ethyl)-1H-indazol-3-ylamino]-acetamide

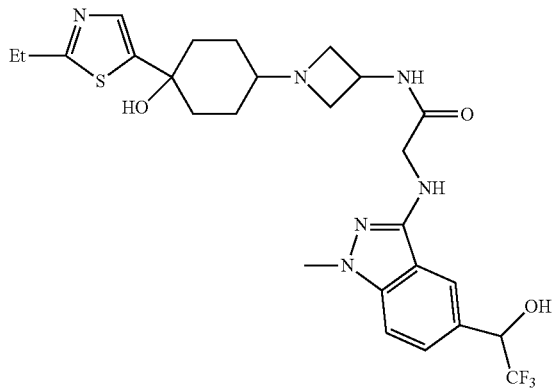 [SMILES: CCc1ncc(C2(O)CCC(N3CC(NC(=O)CNc4nn(C)c5ccc(C(O)C(F)(F)F)cc45)C3)CC2)s1]

The title compound was prepared as a white solid from reaction of N-azetidin-3-yl-2-[1-methyl-5-(2,2,2-trifluoro-1-hydroxy-ethyl)-1H-indazol-3-ylamino]-acetamide TFA salt (as prepared in Example 60, Step B) and 4-(2-ethyl-thiazol-5-yl)-4-hydroxy-cyclohexanone using the procedure described in Step E of Example 1.

The less polar isomer from the silica gel column was tested in vitro as described in Example 107.

Example 63

N-{1-[4-Hydroxy-4-(6-methyl-pyridin-3-yl)-cyclohexyl]-azetidin-3-yl}-2-[1-methyl-5-(2,2,2-trifluoro-1-hydroxy-ethyl)-1H-indazol-3-ylamino]-acetamide

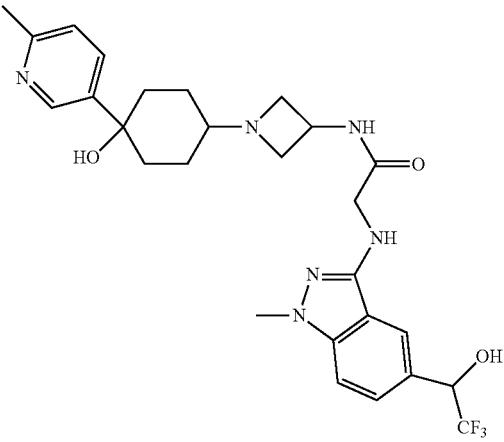 [SMILES: Cc1ccc(C2(O)CCC(N3CC(NC(=O)CNc4nn(C)c5ccc(C(O)C(F)(F)F)cc45)C3)CC2)cn1]

The title compound was prepared as a white solid from reaction of N-azetidin-3-yl-2-[1-methyl-5-(2,2,2-trifluoro-1-hydroxy-ethyl)-1H-indazol-3-ylamino]-acetamide TFA salt (as prepared in Example 60, Step B) and 4-hydroxy-4-(6-methyl-pyridin-3-yl)-cyclohexanone using the procedure described in Step E of Example 1.

The less polar isomer from the silica gel column was tested in vitro as described in Example 107.

$^{1}$H NMR (400 MHz, d$_{4}$-MeOH) δ: 8.55 (d, J=6.0 Hz, 1H), 7.90 (t, J=6.0 Hz, 1H), 7.85 (s, 1H), 7.48 (d, J=5.5 Hz, 1H), 7.30 (t, J=7.0 Hz, 1H), 7.24 (t, J=6.8 Hz, 1H), 5.10 (q, J=7.5 Hz, 1H), 4.50 (m, 1H), 4.05 (s, 2H), 3.80 (s, 3H), 3.65 (t, J=7.5 Hz, 2H), 2.98 (t, J=7.5 Hz, 2H), 2.55 (s, 3H), 2.42 (m, 1H), 2.20 (m, 2H), 1.95 (m, 2H), 1.60 (m, 2H), 1.45 (m, 2H).

Example 64

N-[1-(4-Benzo[1,3]dioxol-5-yl-cyclohexyl)-azetidin-3-yl]-2-[1-methyl-5-(2,2,2-trifluoro-1-hydroxy-ethyl)-1H-indazol-3-ylamino]-acetamide

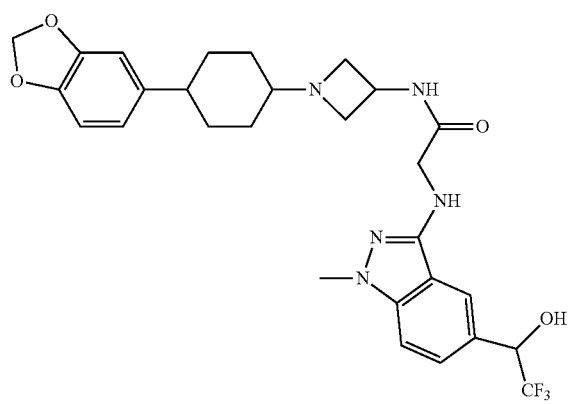 [SMILES: Cn1nc(NCC(=O)NC2CN(C3CCC(c4ccc5c(c4)OCO5)CC3)C2)c2cc(C(O)C(F)(F)F)ccc21]

The title compound was prepared as a white solid from reaction of N-azetidin-3-yl-2-[1-methyl-5-(2,2,2-trifluoro-1-hydroxy-ethyl)-1H-indazol-3-ylamino]-acetamide TFA salt (as prepared in Example 60, Step B) and 4-benzo[1,3]dioxol-5-yl-cyclohexanone using the procedure described in Step E of Example 1.

The less polar isomer from the silica gel column was tested in vitro as described in Example 107.

$^1$H NMR (400 MHz, d$_4$-MeOH) δ: 7.86 (s, 1H), 7.50 (d, J=8.8 Hz, 1H), 7.32 (d, J=8.8 Hz, 1H), 6.75-6.83 (m, 1H), 6.60-6.74 (m, 2H), 5.79-5.93 (m, 2H), 5.11 (d, J=7.1 Hz, 1H), 4.54 (d, J=7.1 Hz, 1H), 4.03-4.17 (m, 1H), 4.01 (s, 2H), 3.82 (s, 3H), 3.69 (t, J=6.6 Hz, 3H), 2.95-3.10 (m, 2H), 2.42 (d, J=7.3 Hz, 3H), 1.95 (s, 4H), 1.65-1.84 (m, 5H), 1.47-1.62 (m, 6H).

Example 65

N-[1-(4-Hydroxy-4-thiazol-5-yl-cyclohexyl)-azetidin-3-yl]-2-[1-methyl-5-(1,2,2,2-tetrafluoro-ethyl)-1H-indazol-3-ylamino]-acetamide

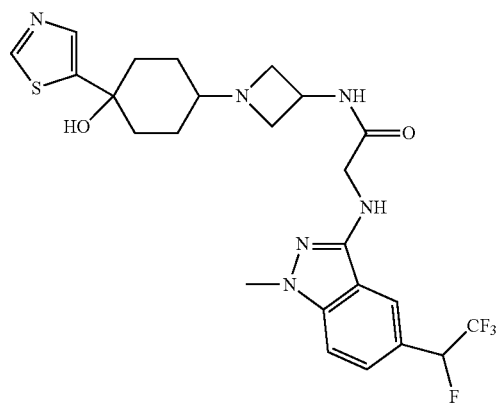 [SMILES: Cn1nc(NCC(=O)NC2CN(C3CCC(O)(c4cncs4)CC3)C2)c2cc(C(F)C(F)(F)F)ccc21]

Step A

2-Fluoro-5-(1,2,2,2-tetrafluoro-ethyl)-benzonitrile

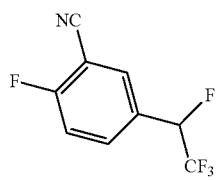 [SMILES: N#Cc1cc(C(F)C(F)(F)F)ccc1F]

2-Fluoro-5-(2,2,2-trifluoro-1-hydroxy-ethyl)-benzonitrile (1 g, 4.56 mmol) in DCM (5 mL) was treated with DAST (Aldrich, 1.12 mL, 9.13 mmol) at −78° C. for 2 hours. The reaction was quenched with saturated NaHCO$_3$ and extracted with DCM. The organic layer was washed with brine, dried over anhydrous Na$_2$SO$_4$, filtered and concentrated to give the crude material, purified by silica gel column (hexanes:ethyl acetate 4:1) to afford the title compound as colorless solid (1.01 g, 100%).

MS: 222 (MH$^+$).

Step B

N-Azetidin-3-yl-2-[1-methyl-5-(1,2,2,2-tetrafluoro-ethyl)-1H-indazol-3-ylamino]-acetamide TFA salt

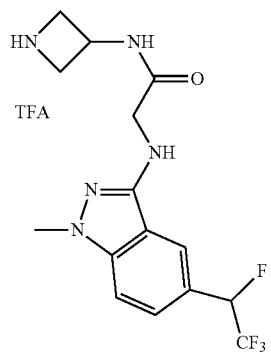 [SMILES: Cn1nc(NCC(=O)NC2CNC2)c2cc(C(F)C(F)(F)F)ccc21]

The title compound was prepared from starting material hydrazine and 2-fluoro-5-(1,2,2,2-tetrafluoro-ethyl)-benzonitrile by following the sequences described in Example 18 (A to D) as a colorless oil.

MS: 360 (MH$^+$).

Step C

N-[1-(4-Hydroxy-4-thiazol-5-yl-cyclohexyl)-azetidin-3-yl]-2-[1-methyl-5-(1,2,2,2-tetrafluoro-ethyl)-1H-indazol-3-ylamino]-acetamide

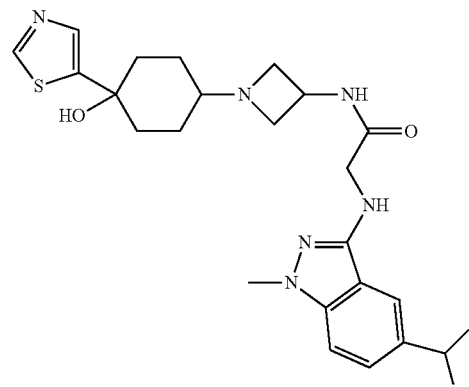

The title compound was prepared as a white solid from reaction of N-azetidin-3-yl-2-[1-methyl-5-(1,2,2,2-tetrafluoro-ethyl)-1H-indazol-3-ylamino]-acetamide TFA salt (as prepared in the previous step) and 4-hydroxy-4-thiazol-5-yl-cyclohexanone using the procedure described in Step E of Example 1.

The less polar isomer from the silica gel column was tested in vitro as described in Example 107.

$^1$H NMR (400 MHz, d$_4$-MeOH) δ: 8.90 (s, 1H), 7.95 (s, 1H), 7.85 (d, J=6.0 Hz, 1H), 7.50 (d, J=7.5 Hz, 1H), 7.38 (d, J=7.0 Hz, 1H), 7.05 (m, 0.5H), 6.95 (m, 0.5H), 4.52 (m, 1H), 4.01 (s, 2H), 3.88 (s, 3H), 3.60 (m, 2H), 3.05 (m, 2H), 2.38 (m, 1H), 2.20 (m, 2H), 1.80 (m, 2H), 1.73 (m, 2H), 1.40 (m, 2H).

Example 66

N-[1-(4-Hydroxy-4-thiazol-2-yl-cyclohexyl)-azetidin-3-yl]-2-[1-methyl-5-(1,2,2,2-tetrafluoro-ethyl)-1H-indazol-3-ylamino]-acetamide

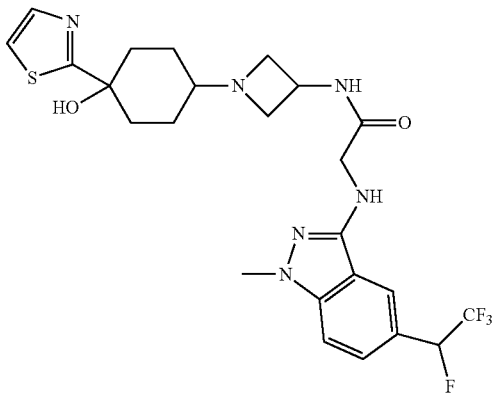 [SMILES: Cn1nc(NCC(=O)NC2CN(C3CCC(O)(c4nccs4)CC3)C2)c2cc(C(F)C(F)(F)F)ccc21]

The title compound was prepared as a white solid from reaction of N-azetidin-3-yl-2-[1-methyl-5-(1,2,2,2-tetrafluoro-ethyl)-1H-indazol-3-ylamino]-acetamide TFA salt (as prepared in Example 65, Step B) and 4-hydroxy-4-thiazol-2-yl-cyclohexanone using the procedure described in Step E of Example 1.

The less polar isomer from the silica gel column was tested in vitro as described in Example 107.

$^1$H NMR (400 MHz, CDCl$_3$) δ: 8.14 (s, 1H), 8.00 (d, J=6.0 Hz, 1H), 7.72 (d, J=6.5 Hz, 1H), 7.65 (m, 1H), 7.63 (s, 1H), 7.53 (t, J=6.8 Hz, 1H), 7.40 (d, J=6.0 Hz, 1H), 7.18 (d, J=6.2 Hz, 1H), 7.01 (m, 0.5H), 6.92 (m, 0.5H), 4.53 (m, 1H), 4.02 (d, J=3.7 Hz, 2H), 3.82 (s, 3H), 3.50 (t, J=7.0 Hz, 2H), 2.98 (t, J=7.0 Hz, 2H), 2.20 (m, 2H), 1.75 (m, 2H), 1.62 (m, 2H), 1.38 (m, 2H).

Example 67

2-(1-Ethyl-5-trifluoromethyl-1H-indazol-3-ylamino)-N-[1-(4-hydroxy-4-thiazol-5-yl-cyclohexyl)-azetidin-3-yl]-acetamide

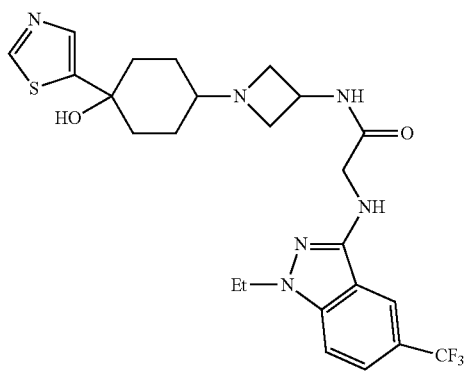 [SMILES: CCn1nc(NCC(=O)NC2CN(C3CCC(O)(c4cncs4)CC3)C2)c2cc(C(F)(F)F)ccc21]

Step A

N-Azetidin-3-yl-2-(1-ethyl-5-trifluoromethyl-1H-indazol-3-ylamino)-acetamide TFA salt

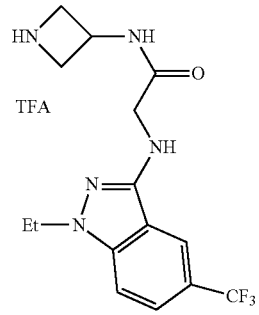 [SMILES: CCn1nc(NCC(=O)NC2CNC2)c2cc(C(F)(F)F)ccc21]

The title compound was prepared from ethyl hydrazine and 2-fluoro-5-(1,2,2,2-tetrafluoro-ethyl)-benzonitrile following the procedures described in Example 18 (A to D) as a colorless oil.

MS: 342 (MH$^+$).

Step B 2-(1-Ethyl-5-trifluoromethyl-1H-indazol-3-ylamino)-N-[1-(4-hydroxy-4-thiazol-5-yl-cyclohexyl)-azetidin-3-yl]-acetamide

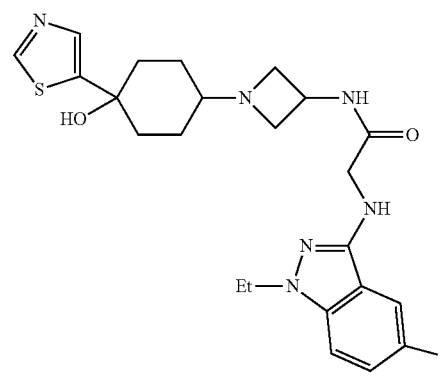

The title compound was prepared as a white solid from reaction of N-azetidin-3-yl-2-(1-ethyl-5-trifluoromethyl-1H-indazol-3-ylamino)-acetamide TFA salt (as prepared in the previous step) and 4-hydroxy-4-thiazol-5-yl-cyclohexanone using the procedure described in Step E of Example 1.

The less polar isomer from the silica gel column was tested in vitro as described in Example 107.

$^1$H NMR (400 MHz, d$_4$-MeOH) δ: 8.90 (s, 1H), 8.10 (s, 1H), 7.75 (s, 1H), 7.60 (d, J=6.0 Hz, 1H), 7.48 (d, J=6.0 Hz, 1H), 4.50 (m, 1H), 4.25 (t, J=4.5 Hz, 2H), 4.02 (s, 2H), 3.65 (t, J=5.0 Hz, 2H), 3.00 (t, J=5.0 Hz, 2H), 2.35 (m, 1H), 2.20 (m, 2H), 1.90 (m, 2H), 1.75 (m, 2H), 1.40 (t, J=6.5 Hz, 3H), 1.38 (m, 2H).

Example 68

2-(1-Ethyl-5-trifluoromethyl-1H-indazol-3-ylamino)-N-[1-(4-hydroxy-4-thiazol-2-yl-cyclohexyl)-azetidin-3-yl]-acetamide

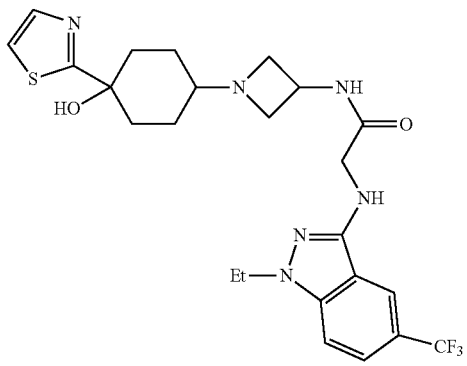 [SMILES: CCn1nc(NCC(=O)NC2CN(C3CCC(O)(c4nccs4)CC3)C2)c2cc(C(F)(F)F)ccc21]

The title compound was prepared as a white solid from reaction of N-azetidin-3-yl-2-(1-ethyl-5-trifluoromethyl-1H-indazol-3-ylamino)-acetamide TFA salt (as prepared in Example 67, Step A) and 4-hydroxy-4-thiazol-2-yl-cyclohexanone using the procedure described in Step E of Example 1.

The less polar isomer from the silica gel column was tested in vitro as described in Example 107.

$^1$H NMR (400 MHz, d$_4$-MeOH) δ: 7.75 (s, 1H), 7.67 (s, 1H), 7.56 (s, 1H), 7.52 (d, J=6.5 Hz, 1H), 7.34 (d, J=6.5 Hz, 1H), 4.55 (m, 1H), 4.20 (q, J=7.0 Hz, 2H), 4.01 (s, 2H), 3.75 (t, J=6.5 Hz, 2H), 3.10 (t, J=6.5 Hz, 2H), 2.45 (m, 3H), 1.85 (m, 2H), 1.60 (m, 2H), 1.30 (t, J=7.0 Hz, 3H), 1.25 (m, 2H).

Example 69

2-(1-Ethyl-5-trifluoromethyl-1H-indazol-3-ylamino)-N-{1-[4-hydroxy-4-(2-methyl-thiazol-5-yl)-cyclohexyl]-azetidin-3-yl}-acetamide

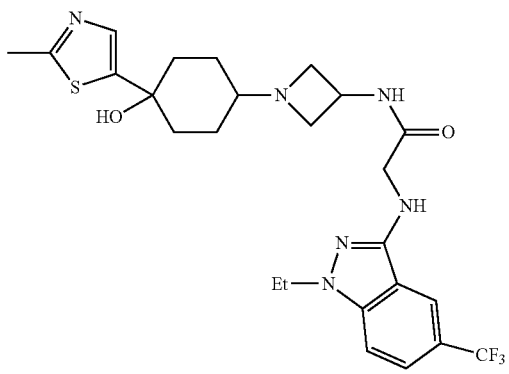 [SMILES: CCn1nc(NCC(=O)NC2CN(C3CCC(O)(c4cnc(C)s4)CC3)C2)c2cc(C(F)(F)F)ccc21]

The title compound was prepared as a white solid from reaction of N-azetidin-3-yl-2-(1-ethyl-5-trifluoromethyl-1H-indazol-3-ylamino)-acetamide TFA salt (as prepared in Example 67, Step A) and 4-hydroxy-4-(2-methyl-thiazol-5-yl)-cyclohexanone using the procedure described in Step E of Example 1.

The less polar isomer from the silica gel column was tested in vitro as described in Example 107.

$^1$H NMR (400 MHz, d$_4$-MeOH) δ: 8.45 (s, 1H), 8.15 (d, J=5.8 Hz, 1H), 8.07 (s, 1H), 7.58 (d, J=6.0 Hz, 1H), 4.52 (m, 1H), 4.25 (q, J=7.5 Hz, 2H), 4.01 (s, 2H), 3.52 (t, J=6.0 Hz, 2H), 2.92 (t, J=6.0 Hz, 2H), 2.45 (m, 1H), 2.32 (s, 3H), 2.02 (m, 2H), 1.80 (m, 4H), 1.30 (t, J=7.0 Hz, 3H), 1.25 (m, 2H).

Example 70

4-{3-[2-(1-Ethyl-5-trifluoromethyl-1H-indazol-3-ylamino)-acetylamino]-azetidin-1-yl}-cyclohexanecarboxylic acid ethyl ester

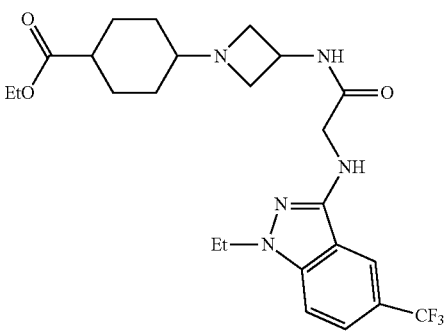 [SMILES: CCOC(=O)C1CCC(N2CC(NC(=O)CNc3nn(CC)c4ccc(C(F)(F)F)cc34)C2)CC1]

The title compound was prepared as a white solid from reaction of N-azetidin-3-yl-2-(1-ethyl-5-trifluoromethyl-1H-indazol-3-ylamino)-acetamide TFA salt (as prepared in Example 67, Step A) and 4-oxo-cyclohexanecarboxylic acid ethyl ester using the procedure described in Step E of Example 1.

The less polar isomer from the silica gel column was tested in vitro as described in Example 107.

$^1$H NMR (400 MHz, d$_4$-MeOH) δ: 8.11 (s, 1H), 7.56 (d, J=6.0 Hz, 1H), 7.48 (d, J=6.0 Hz, 1H), 4.51 (m, 1H), 4.25 (q, J=8.0 Hz, 2H), 4.14 (q, J=7.5 Hz, 2H), 4.05 (s, 2H), 3.62 (t, J=7.4 Hz, 2H), 3.05 (t, J=7.4 Hz, 2H), 2.51 (m, 1H), 2.20 (m, 1H), 2.05 (m, 2H), 1.56 (m, 4H), 1.40 (t, J=7.5 Hz, 3H), 1.25 (m, 2H), 1.20 (t, J=7.0 Hz, 3H).

Example 71

2-(1-Ethyl-5-trifluoromethyl-1H-indazol-3-ylamino)-N-[1-(4-isopropyl-cyclohexyl)-azetidin-3-yl]-acetamide

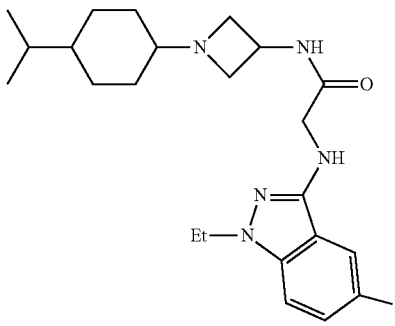

The title compound was prepared as a white solid from reaction of N-azetidin-3-yl-2-(1-ethyl-5-trifluoromethyl-1H-indazol-3-ylamino)-acetamide TFA salt (as prepared in Example 67, Step A) and 4-isopropyl-cyclohexanone using the procedure described in Step E of Example 1.

The less polar isomer from the silica gel column was tested in vitro as described in Example 107.

$^1$H NMR (400 MHz, $d_4$-MeOH) δ: 8.10 (s, 1H), 7.55 (d, J=6.0 Hz, 1H), 7.45 (d, J=6.0 Hz, 1H), 4.48 (m, 1H), 4.25 (q, J=8.0 Hz, 2H), 4.05 (s, 2H), 3.50 (t, J=7.4 Hz, 2H), 2.95 (t, J=7.4 Hz, 2H), 2.21 (m, 1H), 1.40 (m, 8H), 1.35 (t, J=7.5 Hz, 3H), 1.10 (m, 1H), 0.85 (t, J=7.0 Hz, 6H).

Example 72

4-(3-{2-[1-(2,2,2-Trifluoro-ethyl)-5-trifluoromethyl-1H-indazol-3-ylamino]-acetylamino}-azetidin-1-yl)-cyclohexane carboxylic acid ethyl ester

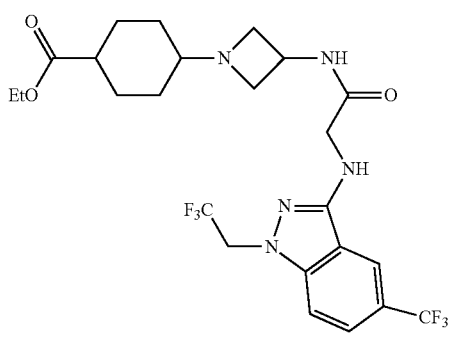 [SMILES: CCOC(=O)C1CCC(N2CC(NC(=O)CNc3nn(CC(F)(F)F)c4ccc(C(F)(F)F)cc34)C2)CC1]

Step A

N-(azetidin-3-yl)-2-((1-(2,2,2-trifluoroethyl)-5-(trifluoromethyl)-1H-indazol-3-yl)amino)acetamide TFA salt

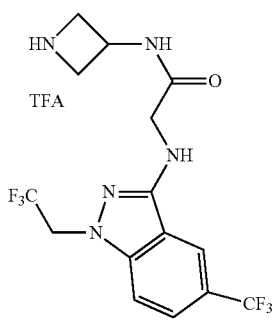 [SMILES: O=C(CNc1nn(CC(F)(F)F)c2ccc(C(F)(F)F)cc12)NC1CNC1]

The title compound was prepared from starting material (2,2,2-trifluoro-ethyl)-hydrazine and 2-fluoro-5-trifluoromethylbenzonitrile by following the sequences described in Example 18 (A to D) as a colorless oil.

MS: 382 (MH$^+$).

Step B 4-(3-{2-[1-(2,2,2-Trifluoro-ethyl)-5-trifluoromethyl-1H-indazol-3-ylamino]-acetylamino}-azetidin-1-yl)-cyclohexanecarboxylic acid ethyl ester

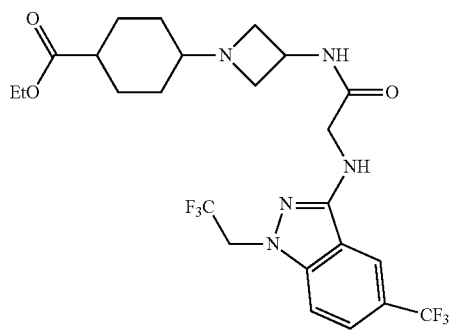 [SMILES: CCOC(=O)C1CCC(N2CC(NC(=O)CNc3nn(CC(F)(F)F)c4ccc(C(F)(F)F)cc34)C2)CC1]

The title compound was prepared as a white solid from reaction of N-(azetidin-3-yl)-2-((1-(2,2,2-trifluoroethyl)-5-(trifluoromethyl)-1H-indazol-3-yl)amino)acetamide TFA salt (as prepared in the previous step) and 4-oxo-cyclohexanecarboxylic acid ethyl ester using the procedure described in Step E of Example 1.

The less polar isomer from the silica gel column was tested in vitro as described in Example 107.

$^1$H NMR (400 MHz, $d_4$-MeOH) δ: 7.95 (s, 1H), 7.49 (d, J=7.0 Hz, 1H), 7.35 (d, J=7.0 Hz, 1H), 5.12 (q, J=9.5 Hz, 2H), 4.48 (m, 1H), 4.21 (s, 2H), 4.12 (q, J=10.0 Hz, 2H), 3.60 (t, J=6.5 Hz, 2H), 2.95 (t, J=6.5 Hz, 2H), 2.50 (m, 1H), 2.20 (m, 2H), 2.10 (m, 1H), 1.70 (m, 4H), 1.35 (m, 2H), 1.28 (t, J=9.5 Hz, 3H).

Example 73

N-{1-[4-(2-Ethyl-thiazol-5-yl)-4-hydroxy-cyclohexyl]-azetidin-3-yl}-2-[1-(2,2,2-trifluoro-ethyl)-5-trifluoromethyl-1H-indazol-3-ylamino]-acetamide

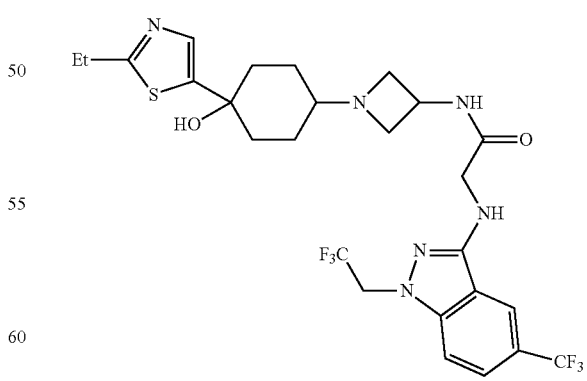

The title compound was prepared as a white solid from reaction of N-(azetidin-3-yl)-2-((1-(2,2,2-trifluoroethyl)-5-(trifluoromethyl)-1H-indazol-3-yl)amino)acetamide TFA salt (as prepared in Example 72, Step A) and 4-(2-ethylthiazol-5-yl)-4-hydroxy-cyclohexanone using the procedure described in Step E of Example 1.

The less polar isomer from the silica gel column was tested in vitro as described in Example 107.

MS: 605 (MH+).

Example 74

2-[1-(2-Hydroxy-ethyl)-5-trifluoromethyl-1H-indazol-3-ylamino]-N-{1-[4-hydroxy-4-(6-methyl-pyridin-3-yl)-cyclohexyl]-azetidin-3-yl}-acetamide

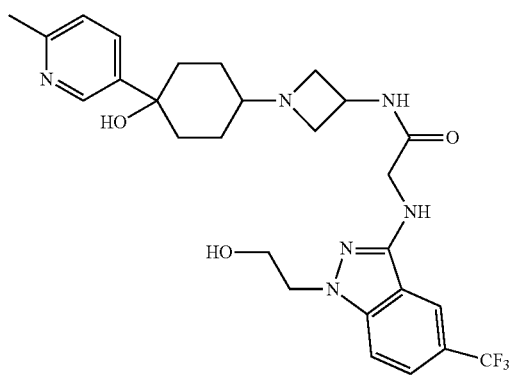 [SMILES: Cc1ccc(C2(O)CCC(N3CC(NC(=O)CNc4nn(CCO)c5ccc(C(F)(F)F)cc45)C3)CC2)cn1]

Step A

N-Azetidin-3-yl-2-[1-(2-hydroxy-ethyl)-5-trifluoromethyl-1H-indazol-3-ylamino]-acetamide TFA salt

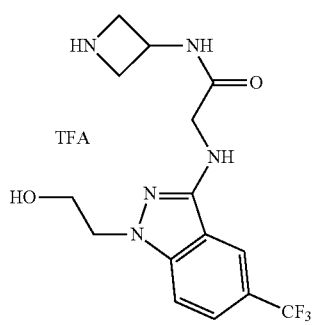 [SMILES: O=C(CNc1nn(CCO)c2ccc(C(F)(F)F)cc12)NC1CNC1]

The title compound was prepared from starting material 2-hydrazino-ethanol and 2-fluoro-5-trifluoromethylbenzonitrile by following the sequences described in Example 18 (A to D) as a colorless oil.

MS: 358 (MH+).

Step B

2-[1-(2-Hydroxy-ethyl)-5-trifluoromethyl-1H-indazol-3-ylamino]-N-{1-[4-hydroxy-4-(6-methyl-pyridin-3-yl)-cyclohexyl]-azetidin-3-yl}-acetamide

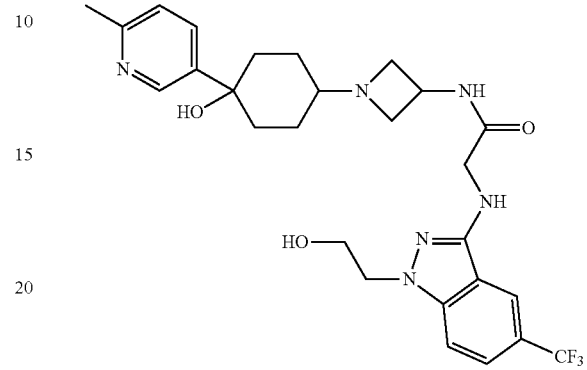

The title compound was prepared as a white solid from reaction of N-azetidin-3-yl-2-[1-(2-hydroxy-ethyl)-5-trifluoromethyl-1H-indazol-3-ylamino]-acetamide TFA salt (as prepared in the previous step) and 4-hydroxy-4-(6-methyl-pyridin-3-yl)-cyclohexanone using the procedure described in Step E of Example 1.

The less polar isomer from the silica gel column was tested in vitro as described in Example 107.

$^1$H NMR (400 MHz, $d_4$-MeOH) δ: 8.55 (d, J=2.2 Hz, 1H), 7.84 (dd, J=2.4, 8.1 Hz, 1H), 7.20-7.39 (m, 1H), 3.97-4.07 (m, 1H), 2.12-2.32 (m, 2H), 1.96-2.10 (m, 2H), 1.76-1.89 (m, 1H), 1.65 (dd, J=3.4, 13.4 Hz, 2H), 1.56 (d, J=13.0 Hz, 2H).

Example 75

2-[1-(2-Hydroxy-ethyl)-5-trifluoromethyl-1H-indazol-3-ylamino]-N-{1-[4-hydroxy-4-(6-methoxy-pyridin-3-yl)-cyclohexyl]-azetidin-3-yl}-acetamide

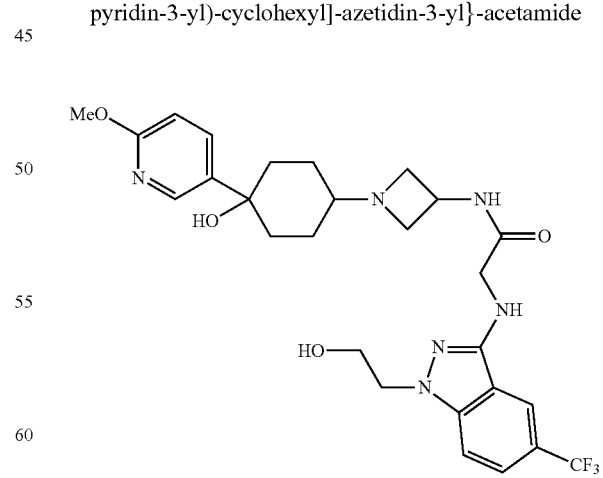

The title compound was prepared as a white solid from reaction of N-azetidin-3-yl-2-[1-(2-hydroxy-ethyl)-5-trifluoromethyl-1H-indazol-3-ylamino]-acetamide TFA salt (as prepared in Example 74, Step A) and 4-hydroxy-4-(6-methoxy-pyridin-3-yl)-cyclohexanone using the procedure described in Step E of Example 1.

The less polar isomer from the silica gel column was tested in vitro as described in Example 107.

$^1$H NMR (400 MHz, CDCl$_3$) δ: 8.30 (d, J=2.2 Hz, 1H), 7.84 (s, 1H), 7.70-7.77 (m, 1H), 7.53-7.59 (m, 1H), 7.29 (d, J=8.8 Hz, 1H), 6.74 (d, J=8.6 Hz, 1H), 4.44 (d, J=4.9 Hz, 1H), 4.25-4.34 (m, 2H), 3.98-4.08 (m, 3H), 3.86-3.98 (m, 4H), 2.10-2.27 (m, 2H), 1.95 (td, J=2.2, 12.8 Hz, 4H), 1.75-1.91 (m, 4H), 1.68 (br. s., 3H), 1.54 (d, J=16.6 Hz, 1H).

Example 76

2-[1-(2-Hydroxy-ethyl)-5-trifluoromethyl-1H-indazol-3-ylamino]-N-[1-(4-hydroxy-4-thiazol-2-yl-cyclohexyl)-azetidin-3-yl]-acetamide

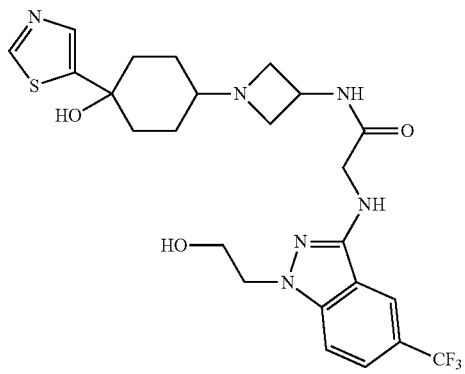 [SMILES: O=C(CNc1nn(CCO)c2ccc(C(F)(F)F)cc12)NC1CN(C2CCC(O)(c3cncs3)CC2)C1]

The title compound was prepared as a white solid from reaction of N-azetidin-3-yl-2-[1-(2-hydroxy-ethyl)-5-trifluoromethyl-1H-indazol-3-ylamino]-acetamide TFA salt (as prepared in Example 74, Step A) and 4-hydroxy-4-thiazol-5-yl-cyclohexanone using the procedure described in Step E of Example 1.

The less polar isomer from the silica gel column was tested in vitro as described in Example 107.

$^1$H NMR (400 MHz, d$_4$-MeOH) δ: 8.91 (s, 1H), 8.10 (s, 1H), 7.85 (s, 1H), 7.58 (d, J=6.0 Hz, 1H), 7.48 (d, J=6.0 Hz, 1H), 4.50 (m, 1H), 4.25 (d, J=4.0 Hz, 2H), 4.05 (d, J=3.5 Hz, 2H), 3.90 (d, J=4.5 Hz, 2H), 3.65 (t, J=6.8 Hz, 2H), 3.05 (d, J=7.0 Hz, 2H), 2.38 (m, 1H), 2.25 (m, 2H), 1.90 (m, 2H), 1.80 (m, 2H), 1.38 (m, 2H).

Example 77

2-[1-(2-Hydroxy-ethyl)-5-trifluoromethyl-1H-indazol-3-ylamino]-N-{1-[4-hydroxy-4-(5-methyl-thiazol-2-yl)-cyclohexyl]-azetidin-3-yl}-acetamide

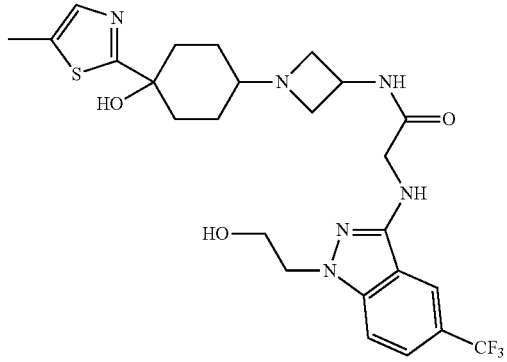 [SMILES: Cc1cnc(C2(O)CCC(N3CC(NC(=O)CNc4nn(CCO)c5ccc(C(F)(F)F)cc45)C3)CC2)s1]

The title compound was prepared as a white solid from reaction of N-azetidin-3-yl-2-[1-(2-hydroxy-ethyl)-5-trifluoromethyl-1H-indazol-3-ylamino]-acetamide TFA salt (as prepared in Example 74, Step A) and 4-hydroxy-4-(5-methyl-thiazol-2-yl)-cyclohexanone using the procedure described in Step E of Example 1.

The less polar isomer from the silica gel column was tested in vitro as described in Example 107.

$^1$H NMR (400 MHz, d$_4$-MeOH) δ: 8.10 (s, 1H), 7.55 (d, J=6.0 Hz, 1H), 7.48 (d, J=6.0 Hz, 1H), 6.98 (s, 1H), 4.48 9 m, 1H), 4.31 (t, J=4.5 Hz, 2H), 4.02 (s, 2H), 3.89 (t, J=5.5 Hz, 2H), 3.58 (t, J=6.5 Hz, 2H), 2.95 (t, J=6.5 Hz, 2H), 2.42 (s, 3H), 2.40 (m, 3H), 1.80 (m, 2H), 1.65 (m, 2H), 1.48 (m, 2H).

Example 78

N-[1-(4-Benzo[1,3]dioxol-5-yl-cyclohexyl)-azetidin-3-yl]-2-[1-(2-hydroxy-ethyl)-5-trifluoromethyl-1H-indazol-3-ylamino]-acetamide

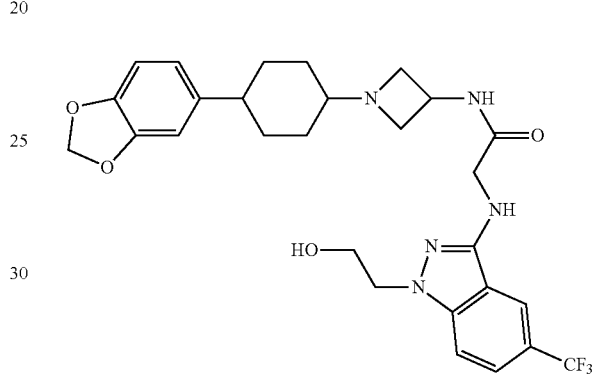

The title compound was prepared as a white solid from reaction of N-azetidin-3-yl-2-[1-(2-hydroxy-ethyl)-5-trifluoromethyl-1H-indazol-3-ylamino]-acetamide TFA salt (as prepared in Example 74, Step A) and 4-benzo[1,3]dioxol-5-yl-cyclohexanone using the procedure described in Step E of Example 1.

The less polar isomer from the silica gel column was tested in vitro as described in Example 107.

MS: 560 (MH$^+$).

Example 79

2-[1-(2-Hydroxy-ethyl)-5-trifluoromethyl-1H-indazol-3-ylamino]-N-[1-(4-methoxymethyl-cyclohexyl)-azetidin-3-yl]-acetamide

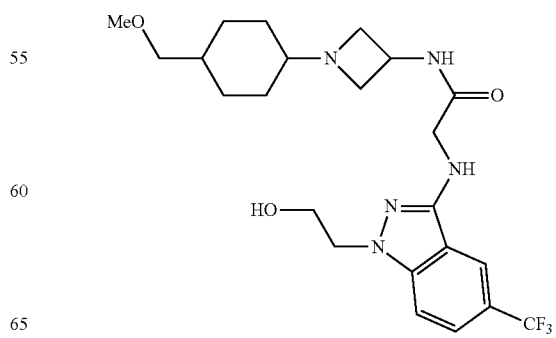

The title compound was prepared as a white solid from reaction of N-azetidin-3-yl-2-[1-(2-hydroxy-ethyl)-5-trifluoromethyl-1H-indazol-3-ylamino]-acetamide TFA salt (as prepared in Example 74, Step A) and 4-methoxymethyl-cyclohexanone using the procedure described in Step E of Example 1.

The less polar isomer from the silica gel column was isolated and characterized by NMR.

$^1$H NMR (400 MHz, d$_4$-MeOH) δ: 8.05 (s, 1H), 7.51 (d, J=7.0 Hz, 1H), 7.46 (d, J=7.0 Hz, 1H), 4.48 (m, 1H), 4.25 (t, J=6.0 Hz, 2H), 3.95 (s, 2H), 3.85 (d, J=6.0 Hz, 2H), 3.60 (m, 2H), 3.38 (s, 3H), 2.90 (t, J=7.0 Hz, 2H), 2.75 (t, J=6.5 Hz, 2H), 2.25 (m, 1H), 1.75 (m, 2H), 1.40 (m, 6H0, 1.02 (m, 1H).

Example 80

3-({[1-(4-Hydroxy-4-thiazol-2-yl-cyclohexyl)-azetidin-3-ylcarbamoyl]-methyl}-amino)-5-trifluoromethyl-indazole-1-carboxylic acid tert-butylamide

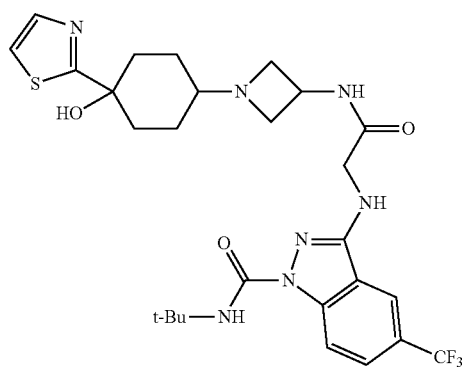 [SMILES: CC(C)(C)NC(=O)n1nc(NCC(=O)NC2CN(C3CCC(O)(c4nccs4)CC3)C2)c2cc(C(F)(F)F)ccc21]

Step A 2-(5-Trifluoromethyl-1H-indazol-3-yl)-isoindole-1,3-dione

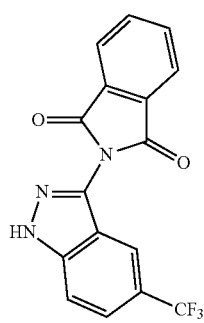 [SMILES: O=C1c2ccccc2C(=O)N1c1n[nH]c2ccc(C(F)(F)F)cc12]

Isobenzofuran-1,3-dione (4.24 g, 28.6 mmol) and 5-trifluoromethyl-1H-indazol-3-ylamine (5.76 g, 28.6 mmol) in dioxane (10 mL) in a sealed tube were heated at 100° C. overnight. The solvent was removed to give the crude product.

MS: 332 (MH$^+$).

Step B 3-(1,3-Dioxo-1,3-dihydro-isoindol-2-yl)-5-trifluoromethyl-indazole-1-carboxylic acid tert-butyl amide

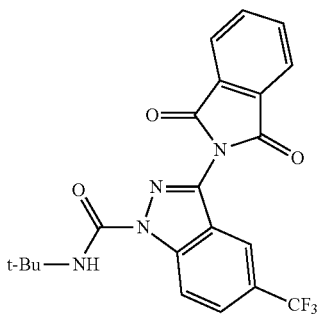 [SMILES: CC(C)(C)NC(=O)n1nc(N2C(=O)c3ccccc3C2=O)c2cc(C(F)(F)F)ccc21]

2-(5-Trifluoromethyl-1H-indazol-3-yl)-isoindole-1,3-dione (1.56 g, 4.71 mmol) in DMF (5 mL) was treated with t-butyl-isocyanate (513 mg, 5.18 mmol) at room temperature overnight. The reaction was partitioned between ethyl acetate and water. The organic layer was washed with brine, dried over anhydrous Na$_2$SO$_4$, filtered and concentrated to give the crude material. Purification by silica gel column (hexanes:ethyl acetate 2:1) afforded the title compound as colorless solid.

$^1$H NMR (400 MHz, CDCl$_3$) δ: 8.61 (d, J=6.0 Hz, 1H), 8.05 (m, 2H), 7.90 (m, 2H), 7.80 (d, J=6.5 Hz, 1H), 7.05 (s, 1H), 1.52 (s, 9H).

Step C

3-Amino-5-trifluoromethyl-indazole-1-carboxylic acid tert-butylamide

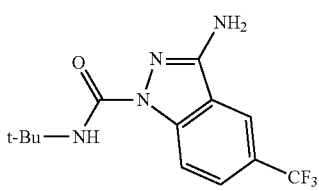 [SMILES: CC(C)(C)NC(=O)n1nc(N)c2cc(C(F)(F)F)ccc21]

3-(1,3-Dioxo-1,3-dihydro-isoindol-2-yl)-5-trifluoromethyl-indazole-1-carboxylic acid tert-butyl amide (1.41 g, 3.28 mmol) in THF (5 mL) was treated with hydrazine (315 mg, 9.84 mmol) at room temperature for 30 min. The solvent was removed and the residue was purified by silica gel column chromatography using 1:1 hexanes and ethyl acetate to afford the title compound as white solid.

MS: 301 (MH$^+$).

Step D

3-[(Azetidin-3-ylcarbamoylmethyl)-amino]-5-trifluoromethyl-indazole-1-carboxylic acid tert-butyl amide TFA salt

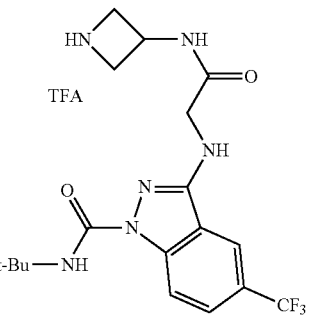

The title compound was prepared as a colorless oil from reductive amination of 3-amino-5-trifluoromethyl-indazole-1-carboxylic acid tert-butylamide and glyoxylic acid, followed by EDCI coupling and TFA de-protection as described in Example 17 (B to D).

MS: 413 (MH+).

Step E

3-({[1-(4-Hydroxy-4-thiazol-2-yl-cyclohexyl)-azetidin-3-ylcarbamoyl]-methyl}-amino)-5-trifluoromethyl-indazole-1-carboxylic acid tert-butylamide

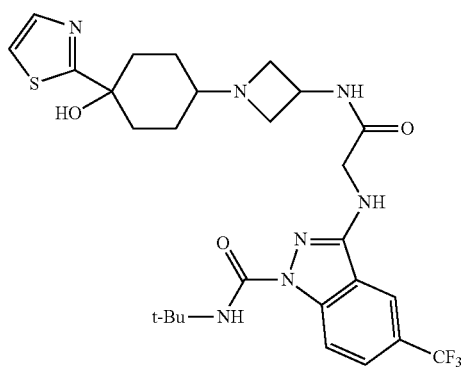 [SMILES: CC(C)(C)NC(=O)n1nc(NCC(=O)NC2CN(C3CCC(O)(c4nccs4)CC3)C2)c2cc(C(F)(F)F)ccc21]

The title compound was prepared as a white solid from reaction of 3-[(azetidin-3-ylcarbamoylmethyl)-amino]-5-trifluoromethyl-indazole-1-carboxylic acid tert-butyl amide TFA salt and 4-hydroxy-4-thiazol-2-yl-cyclohexanone using the procedure described in Step E of Example 1.

The less polar isomer from the silica gel column was tested in vitro as described in Example 107.

$^1$H NMR (400 MHz, CDCl$_3$) δ: 8.35 (d, J=6.0 Hz, 1H), 8.03 (s, 1H), 7.70 (s, 1H), 7.61 (d, J=6.5 Hz, 1H), 7.28 (s, 1H), 7.23 (d, J=6.0 Hz, 1H), 6.15 (s, br, 1H), 4.55 (m, 1H), 4.15 (s, 2H), 3.48 (t, J=7.8 Hz, 2H), 3.15 (t, J=7.8 Hz, 2H), 2.40 (m, 1H), 2.05 (m, 2H), 1.98 (m, 2H), 1.78 (m, 2H), 1.55 (m, 2H), 1.45 (s, 9H).

Example 81

3-({[1-(4-Hydroxy-4-thiazol-2-yl-cyclohexyl)-azetidin-3-ylcarbamoyl]-methyl}-amino)-5-trifluoromethyl-indazole-1-carboxylic acid amide

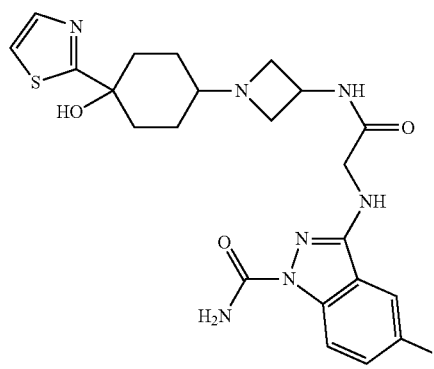

3-({[1-(4-Hydroxy-4-thiazol-2-yl-cyclohexyl)-azetidin-3-ylcarbamoyl]-methyl}-amino)-5-trifluoromethyl-indazole-1-carboxylic acid tert-butylamide (as prepared in Example 80, 150 mg, 0.25 mmol) in TFA (2 mL) in a sealed tube was heated at 80° C. for 6 hours. The TFA was removed, and the residue was partitioned between DCM and saturated NaHCO$_3$. The organic layer was washed with brine, dried over anhydrous Na$_2$SO$_4$, filtered and concentrated to give the crude material, purified by silica gel column (DCM: 7 N NH$_3$ in MeOH 9:1) to afford the title compound as white solid (36 mg, 27%).

$^1$H NMR (400 MHz, d$_4$-MeOH) δ: 8.38 (d, J=6.5 Hz, 1H), 8.21 (s, 1H), 7.71 (d, J=6.0 Hz, 1H), 7.67 (s, 1H), 7.48 (s, 1H), 4.45 (m, 1H), 4.05 (d, J=3.1 Hz, 2H), 3.60 (t, J=7.0 Hz, 2H), 3.02 (t, J=5.0 Hz, 2H), 2.32 (m, 3H), 1.75 (m, 2H), 1.70 (m, 2H), 1.45 (m, 2H).

Example 82

3-[({1-[4-(6-Ethoxy-pyridin-3-yl)-4-hydroxy-cyclohexyl]-azetidin-3-ylcarbamoyl}-methyl)-amino]-5-trifluoromethyl-indazole-1-carboxylic acid tert-butylamide

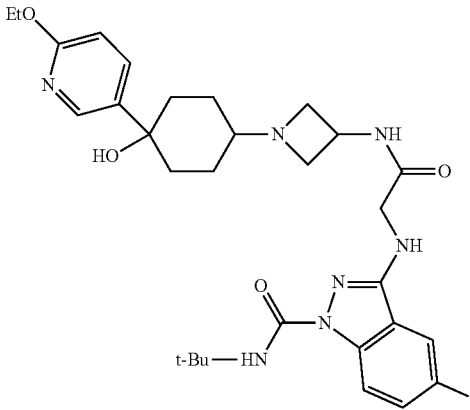

The title compound was prepared as a white solid from reaction of 3-[(azetidin-3-ylcarbamoylmethyl)-amino]-5-trifluoromethyl-indazole-1-carboxylic acid tert-butyl amide TFA salt (as prepared in Example 81, Step D) and 4-(6-ethoxy-pyridin-3-yl)-4-hydroxy-cyclohexanone using the procedure described in Step E of Example 1.

The less polar isomer from the silica gel column was tested in vitro as described in Example 107.

$^1$H NMR (400 MHz, d$_4$-MeOH) δ: 8.32 (d, J=6.5 Hz, 1H), 8.25 (s, 1H), 7.85 (m, 2H), 7.75 (d, J=6.0 Hz, 1H), 6.75 (d, J=7.0 Hz, 1H), 4.50 (m, 1H), 4.32 (q, J=8.5 Hz, 2H), 4.10 (s, 2H), 3.70 (t, J=7.0 Hz, 2H), 3.05 (t, J=6.5 Hz, 2H), 2.42 (m, 1H), 2.20 (m, 2H), 1.90 (m, 4H), 1.51 (s, 9H), 1.42 (t, J=7.5 Hz, 3H).

Example 83

3-[({1-[4-(6-Ethoxy-pyridin-3-yl)-4-hydroxy-cyclohexyl]-azetidin-3-ylcarbamoyl}-methyl)-amino]-5-trifluoromethyl-indazole-1-carboxylic acid amide

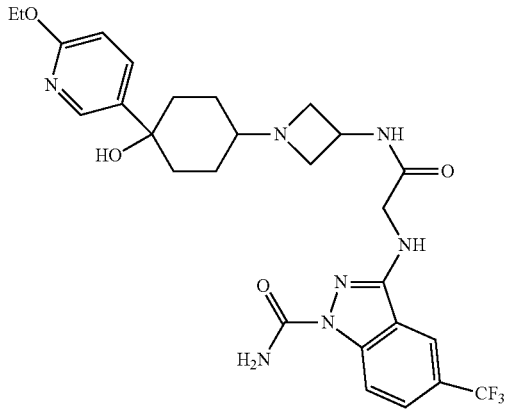 [SMILES: CCOc1ccc(C2(O)CCC(N3CC(NC(=O)CNc4nn(C(N)=O)c5ccc(C(F)(F)F)cc45)C3)CC2)cn1]

The title compound was prepared as a white solid from de-protection of 3-[({1-[4-(6-ethoxy-pyridin-3-yl)-4-hydroxy-cyclohexyl]-azetidin-3-ylcarbamoyl}-methyl)-amino]-5-trifluoromethyl-indazole-1-carboxylic acid tert-butylamide (as prepared in Example 82) with TFA using the procedure described in Example 81.

$^1$H NMR (400 MHz, d$_4$-MeOH) δ: 8.35 (d, J=6.0 Hz, 1H), 8.25 (d, J=7.5 Hz, 2H), 7.85 (d, J=6.0 Hz, 1H), 7.70 (d, J=6.0 Hz, 1H), 6.75 (d, J=7.0 Hz, 1H), 4.60 (m, 1H), 4.30 (q, J=7.0 Hz, 2H), 4.10 (d, J=2.5 Hz, 2H), 3.75 (m, 2H), 2.95 (m, 2H), 2.75 (m, 1H), 2.20 (m, 2H), 1.95 (m, 2H), 1.65 (m, 2H), 1.45 (m, 2H), 1.40 (t, J=7.5 Hz, 3H).

Example 84

3-[({1-[4-(tert-Butyl-dimethyl-silanyloxy)-cyclohexyl]-azetidin-3-ylcarbamoyl}-methyl)-amino]-5-trifluoromethyl-indazole-1-carboxylic acid tert-butylamide

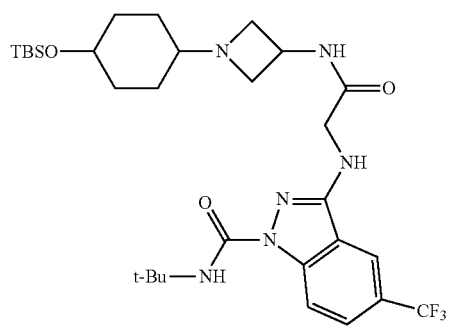 [SMILES: CC(C)(C)NC(=O)n1nc(NCC(=O)NC2CN(C3CCC(O[Si](C)(C)C(C)(C)C)CC3)C2)c2cc(C(F)(F)F)ccc21]

The title compound was prepared as a white solid from reaction of 3-[(azetidin-3-ylcarbamoylmethyl)-amino]-5-trifluoromethyl-indazole-1-carboxylic acid tert-butyl amide TFA salt (as prepared in Example 81, Step D) and 4-(tert-butyl-dimethyl-silanyloxy)-cyclohexanone using the procedure described in Step E of Example 1.

The less polar isomer from the silica gel column was tested in vitro as described in Example 107.

MS: 625 (MH$^+$).

Example 85

3-({[1-(4-Hydroxy-cyclohexyl)-azetidin-3-ylcarbamoyl]-methyl}-amino)-5-trifluoromethyl-indazole-1-carboxylic acid amide

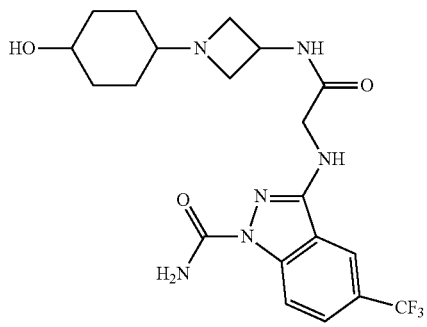 [SMILES: NC(=O)n1nc(NCC(=O)NC2CN(C3CCC(O)CC3)C2)c2cc(C(F)(F)F)ccc21]

The title compound was prepared as a white solid from de-protection of 3-[({1-[4-(tert-butyl-dimethyl-silanyloxy)-cyclohexyl]-azetidin-3-ylcarbamoyl}-methyl)-amino]-5-trifluoromethyl-indazole-1-carboxylic acid tert-butylamide (as prepared in Example 84) with TFA using the procedure described in Example 81.

MS: 455 (MH$^+$).

Example 86

3-({[1-(4-Cyano-cyclohexyl)-azetidin-3-ylcarbamoyl]-methyl}-amino)-5-trifluoromethyl-indazole-1-carboxylic acid tert-butylamide

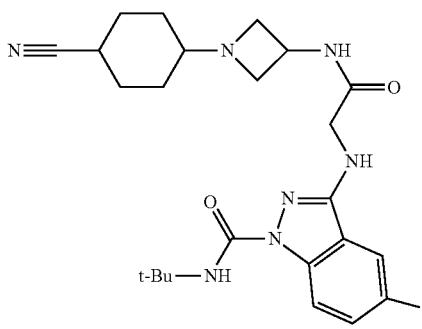

The title compound was prepared as a white solid from reaction of 3-[(azetidin-3-ylcarbamoylmethyl)-amino]-5-trifluoromethyl-indazole-1-carboxylic acid tert-butyl amide TFA salt (as prepared in Example 81, Step D) and 4-cyano-cyclohexanone using the procedure described in Step E of Example 1.

MS: 520 (MH⁺).

Example 87

3-({[1-(4-Cyano-cyclohexyl)-azetidin-3-ylcarbamoyl]-methyl}-amino)-5-trifluoromethyl-indazole-1-carboxylic acid amide

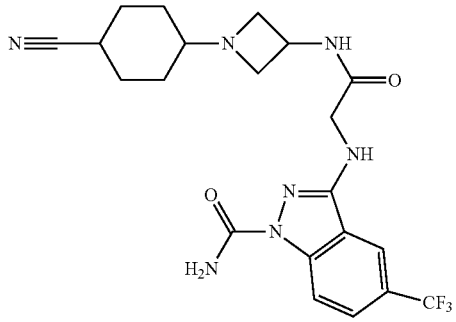 [SMILES: N#CC1CCC(N2CC(NC(=O)CNc3nn(C(N)=O)c4ccc(C(F)(F)F)cc34)C2)CC1]

The title compound was prepared as a white solid from de-protection of 3-({[1-(4-cyano-cyclohexyl)-azetidin-3-ylcarbamoyl]-methyl}-amino)-5-trifluoromethyl-indazole-1-carboxylic acid tert-butylamide (as prepared in Example 86) with TFA using the procedure described in Example 81.

MS: 464 (MH⁺).

Example 88

4-{3-[2-(1-tert-Butylcarbamoyl-5-trifluoromethyl-1H-indazol-3-ylamino)-acetylamino]-azetidin-1-yl}-cyclohexanecarboxylic acid ethyl ester

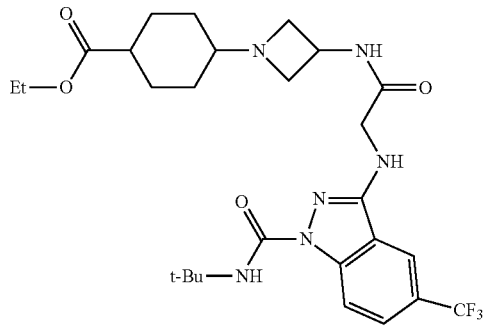 [SMILES: CCOC(=O)C1CCC(N2CC(NC(=O)CNc3nn(C(=O)NC(C)(C)C)c4ccc(C(F)(F)F)cc34)C2)CC1]

The title compound was prepared as a white solid from reaction of 3-[(azetidin-3-ylcarbamoylmethyl)-amino]-5-trifluoromethyl-indazole-1-carboxylic acid tert-butyl amide TFA salt (as prepared in Example 81, Step D) and 4-oxo-cyclohexanecarboxylic acid ethyl ester using the procedure described in Step E of Example 1.

MS; 567 (MH⁺).

Example 89

4-{3-[2-(1-Carbamoyl-5-trifluoromethyl-1H-indazol-3-ylamino)-acetylamino]-azetidin-1-yl}-cyclohexane carboxylic acid ethyl ester

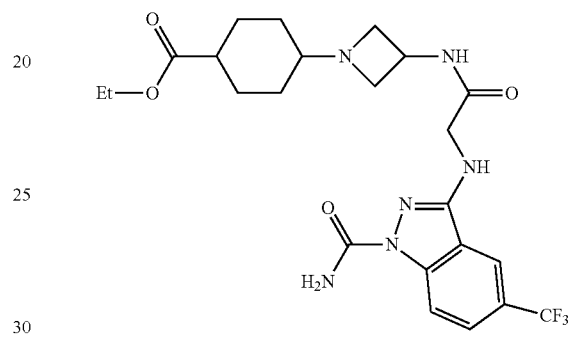

The title compound was prepared as a white solid from de-protection of 4-{3-[2-(1-tert-butylcarbamoyl-5-trifluoromethyl-1H-indazol-3-ylamino)-acetylamino]-azetidin-1-yl}-cyclohexanecarboxylic acid ethyl ester (as prepared in Example 88) with TFA using the procedure described in Example 81.

MS: 511 (MH⁺).

Example 90

-({[1-(4-Phenyl-cyclohexyl)-azetidin-3-ylcarbamoyl]-methyl}-amino)-5-trifluoromethyl-indazole-1-carboxylic acid isopropylamide

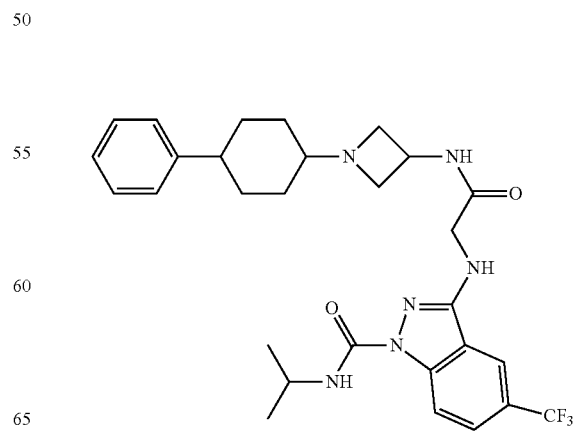

Step A

3-[(Azetidin-3-ylcarbamoylmethyl)-amino]-5-trifluoromethyl-indazole-1-carboxylic acid isopropylamide

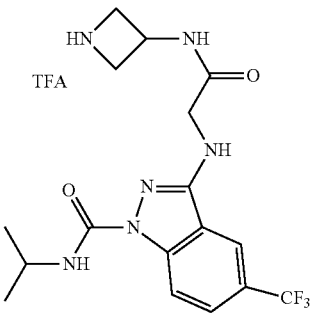 [SMILES: CC(C)NC(=O)n1nc(NCC(=O)NC2CNC2)c2cc(C(F)(F)F)ccc21]

The title compound was prepared as a colorless oil according to the procedure described in Example 80 (A to D), substituting isopropyl-isocyanate for t-butyl-isocyanate.
MS: 399 (MH+).

Step B 3-({[1-(4-Phenyl-cyclohexyl)-azetidin-3-ylcarbamoyl]-methyl}-amino)-5-trifluoromethyl-indazole-1-carboxylic acid isopropylamide

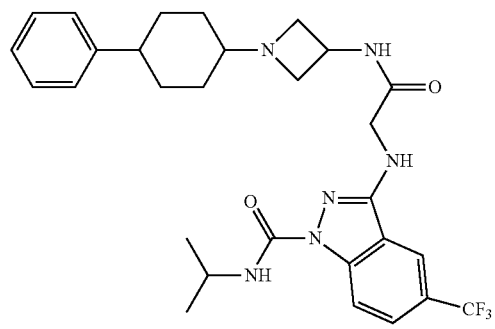 [SMILES: CC(C)NC(=O)n1nc(NCC(=O)NC2CN(C3CCC(c4ccccc4)CC3)C2)c2cc(C(F)(F)F)ccc21]

The title compound was prepared as a white solid from reaction of 3-[(azetidin-3-ylcarbamoylmethyl)-amino]-5-trifluoromethyl-indazole-1-carboxylic acid isopropylamide and 4-phenyl-cyclohexanone using the procedure described in Step E of Example 1.

The less polar isomer from the silica gel column was tested in vitro as described in Example 107.

$^1$H NMR (400 MHz, d$_4$-MeOH) δ: 8.32 (d, J=6.5 Hz, 1H), 8.19 (s, 1H), 7.75 (d, J=6.5 Hz, 1H), 7.25 (m, 4H), 7.12 (m, 1H), 4.67 (m, 1H), 4.11 (s, 2H), 4.05 (m, 1H), 3.95 (m, 2H), 3.33 (m, 2H), 2.80 (br, s, 1H), 2.61 (m, 1H), 1.80 (m, 4H), 1.55 (m, 4H), 1.28 (d, J=5.5 Hz, 6H).

Example 91

3-[({1-[4-(6-Methoxy-pyridin-3-yl)-cyclohexyl]-azetidin-3-ylcarbamoyl}-methyl)-amino]-5-trifluoromethyl-indazole-1-carboxylic acid isopropylamide

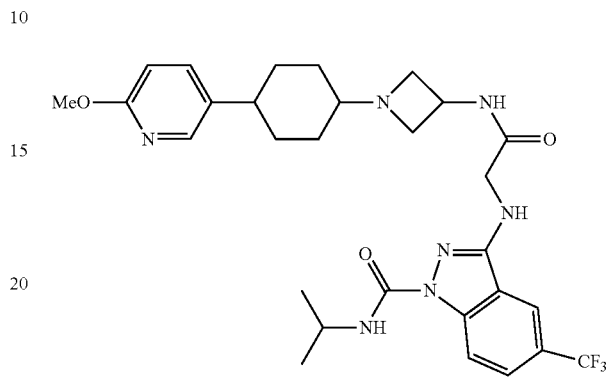

The title compound was prepared as a white solid from reaction of 3-[(azetidin-3-ylcarbamoylmethyl)-amino]-5-trifluoromethyl-indazole-1-carboxylic acid isopropylamide (as prepared in Example 90, Step A) and 4-(6-methoxy-pyridin-3-yl)-cyclohexanone using the procedure described in Step E of Example 1.

The less polar isomer from the silica gel column was tested in vitro as described in Example 107.

$^1$H NMR (400 MHz, d$_4$-MeOH) δ: 8.28 (d, J=6.0 Hz, 1H), 8.20 (s, 1H), 7.95 (s, 1H), 7.78 (d, J=6.0 Hz, 1H), 7.61 (d, J=6.0 Hz, 1H), 6.75 (d, J=6.5 Hz, 1H), 4.55 (m, 1H), 4.11 (s, 2H), 3.90 (s, 3H), 3.69 (t, J=6.5 Hz, 2H), 2.96 (t, J=6.5 Hz, 2H), 2.90 (m, 1H), 2.65 (m, 1H), 2.40 (m, 1H), 1.90 (m, 6H), 1.55 (m, 2H), 1.32 (d, J=4.5 Hz, 2H), 1.21 (d, J=4.5 Hz, 2H).

Example 92

3-({[1-(4-Isopropyl-cyclohexyl)-azetidin-3-ylcarbamoyl]-methyl}-amino)-5-trifluoromethyl-indazole-1-carboxylic acid isopropylamide

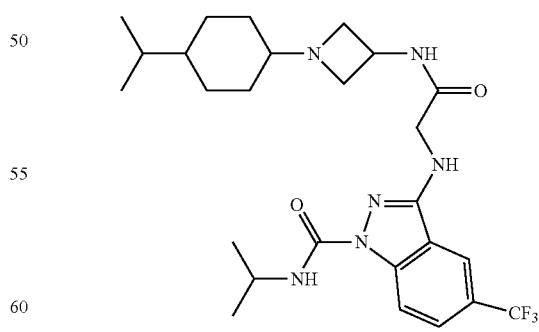

The title compound was prepared as a white solid from reaction of 3-[(azetidin-3-ylcarbamoylmethyl)-amino]-5-trifluoromethyl-indazole-1-carboxylic acid isopropylamide (as prepared in Example 90, Step A) and 4-iso-propyl-cyclohexanone using the procedure described in Step E of Example 1.

The less polar isomer from the silica gel column was tested in vitro as described in Example 107.

¹H NMR (400 MHz, d₄-MeOH) δ: 8.10 (s, 1H0, 7.61 (d, J=6.0 Hz, 1H), 7.45 (d, J=6.0 Hz, 1H), 4.51 (m, 1H), 4.04 (s, 2H), 3.75 (t, J=6.5 Hz, 2H), 3.21 (t, J=6.5 Hz, 2H), 3.19 (m, 1H), 2.55 (m, 1H), 2.22 (m, 2H), 1.90 (m, 2H), 1.75 (m, 2H), 1.45 (d, J=7.5 Hz, 6H), 1.40 (m, 2H), 1.38 (d, J=7.0 Hz, 6H).

Example 93

3-{[(1-Bicyclohexyl-4-yl-azetidin-3-ylcarbamoyl)-methyl]-amino}-5-trifluoromethyl-indazole-1-carboxylic acid isopropylamide

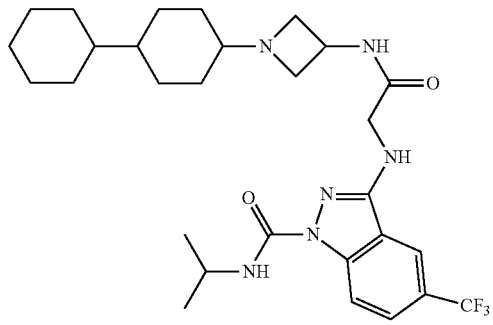 [SMILES: CC(C)NC(=O)n1nc(NCC(=O)NC2CN(C3CCC(C4CCCCC4)CC3)C2)c2cc(C(F)(F)F)ccc21]

The title compound was prepared as a white solid from reaction of 3-[(azetidin-3-ylcarbamoylmethyl)-amino]-5-trifluoromethyl-indazole-1-carboxylic acid isopropylamide (as prepared in Example 90, Step A) and bicyclohexyl-4-one using the procedure described in Step E of Example 1.

The less polar isomer from the silica gel column was tested in vitro as described in Example 107.

¹H NMR (400 MHz, CDCl₃) δ: 9.88 (br, s, 1H), 8.38 (d, J=6.5 Hz, 1H), 8.05 (s, 1H), 7.71 (d, J=6.5 Hz, 1H), 6.78 (d, J=6.0 Hz, 1H), 6.10 (br, s, 1H), 4.78 (m, 1H), 4.20 (s, 2H), 3.69 (m, 2H), 3.10 (m, 2H), 2.70 (m, 1H), 2.05 (m, 1H), 1.80 (m, 14H), 1.55 (m, 2H), 1.30 (d, J=4.5 Hz, 6H), 1.20 (m, 6H).

Example 94

4-{3-[2-(1-Allyl-5-trifluoromethyl-1H-indazol-3-ylamino)-acetylamino]-azetidin-1-yl}-cyclohexanecarboxylic acid ethyl ester

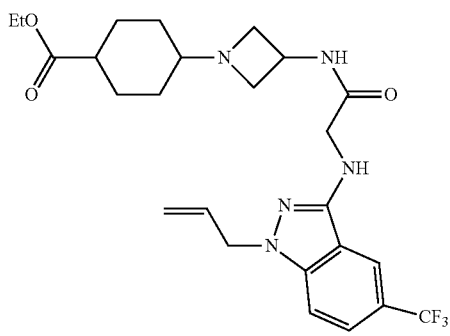 [SMILES: C=CCn1nc(NCC(=O)NC2CN(C3CCC(C(=O)OCC)CC3)C2)c2cc(C(F)(F)F)ccc21]

Step A 2-(1-Allyl-5-trifluoromethyl-1H-indazol-3-yl)-isoindole-1,3-dione

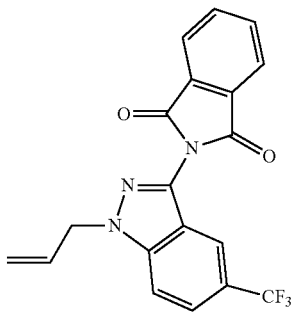 [SMILES: C=CCn1nc(N2C(=O)c3ccccc3C2=O)c2cc(C(F)(F)F)ccc21]

2-(5-Trifluoromethyl-1H-indazol-3-yl)-isoindole-1,3-dione (500 mg, 1.51 mmol), K₂CO₃ (313 mg, 2.26 mmol) and allyl bromide (365 mg, 3.02 mmol) in acetone (10 mL) were heated to reflux overnight. The reaction was filtered, and the residue was concentrated and purified by silica gel column chromatography using hexanes:ethyl acetate 2:1 to give the title compound as white solid.

MS: 372 (MH⁺).

Step B 2-(1-Allyl-5-trifluoromethyl-1H-indazol-3-ylamino)-N-azetidin-3-yl-acetamide

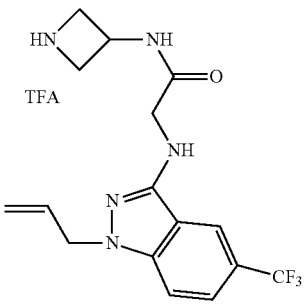 [SMILES: C=CCn1nc(NCC(=O)NC2CNC2)c2cc(C(F)(F)F)ccc21]

The title compound was prepared as a colorless oil from 2-(1-allyl-5-trifluoromethyl-1H-indazol-3-yl)-isoindole-1,3-dione using the sequences described in Example 80 (C-D).

MS: 354 (MH⁺).

Step C

4-{3-[2-(1-Allyl-5-trifluoromethyl-1H-indazol-3-ylamino)-acetylamino]-azetidin-1-yl}-cyclohexane carboxylic acid ethyl ester

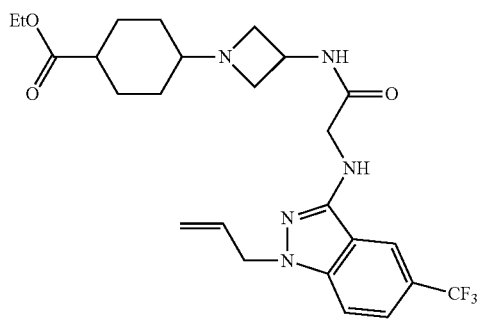 [SMILES: C=CCn1nc(NCC(=O)NC2CN(C3CCC(C(=O)OCC)CC3)C2)c2cc(C(F)(F)F)ccc21]

The title compound was prepared as a white solid from reaction of 2-(1-allyl-5-trifluoromethyl-1H-indazol-3-ylamino)-N-azetidin-3-yl-acetamide and 4-oxo-cyclohexanecarboxylic acid ethyl ester using the procedure described in Step E of Example 1.

The less polar isomer from the silica gel column was tested in vitro as described in Example 107.

$^1$H NMR (400 MHz, $d_4$-MeOH) δ: 8.15 (s, 1H0, 7.58 (d, J=6.0 Hz, 1H), 7.45 (d, J=6.0 Hz, 1H), 5.98 (m, 1H), 5.15 (d, J=9.5 Hz, 1H), 5.05 (m, J=11.5 Hz, 1H), 4.45 (m, 1H), 4.15 (m, 1H), 4.12 (q, J=8.5 Hz, 2H), 4.05 (s, 2H), 3.58 (t, J=7.0 Hz, 3H), 3.00 (t, J=7.0 Hz, 3H), 2.50 (m, 1H), 2.25 (m, 1H), 2.05 (m, 2H), 1.54 (m, 4H), 1.30 (m, 2H), 1.25 (t, J=8.5 Hz, 3H).

Example 95

2-(1-Allyl-5-trifluoromethyl-1H-indazol-3-ylamino)-N-(1-bicyclohexyl-4-yl-azetidin-3-yl)-acetamide

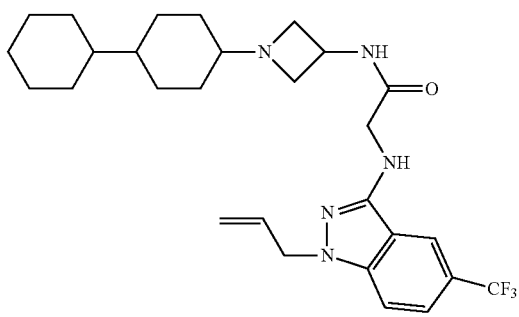 [SMILES: C=CCn1nc(NCC(=O)NC2CN(C3CCC(C4CCCCC4)CC3)C2)c2cc(C(F)(F)F)ccc21]

The title compound was prepared as a white solid from reaction of 2-(1-allyl-5-trifluoromethyl-1H-indazol-3-ylamino)-N-azetidin-3-yl-acetamide and bicyclohexyl-4-one using the procedure described in Step E of Example 1.

The less polar isomer from the silica gel column was tested in vitro as described in Example 107.

$^1$H NMR (400 MHz, $d_4$-MeOH) δ: 8.11 (s, 1H), 7.55 (d, J=6.5 Hz, 1H), 7.42 (d, J=6.5 Hz, 1H), 6.02 (m, 1H), 5.18 (d, J=7.5 Hz, 1H), 5.08 (d, J=9.2 Hz, 1H), 4.48 (m, 1H), 4.02 (s, 2H), 3.65 (m, 2H), 3.61 (t, J=5.8 Hz, 2H), 3.02 (t, J=5.8 Hz, 2H), 1.80 (m, 6H), 1.50-0.90 (m, 14H).

Example 96

2-(1-Benzyl-5-trifluoromethyl-1H-indazol-3-ylamino)-N-{1-[4-hydroxy-4-(6-methoxy-pyridin-2-yl)-cyclohexyl]-azetidin-3-yl}-acetamide

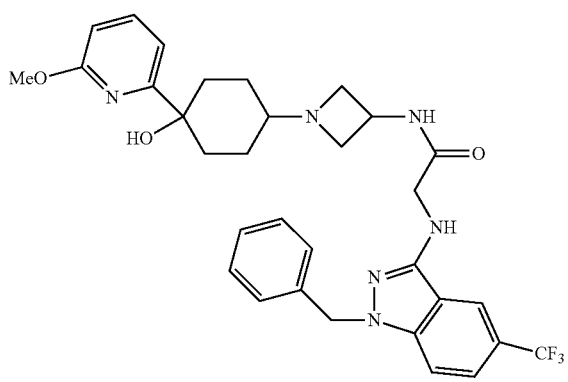 [SMILES: COc1cccc(C2(O)CCC(N3CC(NC(=O)CNc4nn(Cc5ccccc5)c5ccc(C(F)(F)F)cc45)C3)CC2)n1]

Step A

N-Azetidin-3-yl-2-(1-benzyl-5-trifluoromethyl-1H-indazol-3-ylamino)-acetamide

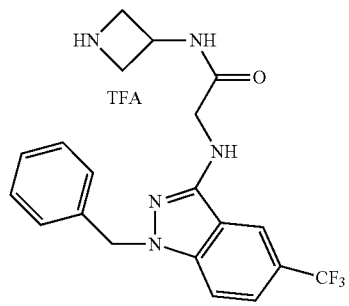 [SMILES: O=C(CNc1nn(Cc2ccccc2)c2ccc(C(F)(F)F)cc12)NC1CNC1]

The title compound was prepared from 2-(1-benzyl-5-trifluoromethyl-1H-indazol-3-yl)-isoindole-1,3-dione as intermediate using the sequences described in Example 80 (A-D) as a colorless oil.

MS: 404 (MH$^+$).

Step B 2-(1-Benzyl-5-trifluoromethyl-1H-indazol-3-ylamino)-N-{1-[4-hydroxy-4-(6-methoxy-pyridin-2-yl)-cyclohexyl]-azetidin-3-yl}-acetamide

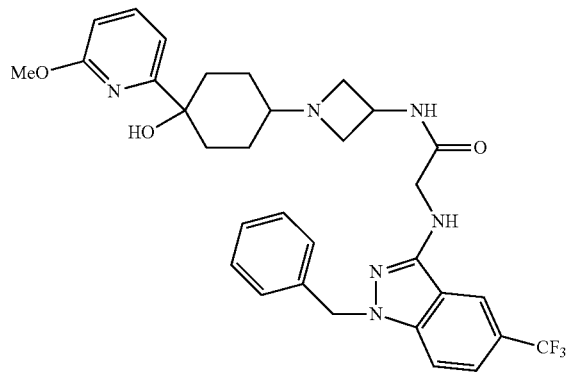 [SMILES: COc1cccc(C2(O)CCC(N3CC(NC(=O)CNc4nn(Cc5ccccc5)c5ccc(C(F)(F)F)cc45)C3)CC2)n1]

The title compound was prepared as a white solid from reaction of N-azetidin-3-yl-2-(1-benzyl-5-trifluoromethyl-1H-indazol-3-ylamino)-acetamide and 4-(6-methoxy-pyridin-2-yl)-cyclohexanone using the procedure described in Step E of Example 1.

The less polar isomer from the silica gel column was tested in vitro as described in Example 107.

$^1$H NMR (400 MHz, d$_4$-MeOH) δ: 8.11 (s, 1H), 7.72 (t, J=5.6 Hz, 1H), 7.56 (d, J=6.7 Hz, 1H), 7.45 (d, J=6.7 Hz, 1H), 7.28 (m, 3H), 7.18 (m, 3H), 6.62 (d, J=7.0 Hz, 1H), 5.41 (s, 2H), 4.44 (m, 1H), 4.02 (s, 2H), 3.95 (s, 3H), 3.55 (t, J=7.5 Hz, 2H), 2.90 (t, J=7.5 Hz, 2H), 2.42 (m, 2H), 2.32 (m, 1H), 1.81 (m, 2H), 1.57 (m, 3H), 1.35 (m, 2H).

Example 97

4-{3-[2-(1-Benzyl-5-trifluoromethyl-1H-indazol-3-ylamino)-acetylamino]-azetidin-1-yl}-cyclohexane carboxylic acid ethyl ester

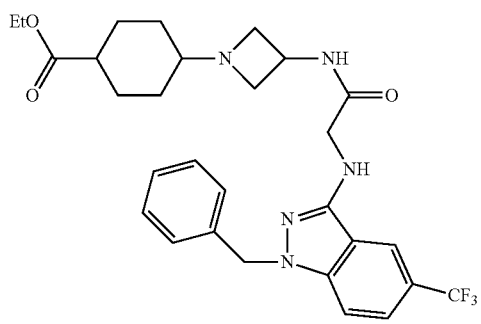 [SMILES: CCOC(=O)C1CCC(N2CC(NC(=O)CNc3nn(Cc4ccccc4)c4ccc(C(F)(F)F)cc34)C2)CC1]

The title compound was prepared as a white solid from reaction of N-azetidin-3-yl-2-(1-benzyl-5-trifluoromethyl-1H-indazol-3-ylamino)-acetamide and 4-oxo-cyclohexanecarboxylic acid ethyl ester using the procedure described in Step E of Example 1.

The less polar isomer from the silica gel column was tested in vitro as described in Example 107.

$^1$H NMR (400 MHz, d$_4$-MeOH) δ: 8.15 (s, 1H), 7.53 (d, J=6.5 Hz, 1H), 7.48 (d, J=6.0 Hz, 1H), 7.28 (m, 4H), 7.19 (d, J=6.0 Hz, 1H), 5.42 (s, 2H), 4.46 (m, 1H), 4.15 (q, J=6.5 Hz, 2H), 4.02 (s, 2H), 3.52 (t, J=8.5 Hz, 2H), 2.90 (t, J=8.5 Hz, 2H), 2.42 (m, 1H), 2.15 (m, 1H), 2.03 (m, 2H), 1.55 (m, 4H), 1.32 (m, 2H), 1.25 (t, J=8.5 Hz, 3H).

Example 98

2-(1-Benzyl-5-trifluoromethyl-1H-indazol-3-ylamino)-N-[1-(4-isopropyl-cyclohexyl)-azetidin-3-yl]-acetamide

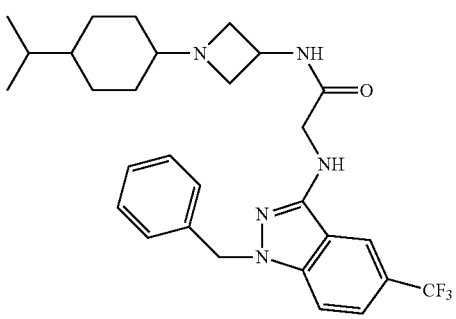 [SMILES: CC(C)C1CCC(N2CC(NC(=O)CNc3nn(Cc4ccccc4)c4ccc(C(F)(F)F)cc34)C2)CC1]

The title compound was prepared as a white solid from reaction of N-azetidin-3-yl-2-(1-benzyl-5-trifluoromethyl-1H-indazol-3-ylamino)-acetamide and 4-isopropyl-cyclohexanone using the procedure described in Step E of Example 1.

The less polar isomer from the silica gel column was tested in vitro as described in Example 107.

$^1$H NMR (400 MHz, d$_4$-MeOH) δ: 8.15 (s, 1H), 7.55 (d, J=7.0 Hz, 1H), 7.45 (d, J=7.0 Hz, 1H), 7.25 (m, 4H), 7.16 (d, J=6.5 Hz, 1H), 5.35 (s, 2H), 4.48 (m, 1H), 4.01 (s, 2H), 3.56 (t, J=7.8 Hz, 2H), 2.90 (t, J=7.8 Hz, 2H), 2.25 (m, 1H), 1.35 (m, 8H), 1.10 (m, 1H), 0.85 (d, J=6.5 Hz, 2H).

Example 99

4-{3-[2-(1-Methanesulfonyl-5-trifluoromethyl-1H-indazol-3-ylamino)-acetylamino]-azetidin-1-yl}-cyclohexane carboxylic acid ethyl ester

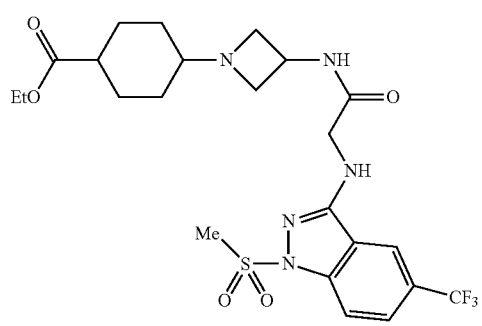 [SMILES: CCOC(=O)C1CCC(N2CC(NC(=O)CNc3nn(S(C)(=O)=O)c4ccc(C(F)(F)F)cc34)C2)CC1]

Step A

2-(1-Methanesulfonyl-5-trifluoromethyl-1H-indazol-3-yl)-isoindole-1,3-dione

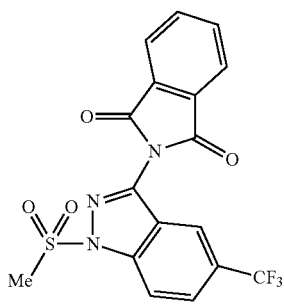 [SMILES: CS(=O)(=O)n1nc(N2C(=O)c3ccccc3C2=O)c2cc(C(F)(F)F)ccc21]

2-(5-Trifluoromethyl-1H-indazol-3-yl)-isoindole-1,3-dione (350 mg, 1.06 mmol), TEA (0.3 mL, 2.12 mmol) in DCM (5 mL) was treated with MsCl (182 mg, 1.59 mmol) at 0° C. for 2 hours. The solvent was removed and the residue was purified by silica gel column chromatography using hexanes: ethyl acetate 1:1 to give the title compound as white solid (305 mg, 69%).

MS: 410 (MH$^+$).

Step B

N-Azetidin-3-yl-2-(1-methanesulfonyl-5-trifluoromethyl-1H-indazol-3-ylamino)-acetamide TFA salt

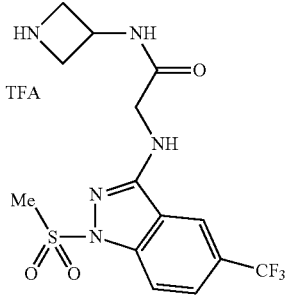 [SMILES: CS(=O)(=O)n1nc(NCC(=O)NC2CNC2)c2cc(C(F)(F)F)ccc21]

The title compound was prepared from 2-(1-methanesulfonyl-5-trifluoromethyl-1H-indazol-3-yl)-isoindole-1,3-dione as intermediate using the sequences described in Example 80 (A-D) as a colorless oil.

MS: 392 (MH$^+$).

Step C

4-{3-[2-(1-Methanesulfonyl-5-trifluoromethyl-1H-indazol-3-ylamino)-acetylamino]-azetidin-1-yl}-cyclohexane carboxylic acid ethyl ester

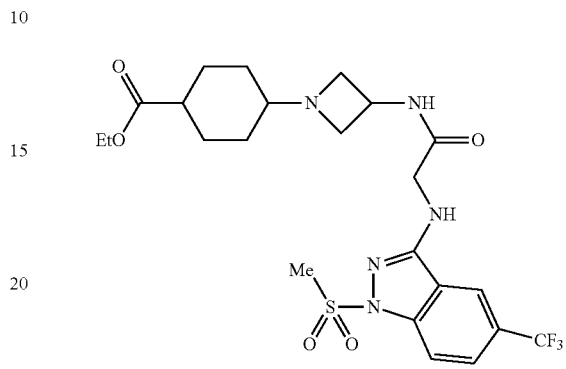

The title compound was prepared as a white solid from reaction of N-azetidin-3-yl-2-(1-methanesulfonyl-5-trifluoromethyl-1H-indazol-3-ylamino)-acetamide TFA salt and 4-oxo-cyclohexanecarboxylic acid ethyl ester using the procedure described in Step E of Example 1.

The less polar isomer from the silica gel column was tested in vitro as described in Example 107.

MS: 546 (MH$^+$).

Example 100

2-(1-Methanesulfonyl-5-trifluoromethyl-1H-indazol-3-ylamino)-N-{1-[4-(6-methoxy-pyridin-3-yl)-cyclohexyl]-azetidin-3-yl}-acetamide

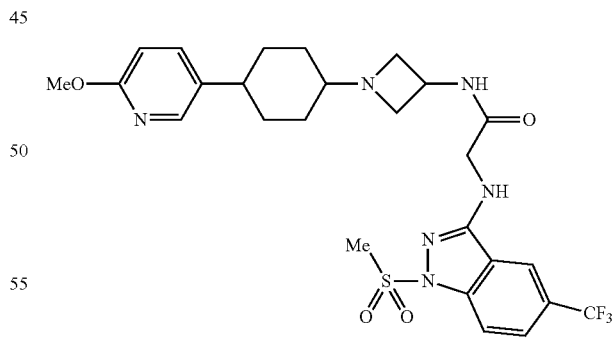

The title compound was prepared as a white solid from reaction of N-azetidin-3-yl-2-(1-methanesulfonyl-5-trifluoromethyl-1H-indazol-3-ylamino)-acetamide TFA salt and 4-(6-methoxy-pyridin-3-yl)-cyclohexanone using the procedure described in Step E of Example 1.

The less polar isomer from the silica gel column was tested in vitro as described in Example 107.

MS: 581 (MH$^+$).

Example 101

N-({1-[4-Hydroxy-4-(6-methyl-pyridin-3-yl)-cyclohexyl]-azetidin-3-ylcarbamoyl}-methyl)-3-(2,2,2-trifluoro-ethoxy)-benzamide

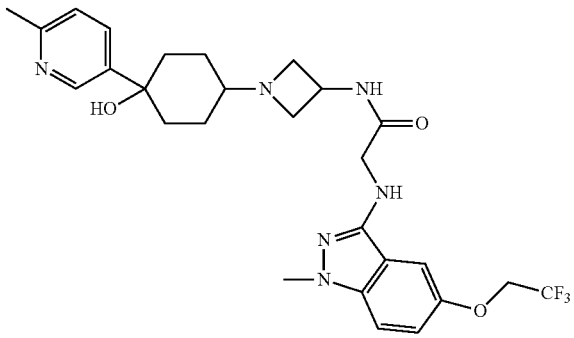 [SMILES: Cc1ccc(C2(O)CCC(N3CC(NC(=O)CNc4nn(C)c5ccc(OCC(F)(F)F)cc45)C3)CC2)cn1]

Step A

2-Fluoro-5-(2,2,2-trifluoro-ethoxy)-benzonitrile

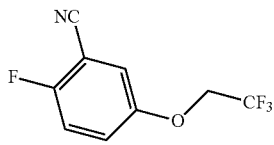 [SMILES: N#Cc1cc(OCC(F)(F)F)ccc1F]

To a solution of 2-fluoro-5-hydroxy-benzonitrile (Alfa Aesar, 137 mg, 1.0 mmol) was added 2-iodo-1,1,1,-trifluoroethane (117 L, 1.2 mmol) and potassium carbonate (165 mg, 1.2 mmol) in DMF (20 mL) and stirred at RT for 24 hours. The reaction was dissolved into EtOAc and washed with water three times and the combined organic layers were dried over anhydrous $Na_2SO_4$ and concentrated. The residue was purified by silica gel column chromatography using hexanes:ethyl acetate 5:1 to give the tile compound as white solid (105 mg, 48%).

$^1$H NMR (400 MHz, $CDCl_3$) δ: 7.26 (s, 1H), 7.18 (dd, J=7.5, 5.0 Hz, 1H), 7.14 (dd, J=6.8, 6.1 Hz, 1H), 4.35 (q, J=8.5 Hz, 2H).

Step B

N-Azetidin-3-yl-2-[1-methyl-5-(2,2,2-trifluoro-ethoxy)-1H-indazol-3-ylamino]-acetamide TFA salt

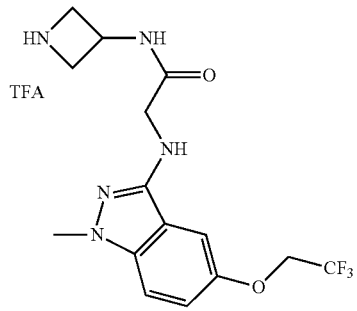 [SMILES: Cn1nc(NCC(=O)NC2CNC2)c2cc(OCC(F)(F)F)ccc21]

The title compound was prepared from 2-fluoro-5-(2,2,2-trifluoro-ethoxy)-benzonitrile as intermediate using the sequences described in Example 80 (A-D) as a colorless oil. MS: 358 (MH$^+$).

Step C

N-({1-[4-Hydroxy-4-(6-methyl-pyridin-3-yl)-cyclohexyl]-azetidin-3-ylcarbamoyl}-methyl)-3-(2,2,2-trifluoro-ethoxy)-benzamide

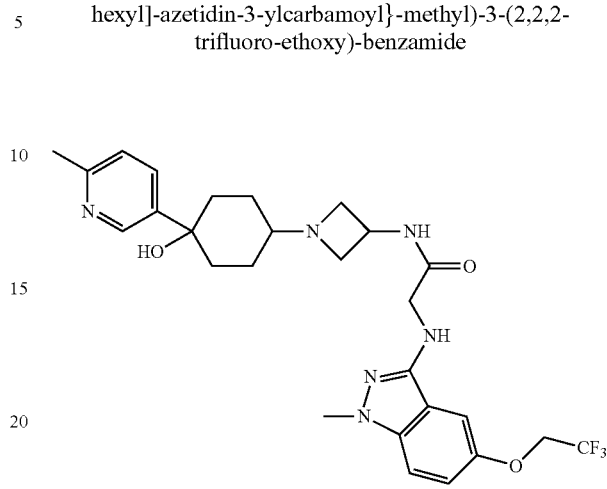

The title compound was prepared as a white solid from reaction of N-azetidin-3-yl-2-[1-methyl-5-(2,2,2-trifluoro-ethoxy)-1H-indazol-3-ylamino]-acetamide TFA salt and 4-(6-methoxy-pyridin-3-yl)-cyclohexanone using the procedure described in Step E of Example 1.

The less polar isomer from the silica gel column was tested in vitro as described in Example 107.

$^1$H NMR (400 MHz, $d_4$-MeOH) δ: 8.54-8.62 (m, 2H), 7.73-7.96 (m, 3H), 7.49-7.62 (m, 2H), 7.43 (t, J=7.9 Hz, 1H), 7.26 (d, J=8.3 Hz, 2H), 7.21 (dd, J=2.6, 8.2 Hz, 1H), 4.60 (q, J=8.3 Hz, 2H), 4.48 (s, 1H), 4.09 (d, J=7.1 Hz, 1H), 4.02 (s, 3H), 3.67 (t, J=7.6 Hz, 2H), 2.96 (t, J=7.7 Hz, 2H), 2.50 (s, 8H), 2.11-2.28 (m, 5H), 1.97-2.11 (m, 4H), 1.74-1.92 (m, 4H), 1.48-1.72 (m, 7H), 1.34-1.48 (m, 2H).

Example 102

N-{1-[4-Hydroxy-4-(6-methoxy-pyridin-3-yl)-cyclohexyl]-azetidin-3-yl}-2-[1-methyl-5-(1,2,2,2-tetrafluoro-1-methoxy-ethyl)-1H-indazol-3-ylamino]-acetamide

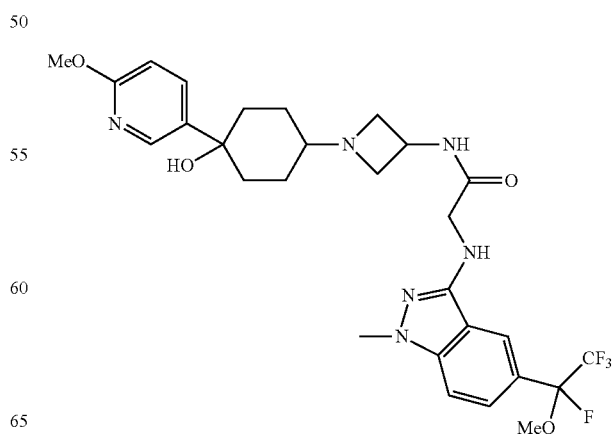

Step A

2-Fluoro-5-(1,2,2,2-tetrafluoro-1-methoxy-ethyl)-benzonitrile

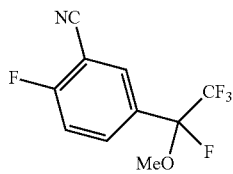 [SMILES: COC(F)(c1ccc(F)c(C#N)c1)C(F)(F)F]

2-Fluoro-5-(2,2,2-trifluoro-1-hydroxy-ethyl)-benzonitrile (1 g, 4.6 mmol) in DCM (20 mL) was treated with Dess-Martin reagent (4.84 g, 11.4 mmol) at room temperature overnight. The reaction was partitioned between DCM and water. The aqueous layer was extracted twice with DCM. The combined organic layers were dried over anhydrous Na$_2$SO$_4$ and concentrated to give crude intermediate, which was then dissolved in DCM (5 mL) and treated with DAST (0.91 mL, 6.91 mmol) at −78° C. for 2 hours. The reaction was warmed to room temperature and stirred overnight. The solution was partitioned between DCM and saturated NaHCO$_3$. The aqueous layer was extracted twice with DCM. The combined organic layers were washed with brine, dried over anhydrous Na$_2$SO$_4$ and concentrated to give the crude product which was purified by silica gel column chromatography using hexanes:ethyl acetate 4:1 to give the title compound as colorless solid (2 steps ~31%).

$^1$H NMR (400 MHz, CDCl$_3$) δ: 8.21 (t, J=5.0 Hz, 1H), 7.51 (dd, J=5.5, 3.0 Hz, 1H), 7.15 (dd, J=5.7, 2.5 Hz, 1H), 3.21 (s, 3H).

MS: 252 (MH$^+$).

Step B

N-Azetidin-3-yl-2-[1-methyl-5-(1,2,2,2-tetrafluoro-1-methoxy-ethyl)-1H-indazol-3-ylamino]-acetamide TFA salt

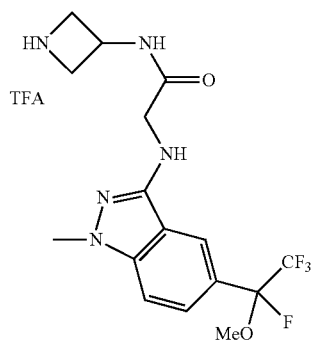 [SMILES: COC(F)(c1ccc2c(c1)c(NCC(=O)NC1CNC1)nn2C)C(F)(F)F]

The title compound was prepared from 2-fluoro-5-(1,2,2,2-tetrafluoro-1-methoxy-ethyl)-benzonitrile as intermediate using the sequences described in Example 80 (A-D) as a colorless oil.

MS: 390 (MH$^+$).

Step C

N-{1-[4-Hydroxy-4-(6-methoxy-pyridin-3-yl)-cyclohexyl]-azetidin-3-yl}-2-[1-methyl-5-(1,2,2,2-tetrafluoro-1-methoxy-ethyl)-1H-indazol-3-ylamino]-acetamide

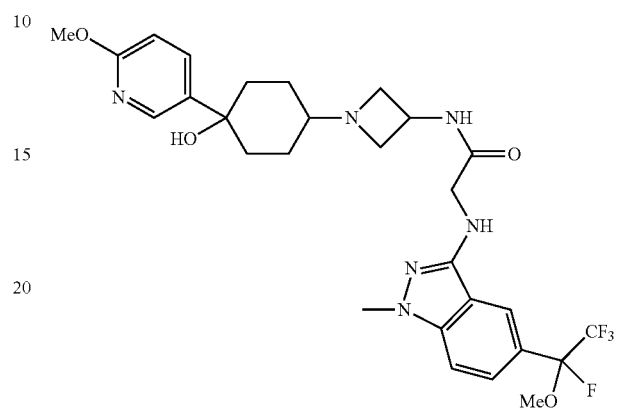

The title compound was prepared as a white solid from reaction of N-azetidin-3-yl-2-[1-methyl-5-(1,2,2,2-tetrafluoro-1-methoxy-ethyl)-1H-indazol-3-ylamino]-acetamide TFA salt and 4-hydroxy-4-(6-methoxy-pyridin-3-yl)-cyclohexanone using the procedure described in Step E of Example 1.

The less polar isomer from the silica gel column was tested in vitro as described in Example 107.

$^1$H NMR (400 MHz, CDCl$_3$) δ: 8.29 (br. s., 2H), 7.79 (s, 1H), 7.72 (br. s., 2H), 7.48 (s, 2H), 7.26-7.36 (m, 10H), 6.72 (s, 2H), 4.65 (br. s., 1H), 4.47 (s, 1H), 3.92 (s, 6H), 3.87 (s, 5H), 3.62 (br. s., 3H), 3.40 (s, 5H), 2.86 (br. s., 3H), 1.58 (br. s., 7H), 1.41 (br. s., 4H), 1.18-1.30 (m, 8H).

Example 103

N-{1-[4-Hydroxy-4-(6-methyl-pyridin-3-yl)-cyclohexyl]-azetidin-3-yl}-2-[1-methyl-5-(1,2,2,2-tetrafluoro-1-methoxy-ethyl)-1H-indazol-3-ylamino]-acetamide

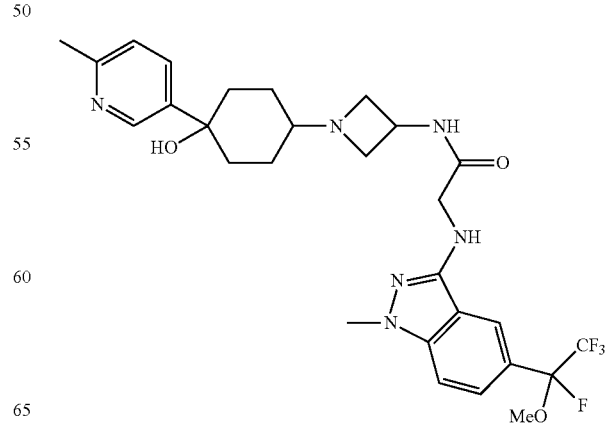

The title compound was prepared as a white solid from reaction of a N-azetidin-3-yl-2-[1-methyl-5-(1,2,2,2-tetrafluoro-1-methoxy-ethyl)-1H-indazol-3-ylamino]-acetamide TFA salt and 4-hydroxy-4-(6-methyl-pyridin-3-yl)-cyclohexanone using the procedure described in Step E of Example 1.

The less polar isomer from the silica gel column was tested in vitro as described in Example 107.

LC-MS: 579 (MH+).

Example 104

N-(1-((1R,4R)-4-hydroxy-4-(thiazol-5-yl)cyclohexyl)azetidin-3-yl)-2-((5-(trifluoromethyl)-1H-pyrazolo[4,3-b]pyridin-3-yl)amino)acetamide

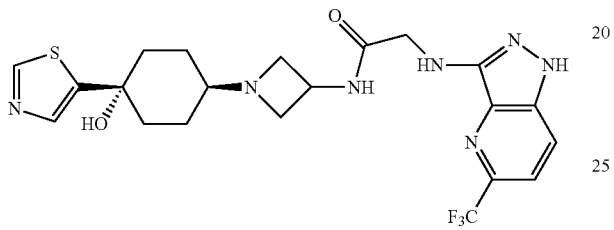

Step A 5-chloro-2-iodopyridine

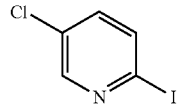

A solution of 2-bromo-5-chloropyridine (1 g, 5.21 mmol, 1.00 equiv) and NaI (2.3 g, 15.33 mmol, 3.00 equiv) in CH₃CN (20 mL) in a 100-mL round-bottom flask was treated with chlorotrimethylsilane (570 mg, 5.23 mmol, 1.00 equiv) dropwise with stirring. The reaction mixture was stirred overnight at reflux. The reaction was then quenched by the addition of 50 mL of sodium hydroxide (aq, 2N). The resulting solution was extracted with 2×20 mL of ethyl acetate. The combined organic layers were washed with 50 mL brine, dried over anhydrous sodium sulfate and concentrated. The residue was purified by chromatography over a silica gel column with ethyl acetate/petroleum ether (1:40) to yield 5-chloro-2-iodopyridine as a yellow solid Step B 5-chloro-2-(trifluoromethyl)pyridine

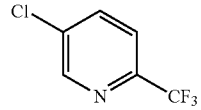

Into a 10-mL sealed tube purged and maintained with an inert atmosphere of nitrogen, was placed a solution of KF (53 mg, 0.91 mmol, 1.10 equiv) in NMP (3 mL), CuI (175 mg, 0.92 mmol, 1.10 equiv), trimethyl(trifluoromethyl)silane (119 mg, 0.84 mmol, 1.00 equiv) and 5-chloro-2-iodopyridine (as prepared in the previous step, 200 mg, 0.84 mmol, 1.00 equiv). The reaction mixture was stirred overnight at 60° C. The reaction was then quenched by the addition of 20 mL of ammonia (12%). The resulting solution was extracted with 2×20 mL of ethyl acetate. The combined organic layers were washed with 50 ml of brine, dried (Na₂SO₄), and concentrated to yield 5-chloro-2-(trifluoromethyl)pyridine as a yellow oil.

Step C 5-chloro-4-iodo-2-(trifluoromethyl)pyridine

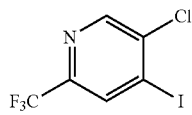

Into a 100-mL 3-necked round-bottom flask purged and maintained with an inert atmosphere of nitrogen, was placed a solution of 5-chloro-2-(trifluoromethyl)pyridine (as prepared in the previous step, 5 g, 27.62 mmol, 1.00 equiv) in tetrahydrofuran (50 mL). LDA (3 g, 28.04 mmol, 1.05 equiv, as a THF solution) was added dropwise with stirring at −78° C. The resulting solution was stirred for 30 min at −78° C. A solution of I₂ (7.4 g, 29.13 mmol, 1.05 equiv) in tetrahydrofuran (10 mL) was added dropwise with stirring at −78° C. The reaction mixture was stirred for an additional 2 h at −78° C., quenched with 15 mL of Na₂S₂O₃ (1M) and diluted with 100 mL of water. The resulting mixture was extracted with 3×50 mL of ether. The combined organic layers were washed with 50 ml brine, dried (Na₂SO₄), and concentrated under vacuum. The residue was purified by chromatography over a silica gel column with ethyl acetate/petroleum ether (0:1), yielding 5-chloro-4-iodo-2-(trifluoromethyl)pyridine as a white solid.

Step D 3-chloro-2-iodo-6-(trifluoromethyl)pyridine

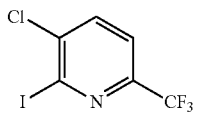 [SMILES: FC(F)(F)c1ccc(Cl)c(I)n1]

Into a 100 mL 3-necked round-bottom flask purged and maintained with an inert atmosphere of nitrogen, was placed a solution of 5-chloro-4-iodo-2-(trifluoromethyl)pyridine (as prepared in the previous step, 2 g, 6.51 mmol, 1.00 equiv) in tetrahydrofuran (20 mL). This was followed by the addition of LDA (730 mg, 6.82 mmol, 1.05 equiv, as a THF solution) dropwise with stirring at −78° C. The resulting solution was stirred for 2 h at −78° C. The reaction was then quenched by the addition of 5 mL of water and diluted with 100 mL DCM. The resulting solution was washed with 50 mL brine, dried (Na₂SO₄), and concentrated. The residue was purified by silica gel column with ethyl acetate/petroleum ether (1:10) eluent, yielding 3-chloro-2-iodo-6-(trifluoromethyl)pyridine as a yellow solid.

Step E 3-chloro-6-(trifluoromethyl)picolinonitrile

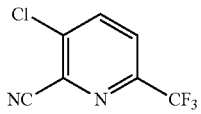

Into a 10-mL sealed tube purged and maintained with an inert atmosphere of nitrogen, was placed a solution of 3-chloro-2-iodo-6-(trifluoromethyl)pyridine (as prepared in the previous step, 4.0 g, 13.03 mmol, 1.00 equiv) in N,N-dimethylformamide (2 mL), Zn(CN)$_2$ (1.2 g, 10.34 mmol, 0.80 equiv), and Pd(PPh$_3$)$_4$ (0.8 g, 0.69 mmol, 0.05 equiv). The reaction solution was stirred overnight at 110° C. The resulting mixture was concentrated under vacuum and purified by silica gel column chromatography with ethyl acetate/petroleum ether (1:100). The title compound was obtained as yellow oil Step F 5-(trifluoromethyl)-1H-pyrazolo[4,3-b]pyridin-3-amine

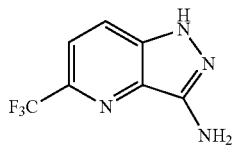

Into a 50 mL round-bottom flask, was placed a solution of 3-chloro-6-(trifluoromethyl)picolinonitrile (as prepared in the previous step, 200 mg, 0.97 mmol, 1.00 equiv) in ethanol (15 mL) and NH$_2$NH$_2$.H$_2$O (145 mg, 2.90 mmol, 3.00 equiv). The reaction mixture was stirred overnight at 90° C. The resulting mixture was concentrated under vacuum and purified by silica gel column chromatography with dichloromethane/methanol (100:1) to give 5-(trifluoromethyl)-1H-indazol-3-amine as a yellow solid. LC-MS-(ES, m/z) 203 [M+H]

Step G 2-((5-(trifluoromethyl)-1H-pyrazolo[4,3-b]pyridin-3-yl)amino)acetic acid

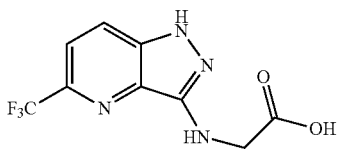 [SMILES: O=C(O)CNc1n[nH]c2ccc(C(F)(F)F)nc12]

Into a 50-mL round-bottom flask, was placed a solution of 5-(trifluoromethyl)-1H-indazol-3-amine (as prepared in the previous step, 50 mg, 0.25 mmol, 1.00 equiv) in MeOH (10 mL), 2-oxoacetic acid (80% in water) (27.6 mg, 0.37 mmol, 1.20 equiv) and NaBH$_3$CN (105 mg, 0.50 mmol, 2.00 equiv). The reaction mixture was stirred for 2 h at room temperature, then concentrated under vacuum to give 2-(5-(trifluoromethyl)-1H-indazol-3-ylamino)acetic acid as a yellow solid. LC-MS-(ES, m/z) 261[M+H]$^+$ Step H tert-butyl (1-((1r, 4r)-4-hydroxy-4-(thiazol-5-yl)cyclohexyl)azetidin-3-yl)carbamate

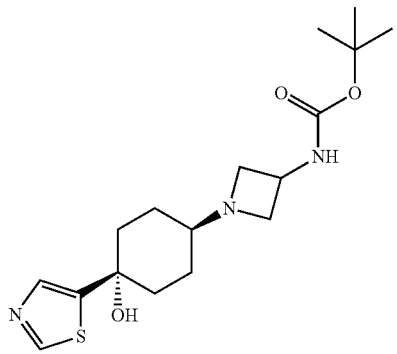 [SMILES: CC(C)(C)OC(=O)NC1CN([C@H]2CC[C@@](O)(c3cncs3)CC2)C1]

A solution of 4-hydroxy-4-(thiazol-5-yl)cyclohexanone (412 mg, 2.09 mmol) and tert-butyl azetidin-3-ylcarbamate (30 mg, 2.09 mmol) in DCM (30 mL) was treated with NaBH(OAc)$_3$ (1.33 g, 6.28 mmol) and stirred overnight at room temperature. The mixture was concentrated in vacuo and the residue purified by flash chromatography (silica gel, 5-20% 7N NH3-MeOH/ethyl acetate) with the titled isomer eluting before the minor isomer.
$^1$H NMR (ACETONITRILE-d$_3$) δ: 8.72 (s, 1H), 7.71 (s, 1H), 5.62 (br. s., 1H), 3.99-4.13 (m, 1H), 3.49 (s, 2H), 3.35-3.45 (m, 1H), 2.72 (s, 2H), 2.16 (s, 6H), 1.70-1.80 (m, 2H), 1.58-1.70 (m, 2H), 1.39 (s, 11H)

Step I (1r, 4r)-4-(3-aminoazetidin-1-yl)-1-(thiazol-5-yl)cyclohexanol

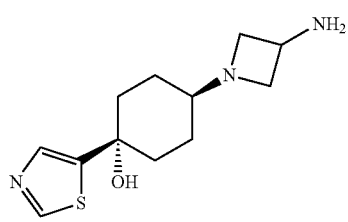 [SMILES: NC1CN([C@H]2CC[C@@](O)(c3cncs3)CC2)C1]

To a solution of tert-butyl (1-((1r, 4r)-4-hydroxy-4-(thiazol-5-yl)cyclohexyl)azetidin-3-yl)carbamate (as prepared in the previous step, 366 mg, 1.04 mmol) in dry DCM (20 mL) was added TFA (1 mL, 13.1 mmol) at room temperature. After stirring overnight at ambient temperature, the reaction mixture was concentrated in vacuo. Trituration of the residue

Step J

N-(1-((1R,4R)-4-hydroxy-4-(thiazol-5-yl)cyclohexyl)azetidin-3-yl)-2-((5-(trifluoromethyl)-1H-pyrazolo[4,3-b]pyridin-3-yl)amino)acetamide

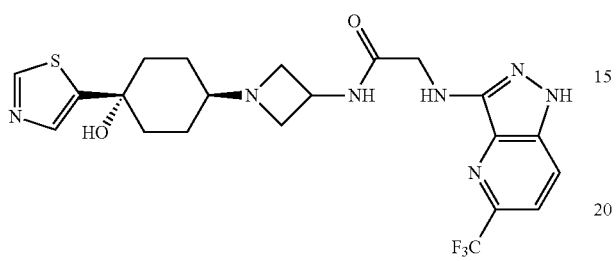

Into a 50-mL round-bottom flask, was placed a solution of 2-(5-(trifluoromethyl)-1H-indazol-3-ylamino)acetic acid (as prepared in Step G, 50 mg, 0.19 mmol, 1.00 equiv) in tetrahydrofuran (10 mL), (1r, 4r)-4-(3-aminoazetidin-1-yl)-1-(thiazol-5-yl)cyclohexanol 2,2,2-trifluoroacetic acid (as prepared in the previous step, 70.8 mg, 0.19 mmol, 1.00 equiv), EDCI (48 mg, 0.25 mmol, 1.30 equiv), HOBt (34 mg, 0.25 mmol, 1.30 equiv) and TEA (58 mg, 0.57 mmol, 3.00 equiv). The reaction mixture was stirred overnight at room temperature. The resulting mixture was diluted with 100 mL of DCM, washed with 50 mL brine, dried ($Na_2SO_4$), and concentrated under vacuum. The crude product was purified by prep-HPLC with the following conditions (1#-Waters 2767-1): Column, SunFire Prep C18, 5 um, 19*100 mm; mobile phase, water in 0.05% $NH_4HCO_3$ and $CH_3CN$ (5% up to 31.5% in 28 min, up to 100% in 2 min, down to 5% in 2 min; Detector, UV 254 nm. The title product was obtained as a yellow solid LC-MS (ES, m/z) 496[M+H]$^+$.

$^1$H NMR (300 MHz, $CD_3OD$) δ8.897 (s, 1H), 7.936-7.906 (d, J=9 Hz, 1H), 7.819 (s, 1H), 7.727-7.697 (d, J=9 Hz, 11H), 4.504-4.458 (t, J=6.9 Hz, 1H), 4.084 (s, 2H), 3.652-3.601 (t, 2H), 3.012-2.962 (t, 2H), 2.334-2.174 (m, 3H), 1.879-1.718 (m, 4H), 1.346-1.315 (t, J=3 Hz, 2H).

Examples 105 and 106

N-(1-((1R,4S)-4-((S)-1-hydroxypropyl)cyclohexyl)azetidin-3-yl)-2-((5-(trifluoromethyl)-1H-pyrazolo[3,4-b]pyridin-3-yl)amino)acetamide and N-(1-((1R,4R)-4-((R)-1-hydroxypropyl)cyclohexyl)azetidin-3-yl)-2-((5-(trifluoromethyl)-1H-pyrazolo[3,4-b]pyridin-3-yl)amino)acetamide

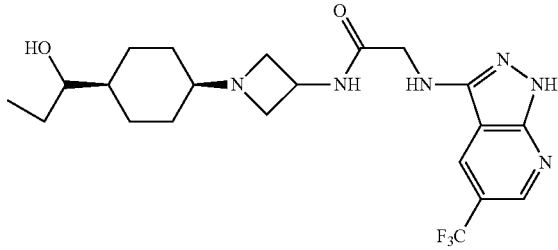 [SMILES: CCC(O)[C@H]1CC[C@@H](N2CC(NC(=O)CNc3n[nH]c4ncc(C(F)(F)F)cc34)C2)CC1]

Example 105

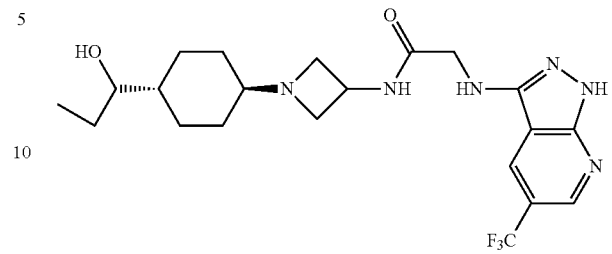

Example 106

Step A 2-chloro-5-(trifluoromethyl)nicotinoyl chloride

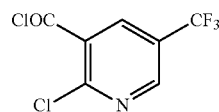

To a suspension of 2-chloro-5-(trifluoromethyl)nicotinic acid (1.147 g, 4.83 mmol) in DCM (20 mL) was added oxalyl chloride (630 L, 7.35 mmol) dropwise with stirring. A single drop of DMF was added and the reaction mixture was stirred 40° C. for 1 hour. Concentration of the reaction mixture in vacuo resulted in the title compound as a brown oil.

$^1$H NMR(CHLOROFORM-d) δ: 8.86 (d, J=1.5 Hz, 1H), 8.58 (d, 1H)

Step B 2-chloro-5-(trifluoromethyl)nicotinamide

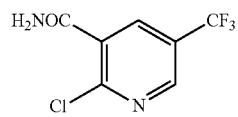

An ice-cold solution of ammonia in water was treated with a solution of 2-chloro-5-(trifluoromethyl)nicotinoyl chloride (as prepared in the previous step, 1.18 g, 4.8 mmol) in dioxane. After stirring at ice bath temperature for 1 hour, the resulting precipitate was dissolved in ethyl acetate and the organic extract dried over anhydrous sodium sulfate. Concentration in vacuo followed by drying on the high vacuum afforded the product as a white solid.

¹H NMR (CHLOROFORM-d) δ: 8.76 (d, J=1.7 Hz, 1H), 8.50 (d, J=2.2 Hz, 1H), 6.46-6.96 (br s, 1H), 6.13 (br s, 1H)

Step C 2-chloro-5-(trifluoromethyl)nicotinonitrile

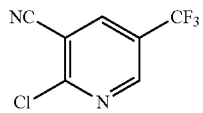

To a solution of 2-chloro-5-(trifluoromethyl)nicotinamide (as prepared in the previous step, 788 mg, 3.51 mmol) in dry DCM was added TEA (1.1 mL, 7.89 mmol). After cooling to 0° C. under argon, trifluoroacetic anhydride (0.54 mL, 3.88 mmol) was added dropwise. After stirring for 1.5 hours at 0° C., DCM (30 mL) and saturated aqueous sodium bicarbonate were introduced. The organic layer was removed and concentrated in vacuo. The resulting residue was purified by flash chromatography (silica gel, DCM) to afford the product as a tan solid.

¹H NMR(CHLOROFORM-d) δ: 8.87 (d, J=1.5 Hz, 1H), 8.25 (d, 1H)

Step D 1-methyl-5-(trifluoromethyl)-1H-pyrazolo[3,4-b]pyridin-3-amine

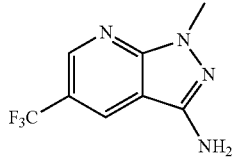

A solution of 2-chloro-5-(trifluoromethyl)nicotinonitrile (as prepared in the previous step, 342 mg, 1.65 mmol) in ethanol (10 mL) in a 50-mL round-bottom flask, was treated with MeNH₂NH₂ (100 L, 2.05 mmol). The reaction mixture was stirred overnight at 90° C. The resulting mixture was concentrated under vacuum. The residue was purified by chromatography over a silica gel column with dichloromethane/ethylacetate (1:1), to give the title compound as a yellow solid.

¹H NMR(CHLOROFORM-d) δ: 8.69 (d, J=1.5 Hz, 1H), 8.15 (s, 1H), 4.24 (br. s., 2H), 3.97 (s, 3H); LC-MS (ES, m/z) 217[M+H]⁺

Step E 2-((1-methyl-5-(trifluoromethyl)-1H-pyrazolo[3,4-b]pyridin-3-yl)amino)acetic acid

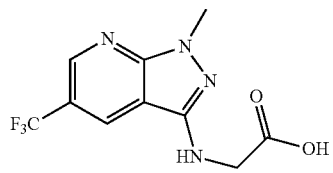 [SMILES: Cn1nc(NCC(=O)O)c2cc(C(F)(F)F)cnc21]

Into a 50-mL round-bottom flask, was placed a solution of 1-methyl-5-(trifluoromethyl)-1H-pyrazolo[3,4-b]pyridin-3-amine (as prepared in the previous step, 284 mg, 1.31 mmol) in MeOH (20 mL), 2-oxoacetic acid (184 mg, 1.577 mmol) and NaBH₃CN (86 mg, 1.37 mmol). The reaction mixture was stirred for 2 h at room temperature. The resulting mixture was concentrated under vacuum. After flash chromatography (silica gel, ethyl acetate) the title compound was isolated as a yellow solid.

¹H NMR (MeOD) δ: 8.65 (d, J=1.5 Hz, 1H), 8.50 (s, 1H), 4.09 (s, 2H), 3.88 (s, 3H); LC-MS (ES, m/z) 275 [M+H]⁺

Step F tert-butyl 3-(2-((1-methyl-5-(trifluoromethyl)-1H-pyrazolo[3,4-b]pyridin-3-yl)amino)acetamido)azetidine-1-carboxylate

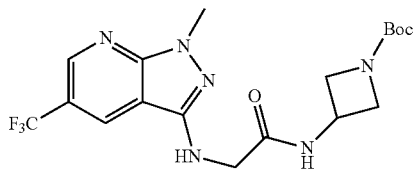 [SMILES: Cn1nc(NCC(=O)NC2CN(C(=O)OC(C)(C)C)C2)c2cc(C(F)(F)F)cnc21]

Into a 50-mL round-bottom flask, was placed 2-((1-methyl-5-(trifluoromethyl)-1H-pyrazolo[3,4-b]pyridin-3-yl)amino)acetic acid (as prepared in the previous step, 134 mg, 0.49 mmol) followed by DCM (20 mL), tert-butyl 3-aminoazetidine-1-carboxylate (104 mg, 0.60 mmol), EDCI (104 mg, 0.54 mmol) and HOBt (75 mg, 0.49 mmol). The reaction mixture was stirred overnight at room temperature and then concentrated in vacuo. The resulting residue was purified by flash chromatography (silica gel, 0-20% MeOH/ethyl acetate) to afford the title compound in sufficient purity to conduct the next step.

Step G

N-(azetidin-3-yl)-2-((1-methyl-5-(trifluoromethyl)-1H-pyrazolo[3,4-b]pyridin-3-yl)amino)acetamide

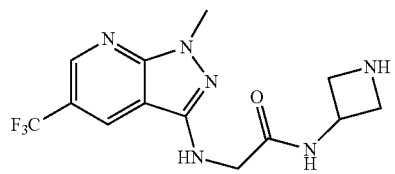 [SMILES: Cn1nc(NCC(=O)NC2CNC2)c2cc(C(F)(F)F)cnc21]

To a 50-mL round-bottom flask containing tert-butyl 3-(2-((1-methyl-5-(trifluoromethyl)-1H-pyrazolo[3,4-b]pyridin-3-yl)amino)acetamido)azetidine-1-carboxylate (as prepared in the previous step, 67 mg, 0.156 mmol) in DCM (10 mL) was added TFA (0.02 mL, 2.6 mmol). The reaction mixture was stirred at room temperature overnight and then concentrated in vacuo. Drying the residue on the high vacuum resulted in crude N-(azetidin-3-yl)-2-((1-methyl-5-(trifluoromethyl)-1H-pyrazolo[3,4-b]pyridin-3-yl)amino)acetamide as a yellow gum (TFA salt). LC-MS (ES, m/z) 329[M+H]$^+$ Step H N-(1-((1R,4S)-4-((S)-1-hydroxypropyl)cyclohexyl)azetidin-3-yl)-2-((5-(trifluoromethyl)-1H-pyrazolo[3,4-b]pyridin-3-yl)amino)acetamide and N-(1-((1R,4R)-4-((R)-1-hydroxypropyl)cyclohexyl)azetidin-3-yl)-2-((5-(trifluoromethyl)-1H-pyrazolo[3,4-b]pyridin-3-yl)amino)acetamide

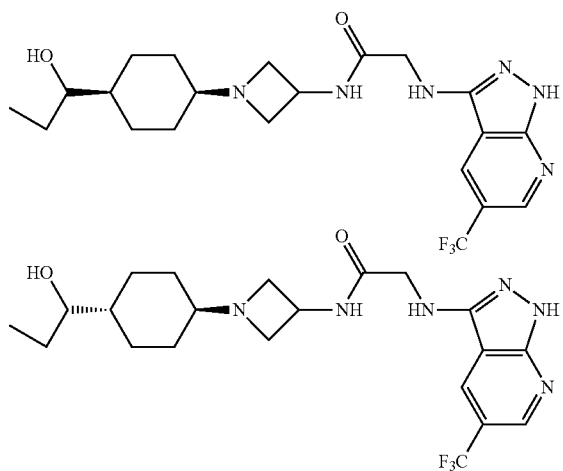

Into a 50-mL round-bottom flask containing N-(azetidin-3-yl)-2-((1-methyl-5-(trifluoromethyl)-1H-pyrazolo[3,4-b]pyridin-3-yl)amino)acetamide (as prepared in the previous step, 79 mg, 0.118 mmol) was added 4-(1-hydroxypropyl)cyclohexanone (29 mg, 0.186 mmol), TEA (0.02 mL, 0.143 mmol) and NaBH(OAc)$_3$ (75 mg, 0.354 mmol). The reaction mixture was stirred overnight at room temperature and then concentrated in vacuo. A saturated solution of NaHCO$_3$ was added to the residue and the mixture extracted with ethyl acetate. Concentration of the organic layer followed by purification of the residue (silica gel, 0-10% 7N NH$_3$-MeOH/ethyl acetate) yielded both the cis (first eluting) and trans (second eluting) isomers.

LC-MS (ES, m/z) 455[M+H]$^+$

Cis:

$^1$H NMR (MeOH) δ: 8.67 (s, 1H), 8.47 (s, 1H), 4.45-4.53 (m, 1H), 4.00 (s, 2H), 3.88 (s, 3H), 3.57-3.67 (m, 3H), 2.90-2.99 (m, 2H), 2.19-2.35 (m, 1H), 1.21-1.67 (m, 17H), 0.89-0.98 (m, 4H)

Trans:

$^1$H NMR (MeOH) δ: 8.67 (s, 1H), 8.49 (s, 1H), 4.44-4.53 (m, 1H), 4.00 (s, 2H), 3.89 (s, 3H), 3.57-3.69 (m, 4H), 3.12-3.23 (m, 1H), 2.87-3.04 (m, 3H), 2.22-2.33 (m, 1H), 1.78-1.91 (m, 2H), 1.24 (s, 22H), 0.94 (m, 8H)

Example 107

In Vitro Biological Data

Compounds of the invention were subjected to various representative biological tests.

The results of these tests are intended to illustrate the invention in a non-limiting fashion.

MCP-1 Receptor Binding Assay in THP-1 Cells

Human monocytic cell line THP-1 cells were obtained from American Type Culture Collection (Manassas, Va., USA). The THP-1 cells were grown in RPMI-1640 (RPMI: Roswell Park Memorial Institute Medium-cell culture growth media) supplemented with 10% fetal bovine serum in a humidified 5% CO$_2$ atmosphere at 37° C. The cell density was maintained between 0.5×10$^6$ cells/mL.

THP-1 (cells were incubated with 0.5 nM $^{125}$I labeled MCP-1 (Perkin-Elmer Life Sciences, Inc. Boston, Mass.) in the presence of varying concentrations of either unlabeled MCP-1 (R & D Systems, Minneapolis, Minn.) or test compound for 2 hours at 30° C. in a 96 well plate. Cells were then harvested onto a filter plate, dried, and 20 µL of Microscint 20 was added to each well. Plates were counted in a TopCount NXT, Microplate Scintillation & Luminescence Counter (Perkin-Elmer Life Sciences, Inc. Boston, Mass.). Blank values (buffer only) were subtracted from all values and drug treated values were compared to vehicle treated values. 1 µM cold MCP-1 was used for nonspecific binding.

Table 1 lists IC$_{50}$ values for inhibition of MCP-1 binding to CCR2 obtained for test compounds of the invention. Where an IC$_{50}$ value was not obtained for a particular compound, the percent inhibition is provided at a test concentration of 25 µM.

TABLE 1

Inhibition of MCP-1 Binding IC$_{50}$

| Example | CCR2 Binding (nM) |
| --- | --- |
| 1 | 36 |
| 2 | 23 |
| 3 | 31 |
| 4 | 31 |
| 5 | 330 |
| 6 | 29 |
| 7 | 170 |
| 8 | 7,700 |
| 9 | 770 |
| 10 | 750 |
| 11 | 2,900 |
| 12 | 390 |
| 13 | 450 |
| 14 | 360 |
| 15 | 10 |
| 16 | 71 |
| 17 | 750 |
| 18 | 9.4 |
| 19 | 56 |
| 20 | 4.8 |
| 21 | 28 |
| 22 | 13 |
| 23 | 180 |
| 24 | 5.3 |
| 25 | 200 |
| 26 | 146 |
| 27 | 1,400 |
| 28 | 19 |
| 29 | 19 |
| 30 | 7.5 |
| 31 | 76 |
| 32 | 13 |
| 33 | 44 |
| 34 | 27 |
| 35 | 23 |
| 36 | 228 |
| 37 | 136 |
| 38 | 150 |
| 39 | 380 |
| 40 | 300 |
| 41 | 31 |
| 42 | 16 |
| 43 | 5.8 |

TABLE 1-continued

Inhibition of MCP-1 Binding $IC_{50}$

| Example | CCR2 Binding (nM) |
|---|---|
| 44 | 16 |
| 45 | 6.6 |
| 46 | 13 |
| 47 | 12 |
| 48 | 430 |
| 49 | no data |
| 50 | 27 |
| 51 | 87 |
| 52 | 370 |
| 53 | 63 |
| 54 | 35 |
| 55 | 42 |
| 56 | 27 |
| 57 | 60 |
| 58 | 45 |
| 59 | 340 |
| 60 | 2,090 |
| 61 | 1,700 |
| 62 | 1,500 |
| 63 | 3,400 |
| 64 | 300 |
| 65 | 100 |
| 66 | 37 |
| 67 | 8.4 |
| 68 | 51 |
| 69 | 8.6 |
| 70 | 15 |
| 71 | 730 |
| 72 | 230 |
| 73 | 160 |
| 74 | 55 |
| 75 | 32 |
| 76 | 29 |
| 77 | 31 |
| 78 | 21 |
| 79 | no data |
| 80 | 75 |
| 81 | 29 |
| 82 | 34 |
| 83 | 22 |
| 84 | 870 |
| 85 | 530 |
| 86 | 750 |
| 87 | 520 |
| 88 | 360 |
| 89 | 56 |
| 90 | 29 |
| 91 | 14 |
| 92 | 1,600 |
| 93 | 3,100 |
| 94 | 53 |
| 95 | 3,600 |
| 96 | 270 |
| 97 | 170 |
| 98 | 5,900 |
| 99 | 230 |
| 100 | 3,700 |
| 101 | 1,100 |
| 102 | 33 |
| 103 | 22 |
| 104 | 230 |
| 105 | 330 |
| 106 | 330 |

Example 108

Animals

Mouse CCR2 knock-out/human CCR2 knock-in mice are generated using targeted 129Sv/Evbrd embryonic stem cell clones injected into C57BL/6 mice. Expression of the hCCR2 transcript is confirmed by quantitative reverse transcription-polymerase chain reaction performed on spleen and blood total RNA from homozygous hCCR2 knock-in mice. Backcrossing into C57BL/6 genetic background continued to the eighth generation. Transgenic mice are housed in a specific-pathogen-free, temperature-controlled facility that maintained a 12-hour light/12-hour dark cycle. Mice have free access to water and food. Experimental procedures are carried out in accordance with institutional standards for animal care and are approved by the institute's animal care and use committee.

Example 109

Murine In Vivo Cell Migration Assay

Animals are orally dosed with vehicle or CCR2 antagonists at 3, 10 and 30 mg/kg bid. Animals undergo anesthesia and laparotomy. A distal loop of small bowel (5 cm in length) is gently eventrated onto moist sterile gauze. Synthetic human MCP-1 (1 mg/100 ml sterile PBS) or PBS alone is administered drop-wise onto the serosa of the eventrated loop. A suture knot is placed into the mesentery to mark the terminus of the treated area. Twenty-four hours later, the animal is sacrificed and the segment of bowel plus the adjacent region is removed. The tissue is opened along the mesenteric border, pinned flat and the mucosa removed. The remaining muscle layer is fixed briefly in 100% EtOH and then stained using Hanker-Yates reagent to detect myeloperoxidase-containing immune cells. At 10 mpk, P.O. bid, a compound is deemed efficacious if the inhibition of cell migration reaches 30% compared with vehicle-treated animals.

Example 110

Thiolycollate-Induced Peritonitis in Mice

Animals are orally dosed with vehicle or CCR2 antagonists at 3, 10, 30 and 100 mg/kg bid). One hour later, the animals are intraperiponeally injected with sterile thioglycollate (25 mL/kg, ip, Sigma) for induction of peritonitis. Animals are orally treated twice daily with vehicle or CCR2 antagonists. At the 72-hour time point, perinoteal cavities are lavaged with 10 mL of sterile saline. Total cell counts in the peritoneal lavage fluid are performed using a microscope and cell differentiation is performed using cytospin analysis after Giemsa staining (Hema Tek 2000). Percent inhibition of the thioglycollate-induced peritonitis is calculated by comparing the change in number of leukocytes of CCR2 antagonist treated mice to the vehicle-treated mice.

Example 111

MCP-1-Induced Monocyte Recruitment to Airway of Mice

Animals are orally treated with vehicle or CCR2 antagonists at 3, 10, and 30 mg/kg po bid). One hour later, the animals are intranasally dosed with 4 g of MCP-1 in sterile saline. The animals are orally treated twice daily with vehicle or CCR2 antagonists. After 48 h, mice are euthanized by intraperitoneal injection of anesthesia solution (Sleepaway-Sodium pentobarbital). Whole bronchoalveolar lavage (BAL) is performed using 1.4 ml of ice-cold PBS containing 3 mM EDTA. Total cell counts in the BAL lavage fluid are performed using a microscope and cell differentiation is performed using cytospin analysis after Giemsa staining (Hema Tek 2000). Percent inhibition is calculated by comparing the change in number of total leukocyte counts (including monocytes/macrophages and lymphocytes) of compound-treated mice to the vehicle-treated mice. Compounds are deemed efficacious if percent inhibition reaches 30%.

Example 112

High-Fat Diet Induced Obesity and Insulin Resistance in Mice

Obesity is induced by a high-fat diet that derived approximately 60% calories from lipids (D-12492; Research Diets Inc.) in animals for 10-24 weeks at age of 7 weeks. Prior to age 7 weeks, animals are fed a standard pellet diet, in which 5% of calories were provided as fat. Obese animals were randomized by body weight and fat mass. The obese animals are orally treated with vehicle or CCR2 antagonists at 3, 10 and 30 mg/kg, po bid. Body weight and food intake and were fasting blood glucose levels monitored. Body mass was determined by a NMR analyzer (Burker MiniSpec). Insulin tolerance test is carried out in animals that were fasted for 3 hours. After an intraperitoneal bolus injection of recombinant human insulin (1.5 U/kg), blood glucose concentrations are measured using a Glucometer before and 15, 30, 45, 60, 90 and 120 minutes after injection. Glucose tolerance tests are performed after an overnight (17-hour) fast. Blood glucose concentrations are measured before and after 15, 30, 60, 90, 120 minutes after an oral dose of glucose dissolved in water (1 g/kg). Energy expenditure analysis was monitored by a complete laboratory animal monitor system. After 40 days treatment with vehicle or CCR2 antagonists, the animals are sacrificed by $CO_2$ asphyxiation. Percent of weight loss is calculated by comparing the body weight changes of the compound-treated mice with the vehicle-treated mice.

Example 113

Mouse Model of Allergic Asthma

Animals are sensitized by intraperitoneal injection of 10 μg chicken egg albumin (OVA) absorbed to 1 mg Imject® in 100 μL phosphate-buffered saline (PBS) on days 0 and 5. Control animals received PBS ip. OVA-immunized animals were challenged by inhalation of 0.5% OVA aerosol for 10 minutes by an ultrasonic nebulizer on days 12, 16 and 20. Control animals were challenged with PBS in similar fashion. The OVA-sensitized animals receive vehicle (0.5% Methocel) or CCR2 antagonists orally at 3, 10, 30 mg/kg twice daily from days 9-20 and once daily on Day 21, 2 hours before sacrifice. Dexamethason (5 mg/kg) and Montelukast (1 mg/kg) are given orally once a day. On day 21, 2 hours post the last dose of CCR2 compounds, bronchial reactivity to aerosolized methacholine is measured using a Buxco whole body plethysmograpgh. On day 21, the animals are sacrificed. Bronchoalveolar lavage fluid is collected (1 mL) and total cells counted. The numbers of eosinophils, lymphocytes, monocytes and neutrophils are determined using cytospin analysis after Giemsa staining (Hema Tek 2000). Percent inhibition of total BAL leukocyte count (and eosinophil count) is calculated by comparing the compound-treated mice with vehicle-treated mice. Compounds are deemed efficacious if the inhibition reaches 30%.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

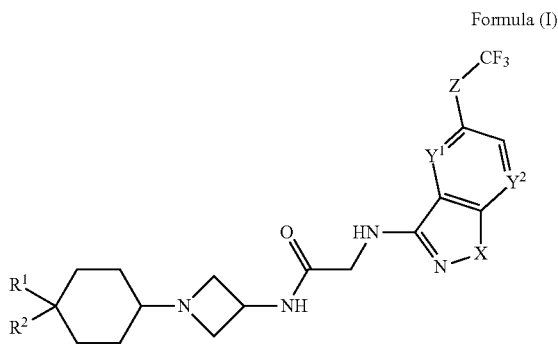

Formula (I)

wherein:
X is O or $NR^3$;
wherein $R^3$ is: H, $C_{(1-6)}$alkyl, $CH_2CF_3$, $C_{(1-6)}$alkylOH, $C_{(2-6)}$alkenyl, $CH_2OC_{(2-6)}$alkenyl, $CH_2OC_{(1-6)}$alkyl, $C(O)C_{(1-6)}$alkyl, $CONH_2$, $CONHC_{(1-6)}$alkyl, $SONH_2$, $CH_2Ph$, $CH_2$heteroaryl, $CH_2$heterocyclyl, $CH_2$cycloalkyl, $C_{(3-6)}$cycloalkyl, or $SO_2C_{(1-2)}$alkyl; wherein said heteroaryl, heterocyclyl, or cycloalkyl may be optionally substituted with up to three substituents selected from the group consisting of: F, $OCH_3$, $CH_3$, and OH;
$Y^1$ and $Y^2$ are CH or N, provided that both $Y^1$ and $Y^2$ are not N;
Z is O, $CH_2$, S, S(O), $SO_2$,

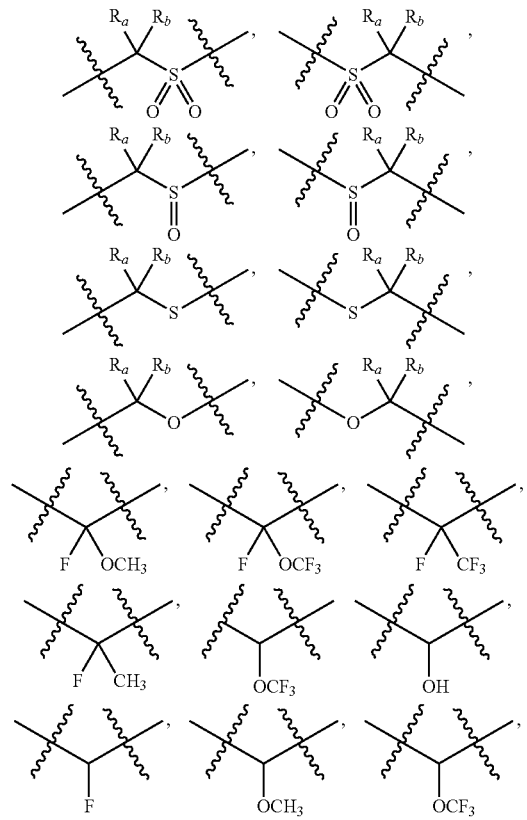

191

-continued

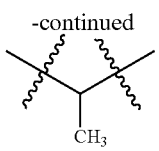

or a direct bond; wherein $R_a$ and $R_b$ are independently selected from the group consisting of: H, OH, F, $CH_3$, $CF_3$, $OCF_3$, and $OCH_3$;

$R^1$ is

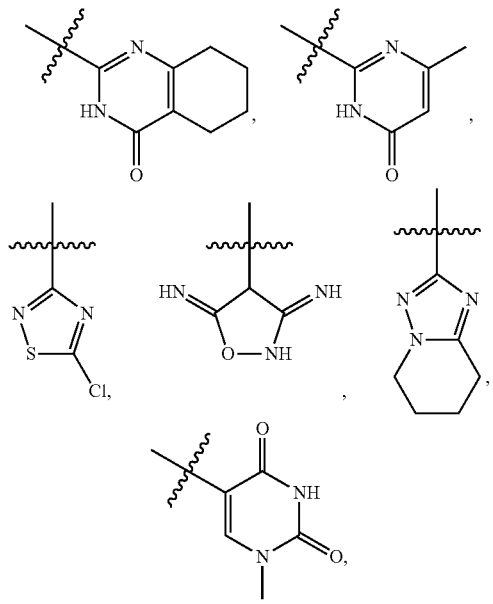

pyridyl, pyridyl-N-oxide, pyrimidyl, pyrazolyl, indolyl, thiazolyl, benzo[1,3]dioxol-5-yl, pyrazolyl, oxazolyl, isoxazolyl, imidazolyl, phenyl, thiazolyl, isothiazolyl, 3-H-thiazol-2-onyl, benzooxazolyl, furyl, [1,2,4]oxadiazolyl, [1,3,4]thiadiazolyl, $C_{(4-7)}$cycloalkyl, $C_{(1-6)}$alkyl, $C_{(1-4)}$alkylOH, $CH_2OC_{(3-6)}$alkenyl, $CH_2OC_{(1-4)}$alkyl, $CH_2C(O)NH_2$, $CO_2C_{(1-4)}$alkyl, —CN, $C(O)NH_2$, $C(O)NHCH_2CH_2OH$, OTBS, OH, $OC_{(1-4)}$alkyl, $OC_{(3-6)}$alkenyl, $NH_2$, NHBOC, or pyridonyl; wherein said pyridyl, pyridyl-N-oxide, pyrimidyl, pyrazolyl, indolyl, thiazolyl, benzo[1,3]dioxol-5-yl, pyrazolyl, oxazolyl, isoxazolyl, imidazolyl, phenyl, thiazolyl, isothiazolyl, 3-H-thiazol-2-onyl, benzooxazolyl, furyl, [1,2,4]oxadiazolyl, [1,3,4]thiadiazolyl, $C_{(4-7)}$cycloalkyl, $C_{(1-6)}$alkyl, or pyridonyl, may be optionally substituted with one or two substituents, independently selected from the group consisting of: $CH_2C(O)NH_2$, $C_{(1-4)}$alkoxy, $OC_{(3-6)}$cycloalkyl, $OCH_2CF_3$, $OCH_2Ph$, F, CN, Cl, $OCF_3$, $CF_3$, $CH_2CN$, $C_{(1-4)}$alkyl, $CH_2CF_3$, $N(C_{(1-4)}alkyl)_2$, $C_{(1-4)}$alkylOH, $Si(CH_3)_3$, —C≡CH, $SCH_3$, $S(O)CH_3$, $SO_2CH_3$, pyrrolidinyl, OH, $NH_2$, NHCN, $CO_2H$, $CONH_2$, $NHCO_2C_{(1-4)}$alkyl, $N(SO_2CH_3)_2$, $NHSO_2CH_3$, $NHC(O)CF_3$, $NHC_{(1-4)}$alkyl, $NHCO_2H$, $NHCO_2C_{(1-4)}$alkyl, $NHCOC_{(1-4)}$alkyl, $NHCONH_2$, $NHCONHC_{(1-4)}$alkyl, and Br;

$R^2$ is F, $NH_2$, H, or OH;

and tautomers, and pharmaceutically acceptable salts thereof.

2. A compound of claim 1 wherein
$Y^1$ and $Y^2$ are CH;
and tautomers, and pharmaceutically acceptable salts thereof.

192

3. A compound of claim 2 wherein:
X is O or $NR^3$;
wherein $R^3$ is: H, $C_{(1-6)}$alkyl, $CH_2CF_3$, $C_{(1-6)}$alkylOH, $C_{(2-6)}$alkenyl, $CH_2OC_{(2-6)}$alkenyl, $CH_2OC_{(1-6)}$alkyl, $C(O)C_{(1-6)}$alkyl, $CONH_2$, $CONHC_{(1-6)}$alkyl, $SONH_2$, $CH_2Ph$, $CH_2$pyridyl, $CH_2$pyrrolyl, $CH_2$pyrimidyl, $CH_2$pyridazyl, $CH_2$imidazolyl, $CH_2$oxazolyl, $CH_2$isoxazolyl, $CH_2$furanyl, or $SO_2C_{(1-2)}$alkyl;

Z is O, $CH_2$,

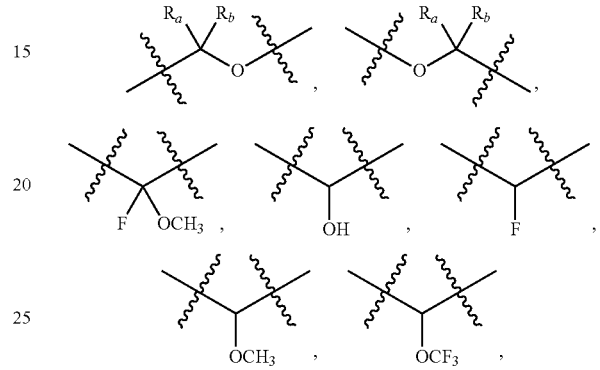

or a direct bond; wherein $R_a$ and $R_b$ are independently selected from the group consisting of: H, OH, F, and $OCH_3$;

$R^1$ is

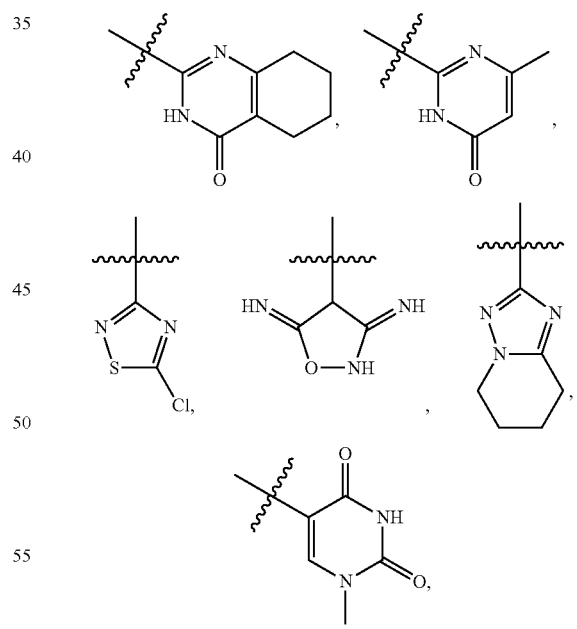

pyridyl, pyrimidyl, pyrazolyl, thiazolyl, benzo[1,3]dioxol-5-yl, pyrazolyl, oxazolyl, isoxazolyl, imidazolyl, phenyl, thiazolyl, isothiazolyl, [1,2,4]oxadiazolyl, [1,3,4]thiadiazolyl, $C_{(4-7)}$cycloalkyl, $C_{(1-6)}$alkyl, $C_{(1-4)}$alkylOH, $CH_2OC_{(3-6)}$alkenyl, $CH_2OC_{(1-4)}$alkyl, $CH_2C(O)NH_2$, $CO_2C_{(1-4)}$alkyl, —CN, $C(O)NH_2$, $C(O)NHCH_2CH_2OH$, OTBS, OH, $OC_{(1-4)}$alkyl, $OC_{(3-6)}$alkenyl, $NH_2$, or NHBOC, or

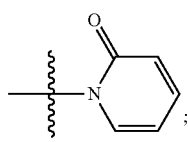 [SMILES: *n1ccccc1=O]

wherein said pyridyl, pyrimidyl, pyrazolyl, thiazolyl, benzo[1,3]dioxol-5-yl, pyrazolyl, oxazolyl, isoxazolyl, imidazolyl, phenyl, $C_{(4-7)}$cycloalkyl or $C_{(1-6)}$alkyl, may be optionally substituted with one substituent selected from the group consisting of: $OC_{(3-6)}$cycloalkyl, $OCH_2CF_3$, $OCH_2Ph$, $C_{(1-3)}$alkyl, OH, $C_{(1-3)}$alkoxy, $NH_2$, $NHCH_3$, $N(CH_3)_2$, $C(O)NH_2$, or $CH_2C(O)NH_2$;

$R^2$ is H, or OH;

and tautomers, and pharmaceutically acceptable salts thereof.

4. A compound of claim 3 wherein:

X is O or $NR^3$;

wherein $R^3$ is: H, $C_{(1-6)}$alkyl, $CH_2CF_3$, $C_{(1-6)}$alkylOH, $C_{(2-6)}$alkenyl, $C(O)C_{(1-6)}$alkyl, $CONH_2$, $CONHC_{(1-6)}$alkyl, $SONH_2$, $CH_2Ph$, $CH_2$pyridyl, $CH_2$pyrrolyl, $CH_2$pyrimidyl, $CH_2$pyridazyl, or $SO_2C_{(1-2)}$alkyl;

Z is O, $CH_2$,

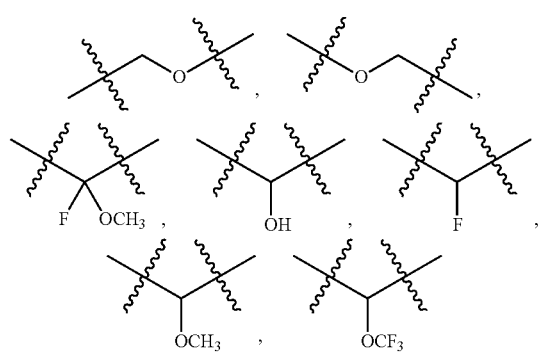

or a direct bond;

$R^1$ is pyridyl, thiazolyl, benzo[1,3]dioxol-5-yl, pyrazolyl, oxazolyl, imidazolyl, phenyl, $C_{(5-6)}$cycloalkyl, $C_{(2-6)}$alkyl, $C_{(1-4)}$alkylOH, $CH_2OC_{(3-6)}$alkenyl, $CH_2OC_{(1-4)}$alkyl, $CH_2C(O)NH_2$, $CO_2C_{(1-4)}$alkyl, —CN, $C(O)NH_2$, $C(O)NHCH_2CH_2OH$, OTBS, OH, $OC_{(1-4)}$alkyl, $OC_{(3-6)}$alkenyl, $NH_2$, NHBOC, or

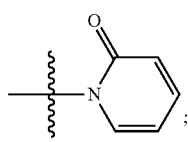 [SMILES: *n1ccccc1=O]

wherein said pyridyl, thiazolyl, benzo[1,3]dioxol-5-yl, pyrazolyl, oxazolyl, imidazolyl, phenyl, or $C_{(5-6)}$cycloalkyl may be optionally substituted with one substituent selected from the group consisting of: $C_{(1-3)}$alkyl, $C_{(1-3)}$alkoxy, $N(CH_3)_2$, or $CH_2C(O)NH_2$;

$R^2$ is H, or OH;

and tautomers, and pharmaceutically acceptable salts thereof.

5. A compound of claim 4 wherein:

X is O or $NR^3$;

wherein $R^3$ is: H, $C_{(1-6)}$alkyl, $CH_2CF_3$, $C_{(1-6)}$alkylOH, $CH_2CH=CH_2$, $CONH_2$, $CONHC_{(1-6)}$alkyl, $CH_2Ph$, $CH_2$pyridyl, or $SO_2C_{(1-2)}$alkyl;

Z is O, $CH_2$,

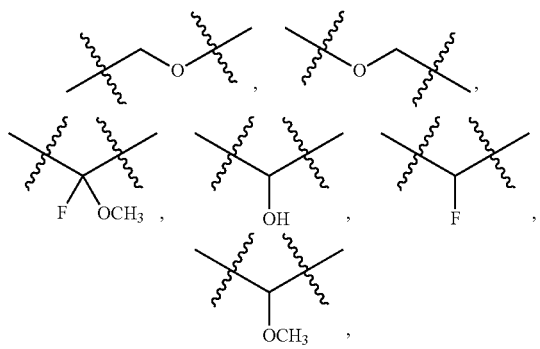

or a direct bond;

$R^1$ is pyrid-3-yl, pyrid-5-yl, pyrid-6-yl, thiazol-2-yl, thiazol-5-yl, benzo[1,3]dioxol-5-yl, pyrazol-4-yl, oxazol-2-yl, imidazol-2-yl, phenyl, cyclohexyl, $C_{(2-6)}$alkyl, $C_{(1-4)}$alkylOH, $CH_2OC_{(3-6)}$alkenyl, $CH_2OC_{(1-4)}$alkyl, $CH_2C(O)NH_2$, $CO_2C_{(1-4)}$alkyl, —CN, $C(O)NH_2$, $C(O)NHCH_2CH_2OH$, OTBS, OH, $OC_{(1-4)}$alkyl, $OC_{(3-6)}$alkenyl, $NH_2$, NHBOC, or

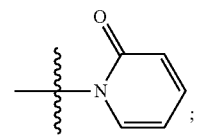

wherein said pyrid-3-yl, pyrid-5-yl, pyrid-6-yl, thiazol-2-yl, thiazol-5-yl, benzo[1,3]dioxol-5-yl, pyrazol-4-yl, oxazol-2-yl, imidazol-2-yl, phenyl, or cyclohexyl may be optionally substituted with one substituent selected from the group consisting of: $C_{(1-3)}$alkyl, $C_{(1-3)}$alkoxy, $N(CH_3)_2$, or $CH_2C(O)NH_2$;

$R^2$ is H, or OH;

and tautomers, and pharmaceutically acceptable salts thereof.

6. A compound of claim 5 wherein:

X is O or $NR^3$;

wherein $R^3$ is: H, $C_{(1-3)}$alkyl, $CH_2CF_3$, $CH_2CH_2OH$, $CH_2CH=CH_2$, $CONH_2$, $CONHC(CH_3)_3$, $CONHCH(CH_3)_2$, $CH_2Ph$, or $SO_2CH_3$;

Z is O,

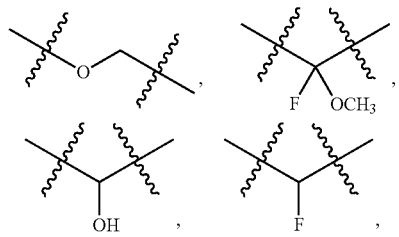

or a direct bond;

$R^1$ is pyrid-3-yl, 2-methoxy-pyrid-5-yl, 2-methoxy-pyrid-6-yl, 2-ethoxy-pyrid-5-yl, 2-methyl-pyrid-5-yl, thiazol- 2-yl, thiazol-5-yl, 2-ethyl-thiazol-5-yl, 2-isopropyl-thiazol-5-yl, 2-methyl-thiazol-5-yl, 5-methyl-thiazol-2-yl, benzo[1,3]dioxol-5-yl, N-1-methyl-pyrazol-4-yl, oxazol-2-yl, N-methyl-imidazol-2-yl, phenyl,

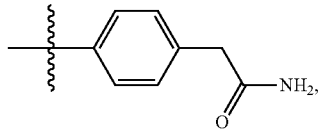

N,N-dimethylamino-phen-3-yl, cyclohexyl, C$_{(2-3)}$alkyl, CH$_2$OH, CH$_2$OCH$_2$CH=CH$_2$, CH$_2$OCH$_2$CH$_3$, CH$_2$OCH$_3$, CH$_2$C(O)NH$_2$, CO$_2$CH$_2$CH$_3$, —CN, C(O)NH$_2$, C(O)NHCH$_2$CH$_2$OH, OTBS, OH, OCH$_2$CH$_3$, OCH$_2$CH=CH$_2$, NH$_2$, NHBOC, or

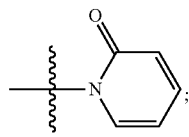 [SMILES: *n1ccccc1=O]

R$^2$ is H, or OH;

and tautomers, and pharmaceutically acceptable salts thereof.

7. A compound selected from the group consisting of:

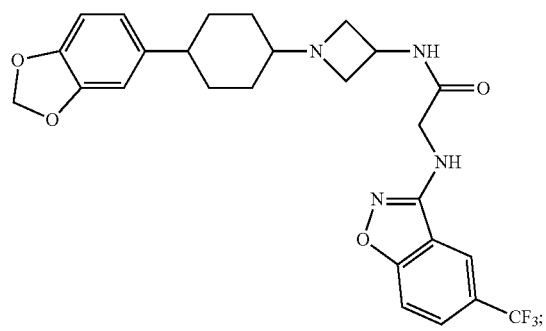

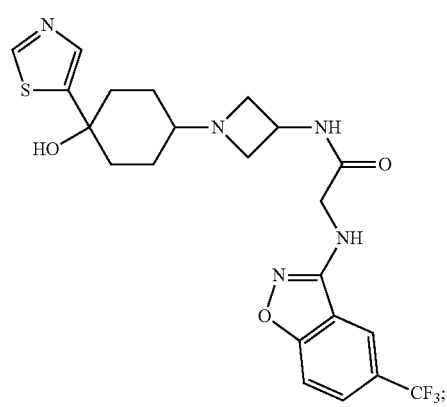

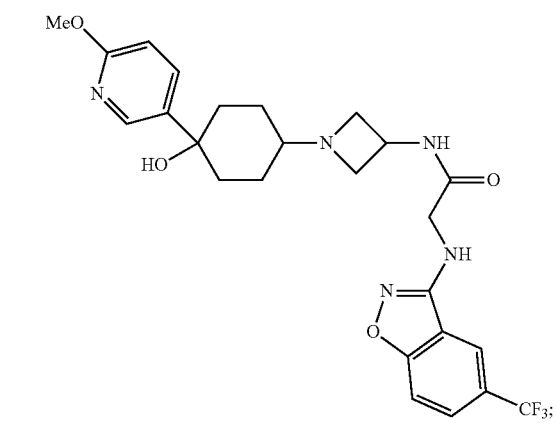

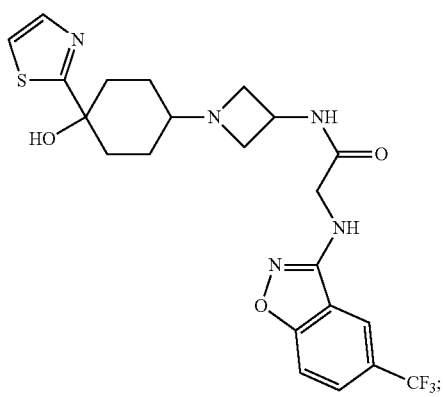

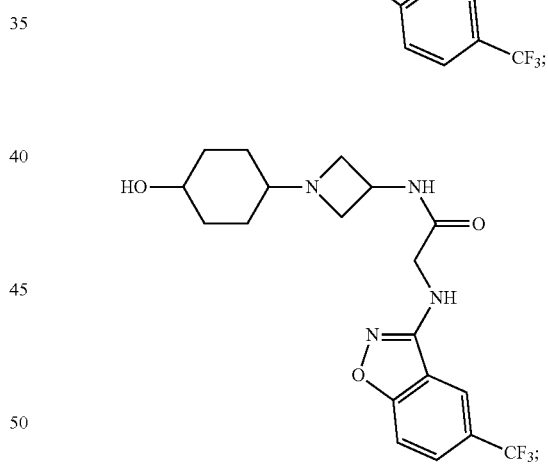

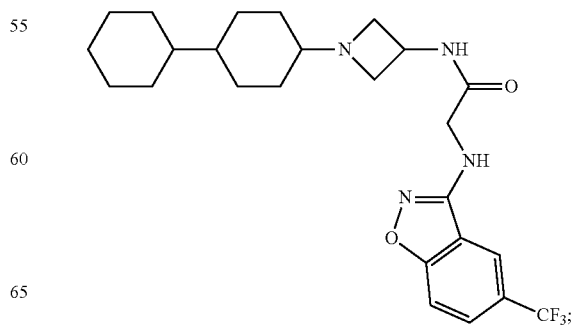

197
-continued
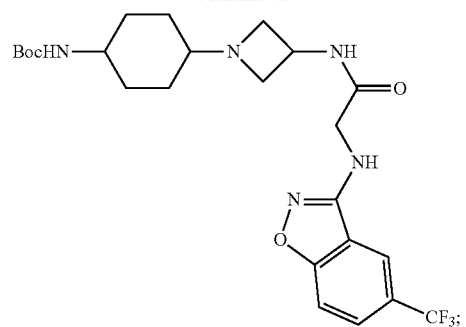
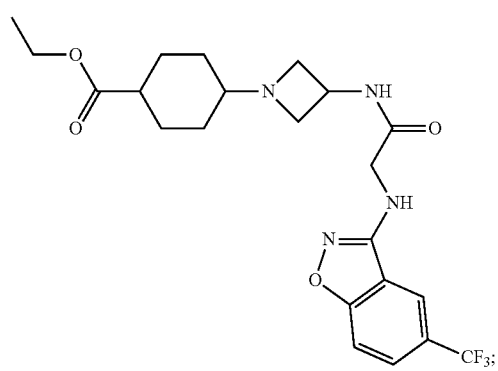
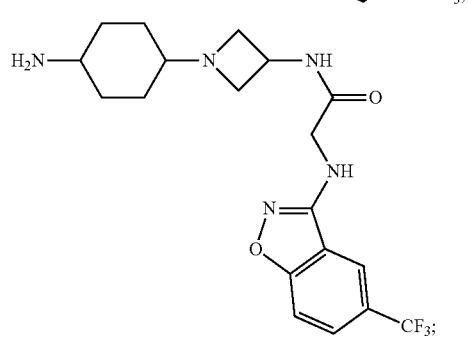
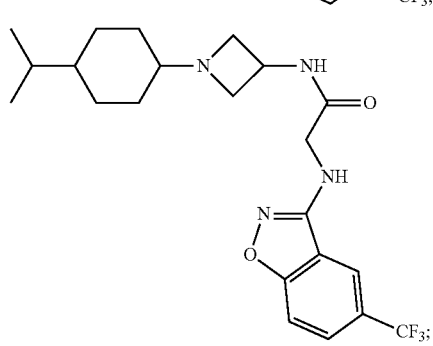
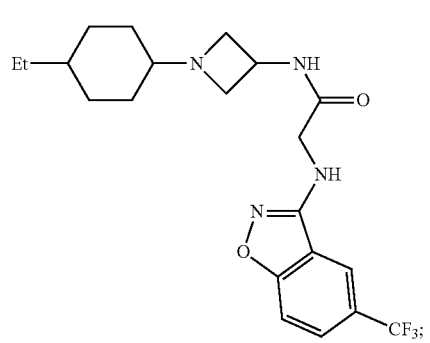
198
-continued
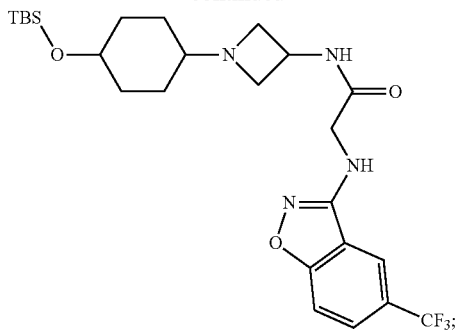
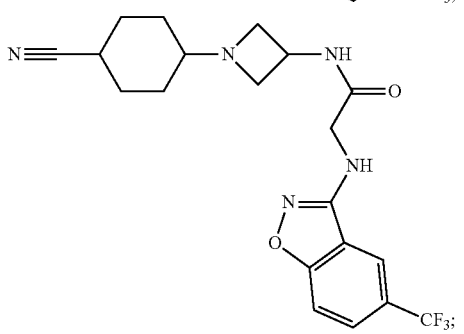
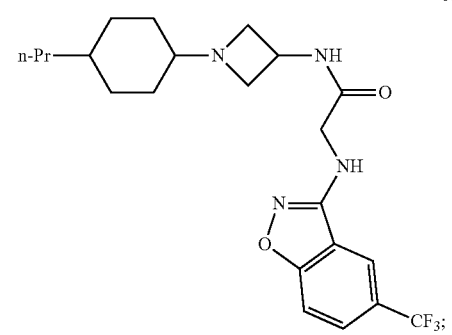
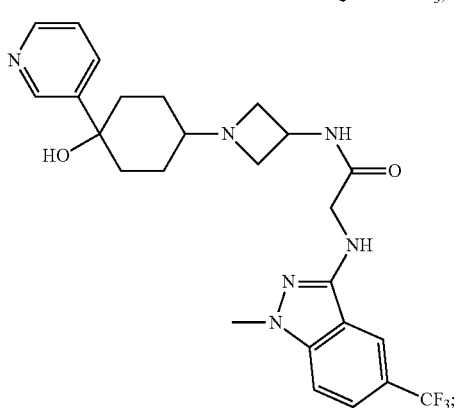
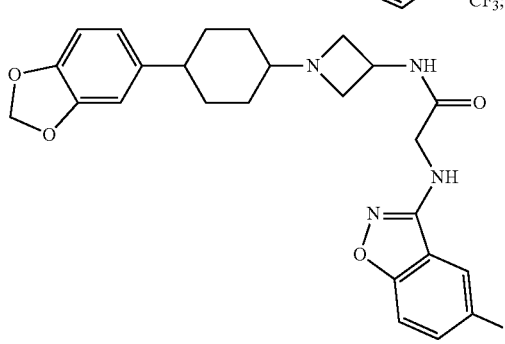

199
-continued
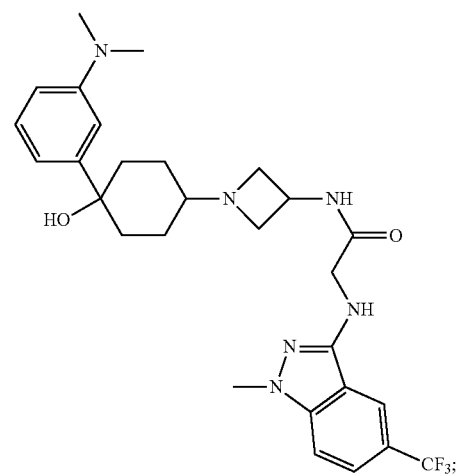
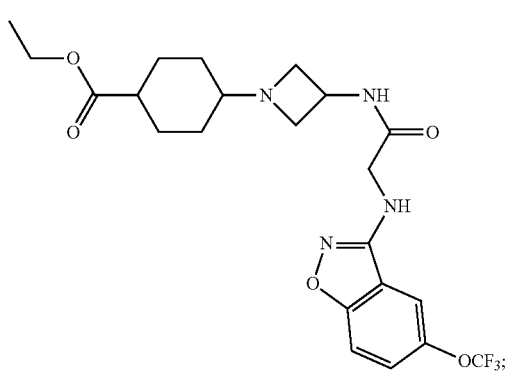
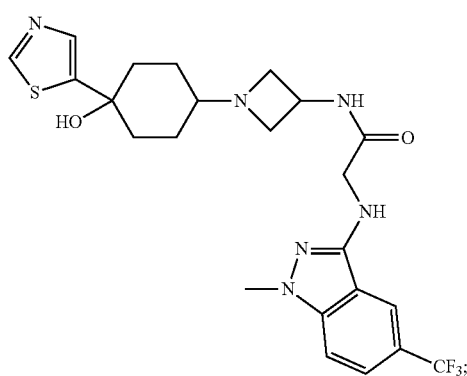
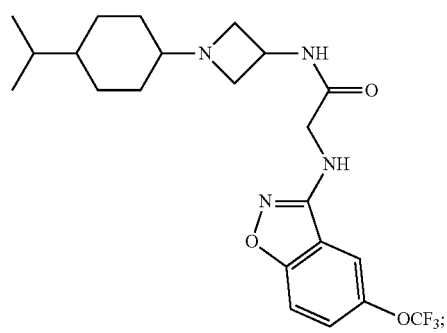
200
-continued
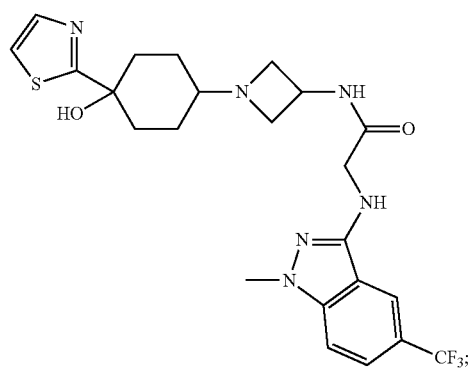
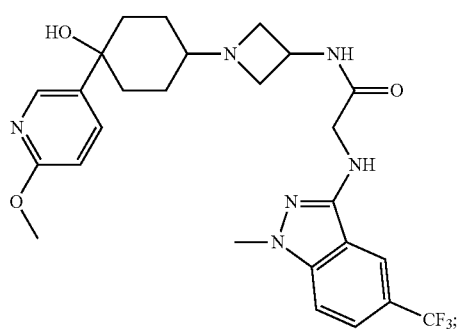
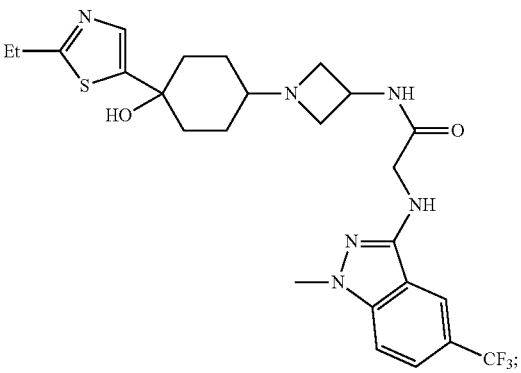
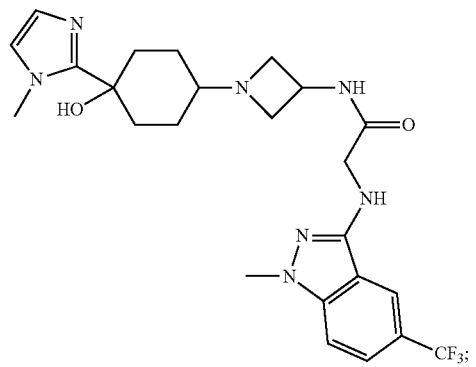

201
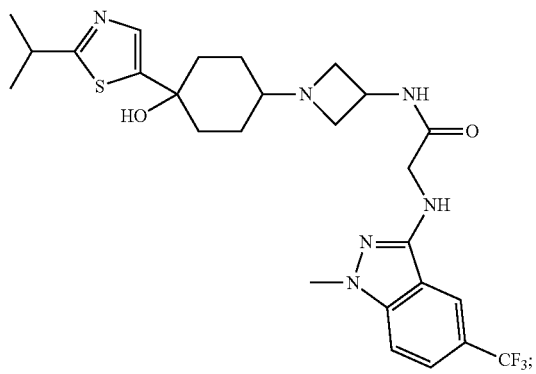
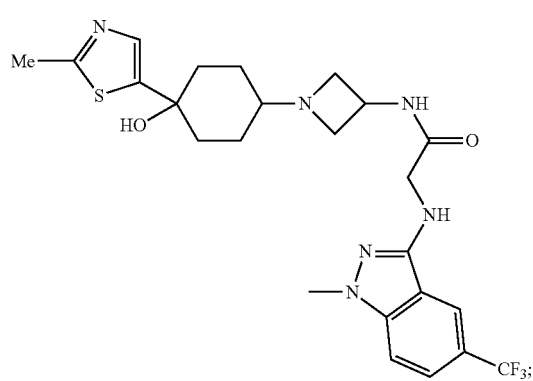
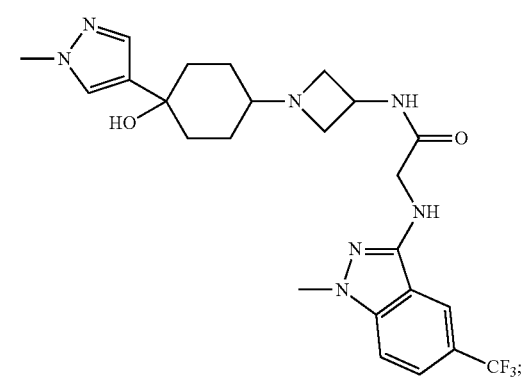
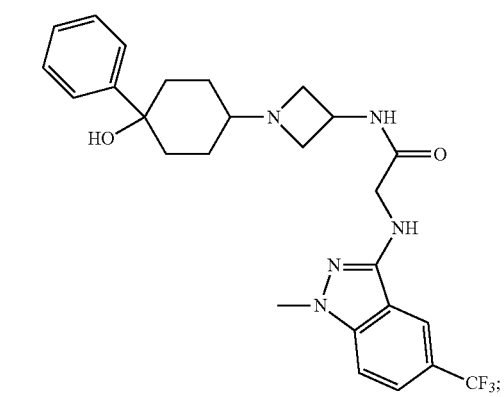
202
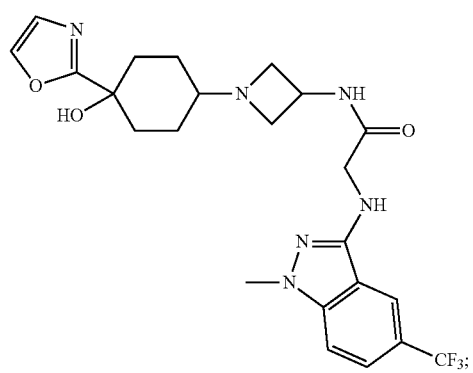
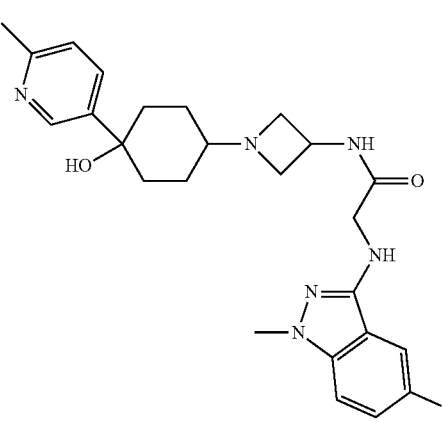
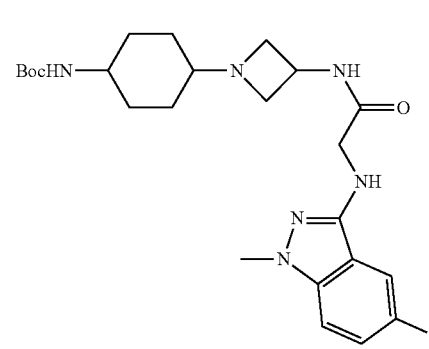
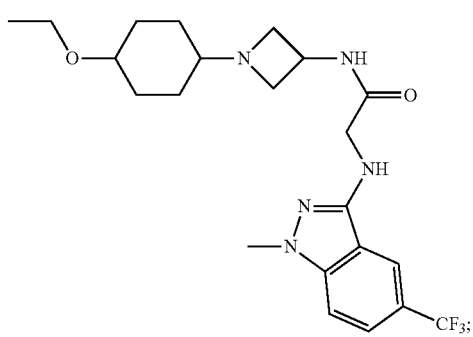

203
-continued
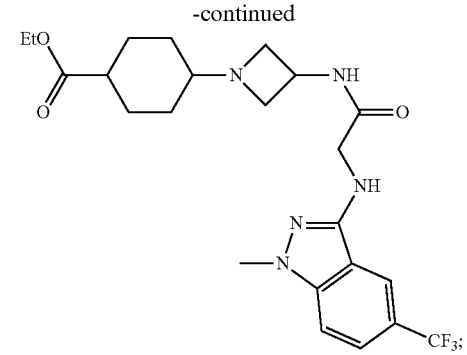
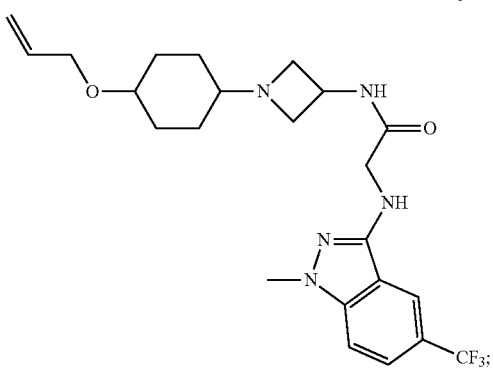
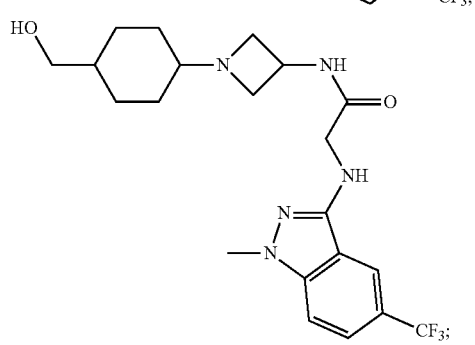
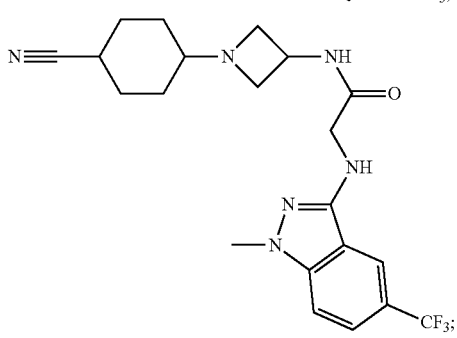
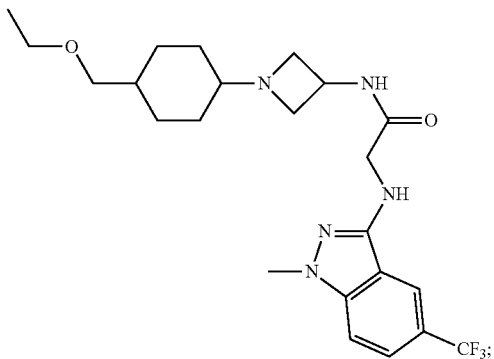
204
-continued
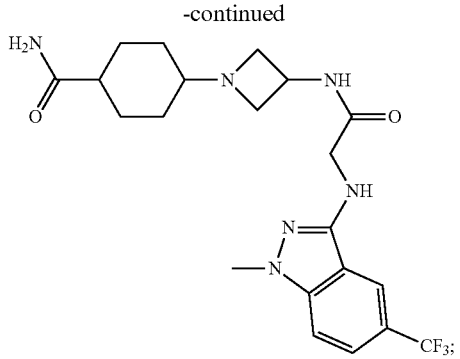
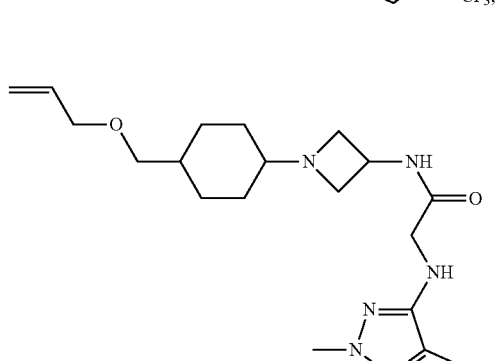
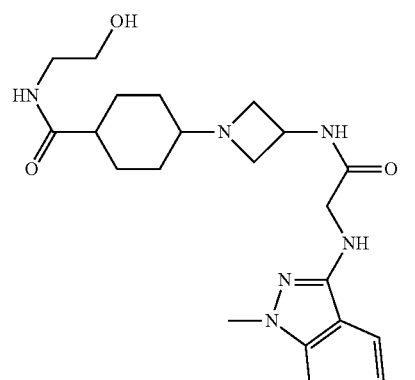
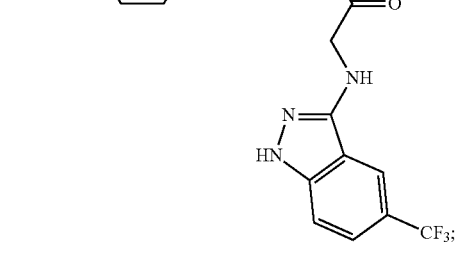

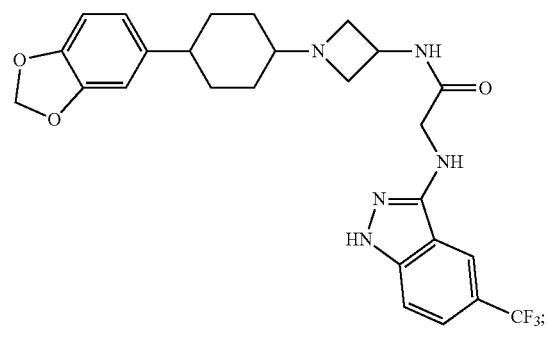
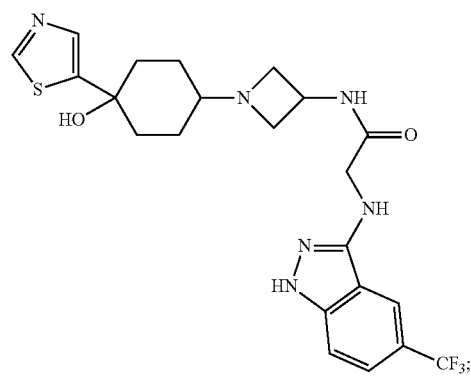
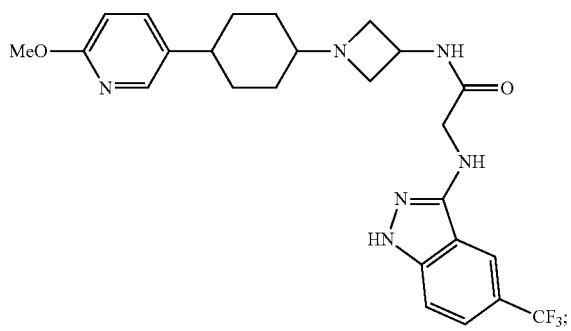
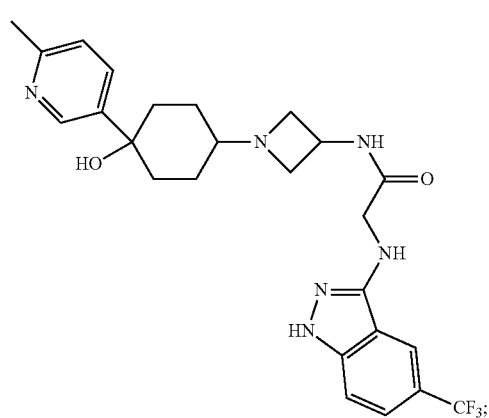
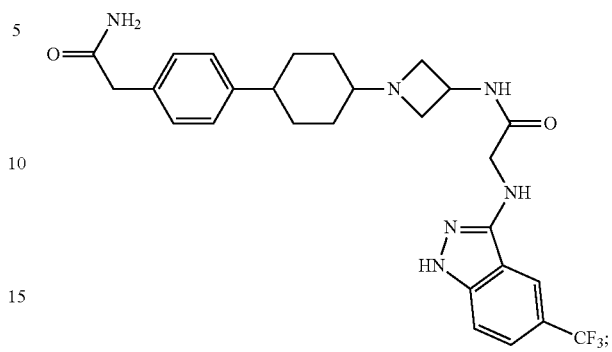
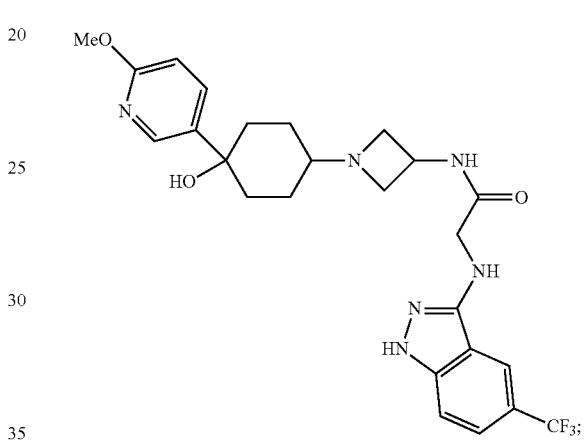
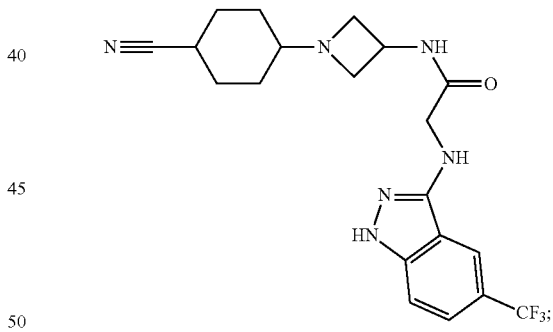
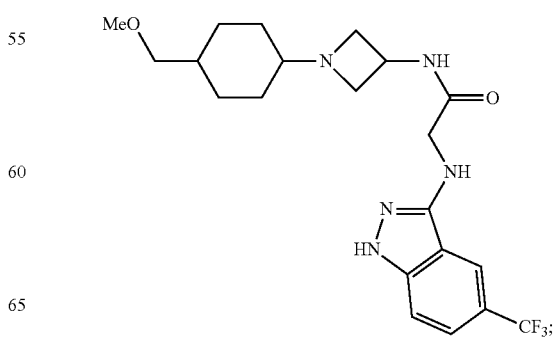

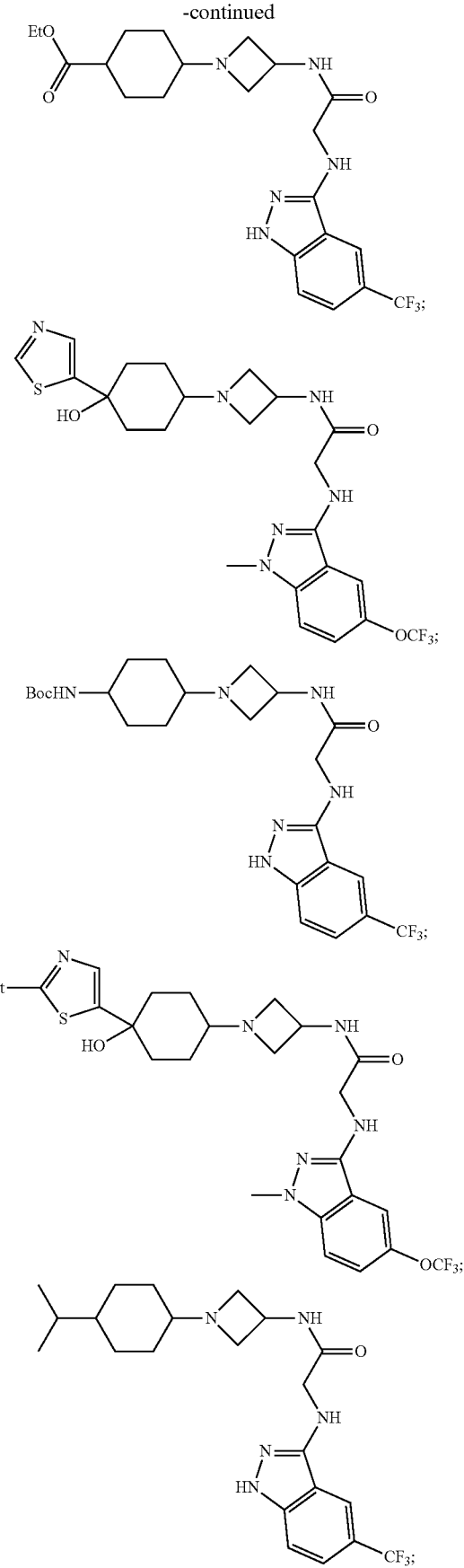
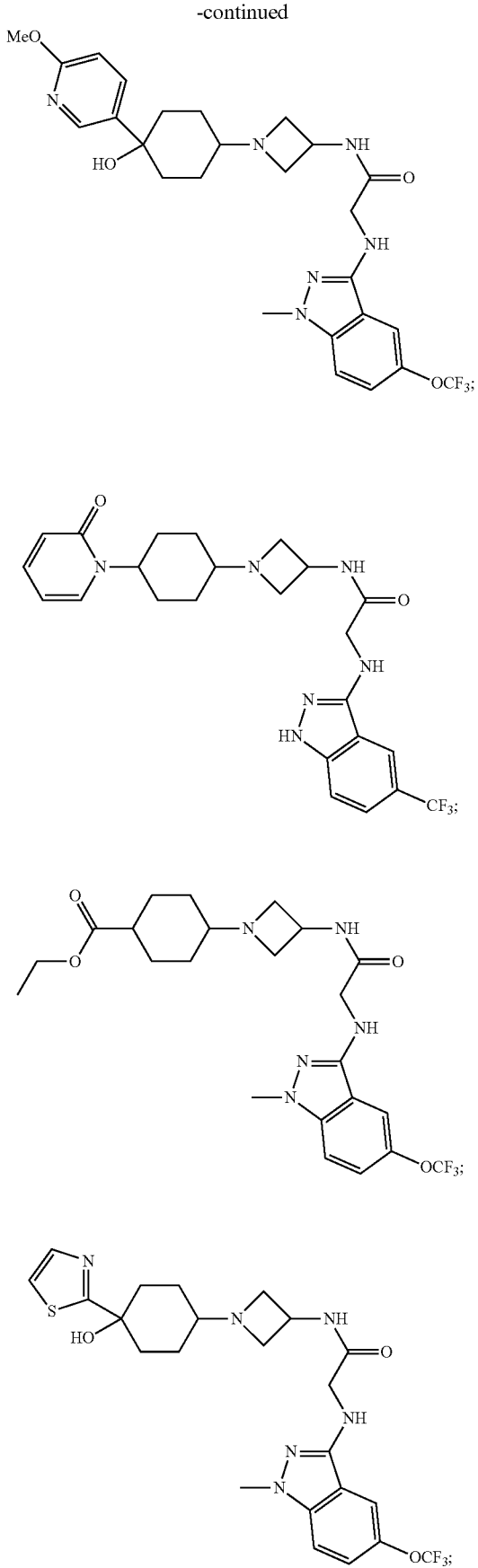

209
-continued
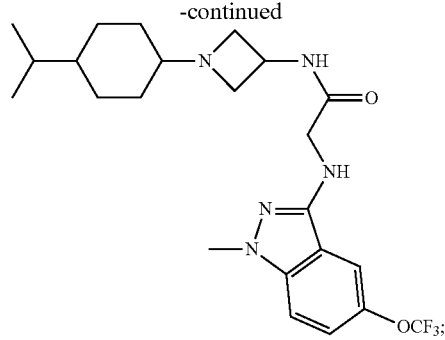
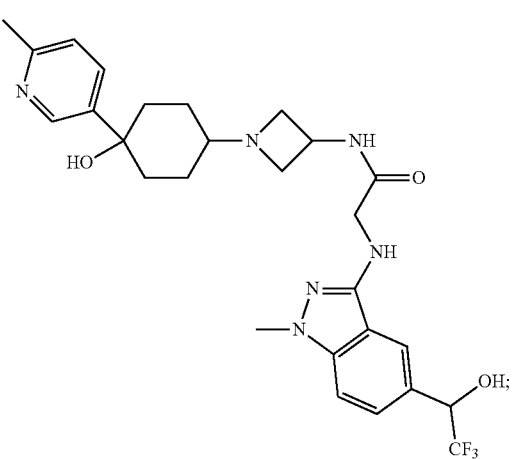
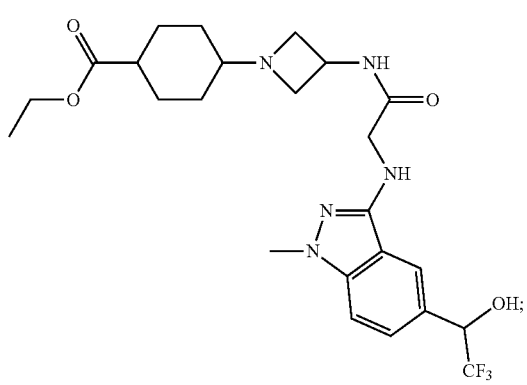
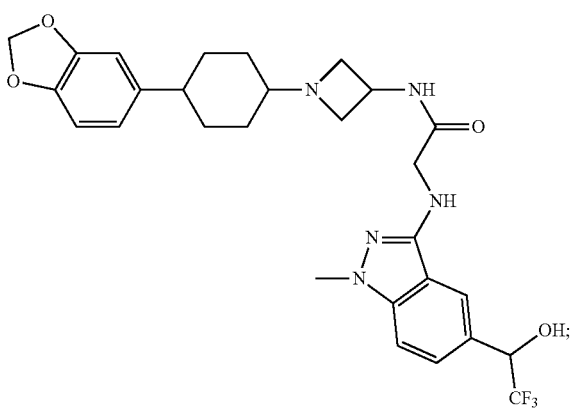
210
-continued
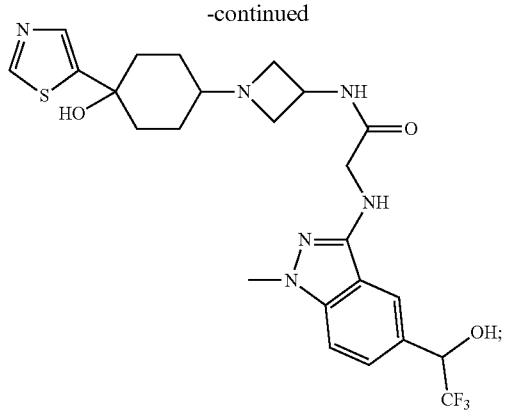
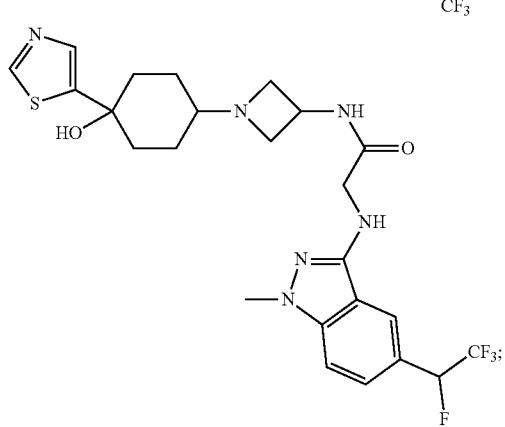
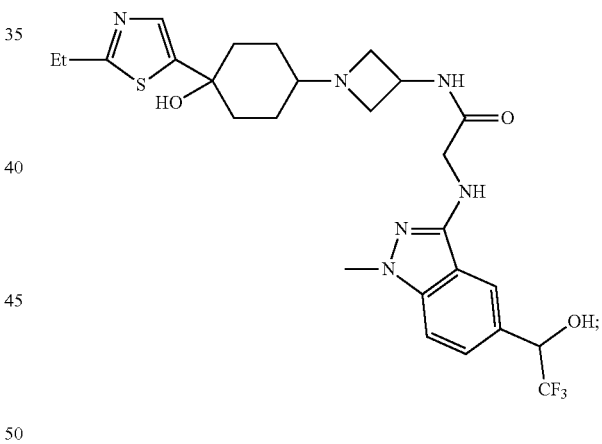
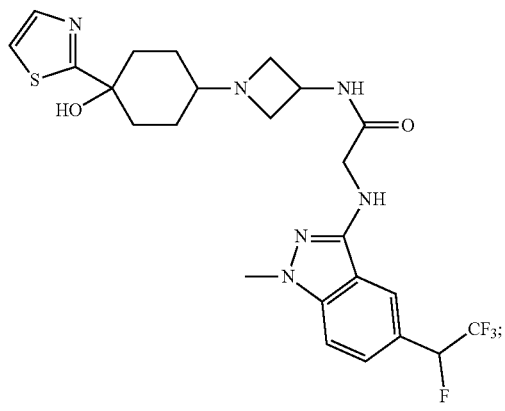

211
-continued
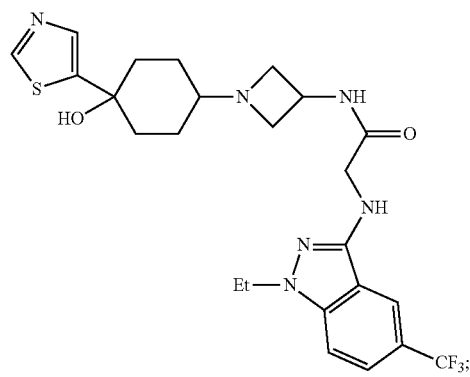
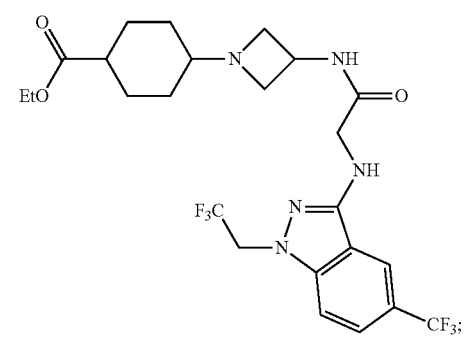
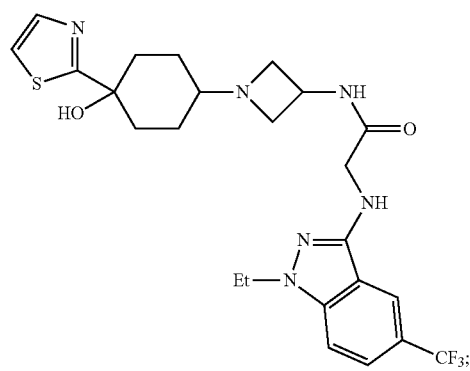
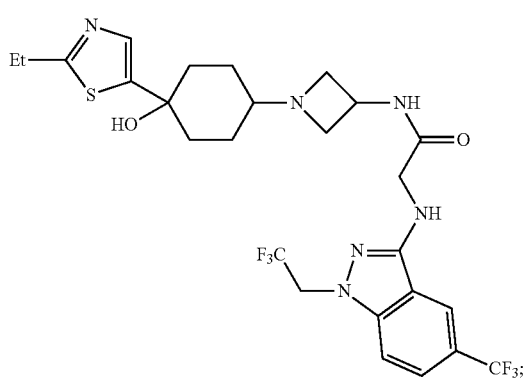
212
-continued
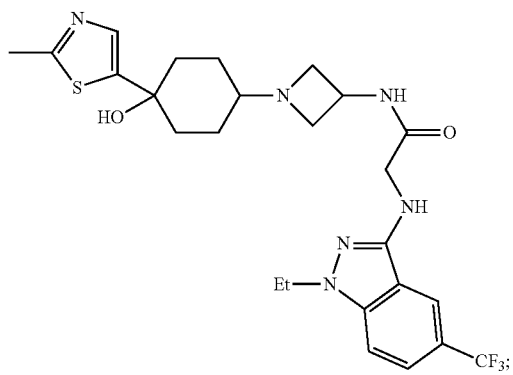
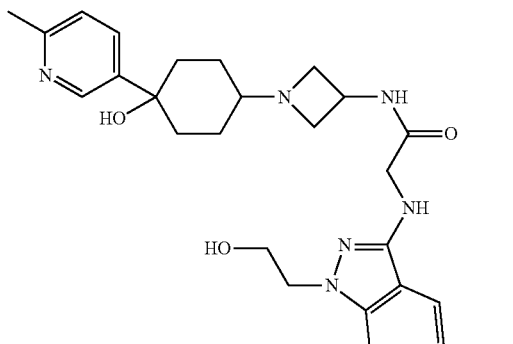
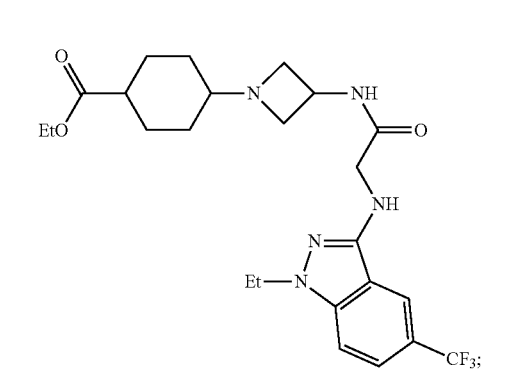
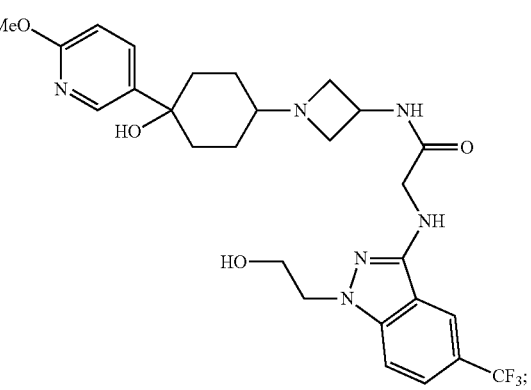

213
-continued
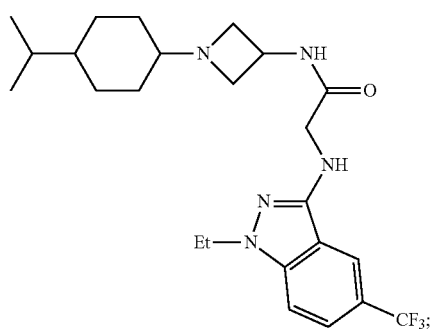
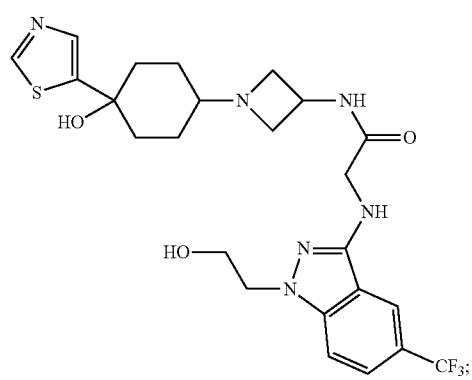
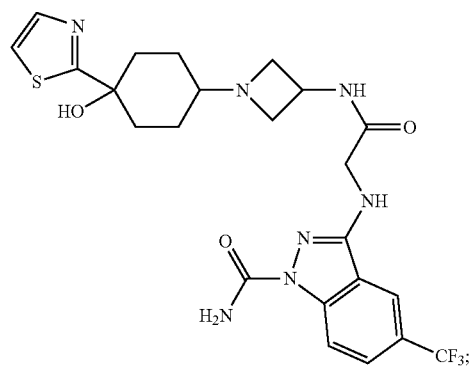
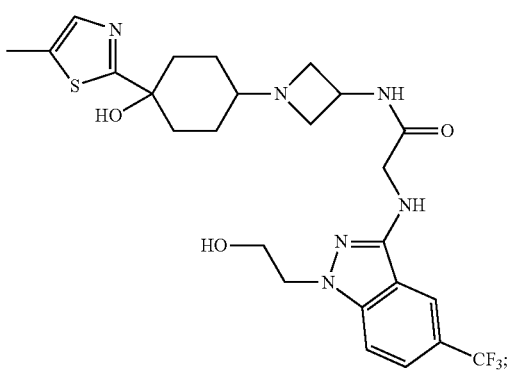
214
-continued
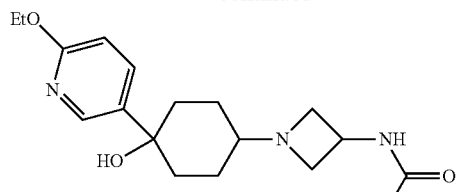
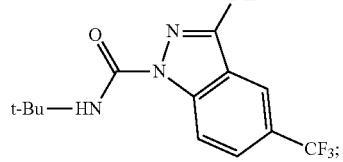
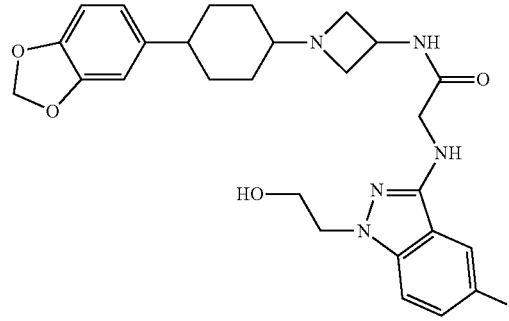
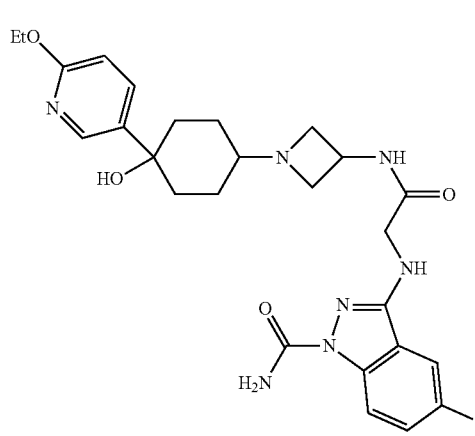
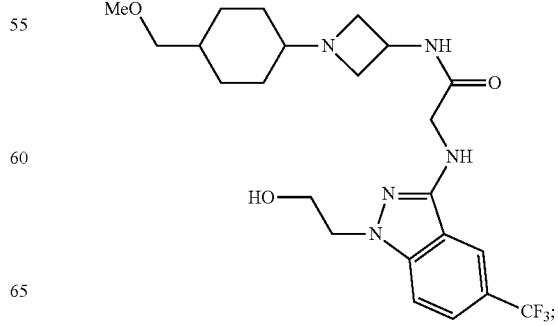

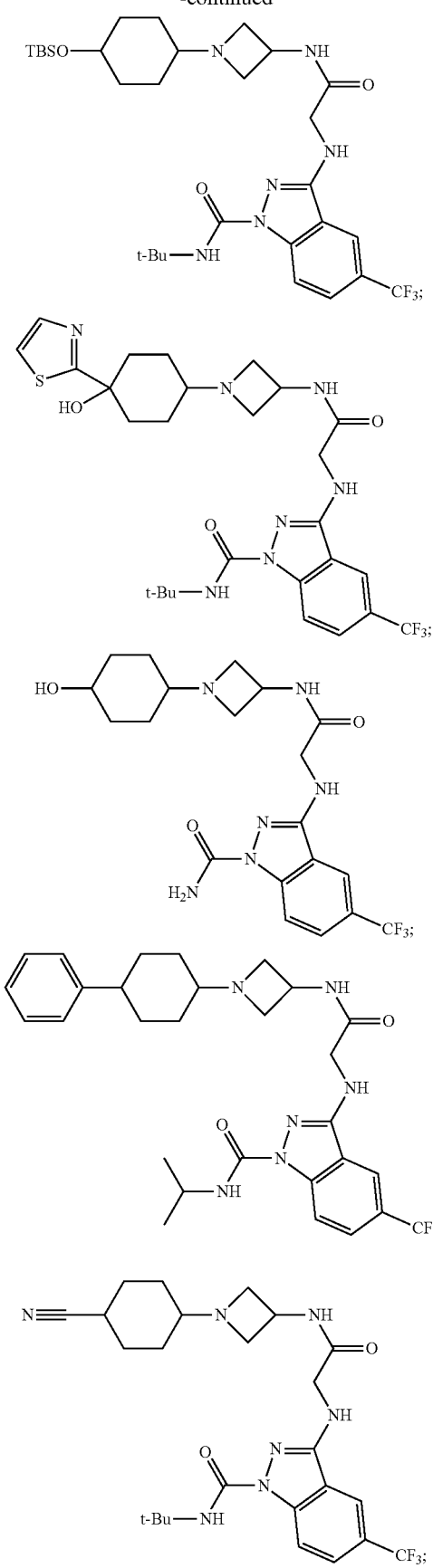
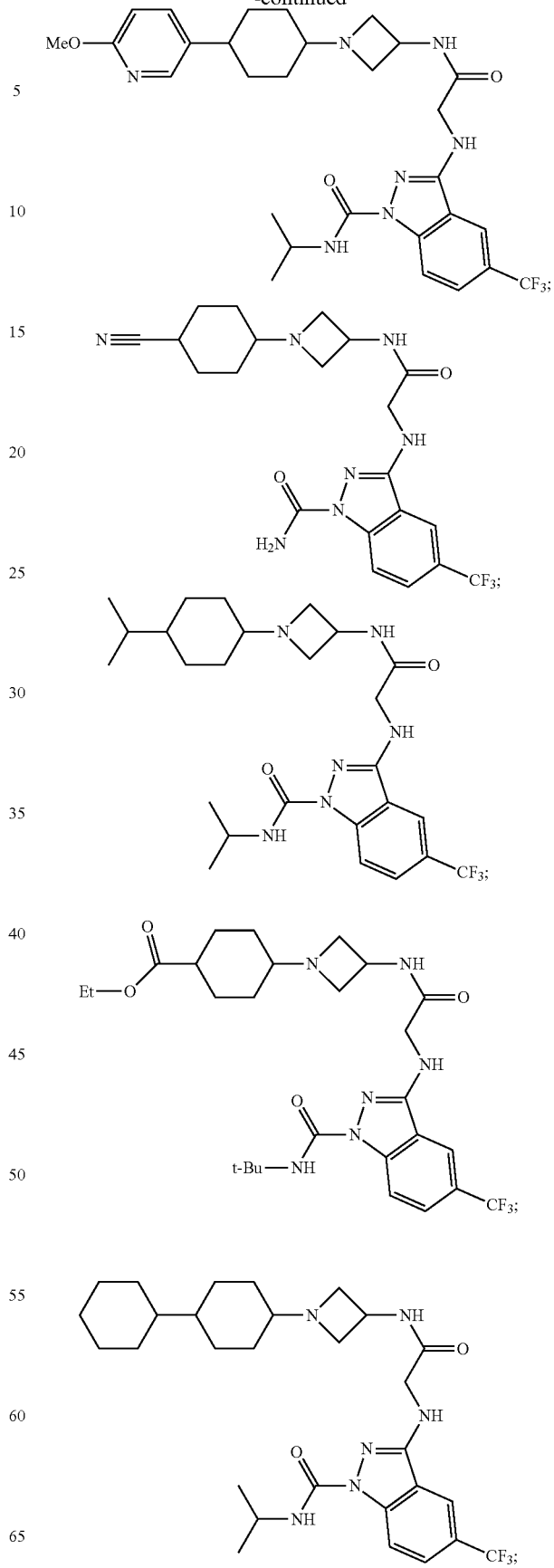

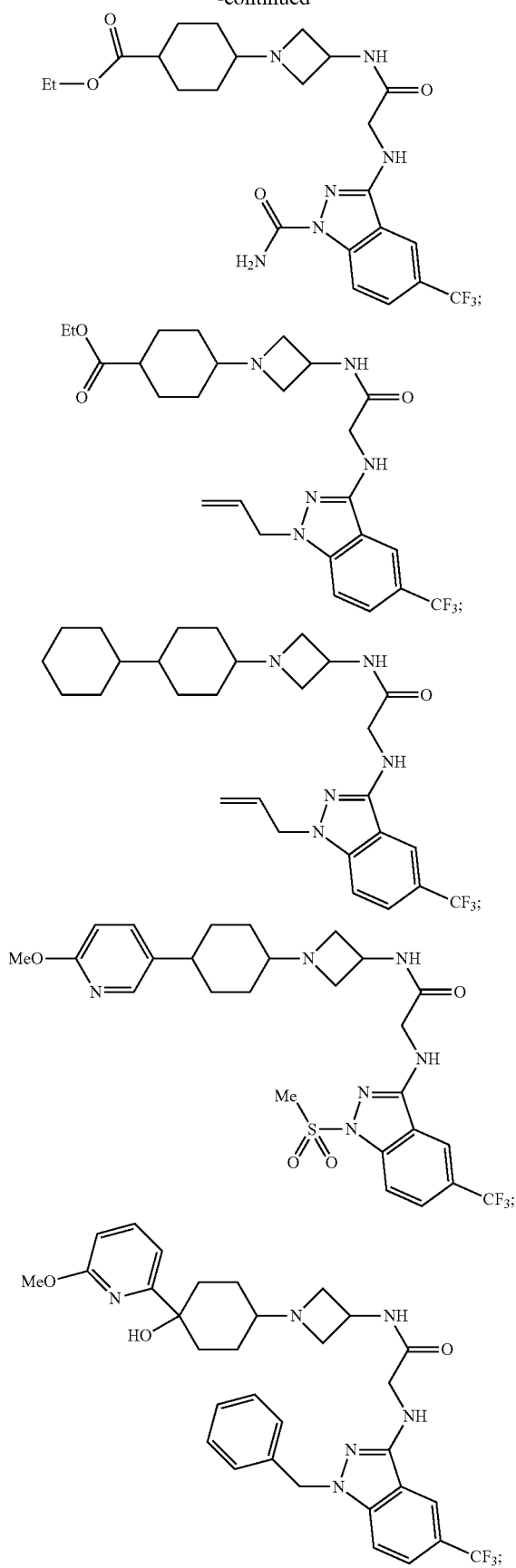
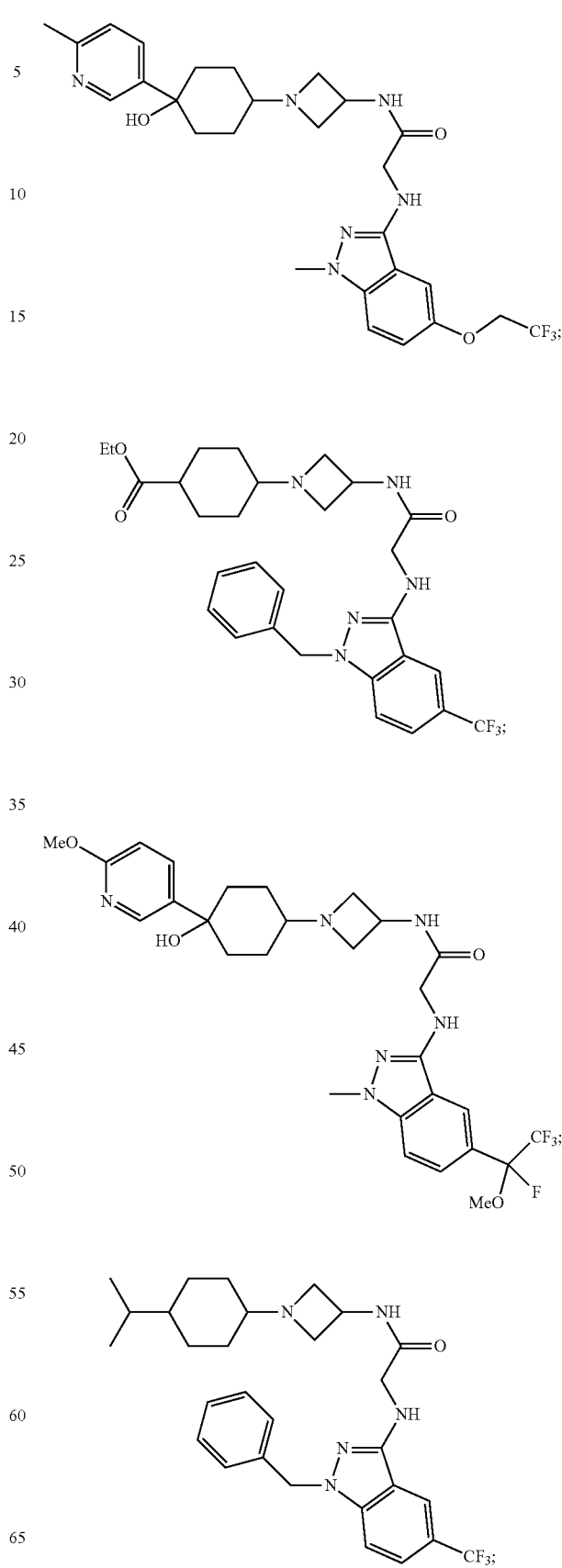

-continued
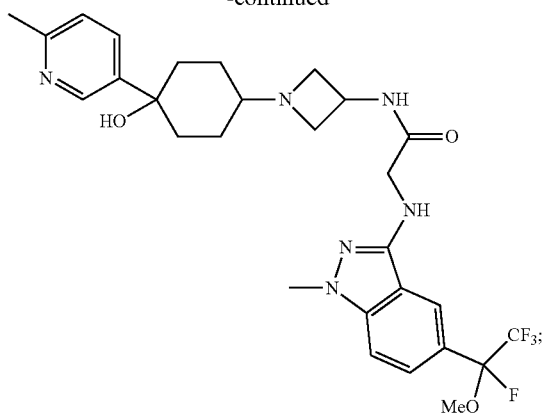
and tautomers, and pharmaceutically acceptable salts thereof.
8. A compound of claim 7 selected from the group consisting of:
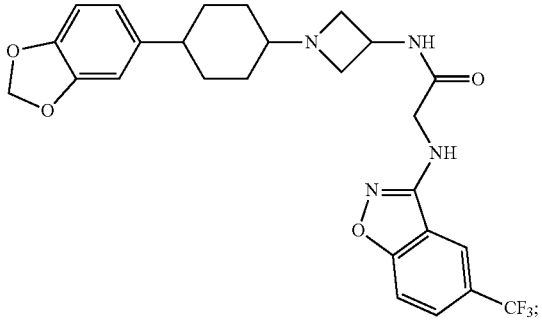
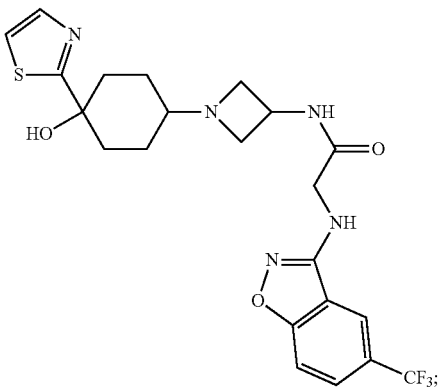
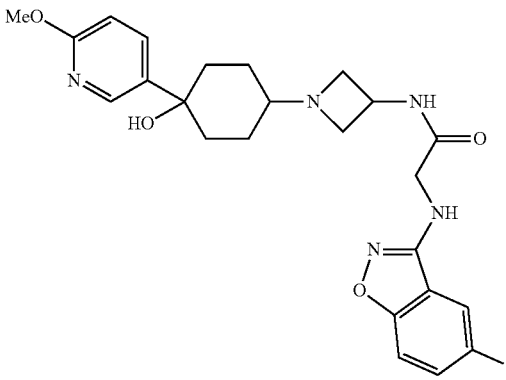
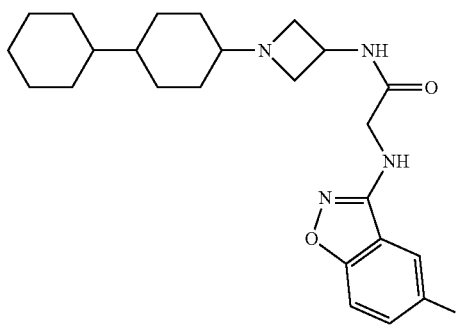

221
-continued
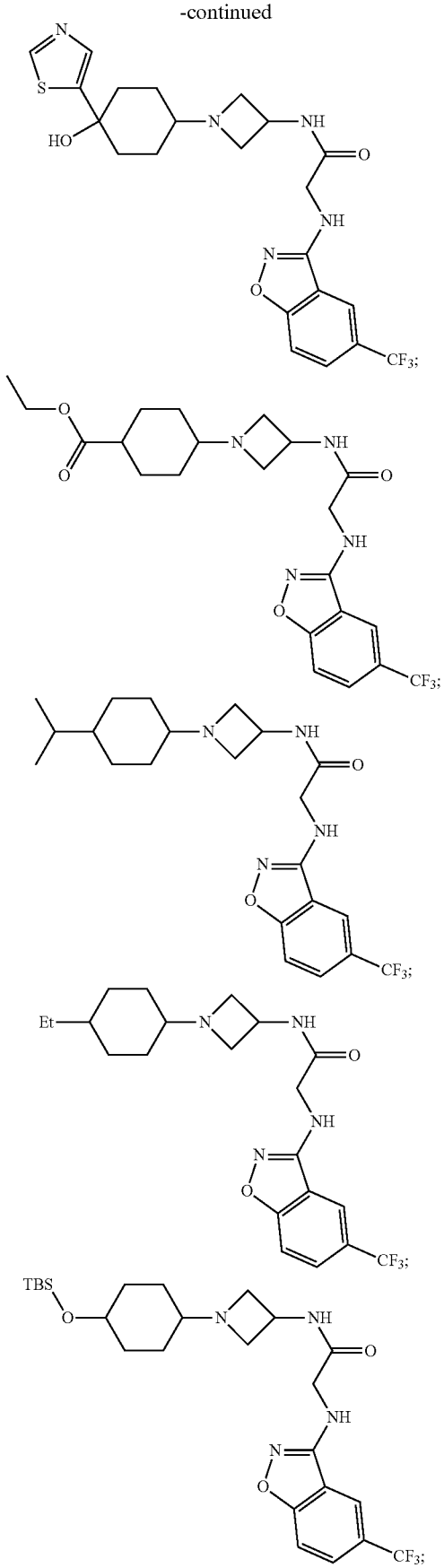
222
-continued
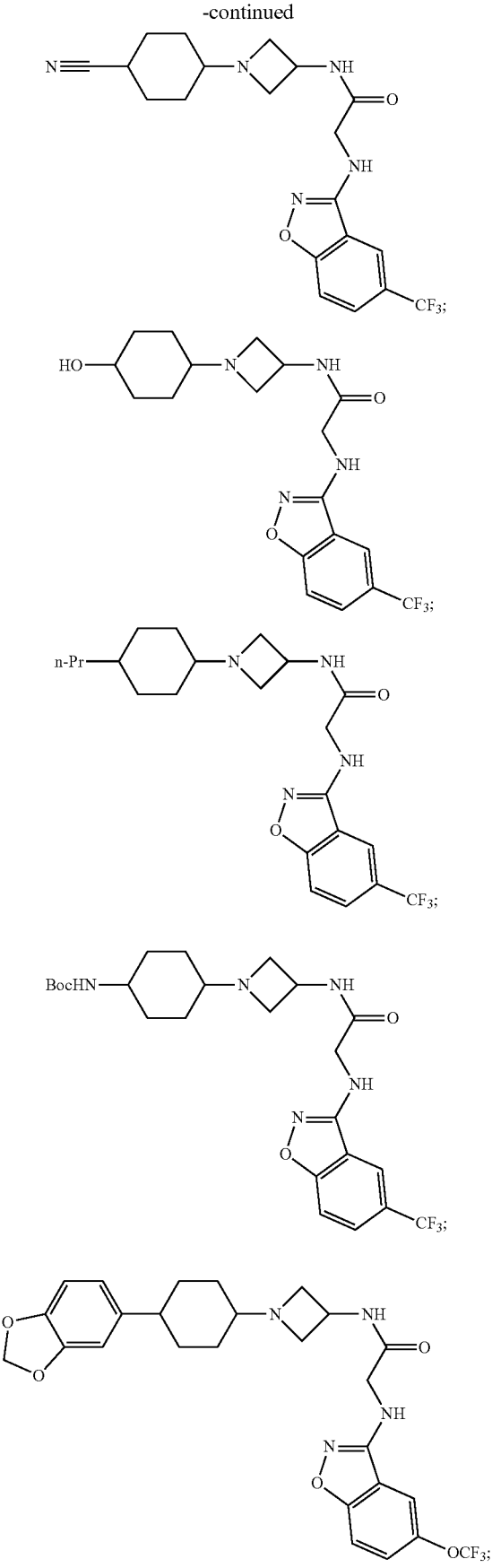

223
-continued
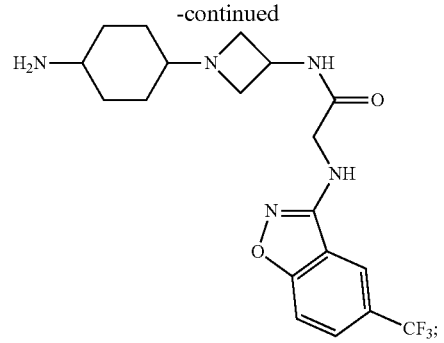
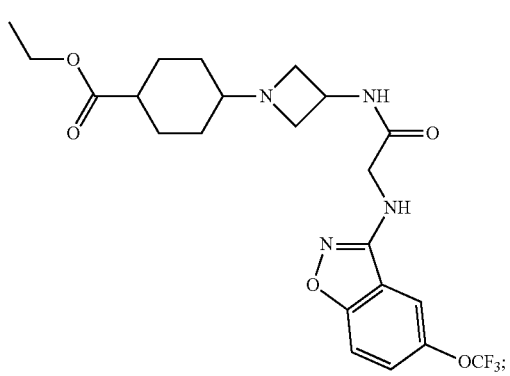
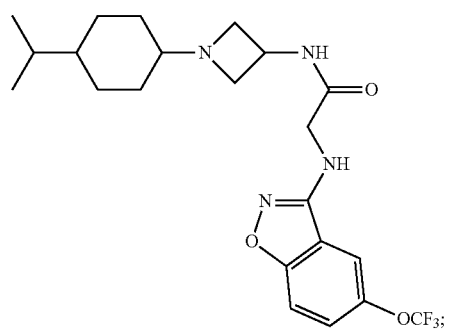
and tautomers, and pharmaceutically acceptable salts thereof.
9. A compound of claim 7 selected from the group consisting of:
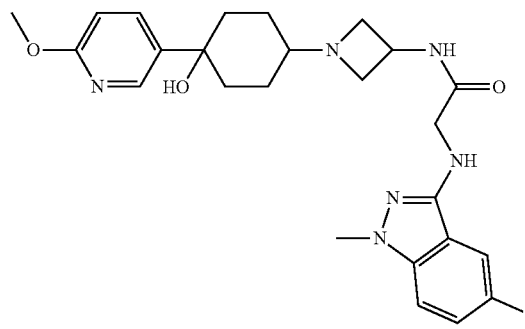
224
-continued
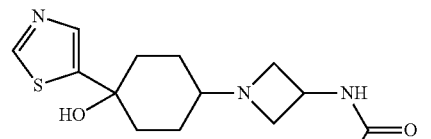
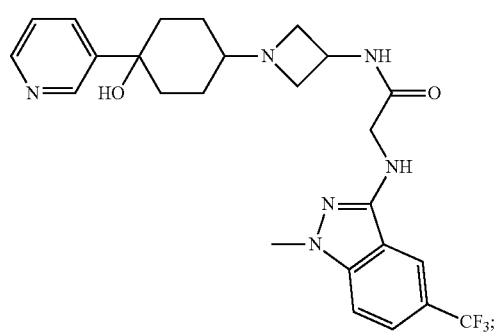
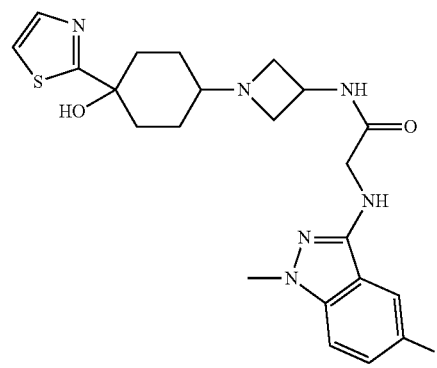
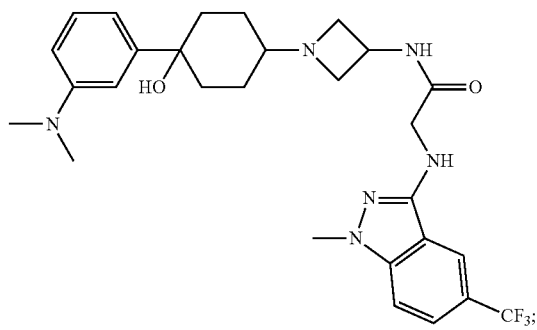

225
-continued
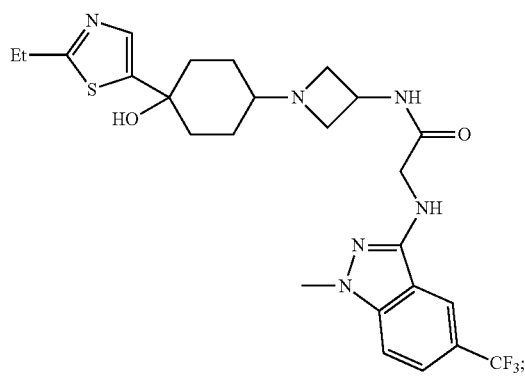
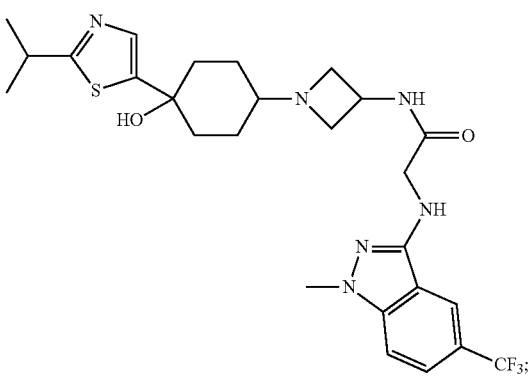
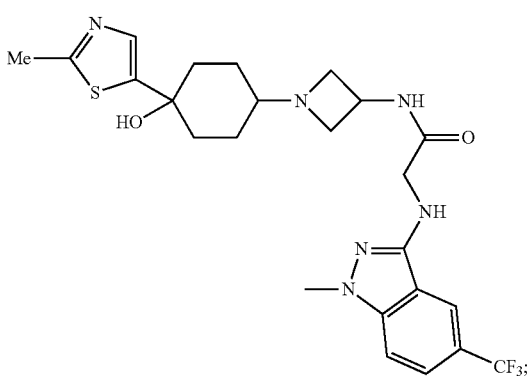
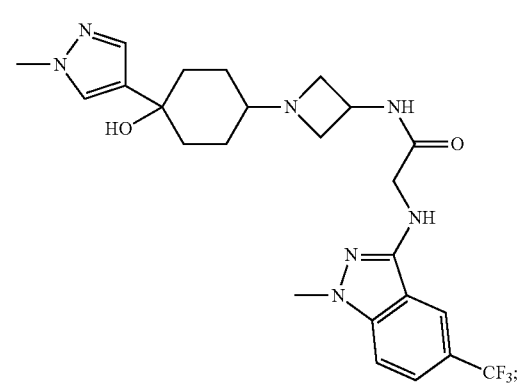
226
-continued
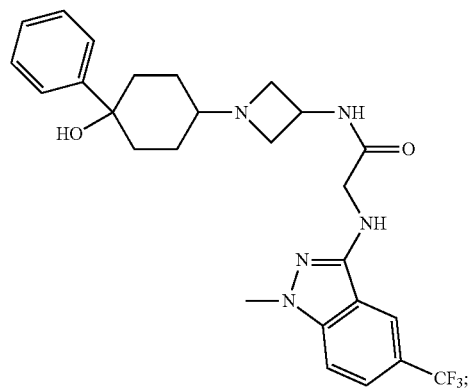
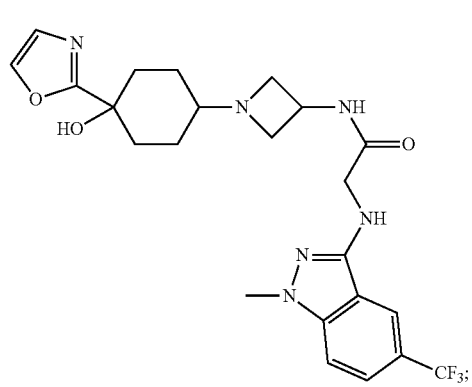
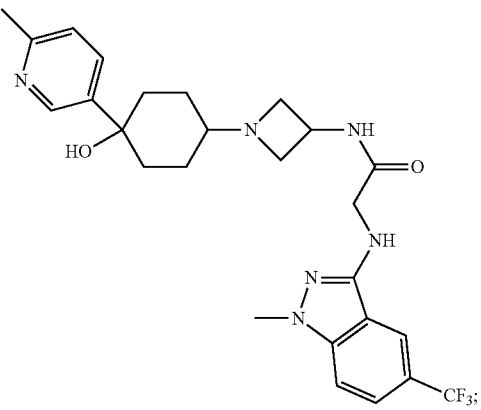
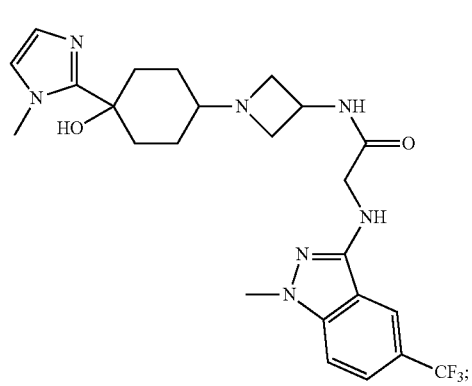

227
-continued
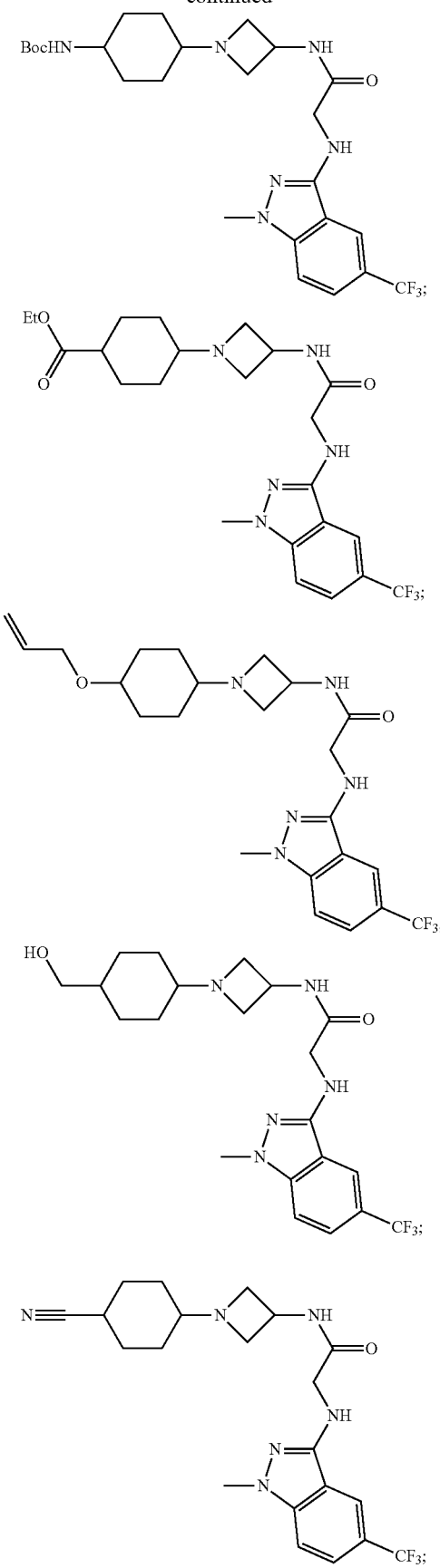
228
-continued
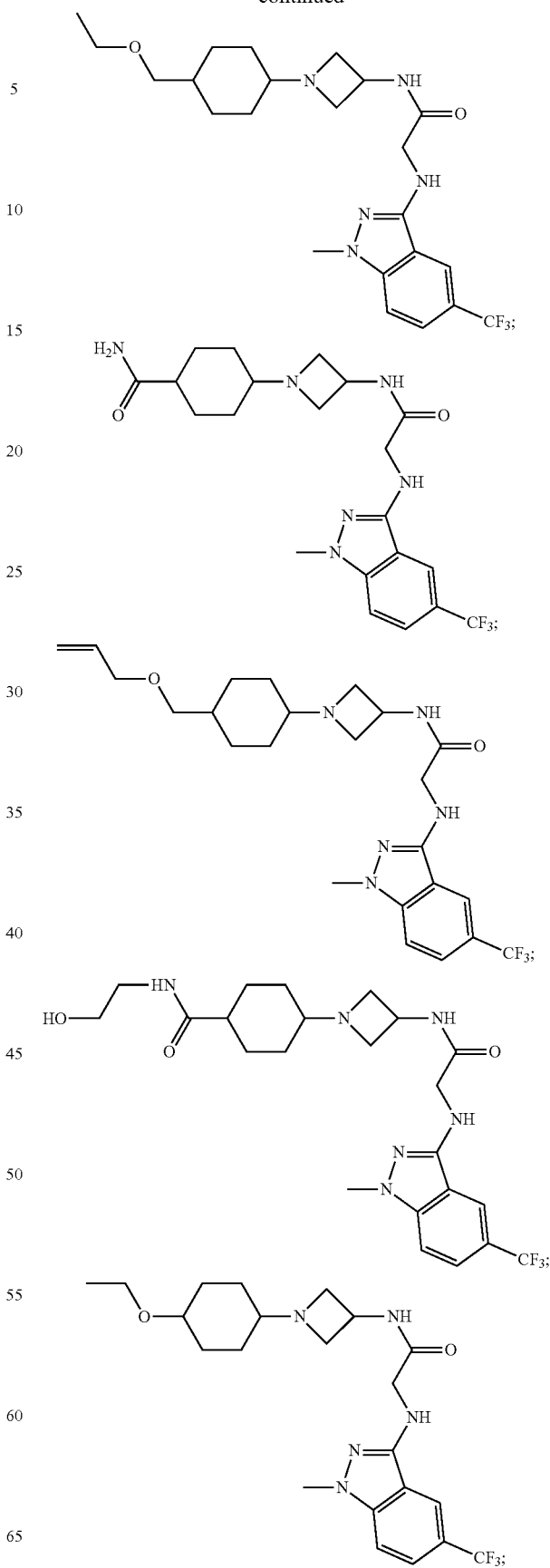

229
-continued
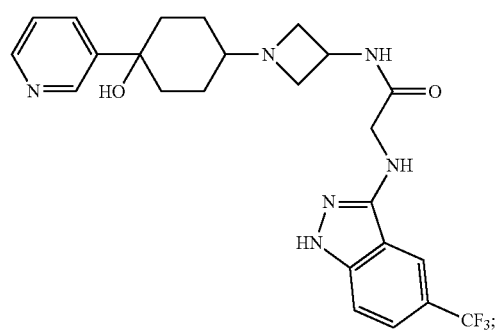
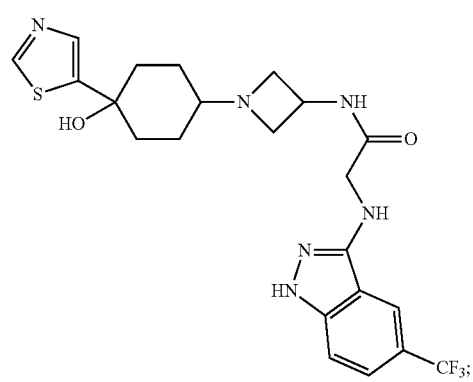
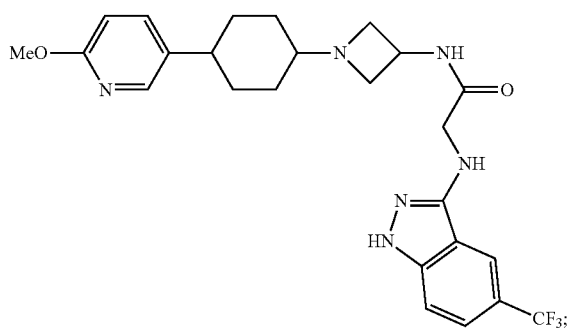
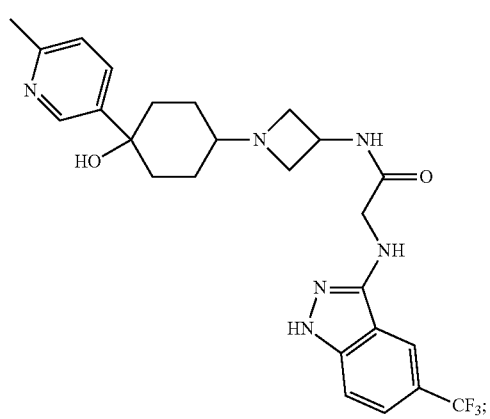
230
-continued
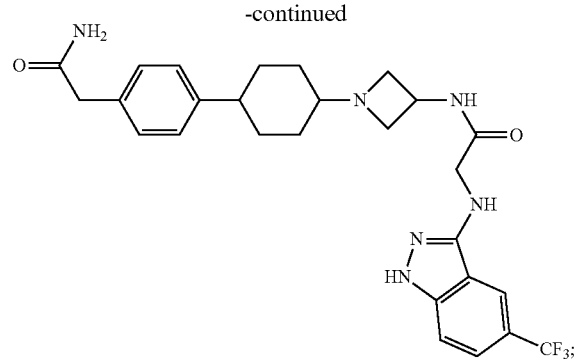
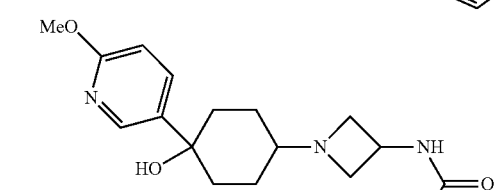
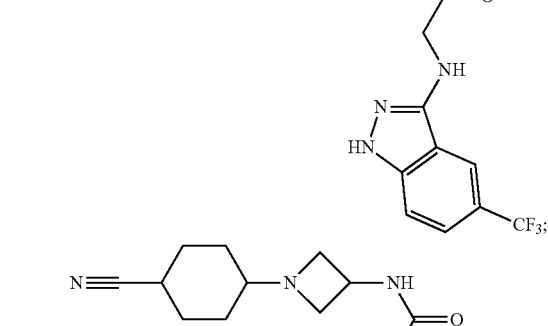
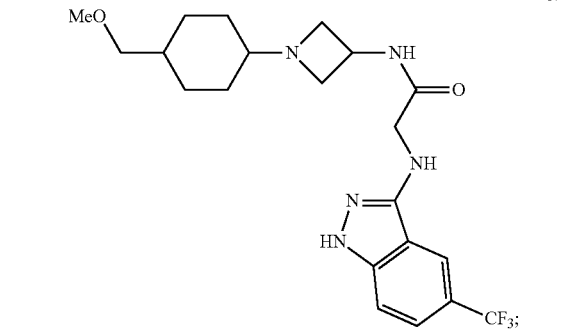

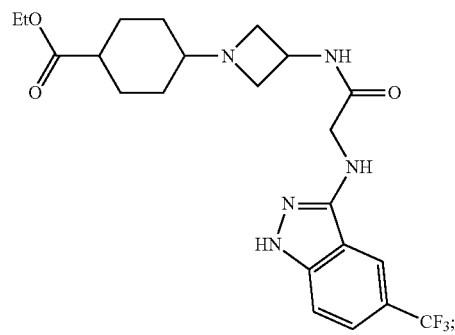
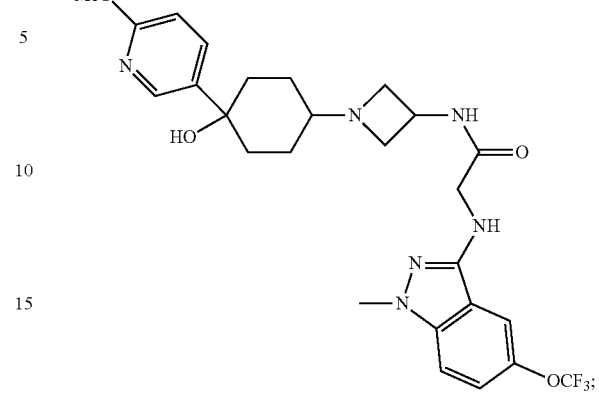
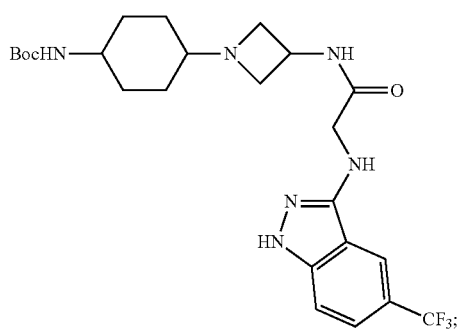
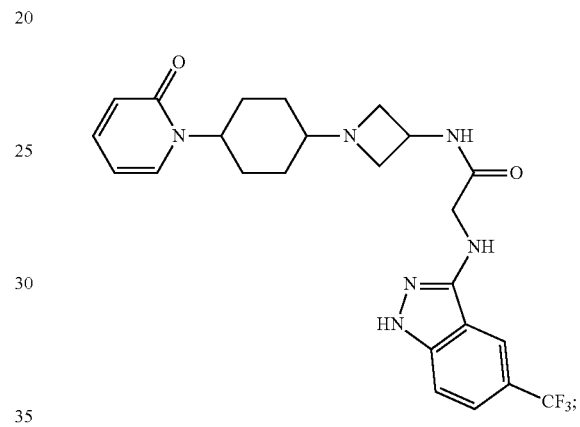
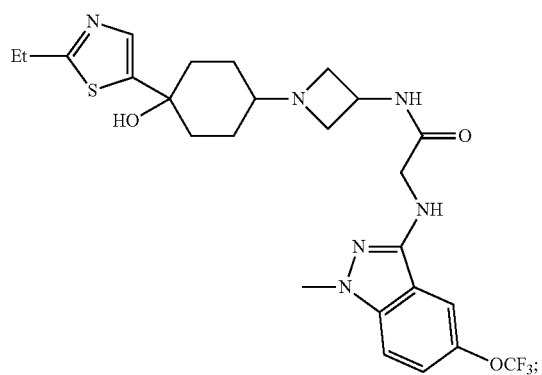
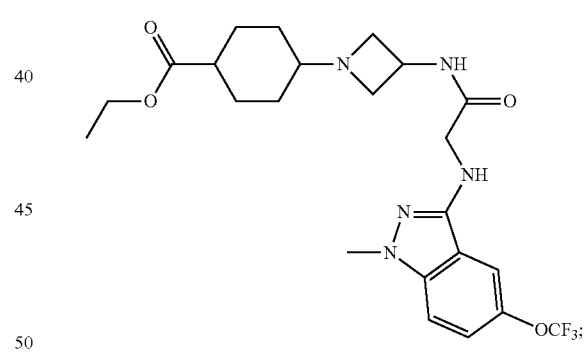
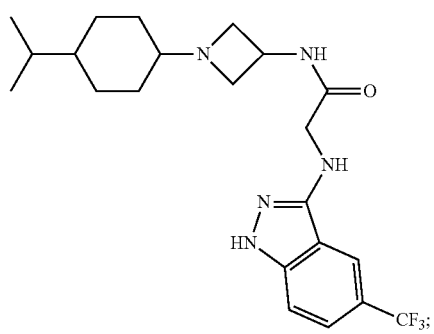
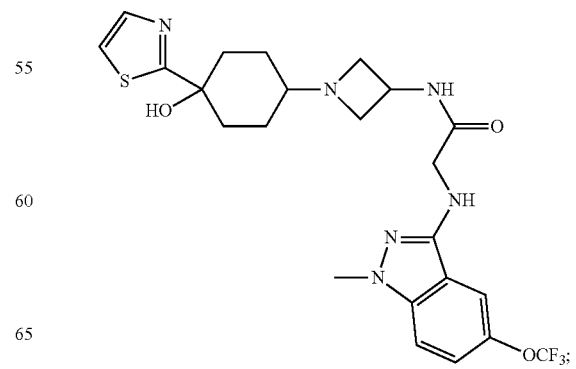

233
-continued
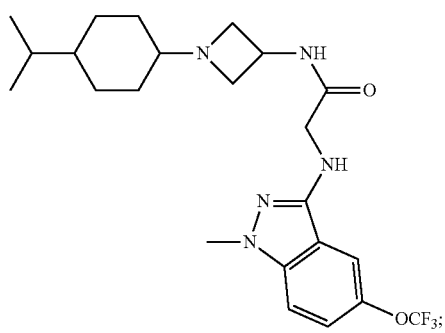
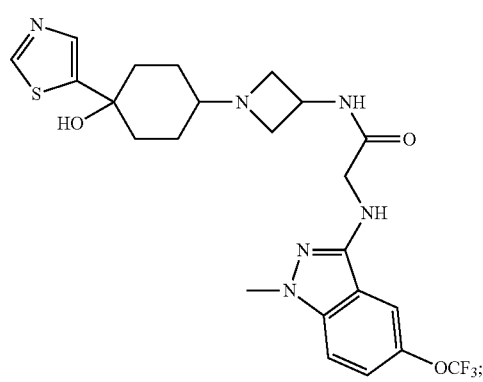
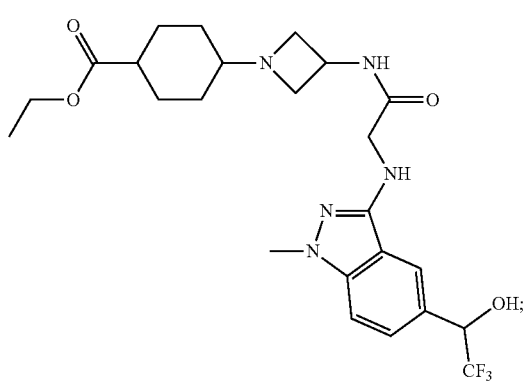
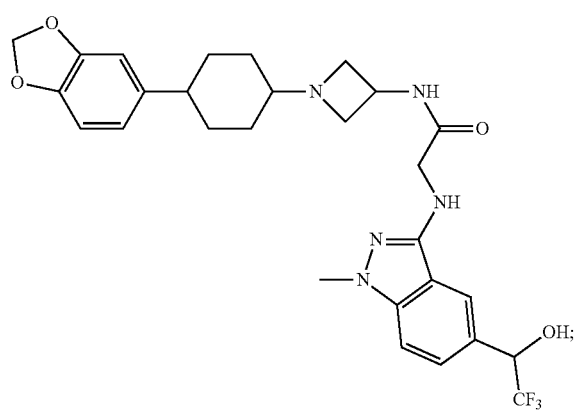
234
-continued
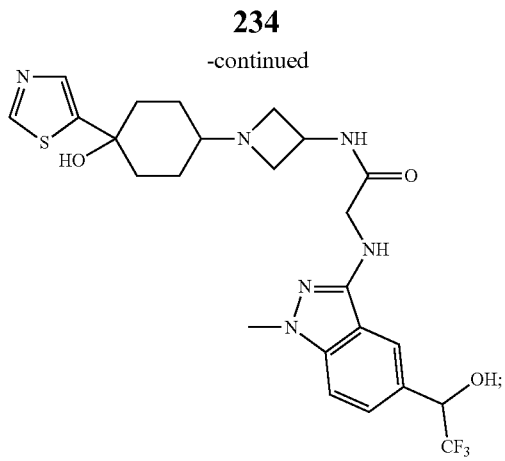
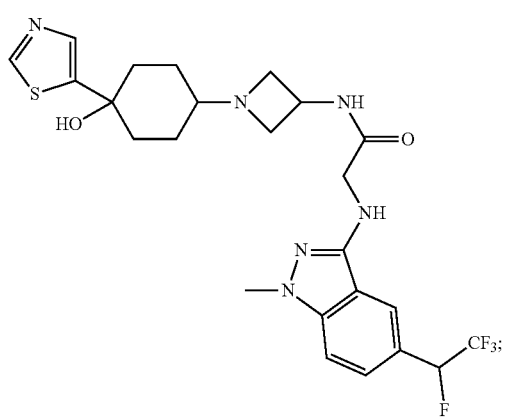
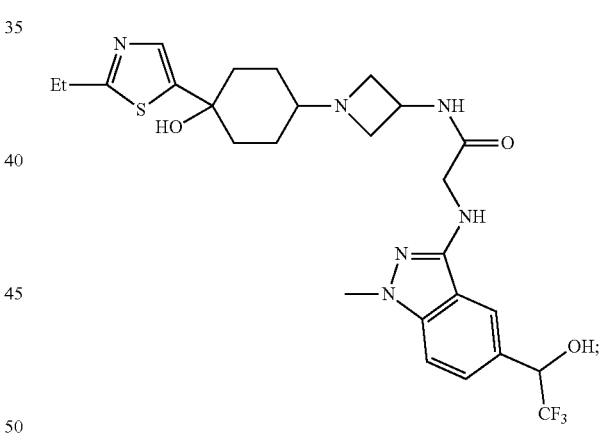
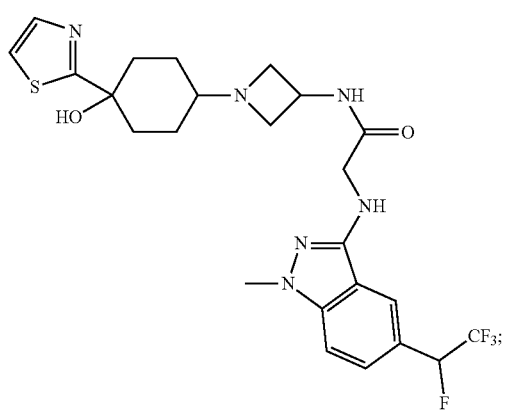

235
-continued
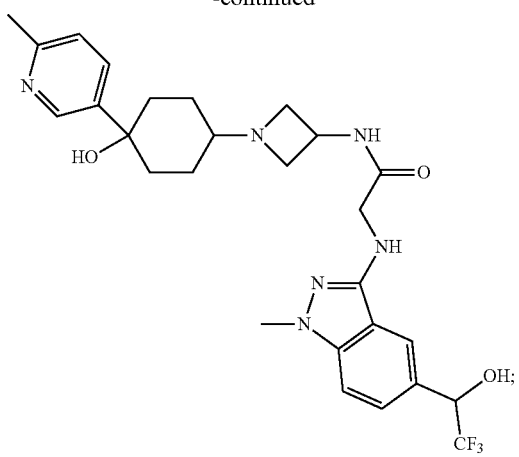
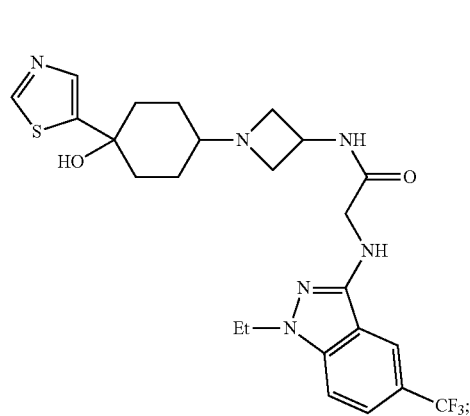
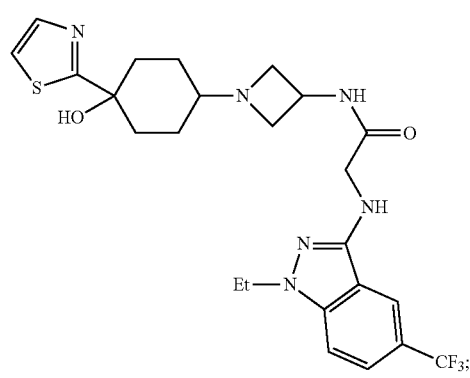
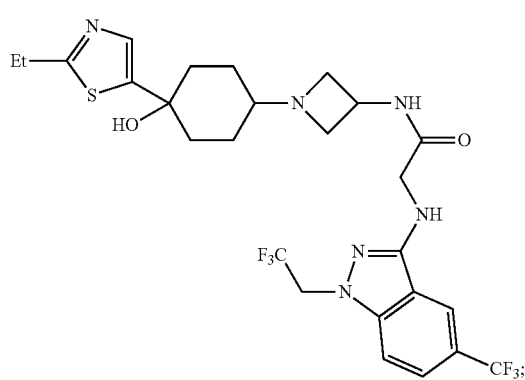
236
-continued
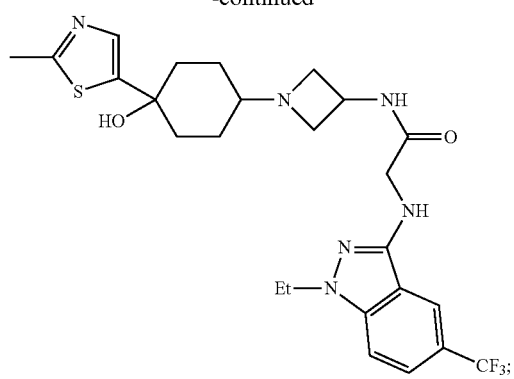
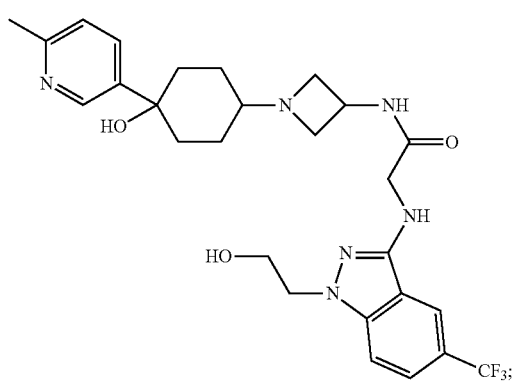
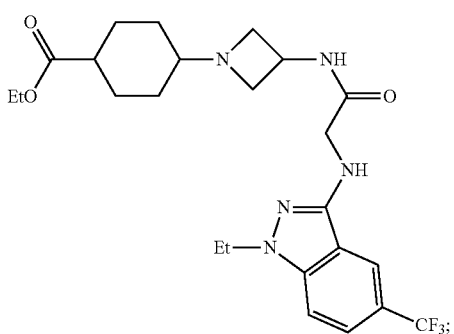
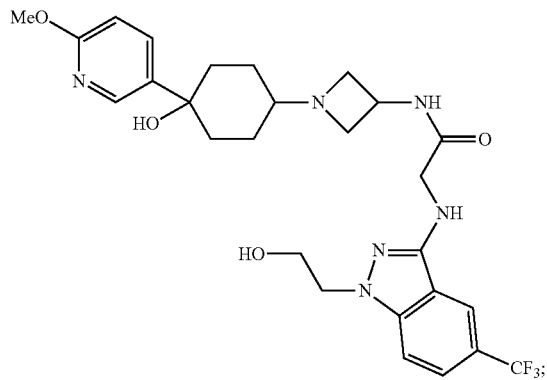

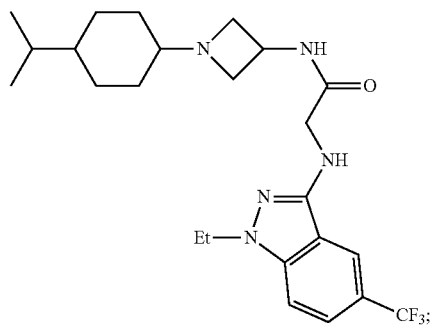
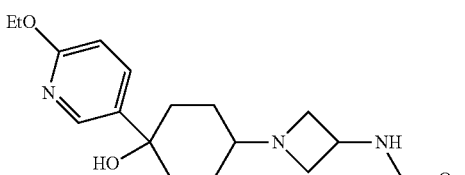
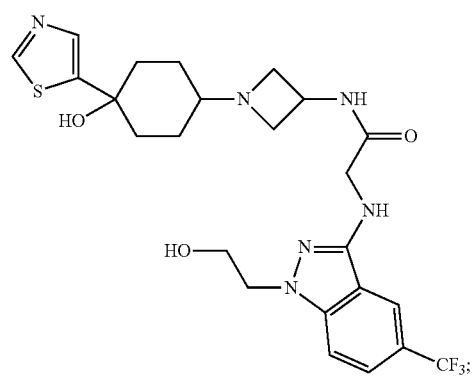
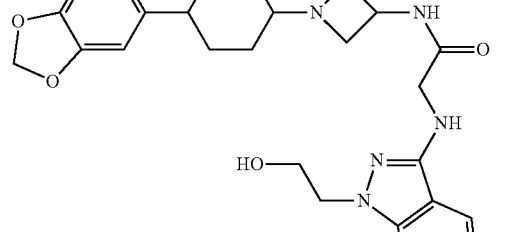
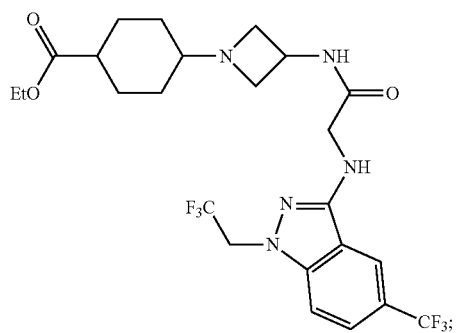
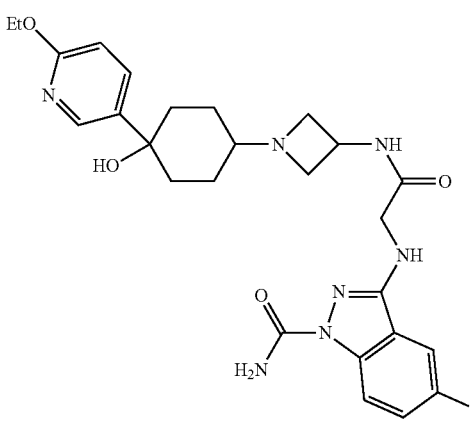
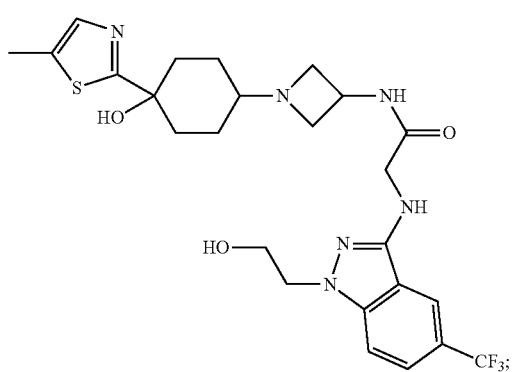
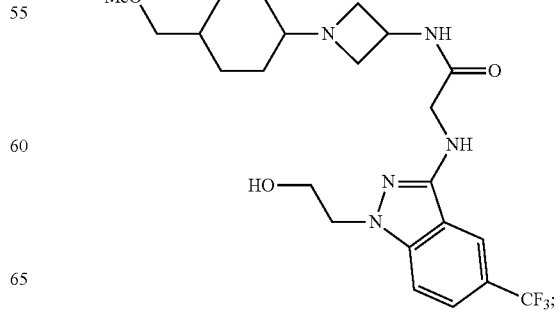

239
-continued
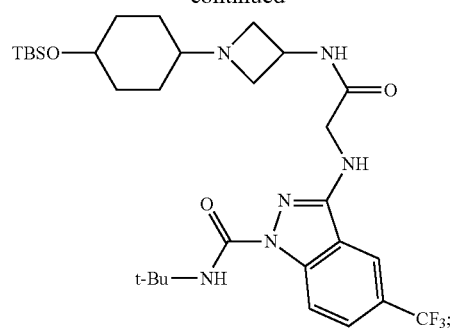
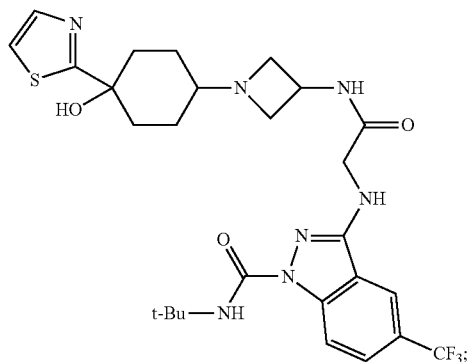
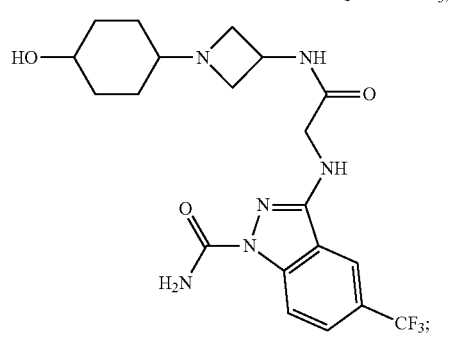
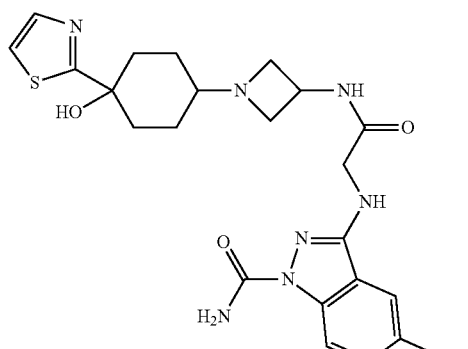
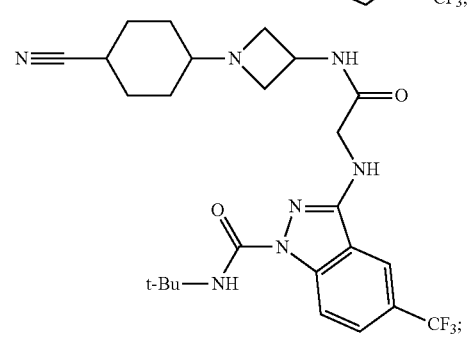
240
-continued
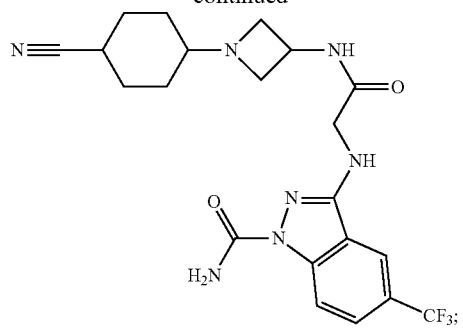
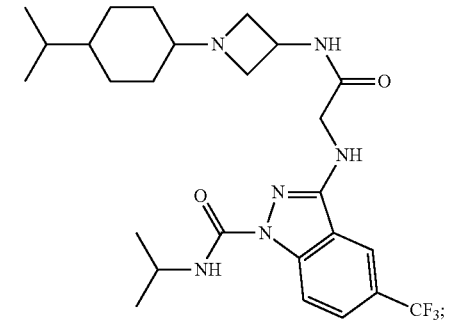
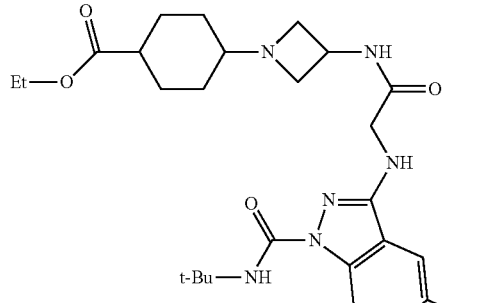
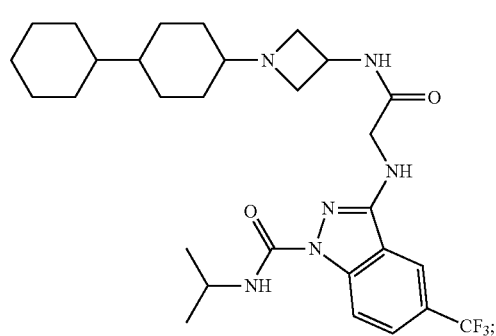
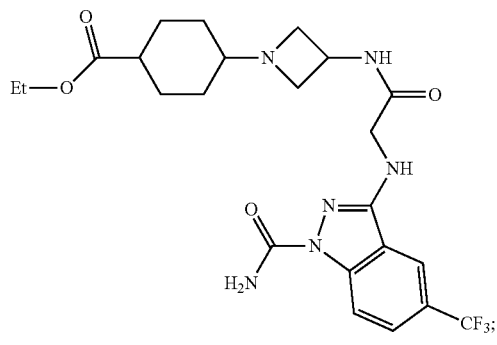

241
-continued
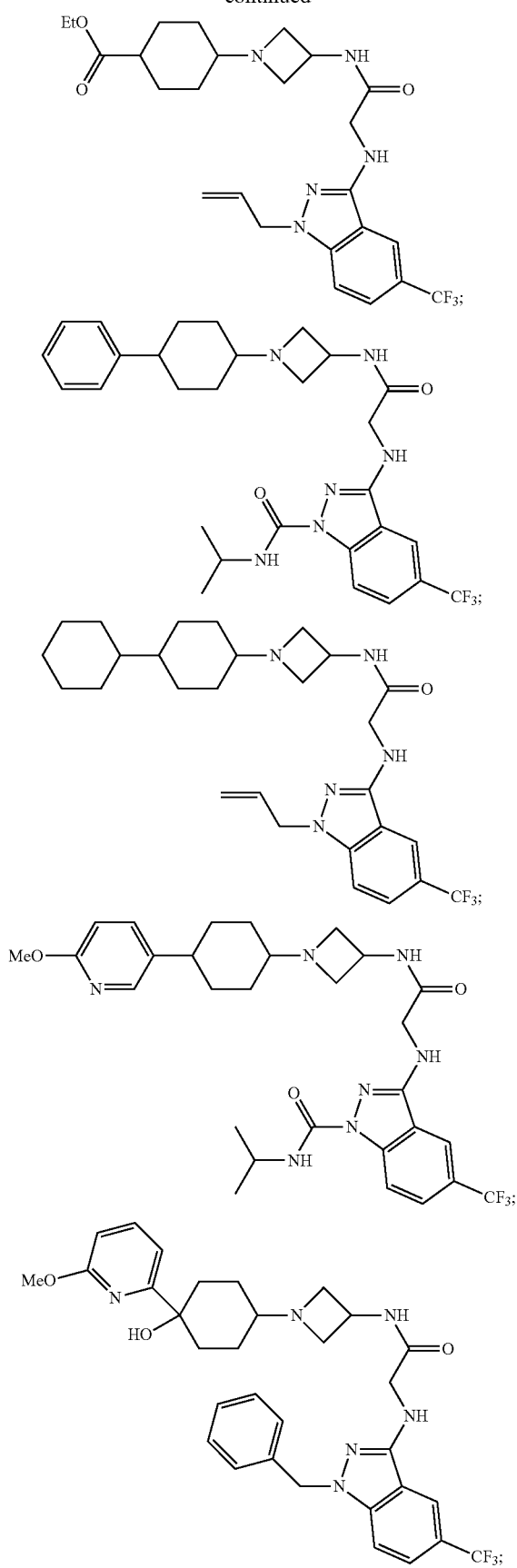
242
-continued
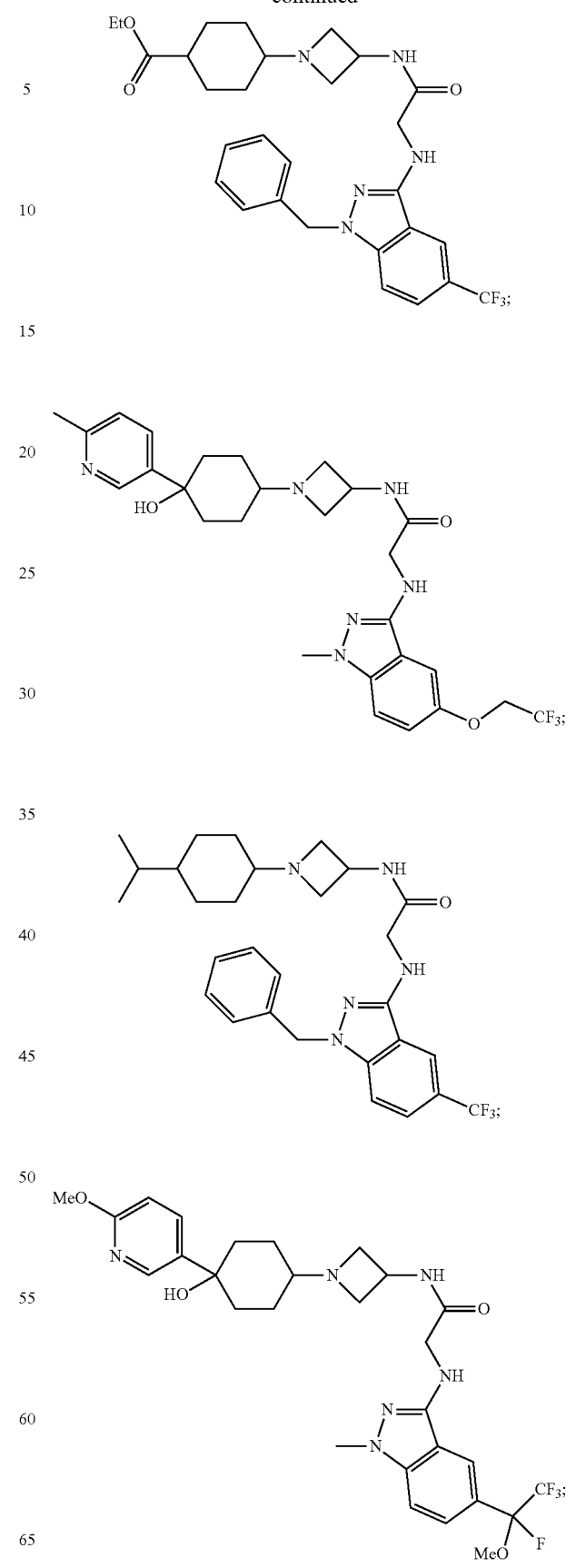

243

-continued

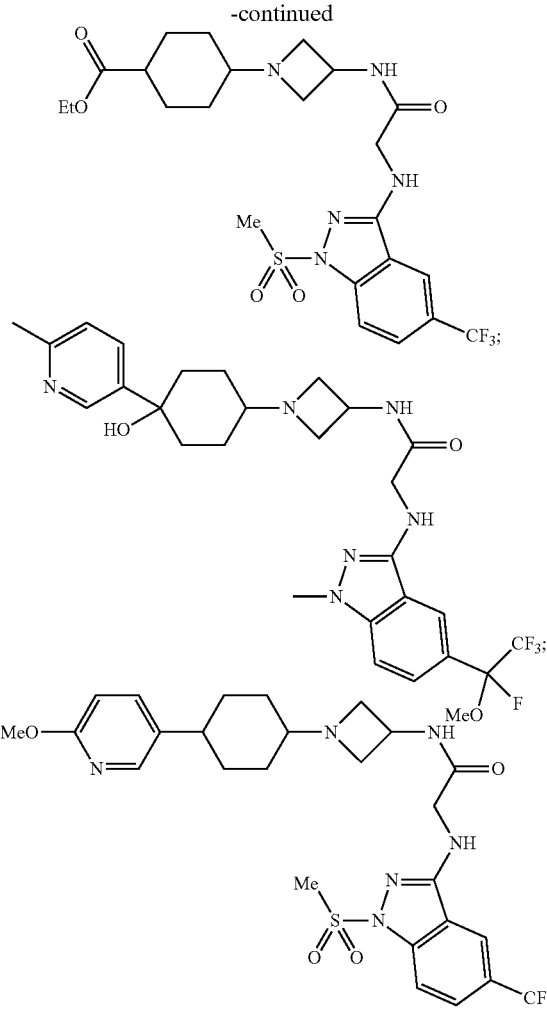

and tautomers, and pharmaceutically acceptable salts thereof.

10. A pharmaceutical composition, comprising a compound of claim 1 and a pharmaceutically acceptable carrier.

11. A pharmaceutical composition comprising a compound of claim 1 made by mixing a compound of claim 1 and a pharmaceutically acceptable carrier.

12. A process for making a pharmaceutical composition comprising mixing a compound of claim 1 and a pharmaceutically acceptable carrier.

13. A process for the preparation of a compound of Formula (I) of claim 1, wherein X is $NR^3$ comprising reacting a compound of Formula (IX)

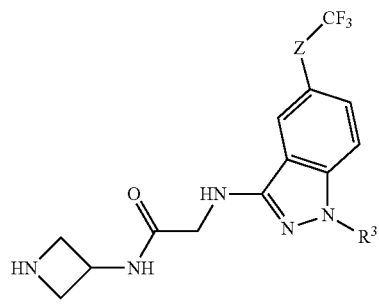

244 with a compound of Formula (X)

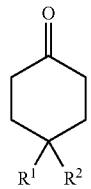

in the presence of a reducing agent to provide the compound of Formula (I).

14. A process for the preparation of a compound of Formula (I) of claim 1, wherein X is O comprising reacting a compound of Formula (XX)

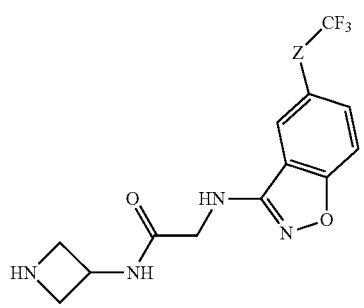

with a compound of Formula (X)

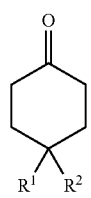

in the presence of a reducing agent to provide the compound of Formula (I).

15. A method of treating or ameliorating a syndrome, disorder or disease, wherein said syndrome, disorder or disease is selected from the group consisting of: type I diabetes, type II diabetes, diabetic complications, diabetic nephropathy, diabetic retinopathy, diabetic retinitis, diabetic microangiopathy, obesity, obesity-associated insulin resistance, metabolic syndrome, asthma, and allergic asthma, comprising administering to a subject in need thereof a therapeutically effective amount of a compound of claim 1.

* * * * *